US012054707B2

(12) United States Patent
Zhu et al.

(10) Patent No.: US 12,054,707 B2
(45) Date of Patent: *Aug. 6, 2024

(54) HIGH FIDELITY RESTRICTION ENDONUCLEASES

(71) Applicant: New England Biolabs, Inc., Ipswich, MA (US)

(72) Inventors: Zhenyu Zhu, Beverly, MA (US); Aine Quimby, Newton, NH (US); Shuang-Yong Xu, Lexington, MA (US); Shengxi Guan, Stoneham, MA (US); Hua Wei, Ipswich, MA (US); Penghua Zhang, Lexington, MA (US); Dapeng Sun, Arlington, MA (US); Siu-hong Chan, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 670 days.

This patent is subject to a terminal disclaimer.

(21) Appl. No.: 17/227,799

(22) Filed: Apr. 12, 2021

(65) Prior Publication Data
US 2021/0230581 A1    Jul. 29, 2021

Related U.S. Application Data

(62) Division of application No. 16/567,332, filed on Sep. 11, 2019, now abandoned, which is a division of
(Continued)

(51) Int. Cl.
*C12N 15/10* (2006.01)
*C12N 9/16* (2006.01)
*C12N 9/22* (2006.01)

(52) U.S. Cl.
CPC ........... *C12N 15/1058* (2013.01); *C12N 9/16* (2013.01); *C12N 9/22* (2013.01); *C12N 15/1034* (2013.01); *C12N 15/1086* (2013.01)

(58) Field of Classification Search
CPC ........ C12N 15/1058; C12N 9/16; C12N 9/22; C12N 15/1034; C12N 15/1086; C12Q 1/44
See application file for complete search history.

(56) References Cited

U.S. PATENT DOCUMENTS 5,663,067 A * 9/1997 Xu ........................... C12N 9/22
435/320.1
6,723,546 B2 4/2004 Zhu et al.
(Continued)

FOREIGN PATENT DOCUMENTS

WO  WO-2007097778 A2 * 8/2007 ............... C12N 9/22
WO  2009/009797 A2    1/2009

OTHER PUBLICATIONS

Witkowski, Andrzej, et al. "Conversion of a β-ketoacyl synthase to a malonyl decarboxylase by replacement of the active-site cysteine with glutamine." Biochemistry 38.36 (1999): 11643-11650. (Year: 1999) (Year: 1999).*

(Continued)

*Primary Examiner* — Manjunath N Rao
*Assistant Examiner* — Erica Nicole Jones-Foster
(74) *Attorney, Agent, or Firm* — New England Biolabs, Inc

(57) ABSTRACT

Compositions and methods are provided for enzymes with altered properties that involve a systematic approach to mutagenesis and a screening assay that permits selection of the desired proteins. Embodiments of the method are particularly suited for modifying specific properties of restriction endonucleases such as star activity. The compositions includes restriction endonucleases with reduced star activity as defined by an overall fidelity index improvement factor.

9 Claims, 49 Drawing Sheets

Specification includes a Sequence Listing.

Related U.S. Application Data application No. 15/882,603, filed on Jan. 29, 2018, now Pat. No. 10,450,559, which is a division of application No. 14/972,844, filed on Dec. 17, 2015, now abandoned, which is a division of application No. 13/736,406, filed on Jan. 8, 2013, now Pat. No. 9,249,396, which is a division of application No. 12/172,963, filed on Jul. 14, 2008, now Pat. No. 8,372,619, said application No. 14/972,844 is a division of application No. 12/172,963, filed on Jul. 14, 2008.

(60) Provisional application No. 60/959,203, filed on Jul. 12, 2007.

(56) References Cited

U.S. PATENT DOCUMENTS

| | | | |
|---|---|---|---|
| 8,372,619 B2 | 2/2013 | Zhu et al. | |
| 2005/0158834 A1* | 7/2005 | Xu | C12Q 1/44<br>435/199 |
| 2009/0029376 A1 | 1/2009 | Zhu et al. | |

OTHER PUBLICATIONS

Sadowski, M. I., and D. T. Jones. "The sequence-structure relationship and protein function prediction." Current opinion in structural biology 19.3 (2009): 357-362. (Year: 2009) (Year: 2009).*
Branden, Carl Ivar, and John Tooze. Introduction to protein structure. Garland Science, 2012. (Year: 2012) (Year: 2012).*
Seffernick, Jennifer L., et al. "Melamine deaminase and atrazine chlorohydrolase: 98 percent identical but functionally different." Journal of bacteriology 183.8 (2001): 2405-2410. (Year: 2001) (Year: 2001).*
New England Biolab (see attached reference) (Year: 2023) (Year: 2023).*
Tang, Jian Xin, et al. "Study on gas control in coal mine by methanotrophic bacteria M02." Advanced Materials Research 602 (2013): 1309-1312. (enzyme) (Year: 2012) (Year: 2012).*
McKane et al Genetics 139 35-43 1993.
Danna et al PNAS 68 2913-2917 1971.
Nasri et al NAR 14 811-821 1986.
New_England_Biolabs_Catalog_and_Technical_Reference_Oct. 2009.
Velculescu et al Science 270 484-487 1995.
Roberts et al NAR 31 1805-1812 2003.
Heitman Genet Eng 15 57-108 1993.
Roberts PNAS 102 5905-5908 2005.
Raleigh et al Bac Genomes Phys Struct Analysis 78-92 1998.
Roberts et al NAR 33 D230-232 2005.
Kelly et al JMB 51 393-409 1970.
Polisky et al PNAS 72 3310-3314 1975.
Walker et al PNAS 89 392-396 1992.
Arber Science 205 361-365 1979.
Carlson et al Mol Microbiol 27 671-676 1998.
Zhu et al J. Mol. Biol 337 573-583, 2004.
Genbank Accession No. AAR96018.1.

* cited by examiner

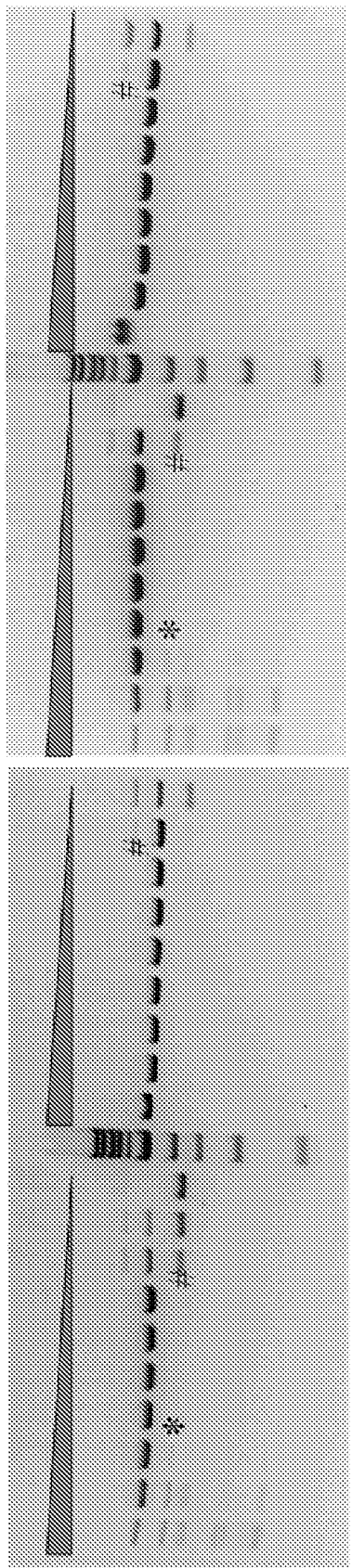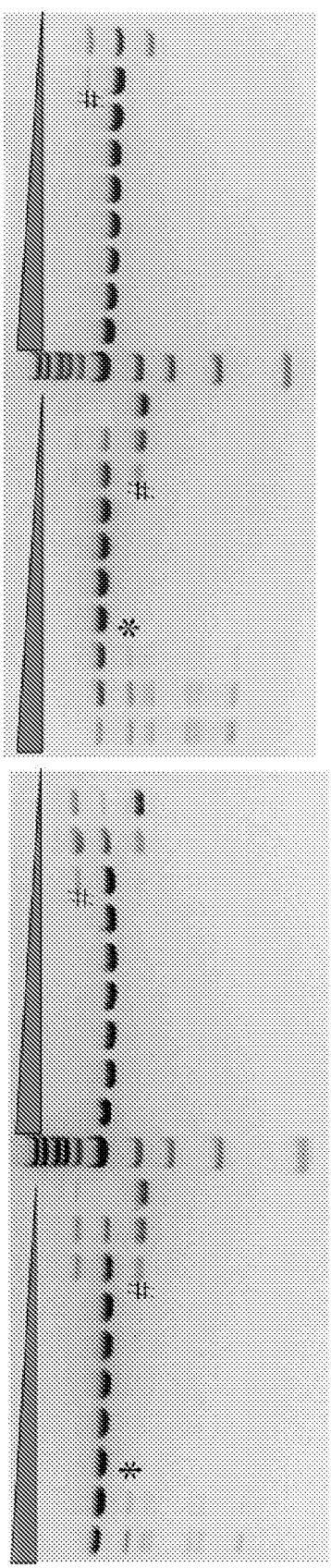

BamHI (E86P)
14 HOURS

BamHI (E86P)
1 HOUR

BamHI-HF(E163A/E167T)

NEB2

BamHI-HF(E163A/E167T)

NEB1

COMPARISON OF
BamHI-HF AND WT BamHI

COMPARISON OF
BamHI-HF AND WT BamHI

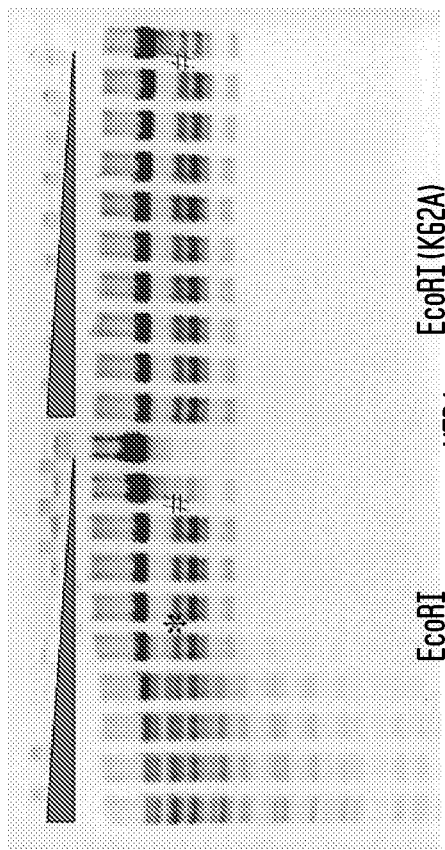
*FIG. 6A* *FIG. 6B*
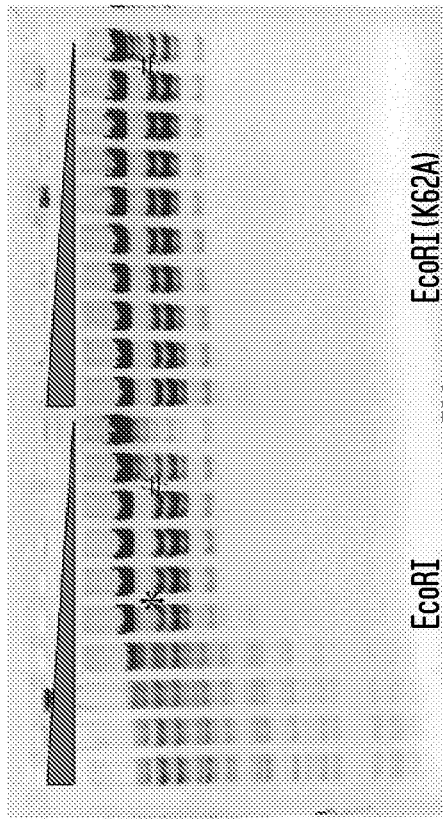
*FIG. 6C* *FIG. 6D*

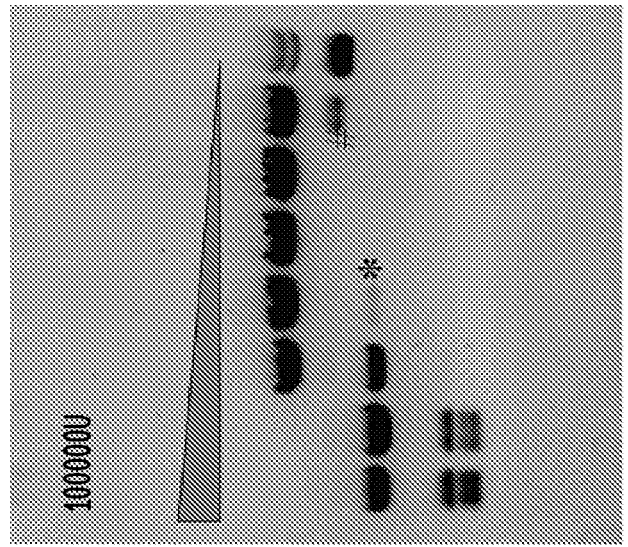
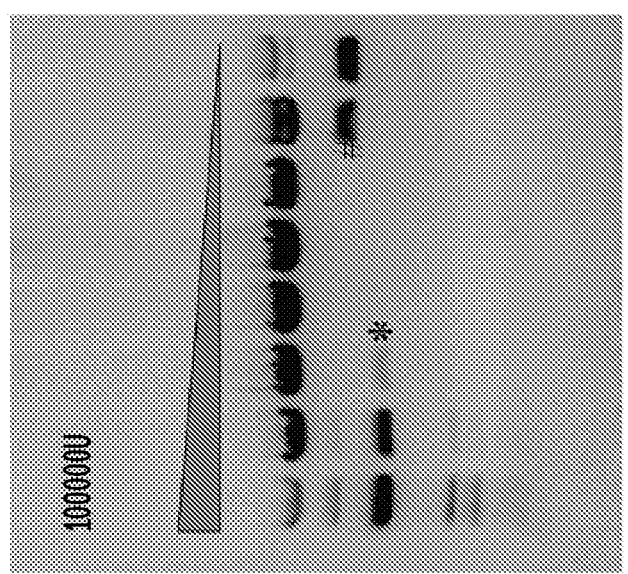
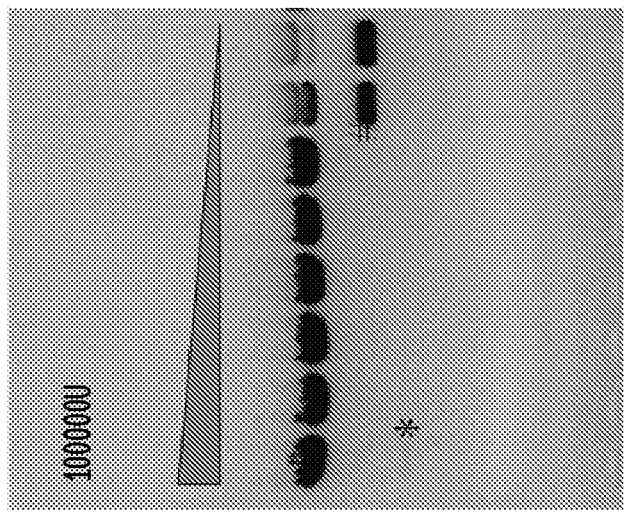

COMPARISON OF
EcoRI-HF AND WT EcoRI

COMPARISON OF
EcoRI-HF AND WT EcoRI

ScaI COMBINATION OF MUTATIONS
NEB2, 37% GLYCEROL

ScaI COMBINATION OF MUTATIONS
NEB2, 5% GLYCEROL

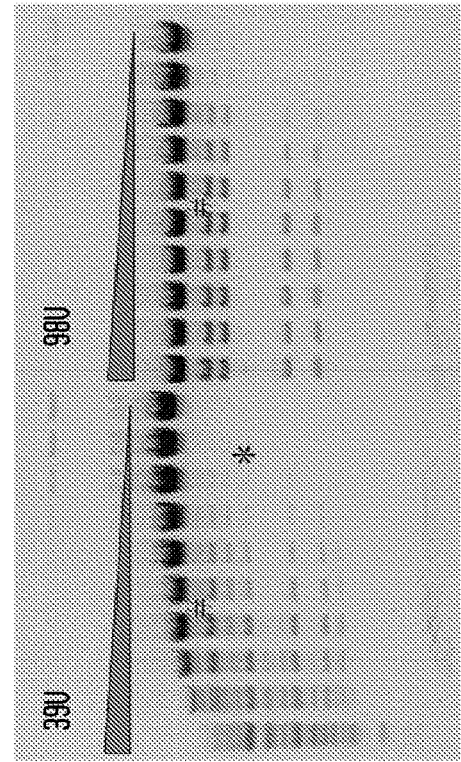
FIG. 10A
ScaI COMPARISON OF ScaI-HF AND WT ScaI
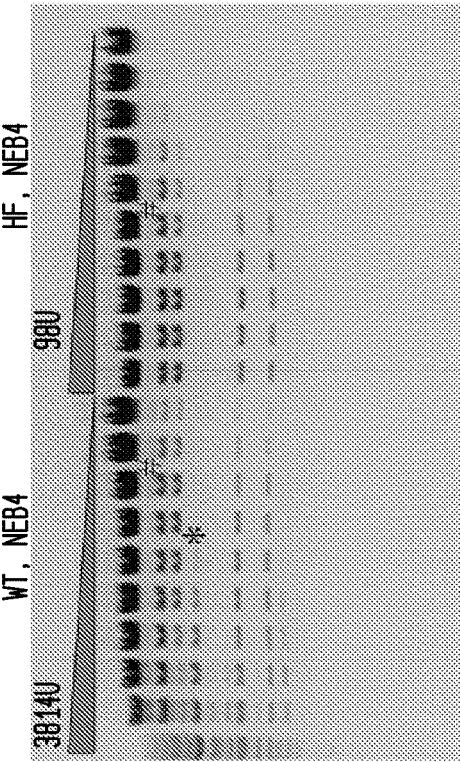
FIG. 10B
ScaI COMPARISON OF ScaI-HF AND WT ScaI
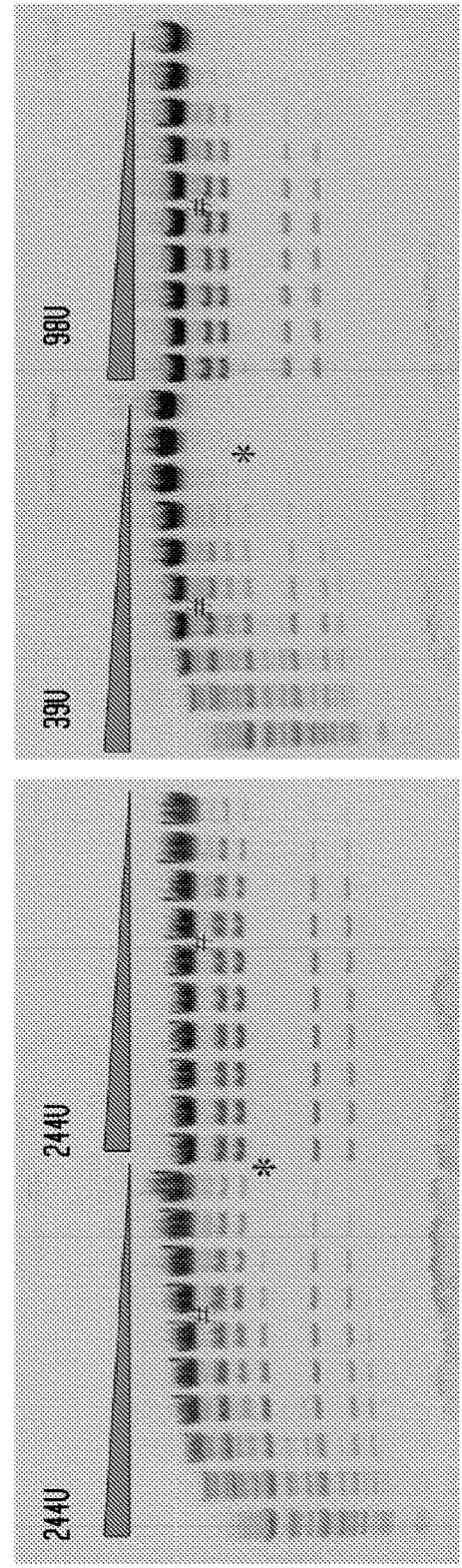
FIG. 10C
ScaI COMPARISON OF ScaI-HF AND WT ScaI
FIG. 10D
ScaI COMPARISON OF ScaI-HF AND WT ScaI

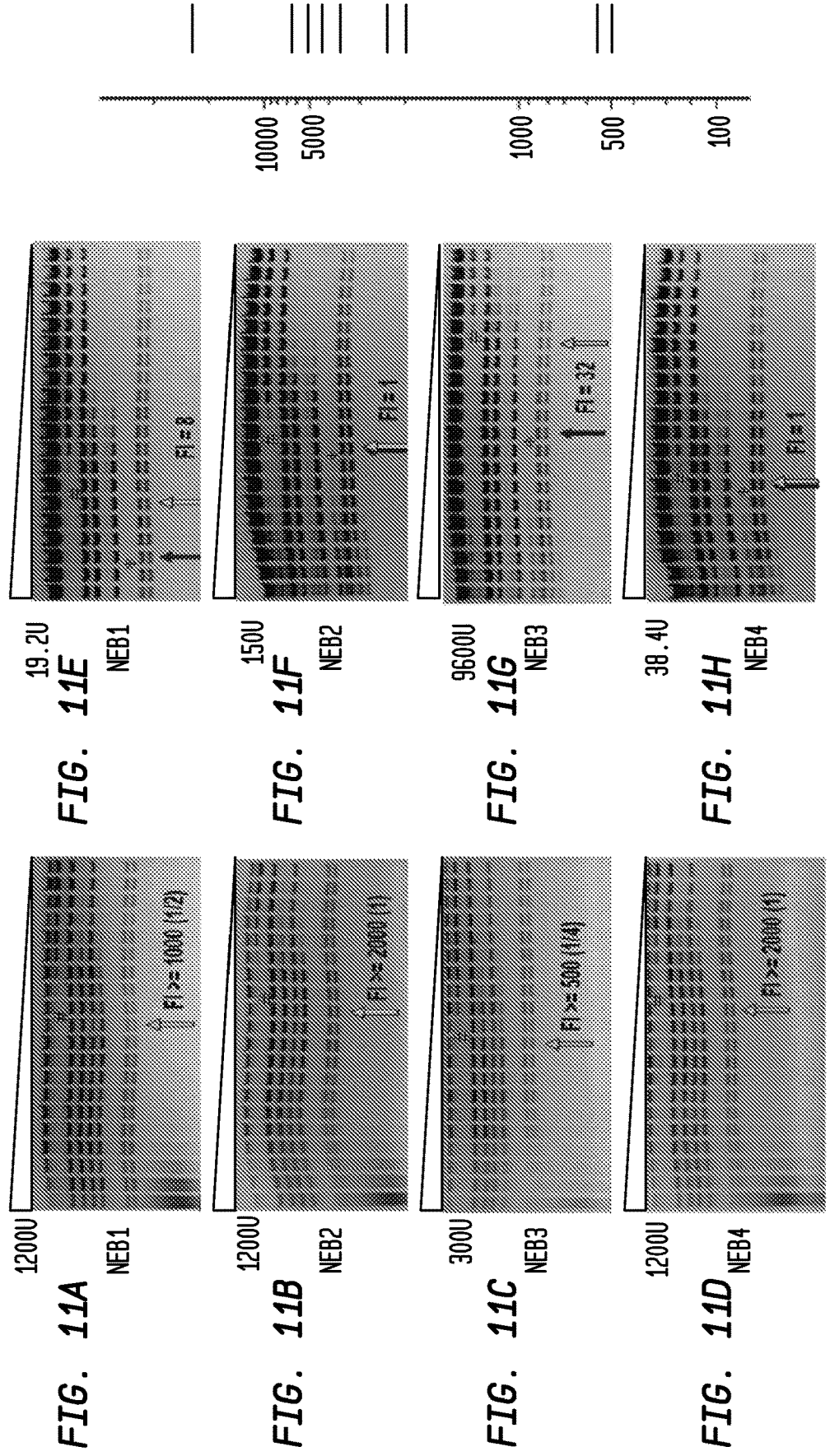

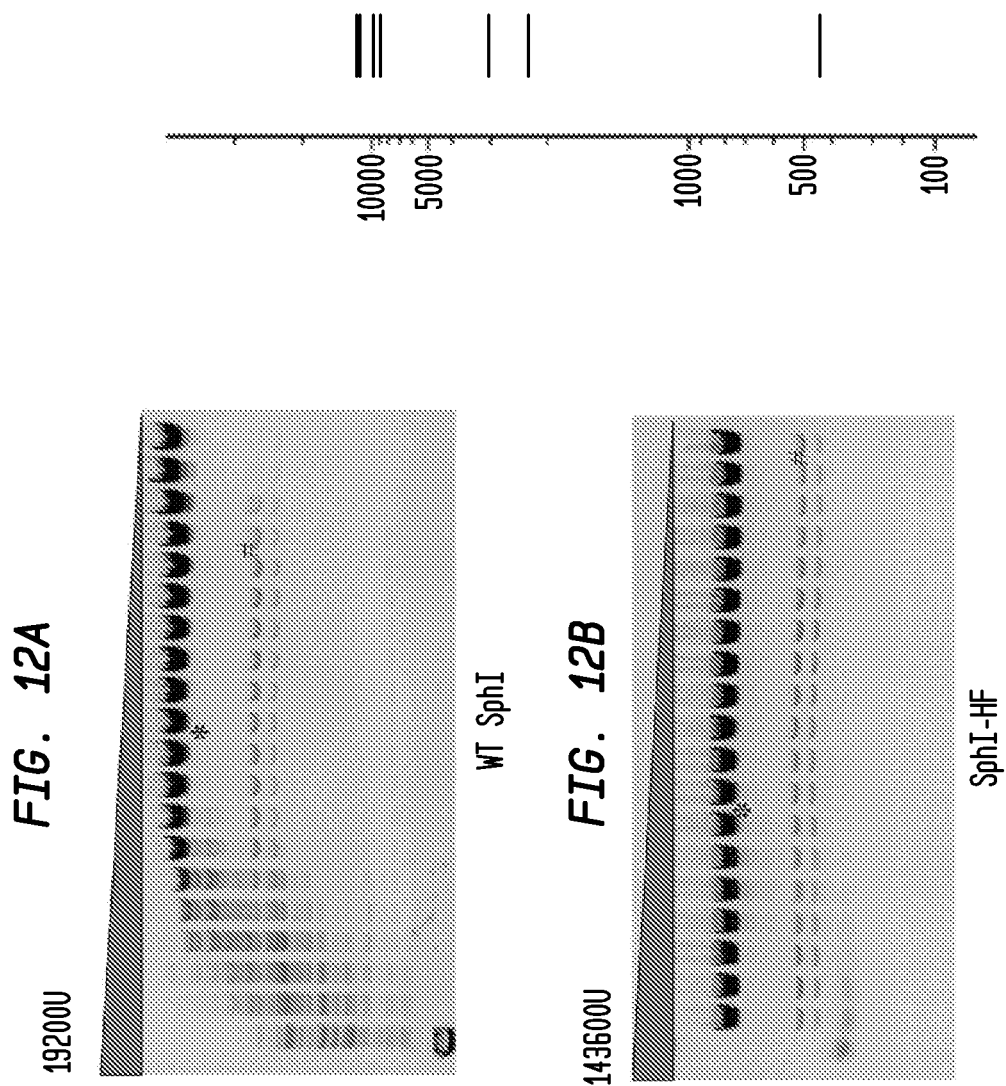
FIG. 12A WT SphI
FIG. 12B SphI-HF

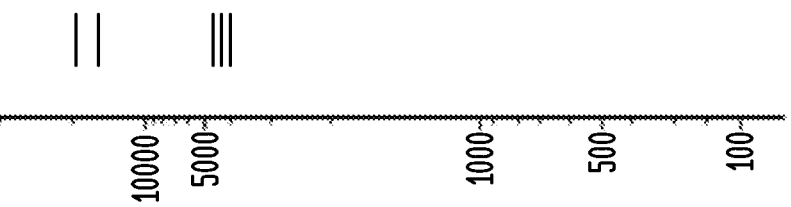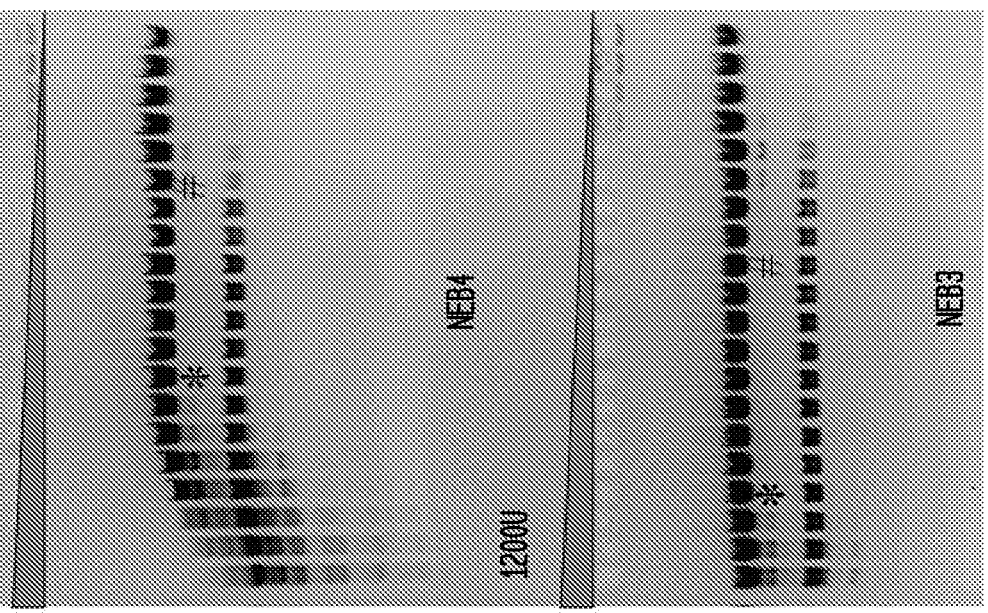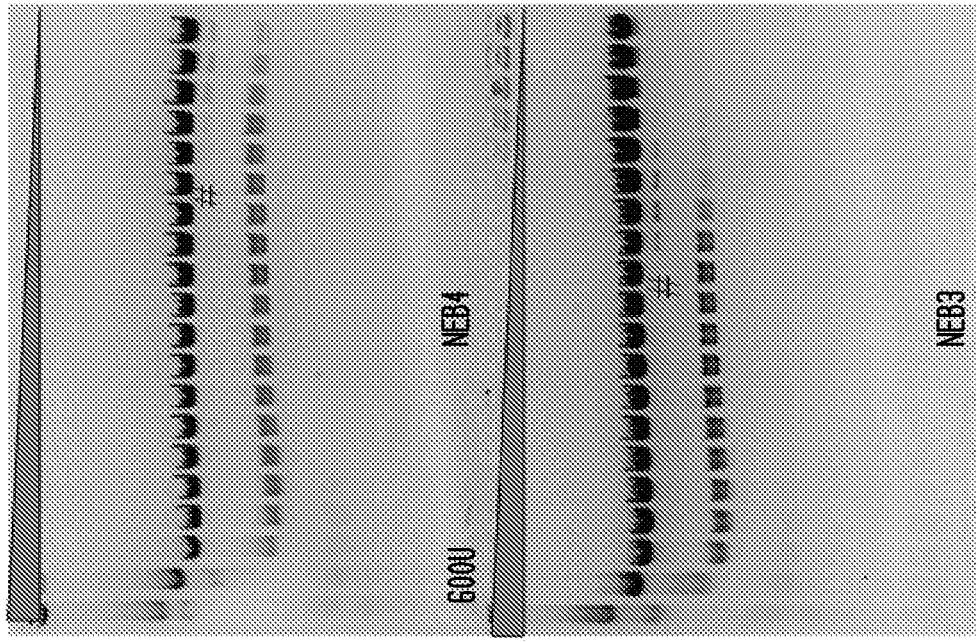
FIG. 14A  FIG. 14B

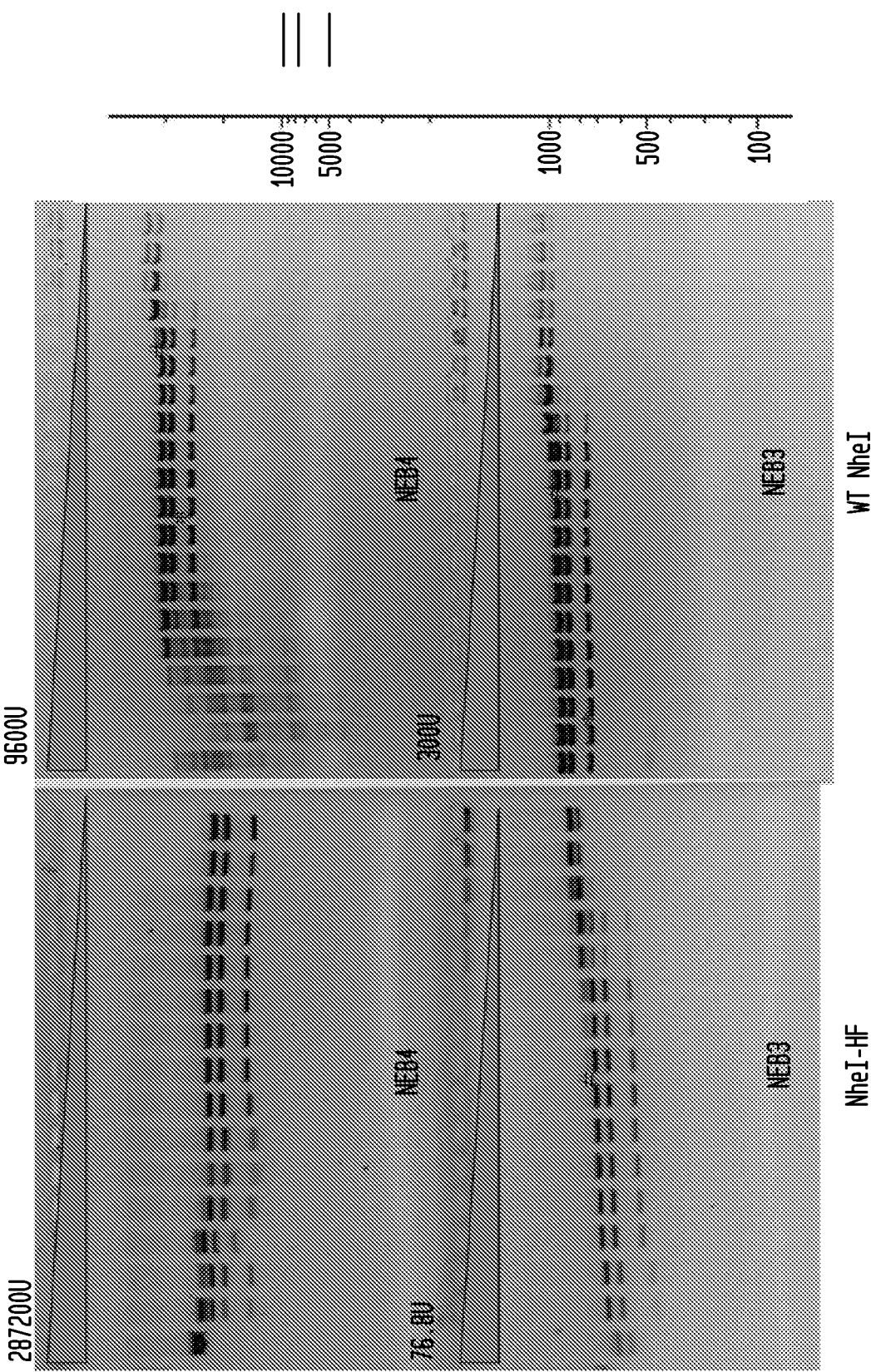

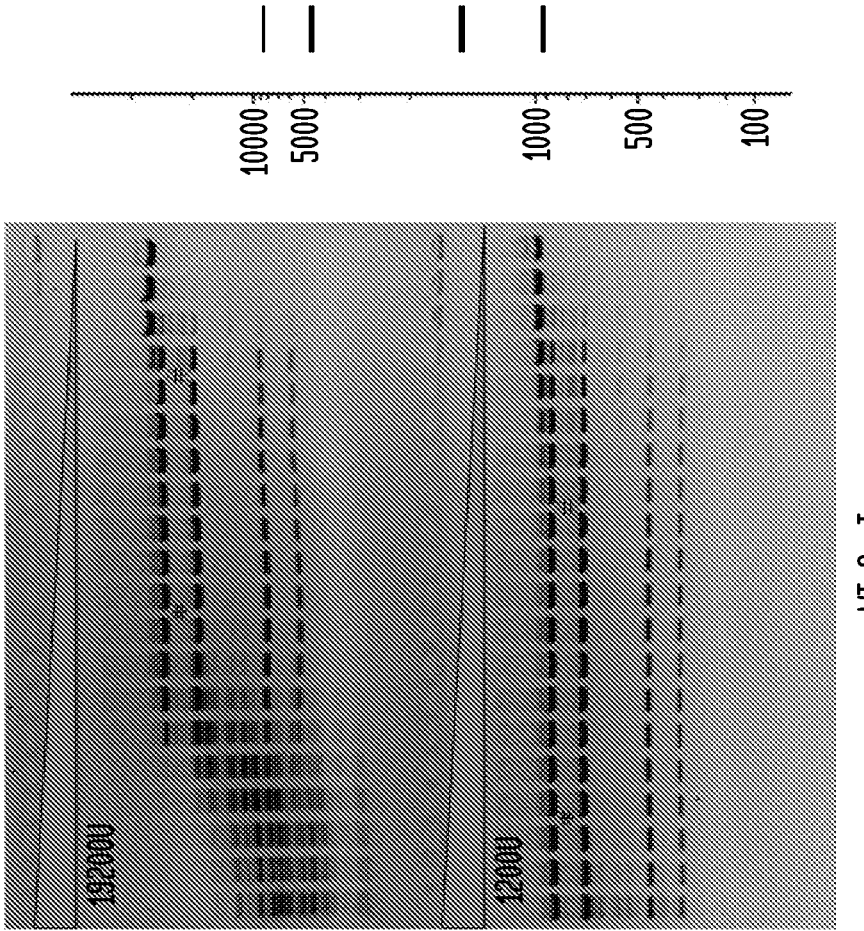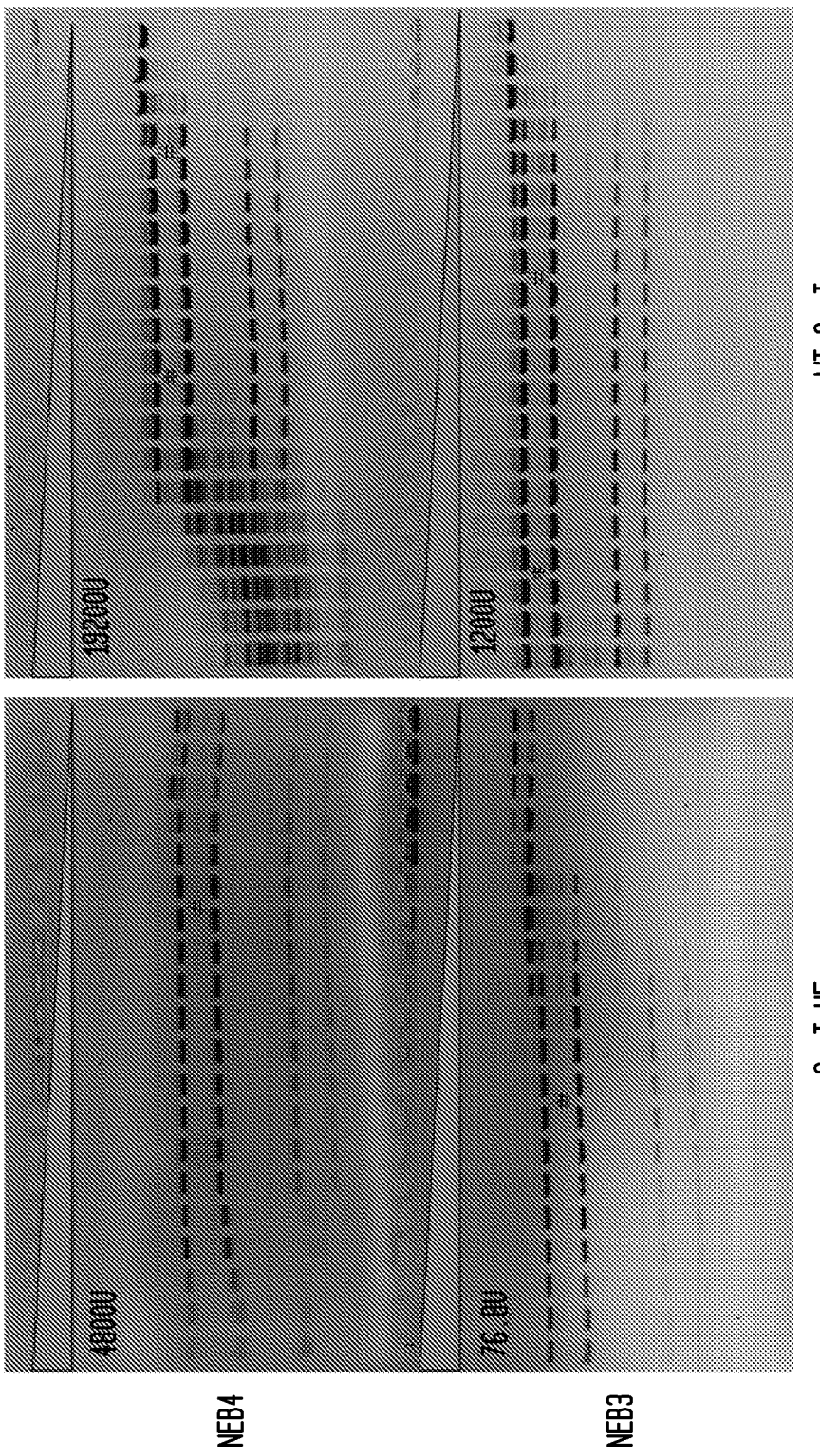

FIG. 31A
SEQ ID NO:1

```
   1 ATGATCAAGT ACTTGGGTAG CAAGCGGACG CTCGTGCCCG TCCTCGGTGA
  51 CATCGCTTCG GCCTCTGAAG CAACAGAGGC GGTTGACCTG TTCACTGGCA
 101 CGACGCGTGT GGCGCAAGAG TTCAAGCGTC GCGGGCTTCG AGTTCTTGCT
 151 AACGACATAG CGACGTACTC CGAGGTTTTA GCCCAGTGCT ATATCGCCAC
 201 CAACGGCCAG GAAGTTGACC GCCGTGCGCT CGAGGCCGCT CTGGCGGAGC
 251 TGAACGCCTT GCCCGGCGAA CCTGGATACT TCACGGAAAC CTTCTGTGAG
 301 GCTTCTCGCT ACTTCCAGCC CAAGAACGGG GCTCGGGTGG ATGCAATCAG
 351 GAATGCGATC GACGACCGGT ACGCGGACTC ATGGATGCGA CCGATCCTCC
 401 TCACGAGCTT GATGCTTGCG GCCGACCGCG TCGACTCCAC TACCGGAGTG
 451 CAGATGGCTT ACCTGAAGCA GTGGGCCGCG CGTGCGCACA ATGATCTAGA
 501 GTTGCGGCTT CCAGACCTAA TCGCAGGTGA CGGTGACGCT GCTCGTGAGG
 551 ATGCGGTGAC TCTCGCACAA GAGCTGCCTC GCGTCCAGCT GATGTACCTT
 601 GATCCTCCCT ATAACCAGCA CAGGTACTTC ACCAACTACC ATATTTGGGA
 651 GACCCTGATT CGTTGGGATG CCCCTGAGAG TTATGGGATC GCCTGTAAGC
 701 GCATTGACTC TCGAGATGAT GCCACCAAGA GCCCTATAA TATGAAGCGG
 751 CGAATGCCCG ACGAGATGCG TCGCCTGCTG ATGACCATCA AGGCGGACCT
 801 CGCGGTTGTA TCTTACAACA ATGAGTCGTG GATTGATCCG GAGACGATGA
 851 TGTCGACCCT GCGCGATGCG GGATATGAGG ACGTGCGTCT GCTCGCTTTC
 901 GACTATAAGC GCTACGTTGG GGCTCAAATC GGGATCTACA ATCCCTCCGG
 951 GGAAAAGGTC GGTCGTGTGA GTCACCTCCG AAACATCGAG TATCTCTTTC
1001 TTGCGGGACC AACGGAGCGC GTTGAGGTGT GCGCCGCGAG TGTTGAACAC
1051 CGAGCACTAC CCAAGGAACC GGAACTCACC GCGTTCTAG
```

FIG. 31B
SEQ ID NO:2

```
MIKYLGSKRT LVPVLGDIAS
ASEATEAVDL FTGTTRVAQE
FKRRGLRVLA NDIATYSEVL
AQCYIATNGQ EVDRRALEAA
LAELNALPGE PGYFTETFCE
ASRYFQPKNG ARVDAIRNAI
DDRYADSWMR PILLTSLMLA
ADRVDSTTGV QMAYLKQWAA
RAHNDLELRL PDLIAGDGDA
AREDAVTLAQ ELPRVQLMYL
DPPYNQHRYF TNYHIWETLI
RWDAPESYGI ACKRIDSRDD
ATKSPYNMKR RMPDEMRRLL
MTIKADLAVV SYNNESWIDP
ETMMSTLRDA GYEDVRLLAF
DYKRYVGAQI GIYNPSGEKV
GRVSHLRNIE YLFLAGPTER
VEVCAASVEH RALPKEPELT
AF
```

FIG. 32
SEQ ID NO:3

```
TTGGAGAATT TTTTGAATAA TTTAGATATT AAAACCTTAG GGCAGGTTTT CACCCCTAAA
AAGATAGTGG ATTTCATGCT CACTCTCAAG CACAATCATG GGAGTGTTTT AGAGCCAAGC
GCGGGCGATG GGAGTTTTTT AAAGCGCTTA AAAAAGGCTG TAGGGATTGA AATCGATCCT
AAAATCTGCC CTAAAAATGC CCTTTGCATG GACTTTTTTG ACTACCCTTT AGAAAATCAA
TTTGACACGA TTATTGGCAA TCCGCCCTAT GTCAAGCACA AGGATATTGC GCCAAGCACG
AAAGAAAAAC TCCATTACAG CCTTTTTGAT GAAAGGAGTA ATCTATACTT GTTTTTCATA
GAAAAAGCGA TCAAGCATTT AAAGCCTAAA GGCGAATTGA TTTTCATCAC CCCAAGGGAT
TTTTTAAAAT CCACTTCTAG CGTGAAATTA AACGAATGGA TTTACAAAGA AGGCACGATA
ACGCATTTTT TTGAATTAGG CGATCAAAAG ATTTTCCCAA ACGCCATGCC TAATTGCGTG
ATTTTTCGTT TTTGTAAAGG TGATTTCAGT AGAATCACCA ACGATGGTTT GCAATTTGTG
TGCAAAAAAG GCATTTGTA TTTCCTCAAC CAATCTTACA CGCAAAAATT AAGCGAGGTT
TTTAAGGTTA AGGTGGGGGC AGTGAGCGGG TGCGATAAGA TTTTTAAAAA TGAAACATAC
GGGAATTTAG AATTTGTCAC CTCAATCACC AAAAGAACCA ATGTTTAGA AAAAATGGTT
TTTGTCAATA AACCTAATGA TTATTTACTC CAGCATAAAG ACAGCTTGAT GCAAAGAAAG
ATTAAAAAAT TCAATGAAAG TAATTGGTTT GAATGGGGGA GGATGCATCA CATATCCCCT
AAAAAACGCA TTTATGTTAA CGCCAAAACG CGCCAAAAAA ACCCCTTTTT CATCCACCAA
TGCCCTAATT ATGACGGCTC TATTTTAGCG CTATTCCCTT ATAACCAAAA TTTGGATTTA
CAAAACCTCT GCGATAAACT CAACGCTATC AACTGGCAAG AATTAGGCTT TGTGTGCGGC
GGGCGTTTTT TGTTTTCGCA GCGCTCTTTA GAAAACGCCC TTTTGCCTAA AGACTTTTTA
AATTAG
```

FIG. 33A
SEQ ID NO:4

```
ATGGGTAAAT CTGAATTAAG TGGAAGATTA AATTGGCAAG CATTGGCTGG ATTAAAAGCT AGTGGTGCTG
AACAAAACTT ATATAACGTG TTTAACGCTG TTTTTGAAGG AACTAAATAC GTTTTATACG AGAAGCCAAA
GCACCTTAAA AATCTATACG CTCAAGTAGT CTTACCTGAT GATGTTATTA AAGAAATTTT TAATCCTTTA
ATTGATTTAT CAACTACTCA ATGGGGTGTT TCTCCAGATT TCGCAATAGA AAATACAGAA ACGCATAAAA
TTCTTTTTGG TGAAATTAAA AGACAAGATG GATGGGTAGA AGGTAAAGAT CCTAGTGCTG GCAGGGGTAA
TGCACATGAG AGATCTTGTA AATTATTTAC TCCTGGATTA TTAAAAGCTT ATAGAACAAT TGGTGGAATT
AACGATGAAG AGATATTGCC ATTCTGGGTT GTATTCGAAG GTGATATAAC ACGAGATCCC AAAAGAGTAA
GAGAAATTAC TTTCTGGTAT GACCACTATC AAGATAATTA TTTCATGTGG CGACCAAATG AATCAGGCGA
AAAATTAGTT CAACACTTCA ATGAAAAATT AAAAAAATAT TTAGATTAA
```

FIG. 33B
SEQ ID NO:5

```
MGKSELSGRL NWQALAGLKA SGAEQNLYNV FNAVFEGTKY VLYEKPKHLK NLYAQVVLPD DVIKEIFNPL
IDLSTTQWGV SPDFAIENTE THKILFGEIK RQDGWVEGKD PSAGRGNAHE RSCKLFTPGL LKAYRTIGGI
NDEEILPFWV VFEGDITRDP KRVREITFWY DHYQDNYFMW RPNESGEKLV QHFNEKLKKY LD
```

FIG. 34A
SEQ ID NO:6

ATGGCTATTA CATTATGTGA CATAAATGGT TGTAGACTTG AGAGAGGACA TACTGGTAAA CATAATAAAT TTCCTGAATT
TGTATGGACT TCTCAATTTA ATAAAAAAGA TATTGATAAG GTCAATAAAG CAGGATATGC AACACCAAGA GGTGGGGACA
AAGGAGCCTA TCAGAACCAT GTTTACAGAA ATAATAAAGT AATTATTCCT TTTGAAAGGT TGGAAAATGT TAATTTAAAT
AACTATCAAG ATGGATATGT TATTAGGTTA TTCCCTAATC AGTACTTTGA ATCAGCCGGG GTAGTTAAGC CGGAATTCTT
ACAACCAAAT TCATTTGTTA AAGTTGGGGA CAATGCATTT ATTTTATATC GCACACATTC ATCTTTTGAG GAATTACCTC
CTCTACCAGA CTGGGAGGTT AGACATCTAA AAAAGAACGG TAATATAGTT ACCAGAAGAA GTAAGGACGT AATCGATGCT
GGACATTATG TCTTACGATT ATCATCAATT AGTAACAAAA AAGAAAGAAA AGAGGGCCCT CCTCAAGGTA TTTTTGCACC
TGAATATGCA AATGCAGAGA CTAATTATCT GTCAAAAGCA TTTTTAGCCT GGTTAATTAT TAAAACTCAA AATAGTCCGT
ATAATGAAGA ACAATTCCAA CACTTAAGAG CGATCTTAAT TAGTCATAAT CTCATCAATA TTTCTCAACT TGAAGAAAAG
GCTATTCTAA AGAATGGTAT CACATGCTGC CCTTTATGCG AGCAAATTAT TTTTTACGAA CAGCTACACG AAATGGTTTC
TTTTGAAGGT GCGTCTGGCC TTGCGAATTC ACAAGAACAG GTTGAGGGTG CAACTAGGTC AACATCAGTT AATTTATTCC
ATATGGTACC ATTAGTATAT GAAACCTTGG AACACAAACC TGATCAAATA GCATGGGGCC ATGCCATTTG TAATACTAGA
CTTGGTCAAA GAGAGTGCCT GCCTCTTAGT AGACTAAAAC AAGAAGGTAC GCCCGTTGGT CTTCTTGATG AAGATTCGAA
TCTTGAAGTA TTAGGATGGA TTAGTAAAGA TAAGCAATTT ATTCGTACAG AAAATGGGGA AGTTTGGATT AAAATTACAG
ATATTGAATT TAACGATGAC TTTGAAGAAT AA

FIG. 34B
SEQ ID NO:7

MAITLCDING CRLERGHTGK HNKFPEFVWT SQFNKKDIDK VNKAGYATPR GGDKGAYQNH VYRNNKVIIP
FERLENVNLN NYQDGYVIRL FPNQYFESAG VVKPEFLQPN SFVKVGDNAF ILYRTHSSFE ELPPLPDWEV
RHLKKNGNIV TRRSKDVIDA GHYVLRLSSI SNKKERKEGP PQGIFAPEYA NAETNYLSKA FLAWLIIKTQ
NSPYNEEQFQ HLRAILISHN LINISQLEEK AILKNGITCC PLCEQIIFYE QLHEMVSFEG ASGLANSQEQ
VEGATRSTSV NLFHMVPLVY ETLEHKPDQI AWGHAICNTR LGQRECLPLS RLKQEGTPVG LLDEDSNLEV
LGWISKDKQF IRTENGEVWI KITDIEFNDD FEE

FIG. 35A
SEQ ID NO:8

```
ATGATTTTTG CTGATATTGA ATTTGAAAAA GAACTTTTTT CAGCTGCTAA TAAATTAAGG GGAAAAATTG CTCCAAGTGA
GTATAAGCAT TATGTTTTGC CTTTGATATT CCTTAGATAT TTATCTCTTA AATACCAACA AAGAAGGAAT GAAATTCAAC
AACAGATAAA TGATTCAAGG GATCACAAGA AAAATCAAGA TGAAGTGTTA AAGATATTGG AAGACAGGAC TGAATACACC
AAAGTAAATG TTTTCTATAT TCCTGAAAAA GCTAGTTGGG AATACTTATT GAAAAATTCC GAAATGATA AAATTAAAGA
AATGATAGAT TCAGCTATGG AAATACTGGA AAATGAATAT GACGAGTTAA AAGGTGTTTT GCCAAAGATA TATAAAAACT
CAAATATACC GAATGAAGTT ATTAGTGATT TACTAAAACT ATTTTCTCAA GAAGTATTTT CAGCACATGA TGGAAGAAAT
GTTGATTTAT TGGGGAGAGT TTATGAATAC TTTATAAGTA ATTTTGCTAC TACAGAAGGT ACTAGAGGTG GTGAATATTT
TACACCGTCT TCAATCGTAA AATTATTGGT AGCAATGCTA GAGCCCATTA AAGGTACAGT TTATGATCCG GCCTGTGGGA
CAGGAGGAAT GTTTATTCAG TCTAATAAAT ATAGAGAAAA TAATCATAAC TTGTGTTTTG TAGGCCAGGA ACAAAACGAG
CTTACTATCA AATTGGCTAA AATGAATGGA ATTCTACATG GAATAAATCC TGAAATTAGA CAAGGTGATT CATTATTAAA
TGACCGTTAT CCAGAATTGA AAGCTGAAAT TGTAATATCT AATCCACCGT TTAATATGAA GGATTGGGGA GCTGAACGCC
TGCCACTTAA TGATAAGCGA TTAATAGGAC CGGTAACAAA CAGTAATGCA AATTACATGT GGATACAGCA TTTTCTATAC
CATTTAAAAG ATGGTGGTTT AGCAGGATTT GTTATTGCTA ATGGAGCTTT GACTAGTAAT CTGGCTGCTG AAAAAATTGT
AAGGAAACAC TTAATAGACA ATGATTATGT AGATTGTGTT GTTCAATTAC CTGAAAAAAT GTTCTTTGGT ACTGGCATTC
CAAGTGCTTT AGTGTTTTA AGTAAGAATC GAAATGGAAG TAACGGCCAT GCCAAAAGAG AAAAAGAGGT TCTATTTATT
GATGCAAGCG ATAAGGGAAC ATTAGTGGGT AAAAAGAATA AAATATTTTT AGATGATGAA ATAAAAGAAA TTGCAGATTT
ATATCATTCA TTTAAATTTT TAAATGATAA TGATTATAAC CATAGTGGTT TTTACAAAAA GGTTAACATT GAAAAAATCG
TGGAAAATGA TTATAAATTA ACTCCAACTC TCTATGTAGG TGTAAAGGAA GAGACTGAAA TGGAGAAGCC ATTTAGAGAA
ATGATAATAG AATATAAAGC GATATTAGAG CAACAATTTG AAGAATCAAA CAAACTACAG CAGAAAATAT AAAGAATTT
AGAGGGATTA TTATGA
```

FIG. 35B
SEQ ID NO:9

```
MIFADIEFEK ELFSAANKLR GKIAPSEYKH YVLPLIFLRY LSLKYQQRRN EIQQQINDSR DHKKNQDEVL KILEDRTEYT
KVNVFYIPEK ASWEYLLKNS ENDKIKEMID SAMEILENEY DELKGVLPKI YKNSIPNEV ISDLLKLFSQ EVFSAHDGRN
VDLLGRVYEY FISNFATTEG TRGGEYFTPS SIVKLLVAML EPIKGTVYDP ACGTGGMFIQ SNKYRENNHN LCFVGQEQNE
LTIKLAKMNG ILHGINPEIR QGDSLLNDRY PELKAEIVIS NPPFNMKDWG AERLPLNDKR LIGPVTNSNA NYMWIQHFLY
HLKDGGLAGF VIANGALTSN LAAEKIVRKH LIDNDYVDCV VQLPEKMFFG TGIPSALVFL SKNRNGSNGH AKREKEVLFI
DASDKGTLVG KKNKIFLDDE IKEIADLYHS FKFLNDNDYN HSGFYKKVNI EKIVENDYKL TPTLYVGVKE ETEMEKPFRE
MIIEYKAILE QQFEESNKLQ QKILKNLEGL L
```

FIG. 36A
SEQ ID NO:10

```
ATGAAAAGTA CTTTGAAGGA ATATAAATTG GGTGATATTA CCGAAGTCGT TAATGGTGCC ACTCCTTCAA
CTAAAAAGCC TGAGTACTAT GAAAATGGTA CAATTCCATG GATTACTCCT AAAGATTTAT CAGGCTATTA
CTTTAAATAT ATATCTCATG GTGAACGTAA TATAACAGAG CTTGGTCTAA GAAATAGTTC AGCTAAGTTG
TTACCAAAAG GAACTGTATT ATTTTCCTCA AGAGCCCCAA TAGGATACGT AGCAATAGCT GATAATTGGT
TAACTACGAA CCAGGGATTT AAAAGTTTTA TATGTAATGA GGAGATTATT ACAATGAAT ACCTTTATTA
TTTTCTTATT GCTAAAAGGG ATTTTATTGA AACATTGCG AATGGGAGTA CGTTTAAAGA GCTTTCATCA
ACTTCTGCAA AGAATATACC AATCAATCTT CCTAGTTTAG AAGAGCAAAA GAAGATTGTG ACAATTTTAG
GGGATTTGGA TAGAAAGATA GAATTAAATT ATAAAATTAT TGAAAGCTTA GAAAAAATAG CAGAAAGAAC
ATATAAATAT TGGTTTGTCG ATGAATTAAA TCAAGATGAA CAGCACATCC GTAATGGATG GGAAACTGCT
AAAATTGGCG ATGTGGTGGA ACTTTTGGGA GGGGGAACCC CTAAAACTTC GGAAAGTAAG TATTGGGAAG
ATGGAGATAT TAATTGGTTT ACTCCTTCAG ATTAACAAA AACTAGACAG CTTTTTGTAC GTGATTCTCA
AAGAAAAATA ACAATTGATG GACTTAATAA CAGTGCAGCG AAATTAATTC CCCCTTATTC CTTGTTAATG
TCAAGTAGAG CTACAATTGG CGAGTTGGCA ATTAATCAAG AATCTGCTAC TACAAATCAA GGGTTTATTG
TATTAATACC AAATGAAAAA ATTTCTATTT ACCAATTATA CTTTTGGGCT AAACTTAATA AGAGCAAAAT
TATTTCAATG GCAAATGGTA GTACTTTTAA AGAAATTAGT AAGCGGGATT TTAAATCTTT GGAGATAATA
TTACCAAAAA ATATAGACAC TTTTAATTCA ATTATGCAAG ATTATTTTAG GAAAATTGAG GAGTTAATTG
ATGAAATAAA AATCTTAAAA ACCGCAAGAG ATAATTTAAT TCCAAAACTT ATAAAATGA
```

FIG. 36B
SEQ ID NO:11

```
MKSTLKEYKL GDITEVVNGA TPSTKKPEYY ENGTIPWITP KDLSGYYFKY ISHGERNITE
LGLRNSSAKL LPKGTVLFSS RAPIGYVAIA DNWLTTNQGF KSFICNEEII YNEYLYYFLI
AKRDFIETFA NGSTFKELSS TSAKNIPINL PSLEEQKKIV TILGDLDRKI ELNYKIIESL
EKIAERTYKY WFVDELNQDE QHIRNGWETA KIGDVVELLG GGTPKTSESK YWEDGDINWF
TPSDLTKTRQ LFVRDSQRKI TIDGLNNSAA KLIPPYSLLM SSRATIGELA INQESATTNQ
GFIVLIPNEK ISIYQLYFWA KLNKSKIISM ANGSTFKEIS KRDFKSLEII LPKNIDTFNS
IMQDYFRKIE ELIDEIKILK TARDNLIPKL IK
```

FIG. 37A
SEQ ID NO:12

ATGAAACAGT TTGCAGATCC TTTTGAAAGA AGATTCCTTG ATGCAATTGA ACATCATCTT GATGGAATTT
CTGAGAAAAT AAAAAAAGAC TTTACACACA AAAACTTTTT AAAAGAATTG AATGGCCTTA AAGGTGATAA
AGTCTATCAT GACTTAGGCT TTGATACCGC TGAATATACT CTGGTACGTC TTATAGGAAG AATGAGCATA
AGCGTTGGGA GAAGGCTGGG GGAGATATAC GATAAAGTCC CTCGTTATGT TGCTGCCGCG CGATTTGGTC
TTCAACCAAA TCAAATTGCA GAAGTATTTG ATGGTCTTGA GTTAGATATA GCTTTGCGCA ATAGCCTTTT
GTCAGATGAT GATAAAATTC ACATAAAAAA AATAACTGAA AAGATGTCAG GCGAAACATA CTCGGGAATC
GGAATCGAAA TTCGTTATAA CTTTAATCCA AATGACAGTT CCCGTTTAAG AAAAGACGTC GATGTAGCTT
CTAAATTGTC GGCCGCGGGG TTATTTCCTG TTTATTTAAT ATTTAGCTCT CTCAGTCCTA GGAATGATGC
AATAGCCCGT CTTAAAAGAG GGGGATGGAG CTTTAAACAG GGGCAGGAAG CCTTAGACTT CCTTACCGAA
CTTTTAGGAG TGGATATTGG GTCTGTTTTA TCTGACCCAA TAATAGCCGC AGAAACTAGG GAGAAAACAT
CAAAAATTAT GAAGTCTATA TTTGAATCAG AGGCATTCCA ATCTGTTATA CCGGGAGAGT GGAGTAAACT
ATAG

FIG. 37B
SEQ ID NO:13

MKQFADPFER RFLDAIEHHL DGISEKIKKD FTHKNFLKEL NGLKGDKVYH DLGFDTAEYT LVRLIGRMSI
SVGRRLGEIY DKVPRYVAAA RFGLQPNQIA EVFDGLELDI ALRNSLLSDD DKIHIKKITE KMSGETYSGI
GIEIRYNFNP NDSSRLRKDV DVASKLSAAG LFPVYLIFSS LSPRNDAIAR LKRGGWSFKQ GQEALDFLTE
LLGVDIGSVL SDPIIAAETR EKTSKIMKSI FESEAFQSVI PGEWSKL

FIG. 38A
SEQ ID NO:14

ATGACAAATT TTTCGCACTC AGCTCTAACG AGCTACGATC TTCTCGGGCA TGAAATTGTC CAAGATTCTG
AAGCTGTTAG CTCGGGTCCA TATCTGGTCA GCTATGACCC GATCCCTGTA CGTCGGTCTA CATTCCTAGC
TGGACTGTCA GAGAACGTTC ACTCGTGGTT TCGTCTCACA CCAAGTTTCG GACCGGATCT AGTTCGAACA
ATCATCAAAC AGATGAATCT TGCGCCGCAC TCACACATCC ATGACCCTTT CTCAGGAGCC GGGACTACCG
CGATTGAGGC TTCGTTAGAG GGCTATGAAG CAAGCTGCGT AGAAGTTAAT CCGTTTCTCT ACTTCGTGGG
GAAAACATCC ATAGATTGGT CTATCAATGC TGATGATGCT GCAGCGCAGC TAGAAAGCAT TAAAAATAAA
TATTATAGCA TGTCTGCAAC CGCTACTTTG GATAACATAG CCGACCTAGG AATAGATATA CCAAAAATAC
ACAATATTCA TCGGTGGTGG AGAAACGATG TTCTTAAAGA TATATTAGTC CTAAAATCTT CTATCAGATC
TTGCACACAA GATAAGTATT GTTCCTTTTT TGAGCTAGCC CTAGCTGCAG TTCTCGTTCC AGATTTGACA
AATGTAACGC TAGGAAAACT ACAACTGCAC TTTGTAAACA AAGACGATAA AGAGATAAAC GTCTGGCCTA
CATATGAATC TCATGCAAAA AAAATGATTC ACGACTTGTC ATTAATTAAT AAGCAAAATT TCGAATTTTT
GCCCAAGATT ATTTATGGTG ATTCAACTCA AAAATCAACA TTTAGCGAGG TGGCAGGGAT AGATGCTATA
ATAACATCCC CTCCGTACCC TAATAGGTAC AGCTATATTT GGAATACTCG CCCTCACCTG TACATTCTTG
ATATGATTTC CGAAGCAAAA GAGGCTTCGC AAATAGATCG TAGAACGATT GGTGGAACAT GGGGGACAGC
AACTTCCGAA TTAGGAAAGG GTATATTTTC TCCAATCAAT GCTGTAGTCA AAGACGCGCT TGAAGGGGTT
CACGAAAGAA TCGCCGGTTC CGATCAACTC ATGGCAAACT ATGTAACTCA TTATTTTAAT CGGCTCTTTT
TACATATAGA AGCTATAAAA CCATCACTTA ATCCAAAAGC AAAGCTTGCT TATGTTGTTG GGAACTCTTG
GATTAAGGGC GAATATGTAG CCACTGACGT AATCTTAGCA AAAATTATCG AAGGGCTTT GCCAGGCTCA
TCAATTGATG GTCTTCATCG TTTCCGTCGC CGGAACAGTG GAAAGAATCT CTTTGAAACT ATAGTTTACT
CCACTCTCCC GGTATAA

FIG. 38B
SEQ ID NO:15

MTNFSHSALT SYDLLGHEIV QDSEAVSSGP YLVSYDPIPV RRSTFLAGLS ENVHSWFRLT PSFGPDLVRT
IIKQMNLAPH SHIHDPFSGA GTTAIEASLE GYEASCVEVN PFLYFVGKTS IDWSINADDA AAQLESIKNK
YYSMSATATL DNIADLGIDI PKIHNIHRWW RNDVLKDILV LKSSIRSCTQ DKYCSFFELA LAAVLVPDLT
NVTLGKLQLH FVNKDDKEIN VWPTYESHAK KMIHDLSLIN KQNFEFLPKI IYGDSTQKST FSEVAGIDAI
ITSPPYPNRY SYIWNTRPHL YILDMISEAK EASQIDRRTI GGTWGTATSE LGKGIFSPIN AVVKDALEGV
HERIAGSDQL MANYVTHYFN RLFLHIEAIK PSLNPKAKLA YVVGNSWIKG EYVATDVILA KIIEGALPGS
SIDGLHRFRR RNSGKNLFET IVYSTLPV

FIG. 39
SEQ ID NO:17

>M1.EarI CTCTTC 1245 nt

```
GTGAATCAGA AAAATGAAAA ATCATTTATG CGTTTGCAAT CAACCTTTAG CGGTGGCAAA
GGTAGTCCAA TGCATGATTG GTACCCATAT TTAGAGGGTT ATTCTCCCGA ATTTGTGAAA
TGCTTGATTT CACGATTTGC TCCTAAAGCC AAAACAATTT TAGATCCATT TTGTGGCTCT
GGAACAACAG CCATTGTTTC CGTTTTAGAG GGTTTAAATA ATTACTATTG CGAAGTAAAC
CCTTTATGCC AATATATTAT TGAAACTAAA CTAATAGCTT TAACATTAAG CGAAGAAGAA
AAAACAAAAT TAGTAAATGA ACTTTATTCT ATTTCTAATG AAATAACTAA TGTACTCAAA
CCTTCTGCAA CCGAGACAGA TCTAGAGAAA TCATTTAAAT CCGTTTTTGG TAATACGAAA
TTTTTTGAGG ATCACATATT TAAAGATATA CTTAGTTATC AATGTTACAT TAGCTCTATC
GAAGATGAAA ATCTTAAGAG ACTTCTGACA ATAGCAGGGA TTAGATCGTT AATCCCTTCC
TCGTTATTGG TAAGACGAGG TGATTTACGA TTCAAGACAC AAAAAGAATT AGAGAAAGGC
AACCAGGGCT TTCGCTTTCA TGTACAAAAA AGCTTAGAAT TAATTGCCAG TGATTTATTA
GACATTACGG AAGGTAGTGG TTTAGCTACC TTCTTATGTG ATGATGCCAA AGAAATATCT
GGGAATAACC TGATTGATGC TGTAATAACA AGCCCGCCAT ATTTAAATGG CACAAATTAT
TTTAGAAATA CTAAAATTGA ACTTTGGTTT ATAGGGAAAT TAAAGACCAA ATCAGATCTA
AGACATTATA GGGATTTAGC TATTACCAGT GGTATTAACG ATGTAACTAA AGGTAAAAGC
TTATCTTCAA ATAATACTAT TATCTCAGAA ATACCATTAT TATCTGAATG TATTAAAGAA
CTAAGCATAA AAGAGTATGA TAGTCGTATT TCAATGATGG TTGAAAACTA CTTTTGGGAC
ATGTTCAAAT TCTTATCAAA ACTCCCAAAA TTACTAACTA ATGATGCGAC TATCTGTATA
GATTTAGGTG ATTCTGTTTA TTGTAACGTC TACATCCCTA CACAAGATAT TTTGAAAGAA
ATGATGTCAA AGTTAGGTTT TGAAGAGAAC GAAAGGGTCA TTCTTCGTGA ACGAAAATCC
CGCAATGGAA CAAAGTTAGT CCAGACTGTT CAGGTTTTTA AATGA
```

FIG. 40
SEQ ID NO:18

>M2.EarI CTCTTC 1140 nt

```
ATGAAAAATA AATATTTTAG TAAAAAATGG GAGCAATTCA AGAAAGAATT ACCCCATCAA
TCAGGTGAAA TGGTAAAGAG AAATTGGGGC CATAACTGGC ACTCTATGTG TTCATACCAA
GGGAAACTTA AACCATCAAT AGCTAGATCT TTAATTGATA CATTCATGCC ATCAAGTAAG
GGACGTATAT TAGATGTCTT CTCAGGTGTT GGCACCATTC CTTTCGAAGC AAGATTACTT
GGTCATACTG CATATGGATT TGATATTAGT CCAGCAGCAG TTAATATTTC ACGCGCAAAA
CTAGAAGTTA TAAGTAAAAA TGAAATCCAA GAGGTAATTA ATAAATTATC TGATTTTATT
GAGCAAAACA AAAATTCAAT AGATTATAAC GAACATAATT TAATAAGGTT TAATGGTTCA
ATTGAATCCT ATTTTCATCC TGAAACTTTT AAGGAAATAC TGTGTGCTCG TAAATTCTTT
TTAATAAAAG GTGAATTAAA TGCATCTGAA TCGTTAGTAC AGTCATGTTT ATTACATATT
TTACATGGTA ATCGTCCGTA TGCATTGAGT AGAAAGTCCC ATCCTATTAC ACCTTTCGCG
CCTACTGGAG ATTTTATATA CAGTAATTTA GTTATAAAGT TAATCAAAAA AGTTGAAAGA
GTCTTGCAAA ATTCTGATGG TATCCCAGAT ACTGGCAGCA AAGTATTTTA TCAGGACTCT
ACAAAAAGTT GGCCTGAAGA AGTAAATAAT TTAGATGCAA TTATAACATC ACCTCCATTT
TATGATAGTA CCCGTTTCTA TTCAGCAAAT TGGATGCGAT TATGGTTTTC TGGTTGGGAA
AAAGATGACT TCCAAACGAA GCCAAAAGAT TTTGTGGACG AAACTCAGAA AAAAAGCTTT
GAAATATATG ATAATATATT CAAACAATCT CAACAATGCT TAAAAAAAGA TGGCGTTTTT
TTAATGCACG TTGGCAAAAG TAAAAAAAGT GATATGGCAG ACAAATTGC TAAAATTGGT
AGTAATTATC TTAGCCTTAT AGATATATTT GACGAAAGTG TTGAACATTG CGAAAGTCAC
GGAATTAAAG ACAAAGGCAC GACAACCCAT CATCAGTACC TTGTCTTTAC GAAAGATTAG
```

WT KpnI

KpnI D16N/E132A/D148E

FIG. 44A

>AgeI ACCGGT 272 aa (SEQ ID NO:79)

MRLDLDFGRG LVAHVMLDNV SEEQYQQISD YFVPLVNKPK LKSRDAIGQA
FVMATEVCPD ANPSDLWHHV LYRIYIREKI GTDPSQSWVR TSGEAFEVAL
VERYNPVLAR HGIRLTALFK GQKGLALTRM GVADRVGSRK VDVMIEKQGG
GRSPDAEGFG VVGGIHAKVS LAERVSDDIP ASRIMMGEGL LSVLSTLDVK
SFPPPHGDLV NRGELGTPDR PSDKRNYIEG HGDFSACFSY NLRTPPSNAT
TPSGRHIYVS ASLVRTTSSP TT

>AvrII CCTAGG 358 aa (SEQ ID NO:80)

MEEDLDLSEN IEAASAELTT LYQVAADAMK DYIEIYLALS KQSDGFSNIN
NLDLTSRNRR LVVIHGLSLE LDPDTSTPEE IKREAERMLA IALDTESAIT
AGVYEKMRLF ASSLVDQLFE QTDELNSLSS EYLSANPGFL PFFQQLAGLR
SKSELKREVG NASDNSISKA VAERILERII RNLRIRTFSK EKLLQAVEPT
LEGIVRDLVG KVLLENIVAD ALSDLQVPFM RESEYQSLKG VIYDFRADFV
IPDAQNPIAF IEVRKSSTRH ASLYAKDKMF SAINWKGKNK RLLGILVVEG
PWTRETLRVM ANVFDYVTPL TRVSQVAEAI RAYLDGDKTR LKWLVNFSIE
EADHDNIT

>AvrII  CCTAGG  1077 nt (SEQ ID NO:110)

ATGGAAGAAG ACCTTGATTT ATCTGAAAAT ATCGAAGCTG CATCTGCGGA
GCTTACGACT CTTTATCAGG TAGCTGCTGA TGCTATGAAA GATTATATTG
AAATCTATCT TGCGCTGAGT AAACAGTCTG ATGGGTTTTC AAATATTAAC
AATCTTGACT TAACTTCTCG TAACAGGCGT TTGGTAGTTA TACATGGACT
TTCGTTAGAG TTAGATCCAG ATACTTCGAC TCCAGAGGAA ATTAAACGTG
AAGCTGAACG AATGCTAGCG ATAGCTCTTG ATACAGAGTC AGCAATTACG
GCAGGAGTAT ATGAAAAAAT GCGTCTCTTC GCAAGCTCTT TAGTAGATCA
GCTATTTGAA CAAACGGATG AACTTAATTC ATTATCATCG AATATTTGT
CAGCAAATCC AGGATTTTTG CCGTTTTTCC AGCAGTTGGC GGGGCTTAGA
AGTAAATCAG AGTTAAAGAG AGAAGTAGGA AATGCCTCTG ACAATAGTAT
TTCTAAAGCG GTTGCAGAGA GAATATTAGA GCGCATTATA CGTAACTTGA
GAATTCGCAC TTTTTCCAAA GAGAAACTAT TACAAGCTGT TGAGCCTACT
TTAGAAGGAA TAGTCAGGGA TCTCGTAGGA AAAGTGTTAT TGGAAAATAT
AGTTGCTGAT GCTTTATCTG ATTTACAAGT TCCTTTCATG CGTGAATCAG
AGTATCAAAG CCTTAAAGGA GTGATTTATG ATTTCCGCGC TGATTTTGTG
ATACCAGACG CACAAAATCC AATTGCTTTT ATCGAGGTGC GAAAAAGCTC
TACACGACAT GCGTCACTCT ATGCCAAGGA TAAGATGTTT TCAGCGATTA
ATTGGAAAGG AAAAAATAAA AGGCTTTTGG GTATTTTGGT TGTGGAAGGA
CCTTGGACAA GAGAAACTCT TCGCGTCATG GCAAATGTGT TTGATTACGT
TACACCTTTA ACTCGTGTTT CCCAAGTTGC AGAAGCTATC AGAGCATATC
TAGATGGGGA TAAAACGAGA CTGAAGTGGT TAGTTAATTT CAGTATTGAA
GAAGCAGACC ACGACAACAT AACCTAA

FIG. 44B

>BsmBI CGTCTC 530 aa (SEQ ID NO:81)

```
MAKYGRGKFL PHQNYIDYMH FIVNHKNYSG MPNAIGEDGR INWQVSSGKT
TSFYEYYQAR FEWWEKKADE LNLPGTGNSN KRFSLAARLI HPTGQRPCRL
CGKYQYVGYM YVSHNLYKRW SKITGREDLF FKKQNIIEAA NIFKSIMGEQ
ALINELTTIF PERKDYFNRL PNIEDFFVSS SHIKNNGNYI SPGFMANPPD
RLDGFHDYGI CCRKEKDPGR HDDNMRLYNH DRRAFMWWSE GDWALADALY
NKAGAGKCAD PDCQKEVEKI SPDHVGPISC GFKQIPFFKP LCASCNSAKN
RRFSYQDVKE LLKYENYTGD SVASWQVRAL WDNCKHLVKN DDDSKLLSNL
MRSLQDYYLR SLYKLFSNGF AHLLSYFLTP EYAHYKITFE GLNTSTLEYE
RYYKTFKKTK STSSLAARIV RIAFEELEIY NSKDINERKL IKFDTSSWEK
DFENIISYAT KNLSLDEEAS KWNKVLTDKN LSSTEKDKKI SSLLEDKNYE
VYKKQFYILK DLLVEHFNKI GEQIAKDYMK
```

>BspQI GCTCTTC 430 aa (SEQ ID NO:16)

```
1   MRRLAKNSRN DSYLSNRDYQ EIVRENTTTI SFPLKEKHTL TLTKKIGLNQ 50
51  TAGFGGWFFP DSPCLLTVTV LSSFGTKVTS KTFSLSKDWN RVGLAWINEH 100
101 SSDTMSIVLE FSDVEIVHTW GLTCDVFNVH ELIIDAIEDQ NKLIDVLNQE 150
151 HLSPETYYLN HDSDTDLIEN LESTEEIKIV NQSQKQISLK KCCYCQRYMP 200
201 VNILVRSNSS FHKHKSKKTG FQNECRACKK WRINNSFNPV RTKDQLHESA 250
251 VITREKKILL KEPEILQKIK NRNNGEGLKS IIWKKFDKKC FNCEKELTIE 300
301 EVRLDHTRPL AYLWPIDEHA TCLCEKCNNT KHDMFPIDFY QGDEDKLRRL 350
351 ARITGLDYES LVKRDVNEVE LARIINNIED FATNVEARTF RSIRNKVKEV 400
401 RPDTDLFEIL KSKNINLYNE LQYELLTRKD                      430
```

>BspQI GCTCTTC 1293 nt (SEQ ID NO:101)

```
ATGAGACGAT TAGCAAAAAA TTCACGGAAC GACAGTTATT TAAGTAATAG
GGATTACCAG GAAATCGTGA GGGAAAATAC CACTACAATA TCGTTTCCCT
TAAAAGAAAA ACATACTCTG ACTTTAACGA AAAAAATAGG GCTAAATCAG
ACTGCTGGAT TCGGAGGATG GTTTTTCCCT GATTCACCAT GTTTATTAAC
AGTAACTGTA CTATCCTCTT TCGGTACAAA GGTAACTTCT AAAACCTTTA
GCCTTTCTAA AGATTGGAAT CGTGTTGGGC TTGCTTGGAT TAACGAGCAT
TCGAGTGACA CCATAAGCAT TGTCCTAGAG TTTAGTGATG TGGAAATAGT
TCATACATGG GGACTTACAT GTGATGTTTT TAATGTCCAT GAATTAATTA
TTGATGCTAT AGAAGATCAA AATAAACTAA TAGACGTGCT AAATCAAGAA
CATTTATCTC CTGAAACATA TTATTTAAAC CATGACTCTG ATACTGATTT
AATTGAGAAT TTGGAATCTA CAGAAGAGAT AAAGATAGTT AACCAAAGCC
AAAAGCAAAT CTCTTTAAAA AAATGCTGTT ATTGTCAACG TTATATGCCT
GTGAACATAT TAGTTCGTTC AAATTCATCA TTTCATAAAC ACAAGAGTAA
GAAAACTGGT TTTCAAAATG AATGTCGGGC TTGTAAGAAG TGGAGAATAA
ATAATTCATT CAATCCAGTC AGAACAAAAG ACCAACTACA TGAATCAGCA
GTTATTACAC GTGAAAAAAA AATATTACTT AAAGAACCTG AAATATTACA
GAAAATCAAA AATAGAAATA ACGGTGAGGG CTTAAAAAGT ATTATATGGA
```

FIG. 44C

```
AAAAATTTGA TAAAAAATGC TTTAATTGTG AAAAAGAATT AACCATTGAA
GAGGTACGCC TAGACCATAC AAGACCACTT GCTTATCTGT GGCCTATCGA
TGAACACGCA ACTTGTTTAT GTGAAAAATG CAACAATACA AAACATGATA
TGTTTCCTAT CGATTTTTAT CAAGGGGACG AAGACAAATT AAGACGTTTA
GCTAGAATTA CGGGGTTAGA TTATGAATCT CTAGTTAAGA GGGACGTAAA
TGAAGTTGAA CTTGCAAGAA TAATCAATAA CATTGAAGAC TTTGCAACTA
ATGTAGAGGC ACGTACTTTT CGCTCAATAA GAAATAAAGT AAAAGAAGTA
CGTCCCGATA CTGACCTATT TGAAATTCTT AAATCTAAAA ATATTAATTT
ATATAATGAA CTTCAATATG AACTTCTTAC CCGTAAGGAT TAA
```

>EagI CGGCCG 301 aa (SEQ ID NO:82)

```
MKKRRDLVEV FGYNPMDLSP EVRALWNLGA CPFLNKECIK INHDQTIIYG
TCSVTSPYGD VIICPNRLYA NDYETLHKVS RDAFGDDVPF LTYSNFIKYR
ATYKDCIVAL GKNSGKEVQV GRALSMDWVL VRITDGELKE YVGVEIQSID
ITGNYRDAWH AYKNLKPIDI IDNLPTSQHG LNWANVHKRL IPQIIRKGVV
YSRSNYVKKG LYFILPEIVY NKFEDVIGAD IPLLKTQTNK SITVHTYSLG
EPAANGEQRK LISEREIIFD LDEFSKRFTT GPNLPKGDDL DAVIKKALGM
M
```

>EcoRI GAATTC 277 aa (SEQ ID NO:83)

```
MSNKKQSNRL TEQHKLSQGV IGIFGDYAKA HDLAVGEVSK LVKKALSNEY
PQLSFRYRDS IKKTEINEAL KKIDPDLGGT LFVSNSSIKP DGGIVEVKDD
YGEWRVVLVA EAKHQGKDII NIRNGLLVGK RGDQDLMAAG NAIERSHKNI
SEIANFMLSE SHFPYVLFLE GSNFLTENIS ITRPDGRVVN LEYNSGILNR
LDRLTAANYG MPINSNLCIN KFVNHKDKSI MLQAASIYTQ GDGREWDSKI
MFEIMFDIST TSLRVLGRDL FEQLTSK
```

>EcoRV GATATC 245 aa (SEQ ID NO:84)

```
MSLRSDLINA LYDENQKYDV CGIISAEGKI YPLGSDTKVL STIFELFSRP
IINKIAEKHG YIVEEPKQQN HYPDFTLYKP SEPNKKIAID IKTTYTNKEN
EKIKFTLGGY TSFIRNNTKN IVYPFDQYIA HWIIGYVYTR VATRKSSLKT
YNINELNEIP KPYKGVKVFL QDKWVIAGDL AGSGNTTNIG SIHAHYKDFV
EGKGIFDSED EFLDYWRNYE RTSQLRNDKY NNISEYRNWI YRGRK
```

>HindIII AAGCTT 300 aa (SEQ ID NO:85)

```
MKKSALEKLL SLIENLTNQE FKQATNSLIS FIYKLNRNEV IELVRSIGIL
PEAIKPSSTQ EKLFSKAGDI VLAKAFQLLN LNSKPLEQRG NAGDVIALSK
EFNYGLVADA KSFRLSRTAK NQKDFKVKAL SEWREDKDYA VLTAPFFQYP
TTKSQIFKQS LDENVLLFSW EHLAILLQLD LEETNIFPFE QLWNFPKKQS
KKTSVSDAEN NFMRDFNKYF MDLFKIDKDT LNQLLQKEIN FIEERSLIEK
EYWKKQINII KNFTREEAIE ALLKDINMSS KIETIDSFIK GIKSNDRLYL
```

FIG. 44D

>HpaI GTTAAC 254 aa (SEQ ID NO:86)

MKYEEINFKV PVESPYYPNY SQCVIERIYS ILRNQKDMGD DRIIINTNLK
KGLPLENINK IAGPMIEAWA EEVFSGIRDN RDNQYNLINV EAQERLGISD
IILQFQVNNN VITGNVDVKA TSNDIPDSGK SPNITSFSRI RTAYVKDPNF
IFIILSIKHS VYVKRNEYTN LMDGIMQIID FNVYDLKYIS DSDISYNPAL
GTGQIQIKDI HYVSSQKRTT WQMCQLLDLK YLRSKKRTIE QFYNEAKRNK
WIKD

>KpnI GGTACC 218 aa (SEQ ID NO:87)

MDVFDKVYSD DNNSYDQKTV SQRIEALFLN NLGKVVTRQQ IIRAATDPKT
GKQPENWHQR LSELRTDKGY TILSWRDMKV LAPQEYIMPH ATRRPKAAKR
VLPTKETWEQ VLDRANYSCE WQEDGQHCGL VEGDIDPIGG GTVKLTPDHM
TPHSIDPATD VNDPKMWQAL CGRHQVMKKN YWDSNNGKIN VIGILQSVNE
KQKNDALEFL LNYYGLKR

>NcoI CCATGG 288 aa (SEQ ID NO:88)

MATAPGHLLG QIIGNVMEEA LKPVLQEMAD RHDLYLDSKG LRPGVRSGAL
VTWTDDLGNN HDLDFVLERG GSATKAGNPA AFIEAAWRRY TKHSKAKAQE
IQGAVLPVLA AWNNVKPTPA AVVAGQWTAP SLQQMRSNGF VVLHLHFPTT
AQVFGGNGIN IEGTGEGTPD AFWQQQCDAY TSKSEADKDS LATALRTAHA
QEFRTFVAEL ERRVVRAIDY VVVTPLHGHG SQYTSIENAI EAVRTYSCGE
ESAPFLRFEI RISYTNGDVI QATFGSSSDA IEFLDTFN

>NheI GCTAGC 328 aa (SEQ ID NO:89)

MSSYHDDLNI LNVDFNHLRL TELIKLADQA EPFYLWVEKI FRQVSGRADS
LETIIEVEER VVLKMAILTC FTSDEKELPK LFNGVGVPYP HIKACYFFFA
WLVRDAATQR LDPLIREAFT QLKSIHPQMK KTELESEIFS QLLVNYRNEL
IHFSWPVIRE VLISRLEGSR RAARGSYLEL FVRTALAQSI TYFYKIYGNY
GKFLDVKIHD KPLKVKNRTY DVVAELIGNN HNTQYLILPV KTRETQGGGH
AHLFTRDIEQ SNNDIRELYP NAVIAPVIIA ENWSDTEKDL ENVGYNDIFH
FSVNPNRFAG FSDVEQIRLN RLVERILL

FIG. 44E

>NotI GCGGCCGC 383 aa (SEQ ID NO:90)

MRSDTSVEPE GANFIAEFFG HRVYPEVVST EAARNDQATG TCPFLTAAKL
VETSCVKAET SRGVCVVNTA VDNERYDWLV CPNRALDPLF MSAASRKLFG
YGPTEPLQFI AAPTLADQAV RDGIREWLDR GVHVVAYFQE KLGGELSISK
TDSSPEFSFD WTLAEVESIY PVPKIKRYGV LEIQTMDFHG SYKHAVGAID
IALVEGIDFH GWLPTPAGRA ALSKKMEGPN LSNVFKRTFY QMAYKFALSG
HQRCAGTGFA IPQSVWKSWL RHLANPTLID NGDGTFSLGD TRNDSENAWI
FVFELDPDTD ASPRPLAPHL EIRVNVDTLI DLALRESPRA ALGPSGPVAT
FTDKVEARML RFWPKTRRRR STTPGGQRGL FDA

>PstI CTGCAG 326 aa (SEQ ID NO:91)

MKELKLKEAK EILKALGLPP QQYNDRSGWV LLALANIKPE DSWKEAKAPL
LPTVSIMEFI RTEYGKDYKP NSRETIRRQT LHQFEQARIV DRNRDLPSRA
TNSKDNNYSL NQVIIDILHN YPNGNWKELI QQFLTHVPSL QELYERALAR
DRIPIKLLDG TQISLSPGEH NQLHADIVHE FCPRFVGDMG KILYIGDTAS
SRNEGGKLMV LDSEYLKKLG VPPMSHDKLP DVVVYDEKRK WLFLIEAVTS
HGPISPKRWL ELEAALSSCT VGKVYVTAFP TRTEFRKNAA NIAWETEVWI
ADNPDHMVHF NGDRFLGPHD KKPELS

>PvuII CAGCTG 157 aa (SEQ ID NO:92)

MSHPDLNKLL ELWPHIQEYQ DLALKHGIND IFQDNGGKLL QVLLITGLTV
LPGREGNDAV DNAGQEYELK SINIDLTKGF STHHHMNPVI IAKYRQVPWI
FAIYRGIAIE AIYRLEPKDL EFYYDKWERK WYSDGHKDIN NPKIPVKYVM
EHGTKIY

FIG. 44F

>SacI GAGCTC 358 aa (SEQ ID NO:93)

MGITIKKSTA EQVLRKAYEA AASDDVFLED WIFLATSLRE VDAPRTYTAA
LVTALLARAC DDRVDPRSIK EKYDDRAFSL RTLCHGVVVP MSVELGFDLG
ATGREPINNQ PFFRYDQYSE IVRVQTKARP YLDRVSSALA RVDEEDYSTE
ESFRALVAVL AVCISVANKK QRVAVGSAIV EASLIAETQS FVVSGHDVPR
KLQACVAAGL DMVYSEVVSR RINDPSRDFP GDVQVILDGD PLLTVEVRGK
SVSWEGLEQF VSSATYAGFR RVALMVDAAS HVSLMSADDL TSALERKYEC
IVKVNESVSS FLRDVFVWSP RDVHSILSAF PEAMYRRMIE IEVREPELDR
WAEIFPET

>SalI GTCGAC 315 aa (SEQ ID NO:94)

MINADKPHRW NDDVQASVRL YNQWFLDAAP KAYRDTRQLT IDEVEQAFQR
TANMTSITPE VLKAHPKTLA TLRMSTAPPI ARDRLVGLSH GSKSLLDTME
KGKLPPRMKG DVLDTHLAKM CAVLTDLLDL DLFHWYPTGE PAEPRQRELA
ATVVADRLCG AIADPIVRNA QERRQLALIE EWLLARGYTK KTHSASLPLN
TMQPGTFSFR QNVVVGSDLP VNIPVDAVIQ PHTPHSHKLP ILIEAKSAGD
FTNTNKRRKE EATKIHQLQL KYGNEISLTL FLCGYFNTGY LGYSAAEGLD
WVWEHRIDDL EAAGA

>SapI GCTCTTC 432 aa (SEQ ID NO:95)

MRRLATQRRE DAYKSNRDYQ TVHEAQSLRV NSTDDDNLSL FLLKDISPRE
DSKNIVGFGG FVKPEIATTM ALTLTTDIDK QIKSVPLSSN WNRISIVAKF
ASNPSVSITL GFDQTPWVDF WGINSDDIGL SFVSDAVPLE MSMIDSIHIA
PETLYLDHSS ACLLDIDPVE STRFKTGHGD PLSLKKCSYC GRLLPIDLER
PGKLSFHKHR AKITNHQNEC RSCKKWRINN SFNPMRTIDQ LNESALITRE
RKIFLQEPEI LQEIKDRTGA GLKSQVWERF HRKCFNCRKD LKLSEVQLDH
TRPLAYLWPI DEHATCLCAQ CNNTKKDRFP VDFYSEQQIR ELSDICGLPY
QDLCARSLNL DQLDRIERNI AEFSKEWDVR TFASTARRIS EVYPARDLFE
TLKKESESAY NKIIEKLKER PDALLDEALP LD

>SbfI CCTGCAGG 323 aa (SEQ ID NO:96)

MNSSDGIDGT VASIDTARAL LKRFGFDAQR YNVRSAVTLL ALAGLKPGDR
WVDSTTPRLG VQKIMDWSGE HWAKPYATGS REDFRKKTLR QWVDNGFAVL
NADNLNIATN SQLNEYCLSD EALQALRAYG TEGFEESLVV FLDEASKAVK
ARAEALQAAM ISVDLPGGEE FLLSPAGQNP LLKKMVEEFV PRFAPRSTVL
YLGDTRGKHS LFEREIFEEV LGLTFDPHGR MPDLILHDEV RGWLFLMEAV
KSKGPFDEER HRSLQELFVT PSAGLIFVNC FENRESMRQW LPELAWETEA
WVAEDPDHLI HLNGSRFLGP YER

FIG. 44G

>ScaI AGTACT 227 aa (SEQ ID NO:97)

MINDQLPRWV REARVGTRTG GPAMRPKTSD SPYFGWDSED WPEVTRQLLS
EQPLSGDTLV DAVLASWESI FESRLGSGFH IGTQIRPTPQ IMGFLLHALI
PLELANGDPS WRADLNSSEK DLVYQPDHKY SIEMKTSSHK DQIFGNRSFG
VENPGKGKKA KDGYYVAVNF EKWSDAPGRL PRIRTIRYGW LDHTDWVAQK
SQTGQQSSLP AVVSNTQLLA IHTGGQR

>SphI GCATGC 235 aa (SEQ ID NO:98)

MTSKDPIVLS ADQIAWLRQL KMSKRAALVR DYILEYGAVT TGKLAELGYS
HPPRAARDLK DAGAGVVTIM VKGPDGRRMA SYAFNGKANE DGAGRVVIPK
AFGEALKRAH GGKCAVCYGD FSERELQCDH RVPFAIAGDK PKLVQEDFMP
LCASDNRAKS WSCENCPNWE LKDEDTCRSC FWASPENYTH VSTRPERRIN
LLFQGDEVEI FDALKNAAAN EGVSLTEATK RKLAD

>SspI AATATT 281 aa (SEQ ID NO:99)

MSKAAYQDFT KRFSLLIKKH PNLITMTLSN IFTMRLIGNK THGDLAEIAI
SEFINQYMYD FKSIHVGKDL YRAKSKEEDI TVENEITKEK FPISLKAYGD
GPLQLSTDKN FLMYPLLEEI GAFINAKEKI EEIFANEAFS CFSEINVLPL
IYDEKRQRCN ILVFDAARAR AETAYIRKET EGSGRKHPAY RFFDKNKNYI
CEVRYGNAAA NALQRGLWTN TKNATSFFDS VTNGWVDYSH NLVLVKLLSH
ALVSSRKGHE AALEEIKKDI LQLKQTNGIN V

HIGH FIDELITY RESTRICTION ENDONUCLEASES

BACKGROUND

Restriction endonucleases are enzymes that cleave double-stranded DNAs in a sequence-specific manner (Roberts, R. J., *Proc Natl Acad Sci USA*, 102:5905-5908 (2005); Roberts, et al., *Nucleic Acids Res*, 31:1805-1812 (2003); Roberts, et al., *Nucleic Acids Res*, 33: D230-232 (2005); Alves, et al., *Restriction Endonucleases*, "Protein Engineering of Restriction Enzymes," ed. Pingoud, Springer-Verlag Berlin Heidelberg, New York, 393-407 (2004)). They are ubiquitously present among prokaryotic organisms (Raleigh, et al., *Bacterial Genomes Physical Structure and Analysis*, Ch. 8, eds. De Bruijin, et al., Chapman & Hall, New York, 78-92 (1998)), in which they form part of restriction-modification systems, which mainly consist of an endonuclease and a methyltransferase. The cognate methyltransferase methylates the same specific sequence that its paired endonuclease recognizes and renders the modified DNA resistant to cleavage by the endonuclease so that the host DNA can be properly protected. However, when there is an invasion of foreign DNA, in particular bacteriophage DNA, the foreign DNA will be degraded before it can be completely methylated. The major biological function of the restriction-modification system is to protect the host from bacteriophage infection (Arber, *Science*, 205:361-365 (1979)). Other functions have also been suggested, such as involvement in recombination and transposition (Carlson, et al., *Mol Microbiol*, 27:671-676 (1998); Heitman, *Genet Eng (NY)*, 15:57-108 (1993); McKane, et al., *Genetics*, 139:35-43 (1995)).

The specificity of the approximately 3,000 known restriction endonucleases for their greater than 250 different target sequences could be considered their most interesting characteristic. After the discovery of the sequence-specific nature of the first restriction endonuclease (Danna, et al., *Proc Natl Acad Sci USA*, 68:2913-2917 (1971); Kelly, et al., *J Mol Biol*, 51:393-409 (1970)), it did not take long for scientists to find that certain restriction endonucleases cleave sequences which are similar but not identical to their defined recognition sequences under non-optimal conditions (Polisky, et al., *Proc Natl Acad Sci USA*, 72:3310-3314 (1975); Nasri, et al., *Nucleic Acids Res*, 14:811-821 (1986)). This relaxed specificity is referred to as star activity of the restriction endonuclease. It has been suggested that water-mediated interactions between the restriction endonuclease and DNA are the key differences between specific complexes and star complexes (Robinson, et al., *J Mol Biol*, 234:302-306 (1993); Robinson, et al., *Proc Natl Acad Sci USA*, 92:3444-3448 (1995), Sidorova, et al., *Biophys J*, 87:2564-2576 (2004)).

Star activity is a problem in molecular biology reactions. Star activity introduces undesirable cuts in a cloning vector or other DNA. In cases such as forensic applications, where a certain DNA substrate needs to be cleaved by a restriction endonuclease to generate a unique fingerprint, star activity will alter a cleavage pattern profile, thereby complicating analysis. Avoiding star activity is also critical in applications such as strand displacement amplification (Walker, et al., *Proc Natl Acad Sci USA*, 89:392-396 (1992)) and serial analysis of gene expression (Velculescu, et al., *Science*, 270:484-487 (1995)).

SUMMARY

In an embodiment of the invention, a composition is provided that includes a restriction endonuclease having at least one artificially introduced mutation and an overall fidelity index (FI) improvement factor of at least two, the restriction endonuclease being capable of cleaving a substrate with at least a similar cleavage activity to that of the restriction endonuclease absent the artificially introduced mutation in a predetermined buffer, the artificially introduced mutation being the product of at least one of a targeted mutation, saturation mutagenesis, or a mutation introduced through a PCR amplification procedure.

In a further embodiment of the invention, at least one of the artificially introduced mutations is a targeted mutation resulting from replacement of a naturally occurring residue with an oppositely charged residue. An Alanine or a Phenylalanine may replace the naturally occurring residue at the target site.

In a further embodiment of the invention, a composition of the type described above includes a restriction enzyme absent the artificially introduced mutation selected from the group consisting of: BamHI, EcoRI, ScaI, SalI, SphI, PstI, NcoI, NheI, SspI, NotI, SacI, PvuII, MfeI, HindIII, SbfI, EagI, EcoRV, AvrII, BstXI, PciI, HpaI, AgeI, BsmBI, BspQI, SapI, KpnI and BsaI.

Further embodiments of the invention include compositions listed in Table 4.

In a further embodiment of the invention, a DNA encoding any of the enzymes listed in Table 4 is provided, a vector comprising the DNA and a host cell for expressing the protein from the vector.

In an embodiment of the invention, a method is provided having the steps of (a) identifying which amino acid residues in an amino acid sequence of a restriction endonuclease having star activity are charged amino acids; (b) mutating one or more codons encoding one or more of the charged residues in a gene sequence encoding the restriction endonuclease; (c) generating a library of gene sequences having one or more different codon mutations in different charged residues; (d) obtaining a set of proteins expressed by the mutated gene sequences; and (e) determining an FI in a predetermined buffer and a cleavage activity for each expressed protein.

An embodiment of the method includes the step of determining an overall FI improvement factor for proteins belonging to the set of proteins in a defined set of buffers where for example, the set of buffers contains NEB1, NEB2, NEB3 and NEB4 buffers.

An embodiment of the method includes the steps described above and additionally mutating codons encoding hydroxylated amino acids or amide amino acids in a same or subsequent step to that of mutating codons for the charged amino acids.

In an embodiment of the invention described above, the codons are mutated to an Alanine except for Tyrosine which is mutated to a Phenylalanine.

In a further embodiment, the overall FI improvement factor is improved using saturation mutagenesis of one or more of the mutated codon.

BRIEF DESCRIPTION OF THE DRAWINGS

For FIGS. 1-32:

The * symbol indicates the lane to its left that contains the lowest concentration of enzyme for which star activity is observed.

The # symbol refers to the lane showing incomplete cleavage, which is adjacent to and to the right side of the lane containing a concentration of enzyme sufficient for complete cleavage of the substrate.

The gray triangle denotes the serial decrease of restriction endonuclease concentration.

"U" denotes units of enzyme.

In each of the reactions described in FIGS. 1-32, the reaction mixture contains a volume of 3 µl unless otherwise specified of a buffer from New England Biolabs, Inc. (NEB), Ipswich, MA, (see Table 1 and NEB catalog), 3 µl unless otherwise specified of a specified restriction endonuclease in a diluent from NEB, Ipswich, MA (See Table 1 and NEB catalog) as well as variable volumes of specified substrate (containing 0.6 µg) substrate and a volume of water to bring the reaction mixture to a total of 30 µl. Reactions were conducted at 37° C. for an incubation time of 1 hour. The results are analyzed on a 0.8% agarose gel. Where the overall volume of the reaction mix, amount of substrate, temperature of the reaction or incubation time varies from above, values are provided in the description of the figures.

The theoretical digestion pattern is provided on the right side of the gel for FIGS. 1, 5, 8, 11-18 and 20-32. Those substrates with only one restriction endonuclease site should be digested into one linear band from supercoiled form.

Figure 1:
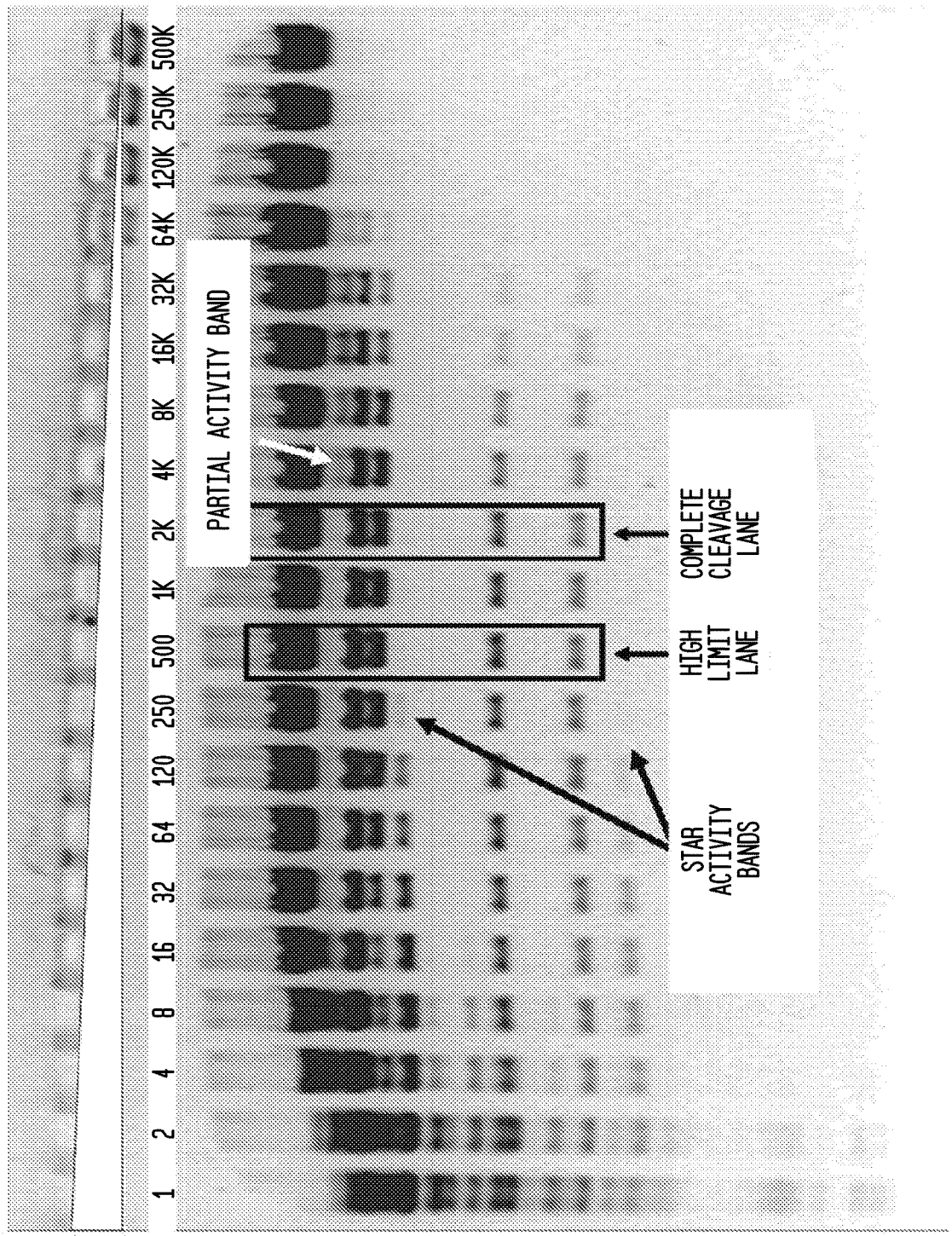

FIG. 1 shows the determination of the FI for wild type (WT) ScaI by digesting 1.2 µl lambda DNA substrate (0.6 µg) with a two-fold serial dilution using diluent A of a preparation of WT ScaI (1,200 U) in NEB3 buffer and examining the digestion products on an agarose gel. The highest concentration of a restriction endonuclease with no star activity is shown with a solid arrow; and the minimum concentration giving rise to complete digestion of substrate is shown with a hollow arrow.

FIGS. 2A-D show the results of digesting 0.5 µl pUC19 substrate (0.5 µg) with WT BamHI or BamHI(E86P) enzyme in a three-fold serial dilution using diluent A for 1 hour at a starting concentration of 172 U or 512 U. The middle lane is the NEB 1 kb marker (New England Biolabs, Inc. (NEB), Ipswich, MA).

FIG. 2A shows results using NEB1 buffer.

FIG. 2B shows results using NEB2 buffer.

FIG. 2C shows results using NEB3 buffer.

FIG. 2D shows results using NEB4 buffer.

Figure 3B:
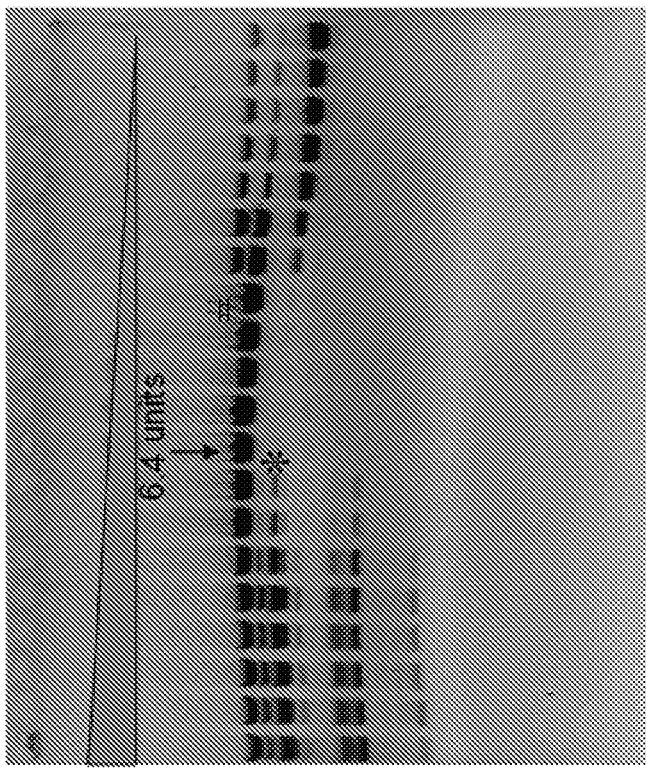
Figure 3A:
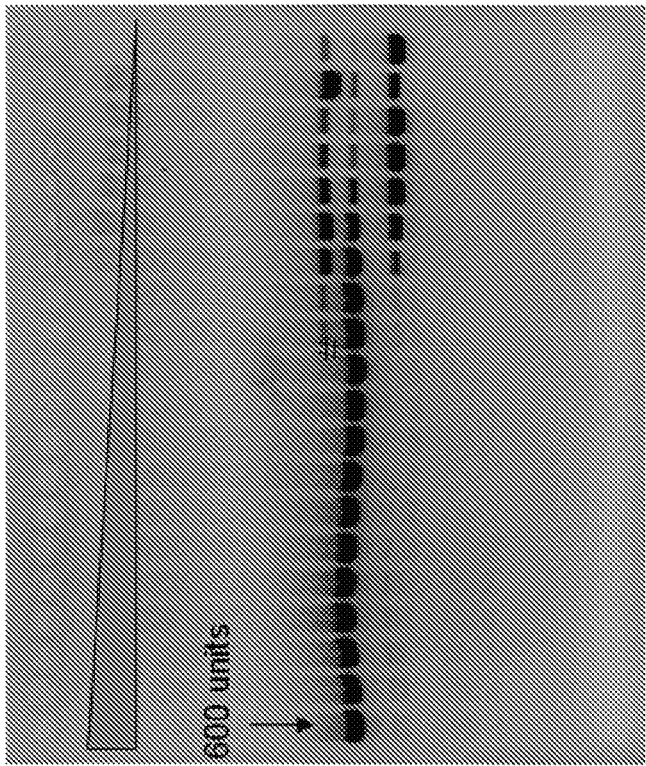

FIGS. 3A-B show a comparison of BamHI(E86P) activity over two time periods using 0.6 µl pBR322 substrate (which contains only 1 BamHI cleavage site) in NEB2 buffer using an initial concentration of 600 U of enzyme in a 2-fold serial dilution using diluent A.

FIG. 3A shows results in 1 hour.

FIG. 3B shows results in 14 hours.

Figure 4A:
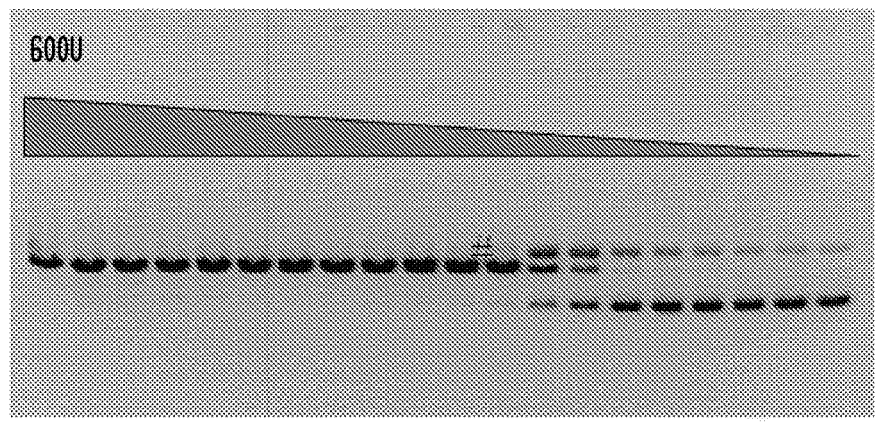
Figure 4B:
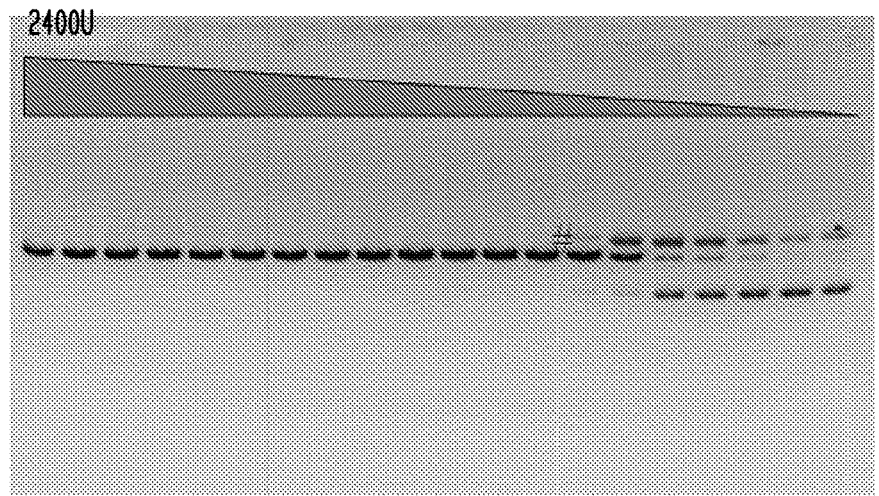

FIGS. 4A-B show the cleavage of 0.6 µl pBR322 substrate in a 2-fold serial dilution of BamHI-HF (E163A/E167T) using diluent A after 14 hours incubation in two different buffers on an agarose gel.

FIG. 4A shows the results with NEB2 buffer with an initial concentration of 600 U of enzyme.

FIG. 4B shows the results with NEB1 buffer with an initial concentration of 2,400 U of enzyme.

Figures 5A, 5B:
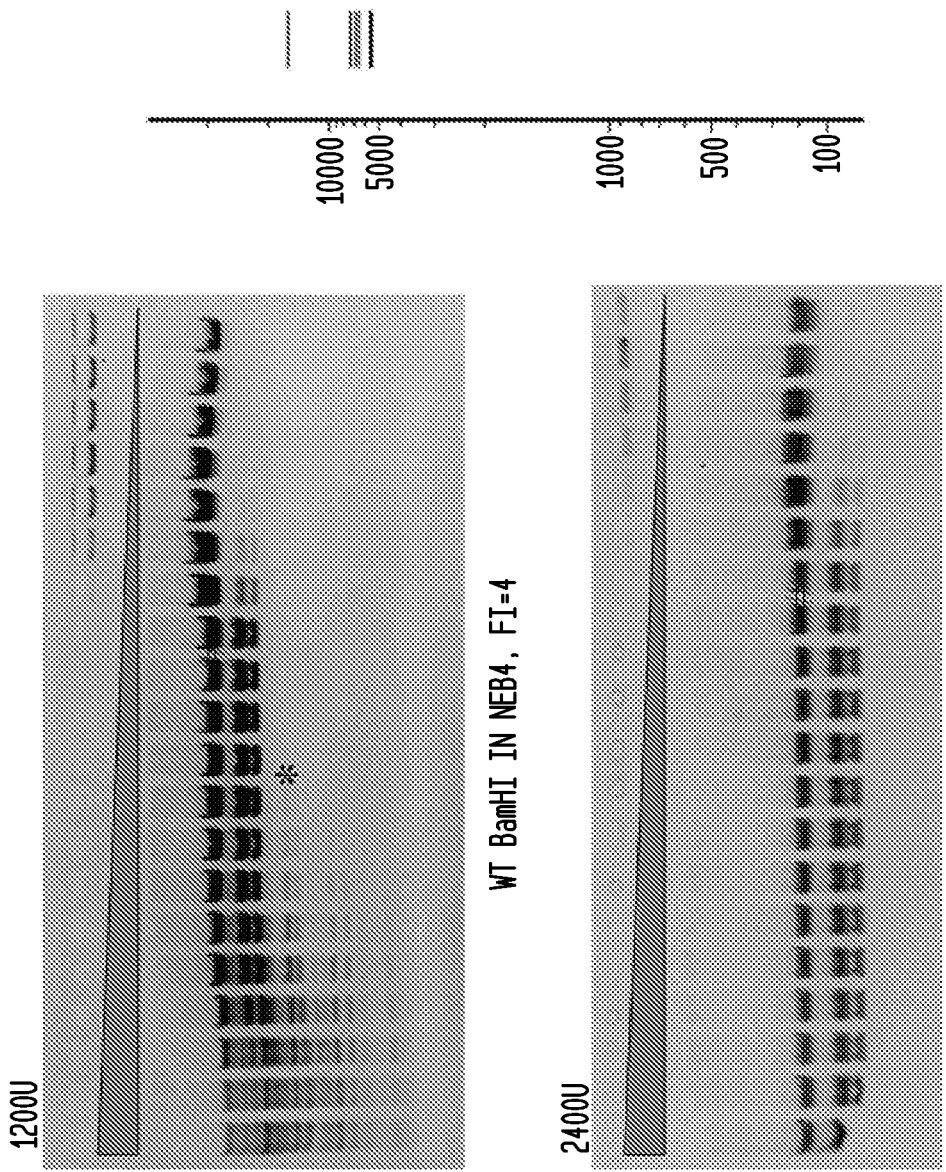

FIGS. 5A-B show a comparison of cleavage reactions using BamHI-HF and WT BamHI in NEB4 buffer. The reaction was carried out in NEB4 buffer using 1.2 µl lambda DNA substrate in a 2-fold serial dilution using diluent A.

FIG. 5A shows WT BamHI with a starting concentration of 1,200 U where the FI equals 4.

FIG. 5B shows BamHI-HF with a starting concentration of 2,400 U where the FI≥4000.

FIGS. 6A-D show a comparison of WT EcoRI and EcoRI(K62A) in NEB1-4 buffers in a 3-fold serial dilution using NEB diluent C. The reaction mixture contained 2 µl lambda DNA substrate (1 µg) in NEB1-4 buffers.

FIG. 6A shows the cleavage results following 2-fold serial dilution, 120 U WT EcoRI and 240 U of EcoRI (K62A) in NEB2 buffer.

FIG. 6B shows the cleavage results following 2-fold serial dilution, 120 U WT EcoRI and 240 U of EcoRI (K62A) in NEB4 buffer.

FIG. 6C shows the cleavage results following 2-fold serial dilution, 60 U WT EcoRI and 120 U of EcoRI (K62A) in NEB1 buffer.

FIG. 6D shows the cleavage results following 2-fold serial dilution, 120 U WT EcoRI and 60 U of EcoRI (K62A) in NEB3 buffer.

FIGS. 7A-C show the cleavage results with 2 different EcoRI mutants and WT EcoRI. The digestion of 100,000 U of enzyme and a 10-fold serial dilution thereof in diluent C over 10 hours using 0.6 µl of Litmus28 substrate in various buffers is shown. There is only one EcoRI cleavage site in Litmus28 substrate.

FIG. 7A: EcoRI mutant K62E in NEB4 buffer.

FIG. 7B: EcoRI mutant K62A in NEB4 buffer.

FIG. 7C: WT EcoRI in EcoRI buffer (see NEB catalog 2007-8).

Figures 8A, 8B:
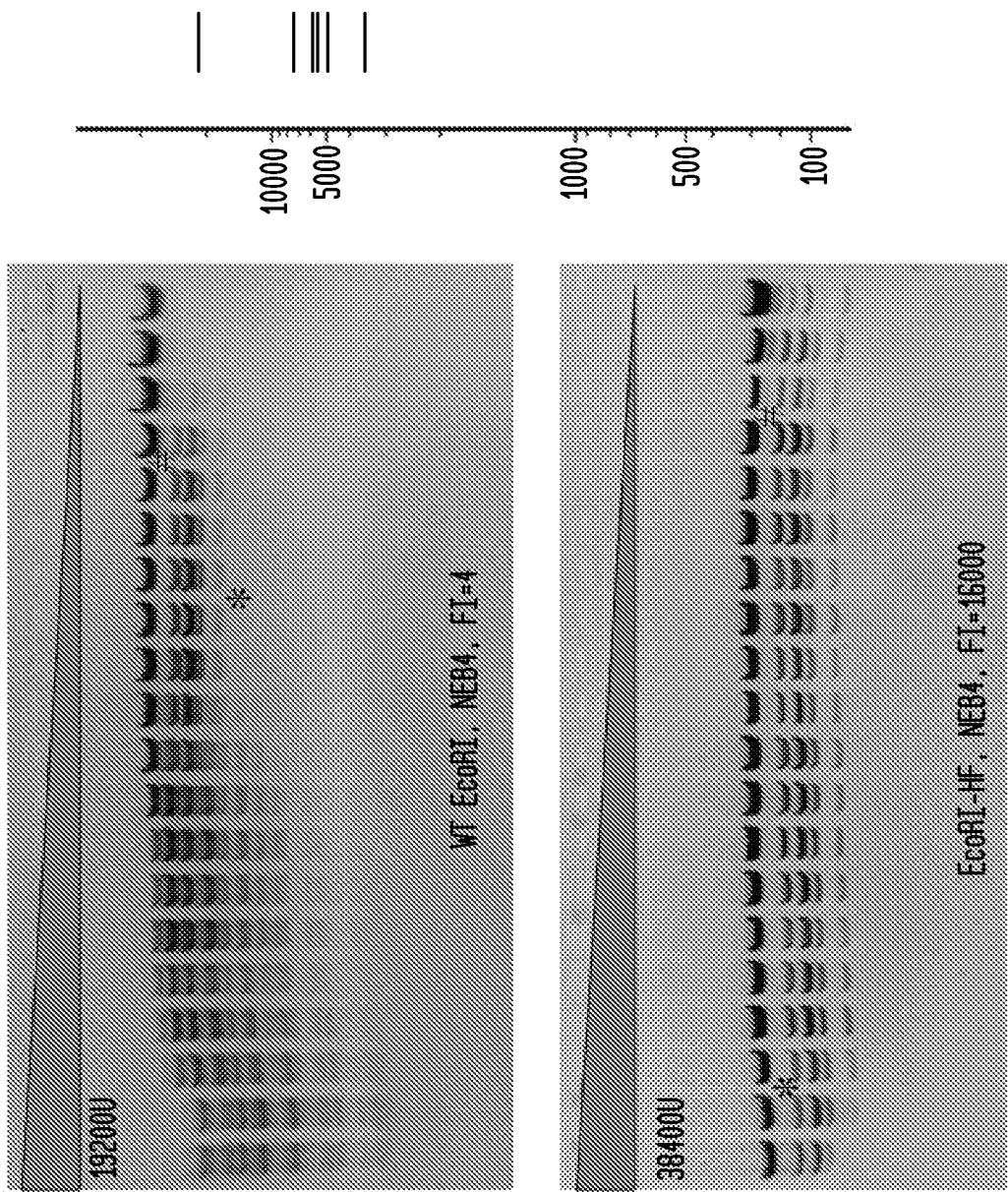

FIGS. 8A-B shows a comparison of EcoRI-HF and WT EcoRI in NEB4 buffer. The reaction utilized 1.2 µl lambda DNA substrate in a 2-fold serial dilution using diluent C.

FIG. 8A: WT EcoRI with a starting concentration of 19,200 U reveals a FI=4 in NEB4 buffer.

FIG. 8B: EcoRI-HF with a starting concentration of 38,400 U reveals a FI=16,000 in NEB4 buffer.

Figure 9B:
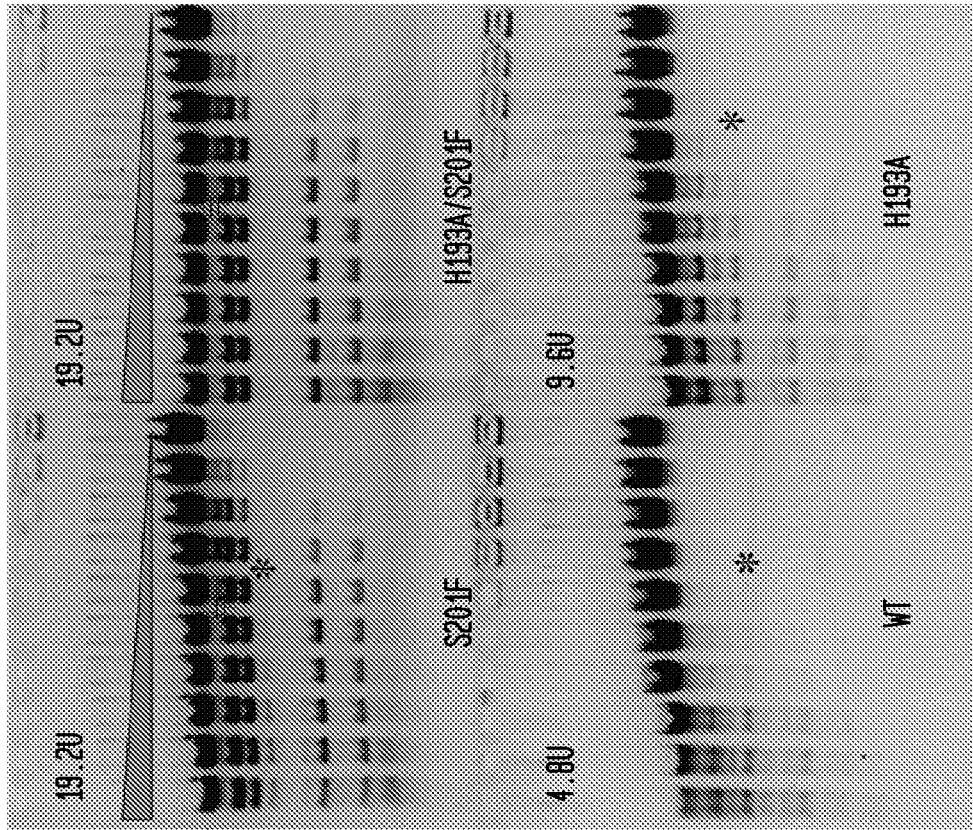
Figure 9A:
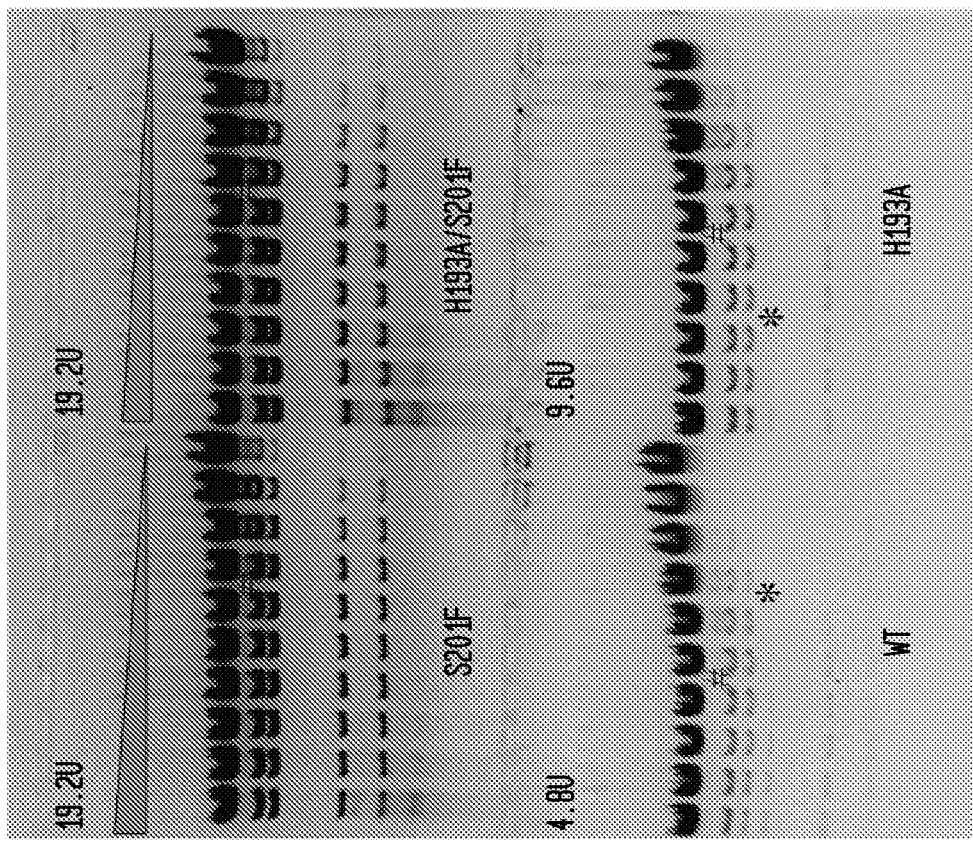

FIGS. 9A-B shows a comparison of serial dilutions of WT ScaI (4.8 U), ScaI(H193A) (9.6 U), ScaI(S201F) (19.2 U), and ScaI(H193A/S201F) (19.2 U). Each sample was initially diluted by 1/10, followed by a 2-fold serial dilution in NEB2 buffer with the specified percentage of glycerol. Each reaction mixture contains 2 µl of lambda DNA substrate (1 µg).

FIG. 9A: 5% glycerol.

FIG. 9B: 37% glycerol.

FIGS. 10A-D shows a comparison of WT ScaI and ScaI-HF (H193A/S201F). The enzymes (unit concentration as specified) were each diluted in a 2.5-fold serial dilution with diluent A. The reaction mixture contains 2 µl lambda DNA substrate and NEB1-4 buffers.

FIG. 10A: cleavage in NEB2 buffer.

FIG. 10B: cleavage in NEB4 buffer.

FIG. 10C: cleavage in NEB1 buffer.

FIG. 10D: cleavage in NEB3 buffer.

FIGS. 11A-H show the FI determination for SalI-HF and WT SalI. Both enzymes were diluted in 2-fold serial dilutions using diluent A. The reaction mixture contains 2 µl HindIII-digested lambda DNA substrate.

FIGS. 11A, B, C and D show a serial dilution of 1,200 U, 1,200 U, 300 U and 1,200 U of SalI-HF demonstrating a FI≥1,000, FI≥2,000, FI≥500 and FI≥2,000 in NEB1, 2, 3 and 4 buffers, respectively.

FIGS. 11E, F, G, and H show a serial dilution of 19.2 U, 150 U, 9,600 U and 38.4 U of WT SalI demonstrating a FI=8, FI=1, FI=32 and FI=1 in NEB1, 2, 3 and 4 buffers, respectively.

FIGS. 12A-B show the results of a 2-fold serial dilution of SphI-HF (19,200 U) in diluent A and WT SphI (143,600 U) in diluent B reacted in NEB 4 buffer with 1.2 µl lambda DNA substrate.

FIG. 12A shows cleavage by WT SphI.

FIG. 12B shows cleavage by SphI-HF.

Figure 13A:
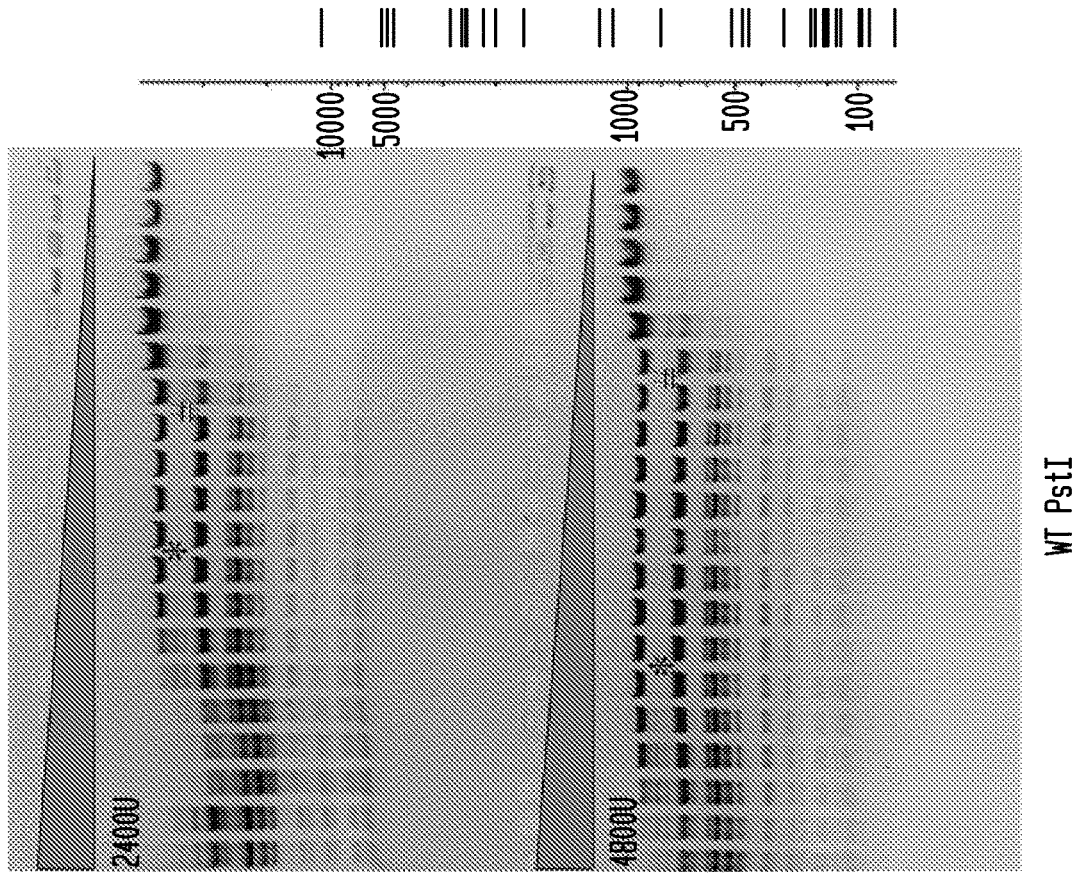
Figure 13B:
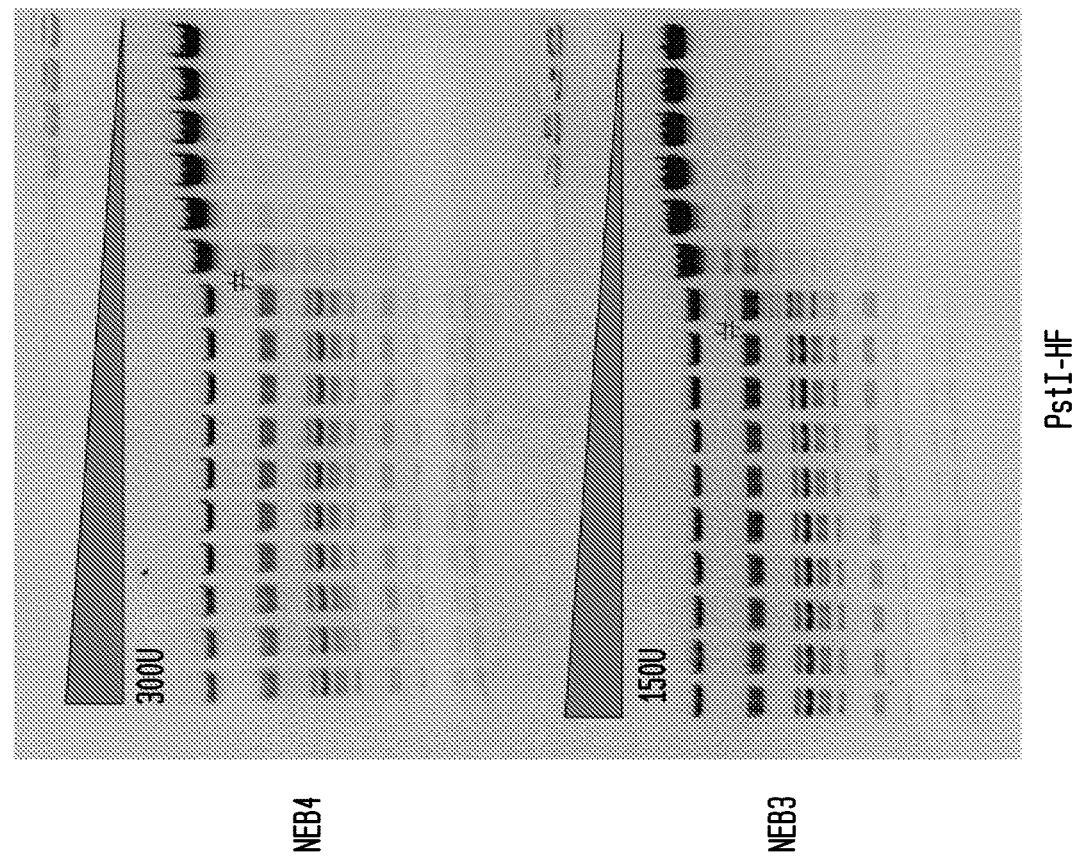

FIGS. 13A-B show cleavage of 1.2 µl lambda DNA substrate using 2-fold serial dilutions of PstI-HF (300 U and 150 U) and 2-fold serial dilutions of WT PstI (2,400 U and 4,800 U) in NEB3 and NEB4 buffers, respectively. Serial dilutions were performed in diluent C.

FIG. 13A shows cleavage by PstI-HF in NEB4 buffer (upper panel) and NEB3 buffer (lower panel).

FIG. 13B shows cleavage by WT PstI in NEB4 buffer (upper panel) and NEB3 buffer (lower panel).

FIGS. 14A-B show cleavage of 1.2 µl lambda DNA substrate using 2-fold serial dilutions of NcoI-HF (4,800 U and 600 U) and 2-fold serial dilutions of WT NcoI (4,800 U and 1,200 U) in NEB3 and NEB4 buffers, respectively. Serial dilutions were performed in diluent A.

FIG. 14A shows cleavage by NcoI-HF in NEB4 buffer (upper panel) and NEB3 buffer (lower panel).

FIG. 14B shows cleavage by WT NcoI in NEB4 buffer (upper panel) and NEB3 buffer (lower panel).

FIGS. 15A-B show cleavage of 1.2 µl pXba DNA substrate using 2-fold serial dilutions of NheI-HF (287,200 U and 76.8 U) and 2-fold serial dilutions of WT NheI (9,600 U and 300 U) in NEB3 and NEB4 buffers, respectively. Serial dilutions were performed in diluent A.

FIG. 15A shows cleavage by NheI-HF in NEB4 buffer (upper panel) and NEB3 buffer (lower panel).

FIG. 15B shows cleavage by WT NheI in NEB4 buffer (upper panel) and NEB3 buffer (lower panel.)

Figures 16A, 16B:
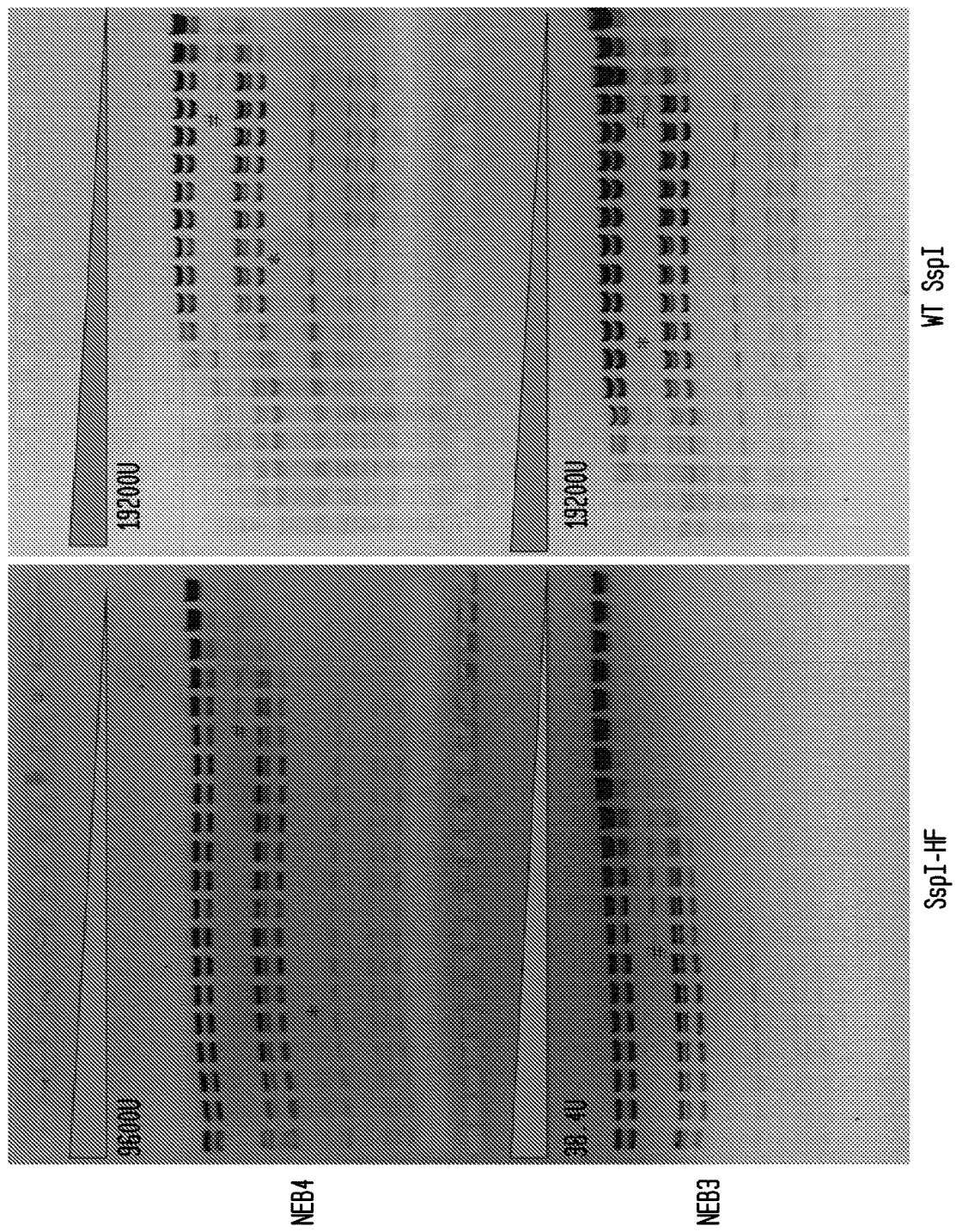

FIGS. 16A-B show cleavage of 1.2 µl lambda DNA substrate using 2-fold serial dilutions of SspI-HF (9,600 U and 38.4 U) and 2-fold serial dilutions of WT SspI (19,200 U and 19,200 U) in NEB3 and NEB4 buffers, respectively. Serial dilutions were performed in diluent C.

FIG. 16A shows cleavage by SspI-HF in NEB4 buffer (upper panel) and NEB3 buffer (lower panel).

FIG. 16B shows cleavage by WT SspI in NEB4 buffer (upper panel) and NEB3 buffer (lower panel).

Figure 17B:
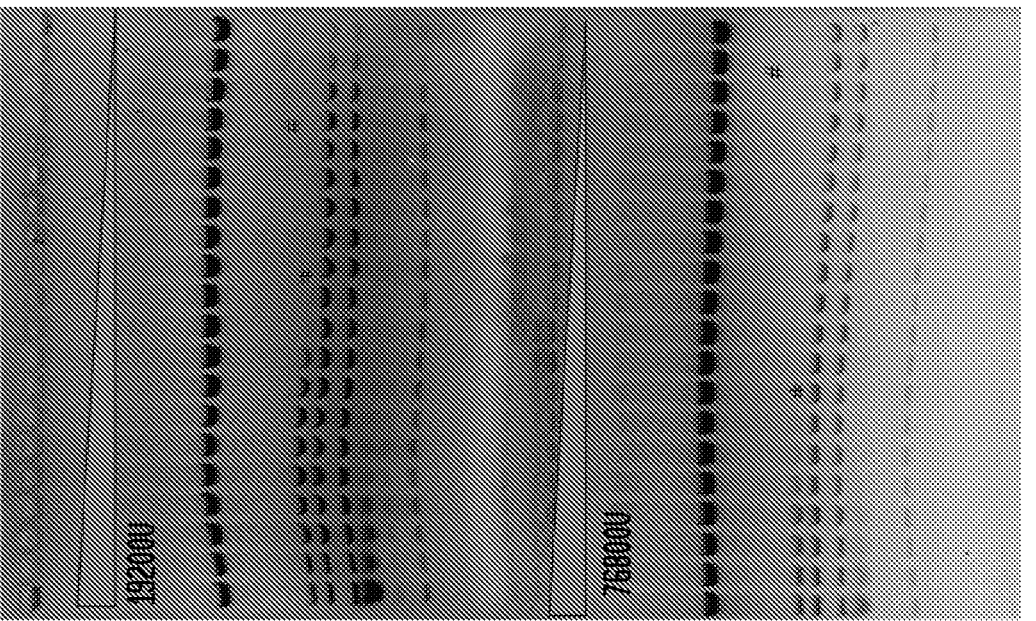
Figure 17A:
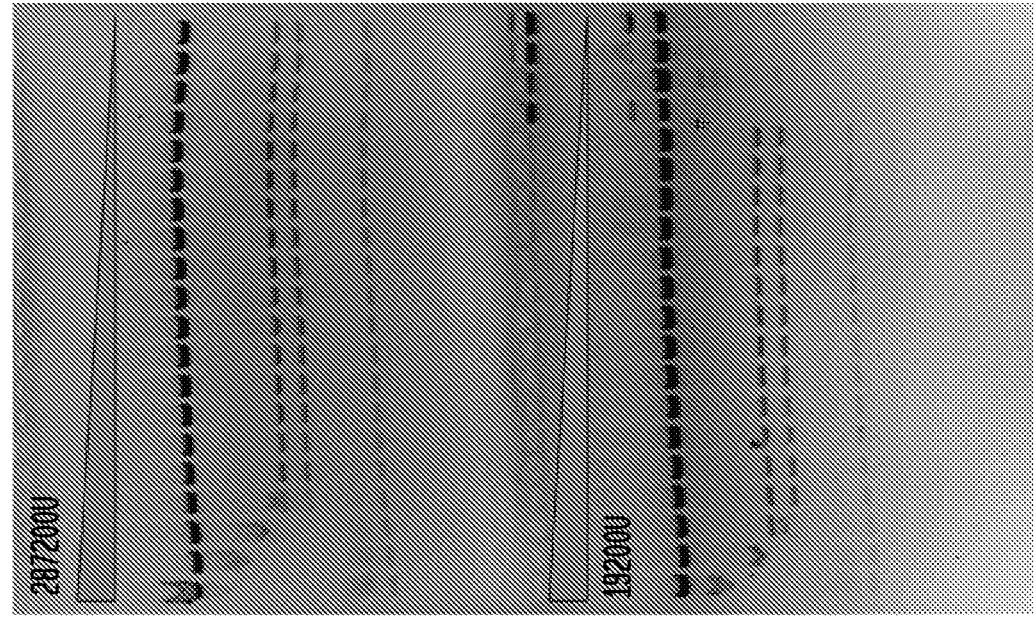

FIGS. 17A-B show cleavage of 1.2 µl pXba DNA substrate using 2-fold serial dilutions of NotI-HF (287,200 U and 19,200 U) and 2-fold serial dilutions of WT NotI (19,200 U and 76,800 U) in NEB3 and NEB4 buffers, respectively. Serial dilutions were performed in diluent C.

FIG. 17A shows cleavage by NotI-HF in NEB4 buffer (upper panel) and NEB3 buffer (lower panel).

FIG. 17B shows cleavage by WT NotI I in NEB4 buffer (upper panel) and NEB3 buffer (lower panel).

FIGS. 18A-B show cleavage of 1.2 µl pXba DNA substrate using 2-fold serial dilutions of SacI-HF (4,800 U and 76.8 U) and 2-fold serial dilutions of WT SacI (19,200 U and 1200 U) in NEB3 and NEB4 buffers, respectively. Serial dilutions were performed in diluent A.

FIG. 18A shows cleavage by SacI-HF in NEB4 buffer (upper panel) and NEB3 buffer (lower panel).

FIG. 18B shows cleavage by WT SacI in NEB4 buffer (upper panel) and NEB3 buffer (lower panel).

Figure 19B:
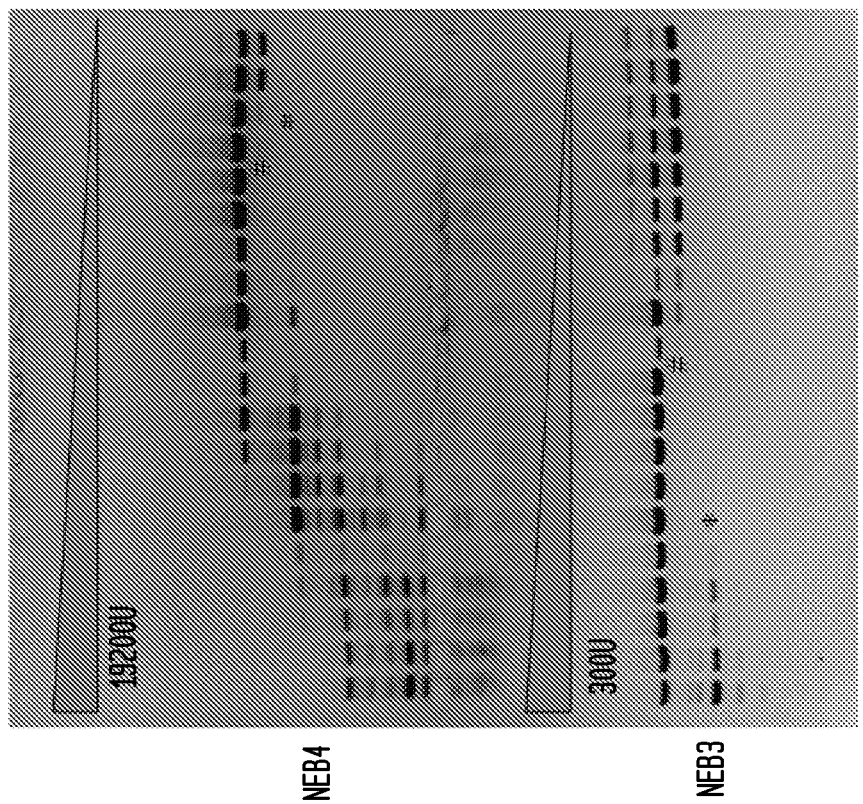
Figure 19A:
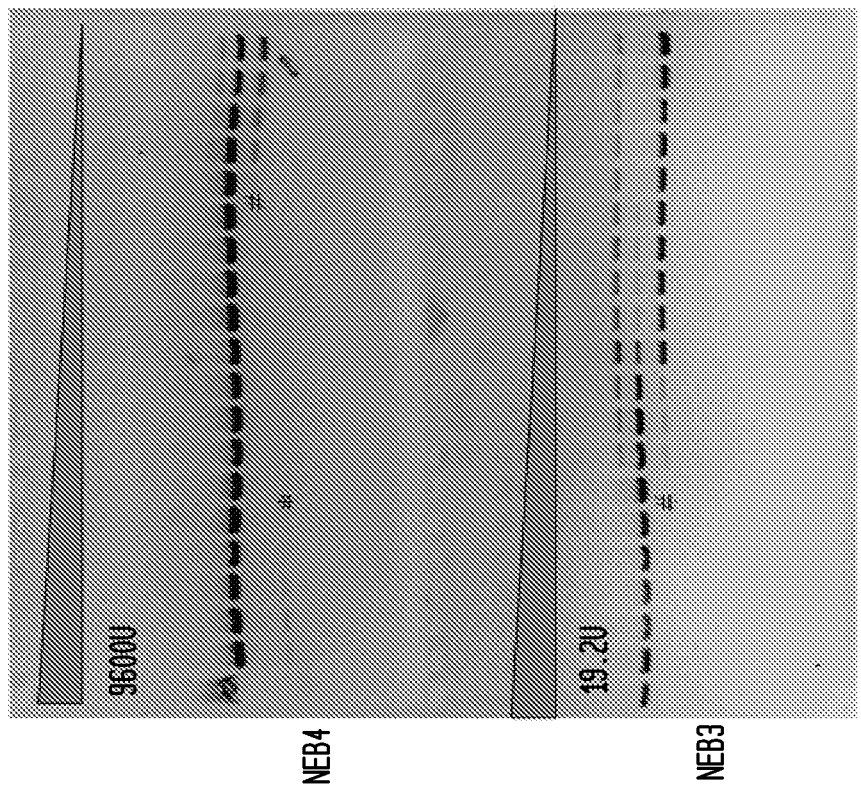

FIGS. 19A-B show cleavage of 0.6 µl pBR322 DNA substrate using 2-fold serial dilutions of PvuII-HF (9,600 U and 19.2 U) and 2-fold serial dilutions of WT PvuII (19,200 U and 300 U) in NEB3 and NEB4 buffers, respectively. Serial dilutions were performed in diluent A.

FIG. 19A shows cleavage by PvuII-HF in NEB4 buffer (upper panel) and NEB3 buffer (lower panel)

FIG. 19B shows cleavage by WT PvuII in NEB4 buffer (upper panel) and NEB3 buffer (lower panel).

Figure 20B:
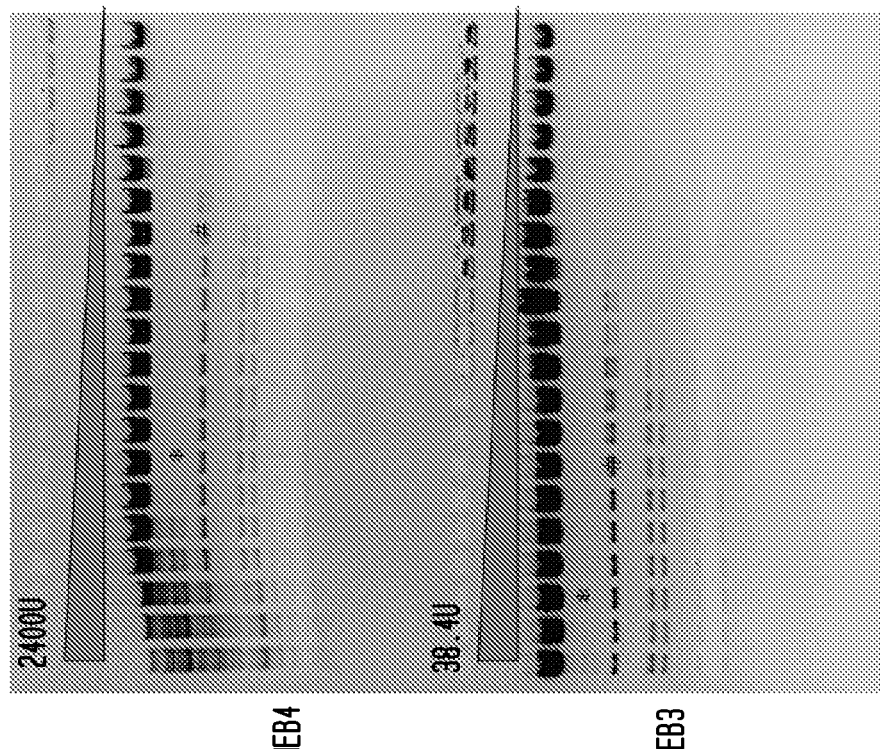
Figure 20A:
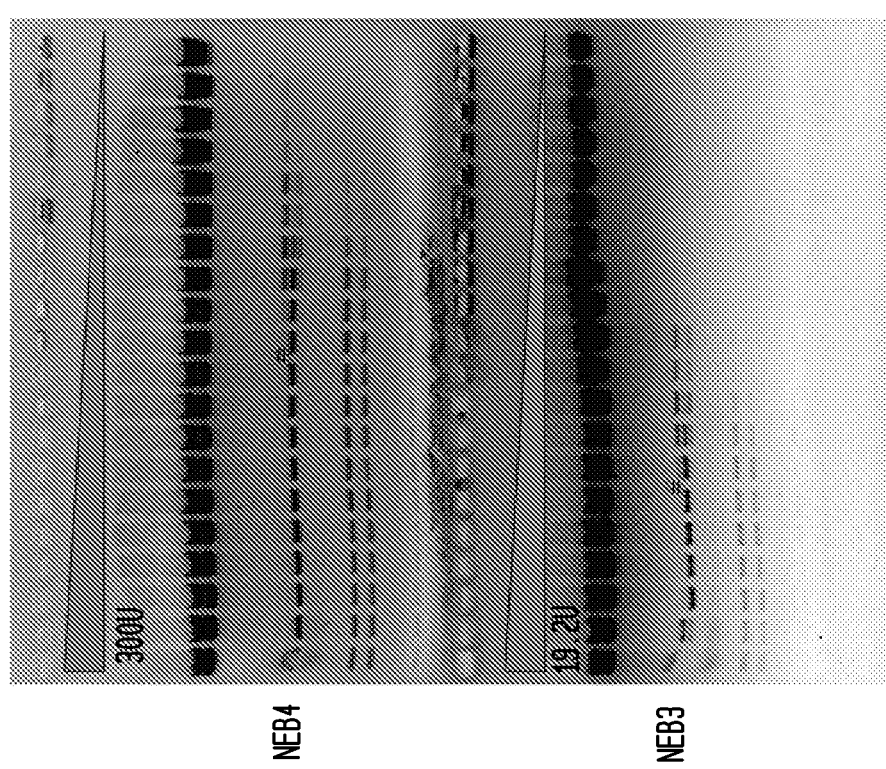

FIGS. 20A-B show cleavage of 1.2 µl lambda DNA substrate using 2-fold serial dilutions of MfeI-HF (300 U and 19.2 U) and 2-fold serial dilutions of WT MfeI (2,400 U and 38.4 U) in NEB3 and NEB4 buffers, respectively. Serial dilutions were performed in diluent A.

FIG. 20A shows cleavage by MfeI-HF in NEB4 buffer (upper panel) and NEB3 buffer (lower panel).

FIG. 20B shows cleavage by WT MfeI in NEB4 buffer (upper panel) and NEB3 buffer (lower panel).

Figure 21B:
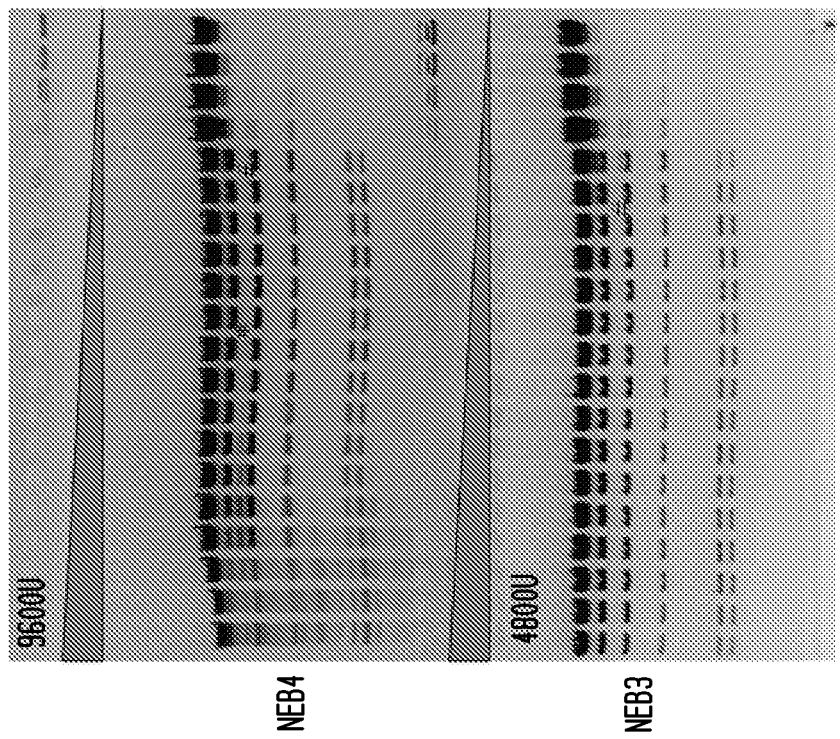
Figure 21A:
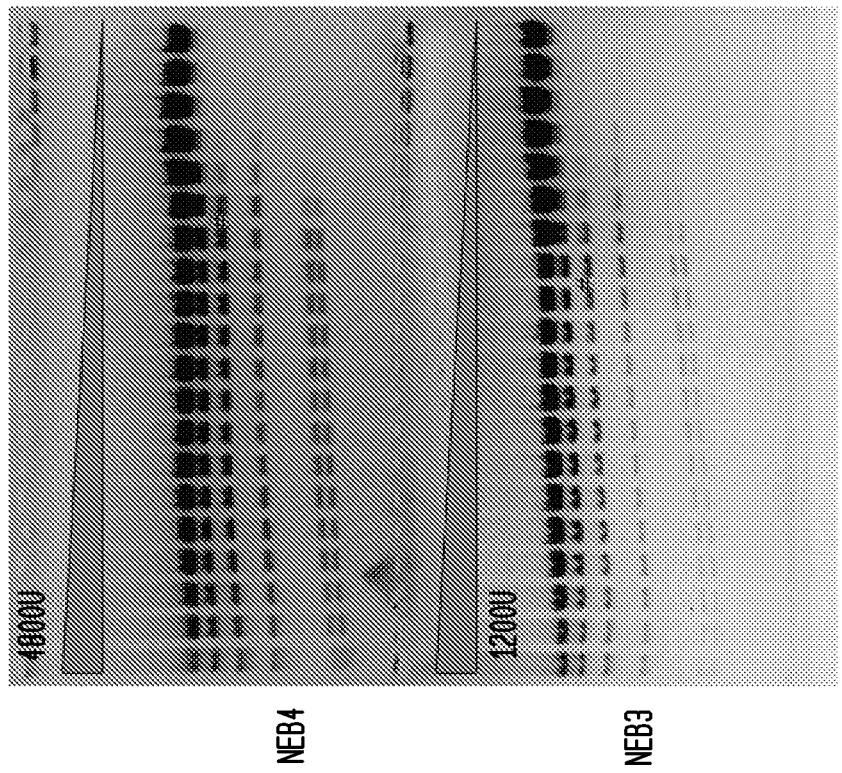

FIGS. 21A-B show cleavage of 1.2 µl lambda DNA substrate using a 2-fold serial dilution of HindIII-HF (4,800 U and 1,200 U) and a 2-fold serial dilution of WT HindIII (9,600 U and 4,800 U) in NEB3 and NEB4 buffers, respectively. Serial dilutions were performed in diluent A.

FIG. 21A shows cleavage by HindIII-HF in NEB4 buffer (upper panel) and NEB3 buffer (lower panel).

FIG. 21B shows cleavage by WT HindIII in NEB4 buffer (upper panel) and NEB3 buffer (lower panel)

Figures 22A, 22B:
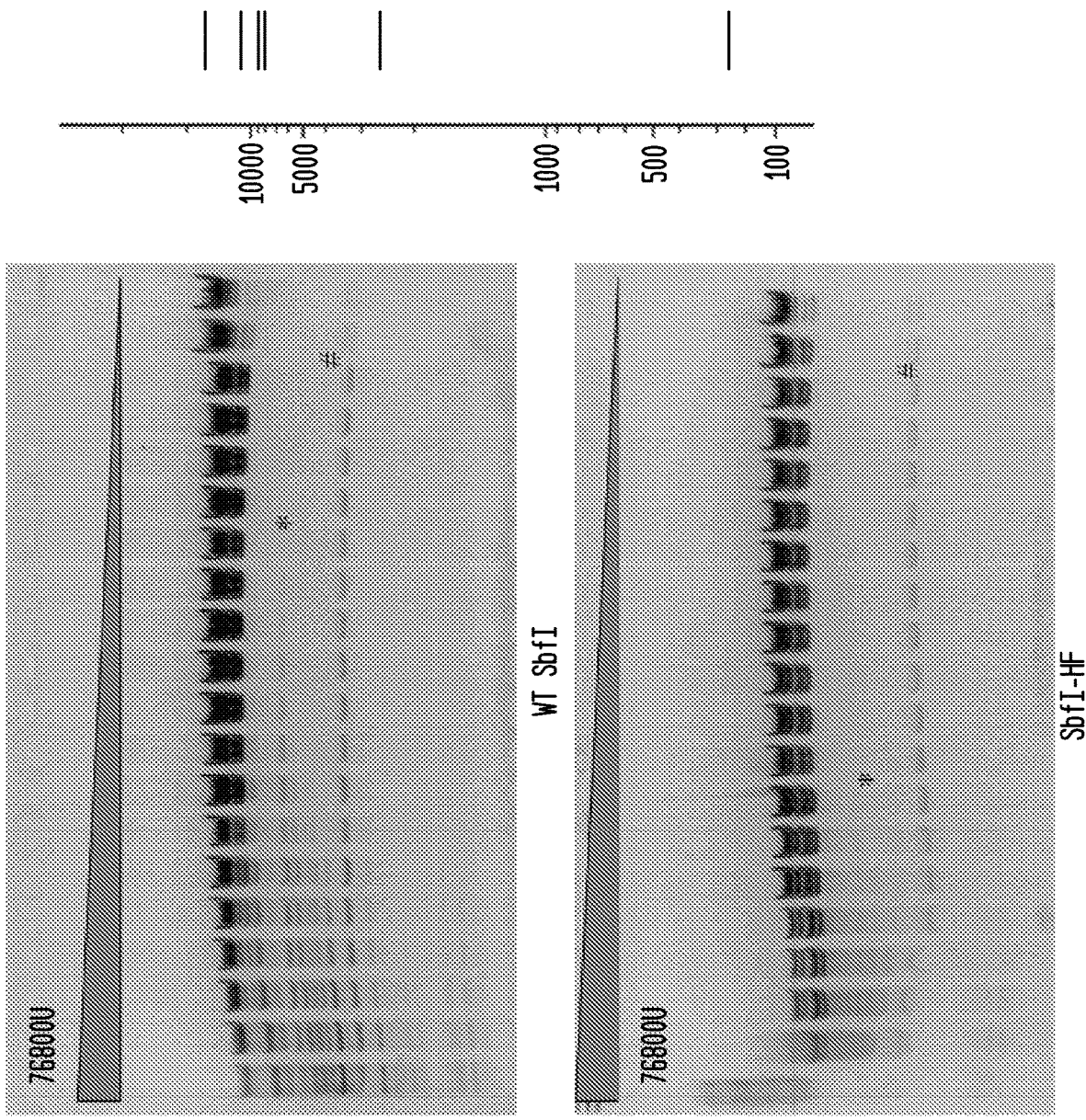

FIGS. 22A-B show cleavage of 1.2 µl lambda DNA substrate in a 2-fold serial dilution using diluent C of SbfI-HF (starting concentration: 76,800 U) and WT SbfI (starting concentration: 76,800 U) in NEB4 buffer.

FIG. 22A shows cleavage by WT SbfI.

FIG. 22B shows cleavage by SbfI-HF.

Figure 23B:
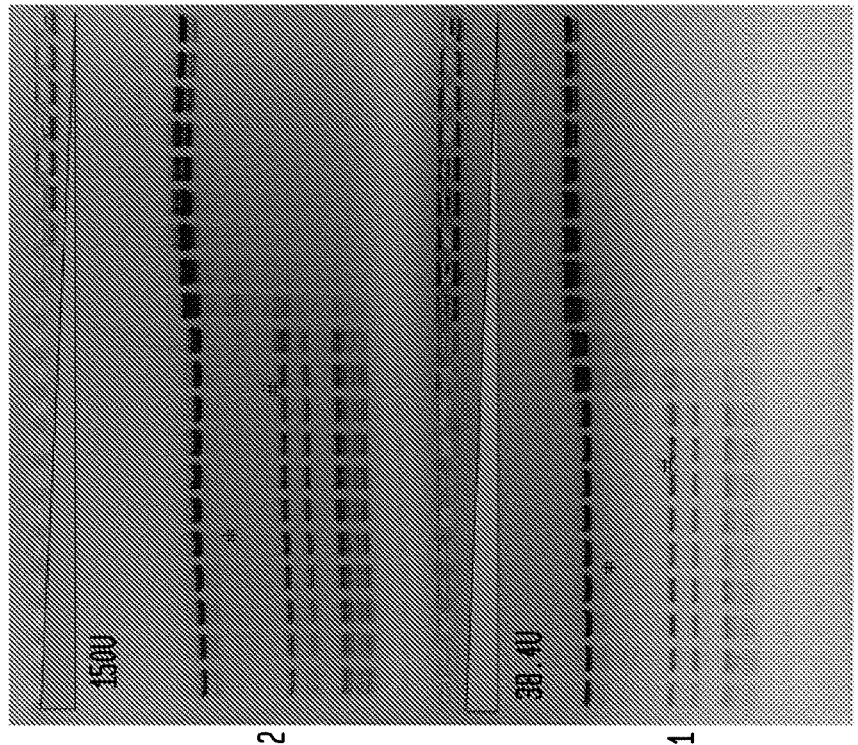
Figure 23A:
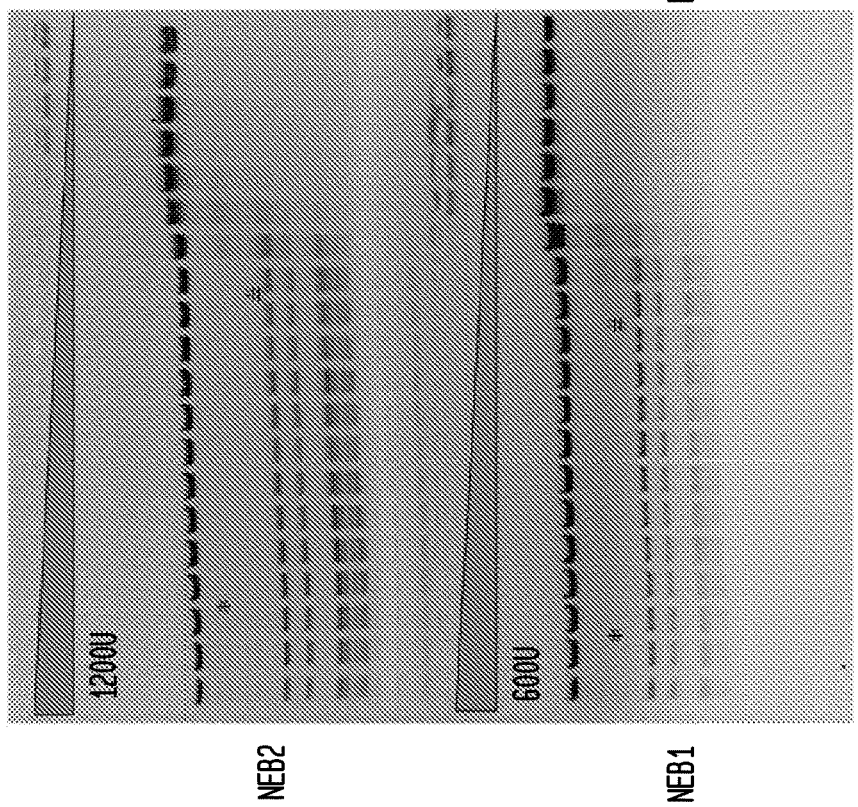

FIGS. 23A-B shows cleavage of 1.2 µl pXba DNA substrate in a 2-fold serial dilution of EagI-HF (1,200 U and 600 U) and a 2-fold serial dilution of WT EagI (150 U and 38.4 U) in NEB2 and NEB1 buffers, respectively, using diluent C.

FIG. 23A shows cleavage by EagI-HF in NEB2 buffer (upper panel) and NEB1 buffer (lower panel).

FIG. 23B shows cleavage by WT EagI in NEB2 buffer (upper panel) and NEB1 buffer (lower panel).

Figures 24A, 24B:
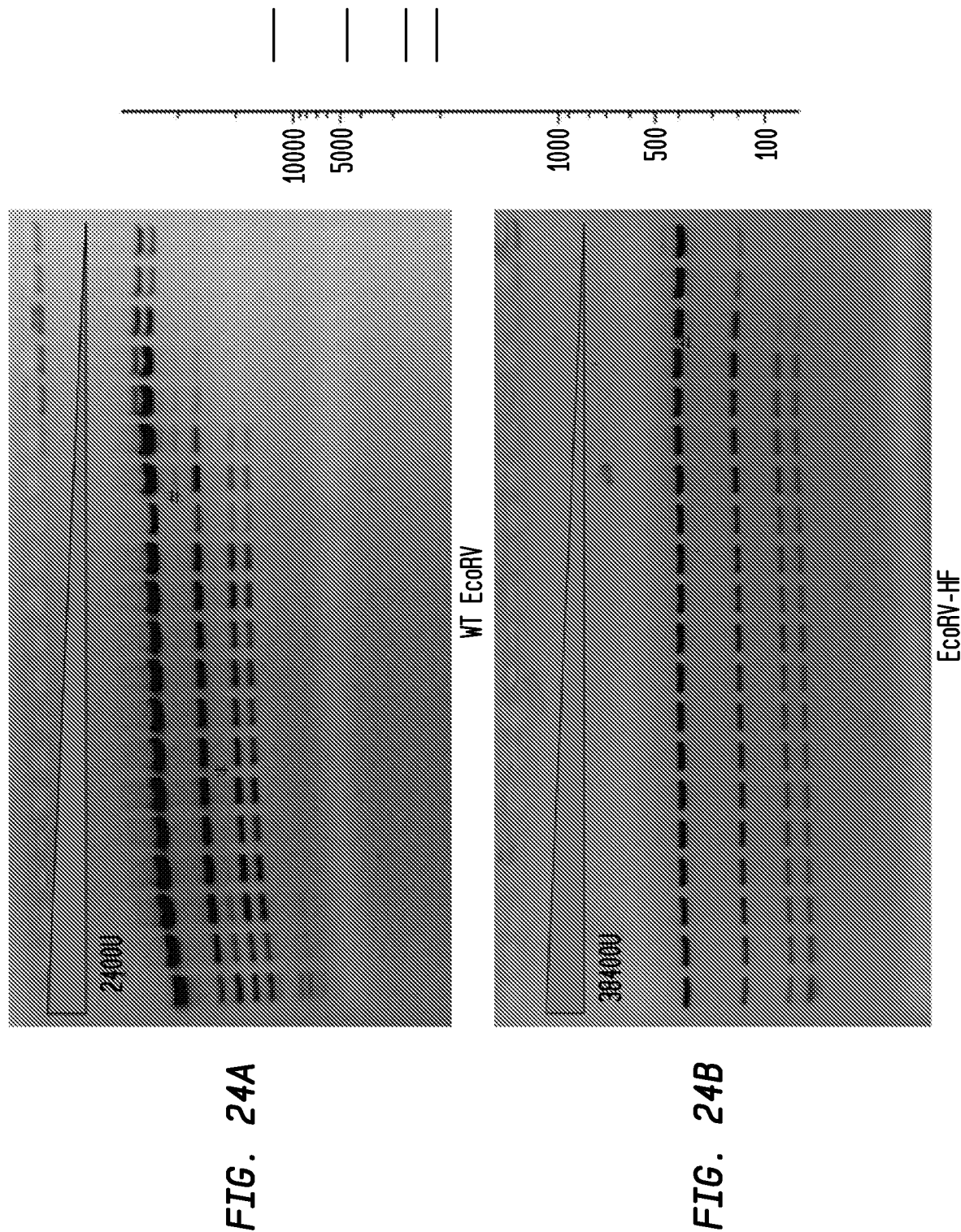

FIGS. 24A-B show cleavage of 1.2 µl pXba DNA substrate in a two-fold serial dilution using diluent A of EcoRV-HF (starting concentration: 38,400 U) and WT EcoRV (starting concentration: 2400 U) in NEB4 buffer.

FIG. 24A shows cleavage by WT EcoRV.

FIG. 24B shows cleavage by EcoRV-HF.

Figures 25A, 25B:
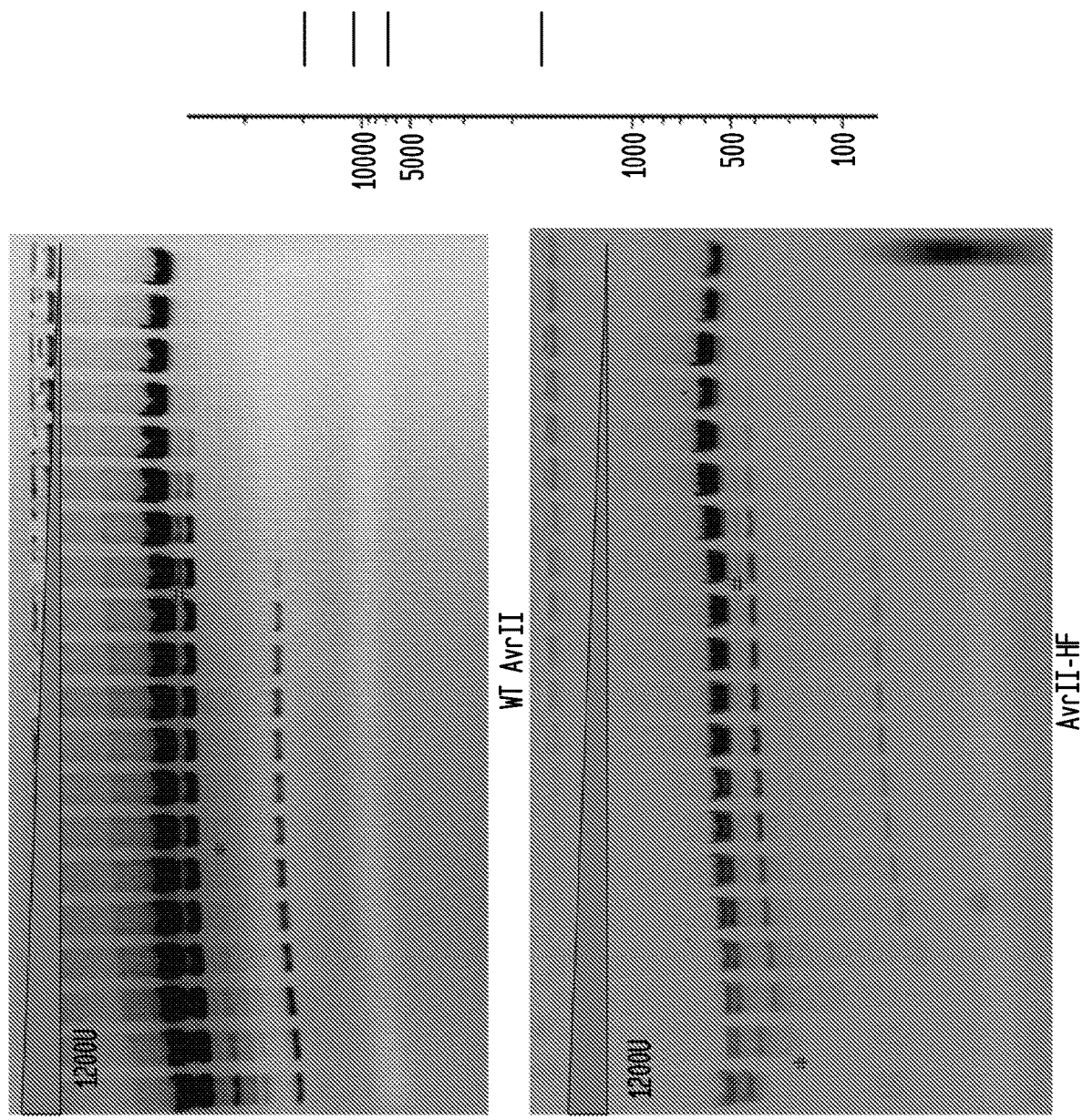

FIGS. 25A-B show cleavage of 1.2 µl T7 DNA substrate in a two-fold serial dilution using diluent A of AvrII-HF (starting concentration: 1,200 U) and WT AvrII (starting concentration: 1,200 U) in NEB4 buffer.

FIG. 25A shows cleavage by WT AvrII.

FIG. 25B shows cleavage by AvrII-HF.

Figures 26A, 26B:
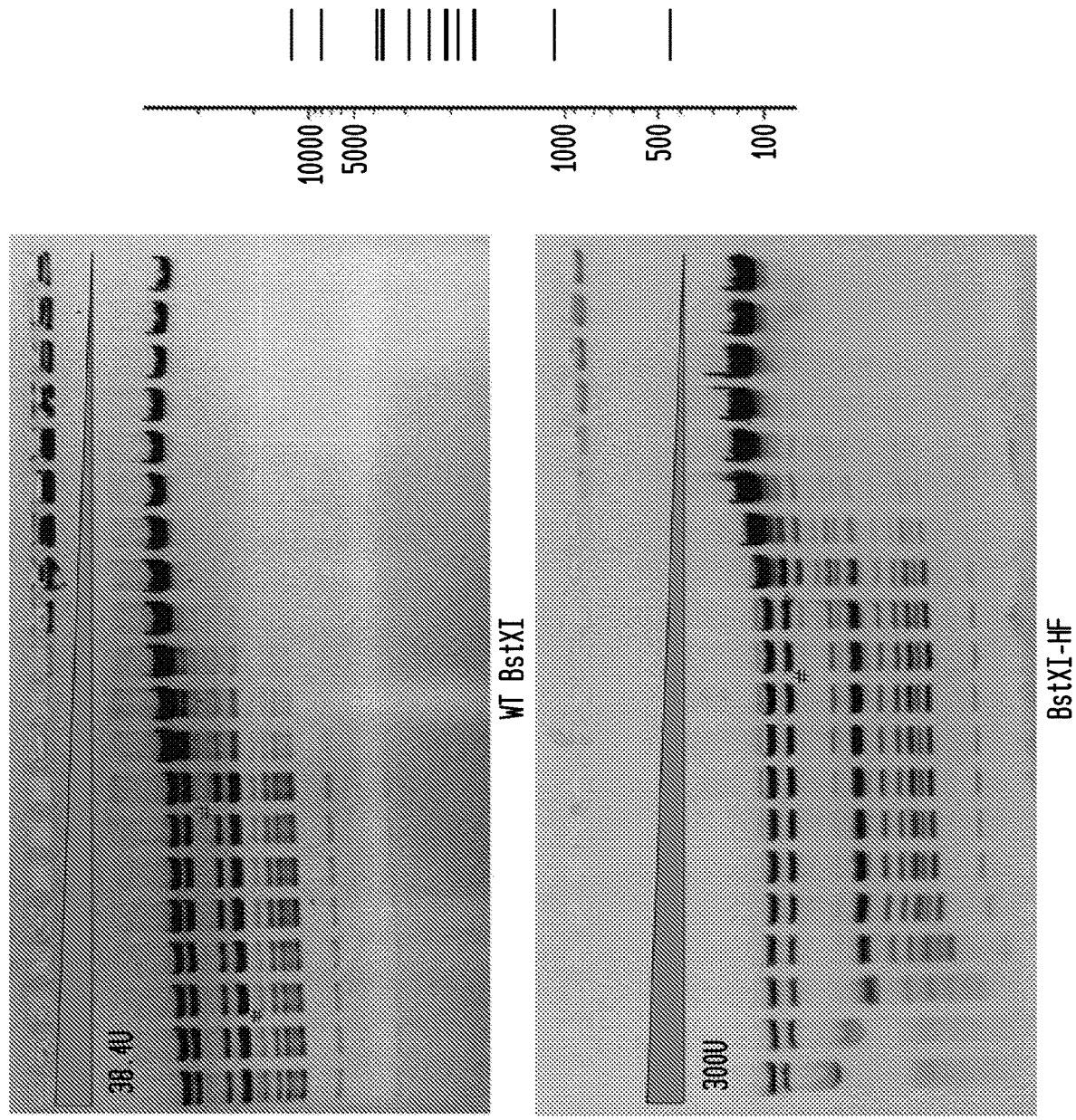

FIGS. 26A-B show cleavage of 1.2 µl lambda DNA substrate by a two-fold serial dilution in diluent A of BstXI-HF (starting concentration: 300 U) and WT BstXI (starting concentration: 38.4 U) in NEB4 buffer. The reaction was performed at 55° C.

FIG. 26A shows cleavage by WT BstXI.

FIG. 26B shows cleavage by BstXI-HF.

Figures 27A, 27B:
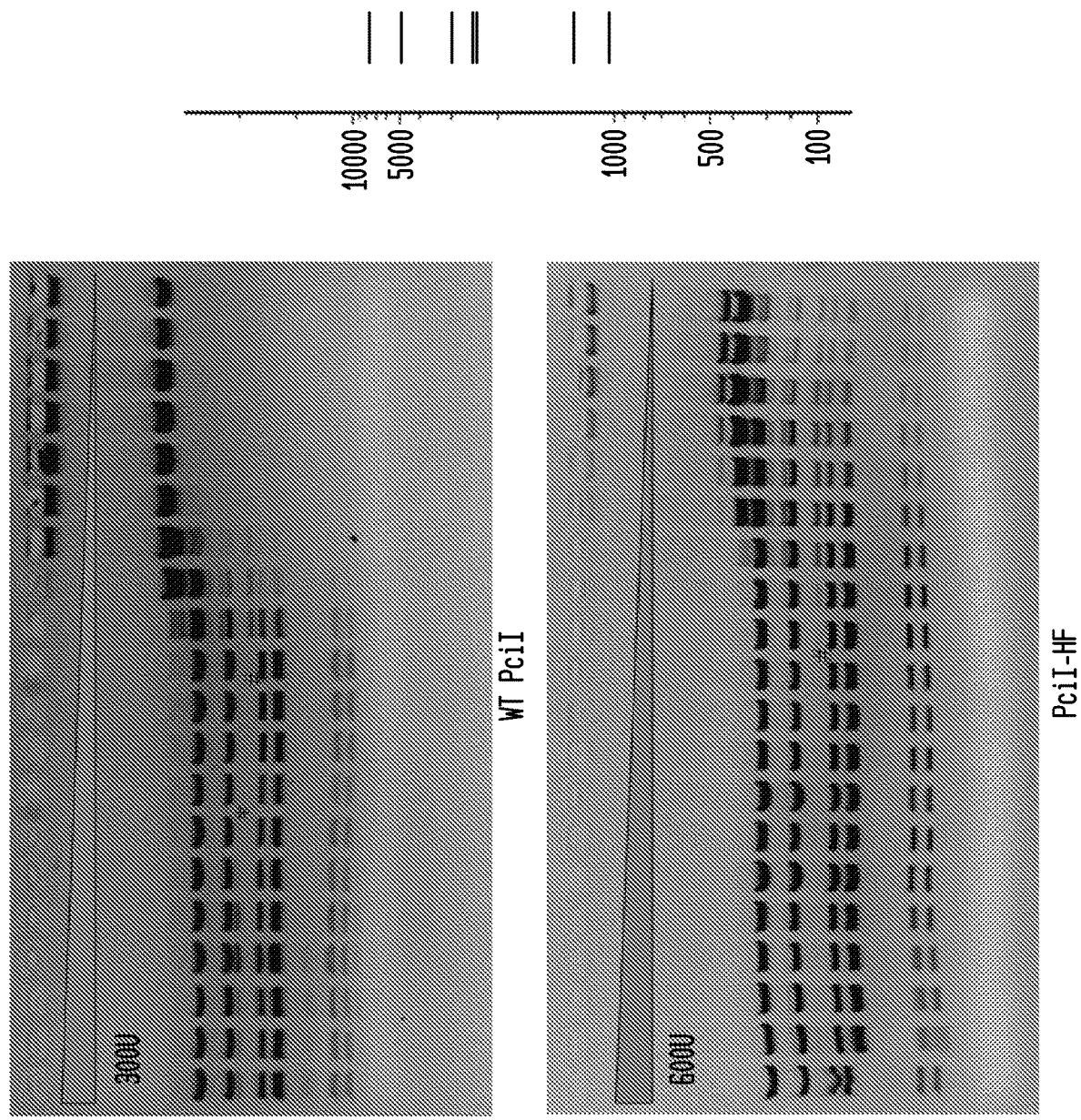

FIGS. 27A-B show cleavage of 1.2 µl pXba DNA substrate in a two-fold serial dilution using diluent A of PciI-HF (starting concentration: 600 U) and WT PciI (starting concentration 300 U) in NEB4 buffer.

FIG. 27A shows cleavage by WT PciI.

FIG. 27B shows cleavage by PciI-HF.

Figures 28A, 28B:
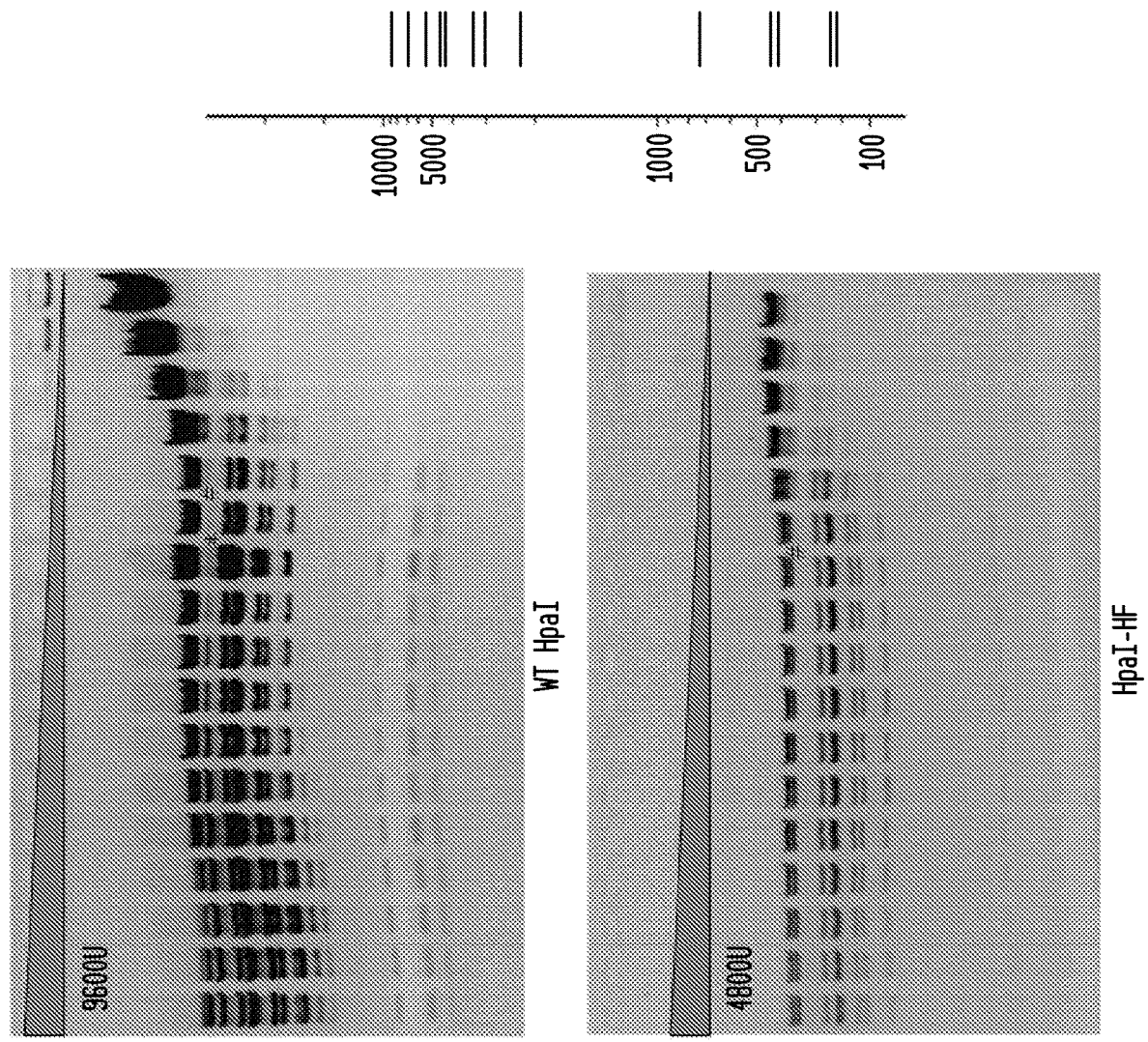

FIGS. 28A-B show cleavage of 1.2 µl lambda DNA substrate in a two-fold serial dilution using diluent A of HpaI-HF (starting concentration: 4,800 U) and WT HpaI (starting concentration 9,600 U) in NEB2 buffer.

FIG. 28A shows cleavage by WT HpaI.

FIG. 28B shows cleavage by HpaI-HF.

Figures 29A, 29B:
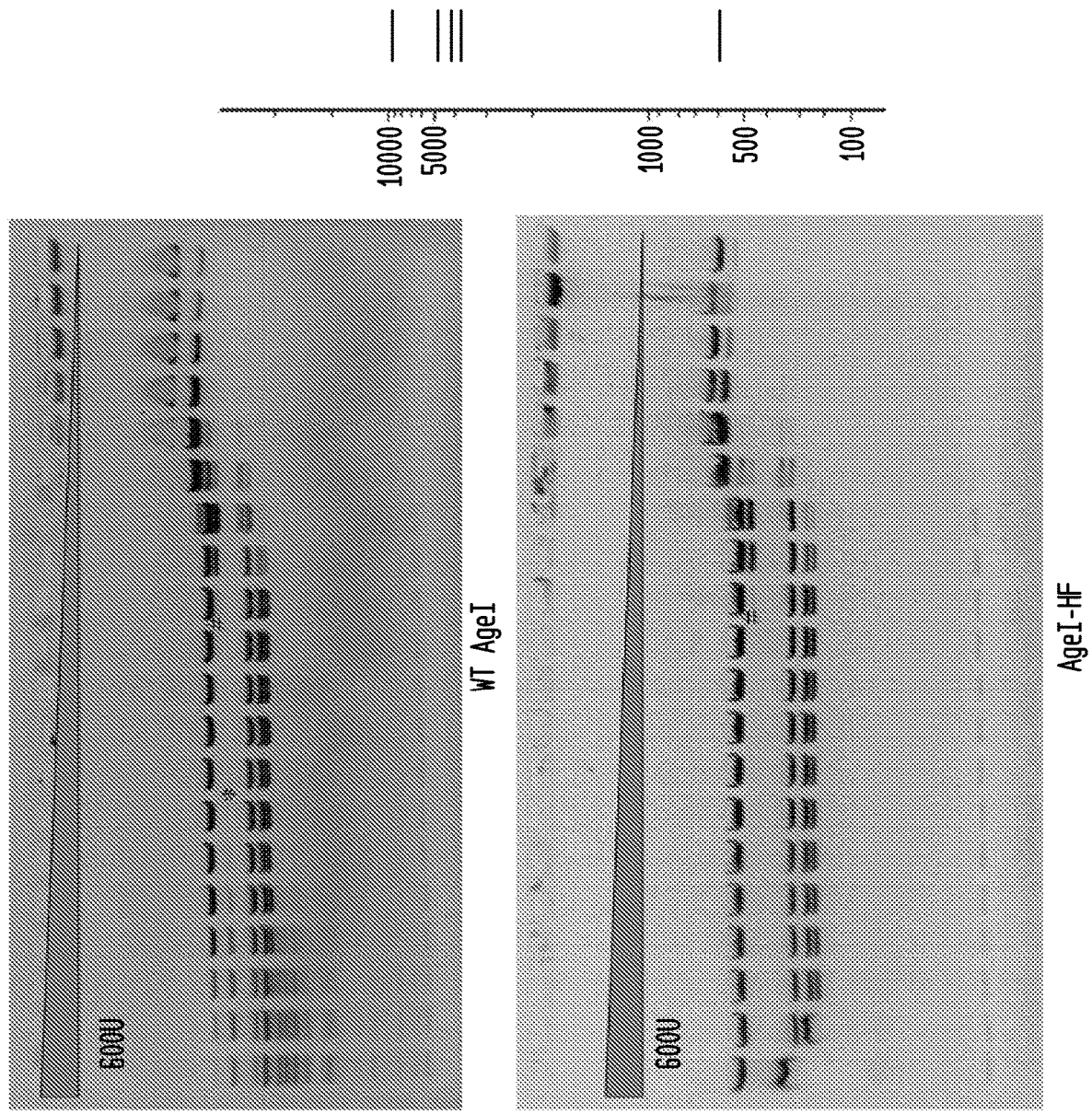

FIGS. 29A-B show cleavage of 1.2 µl pXba DNA substrate in a two-fold serial dilution of AgeI-HF using diluent C (starting concentration: 600 U) and WT AgeI (starting concentration 600 U) in NEB4 buffer.

FIG. 29A shows cleavage by WT AgeI.

FIG. 29B shows cleavage by AgeI-HF.

Figures 30A, 30B:
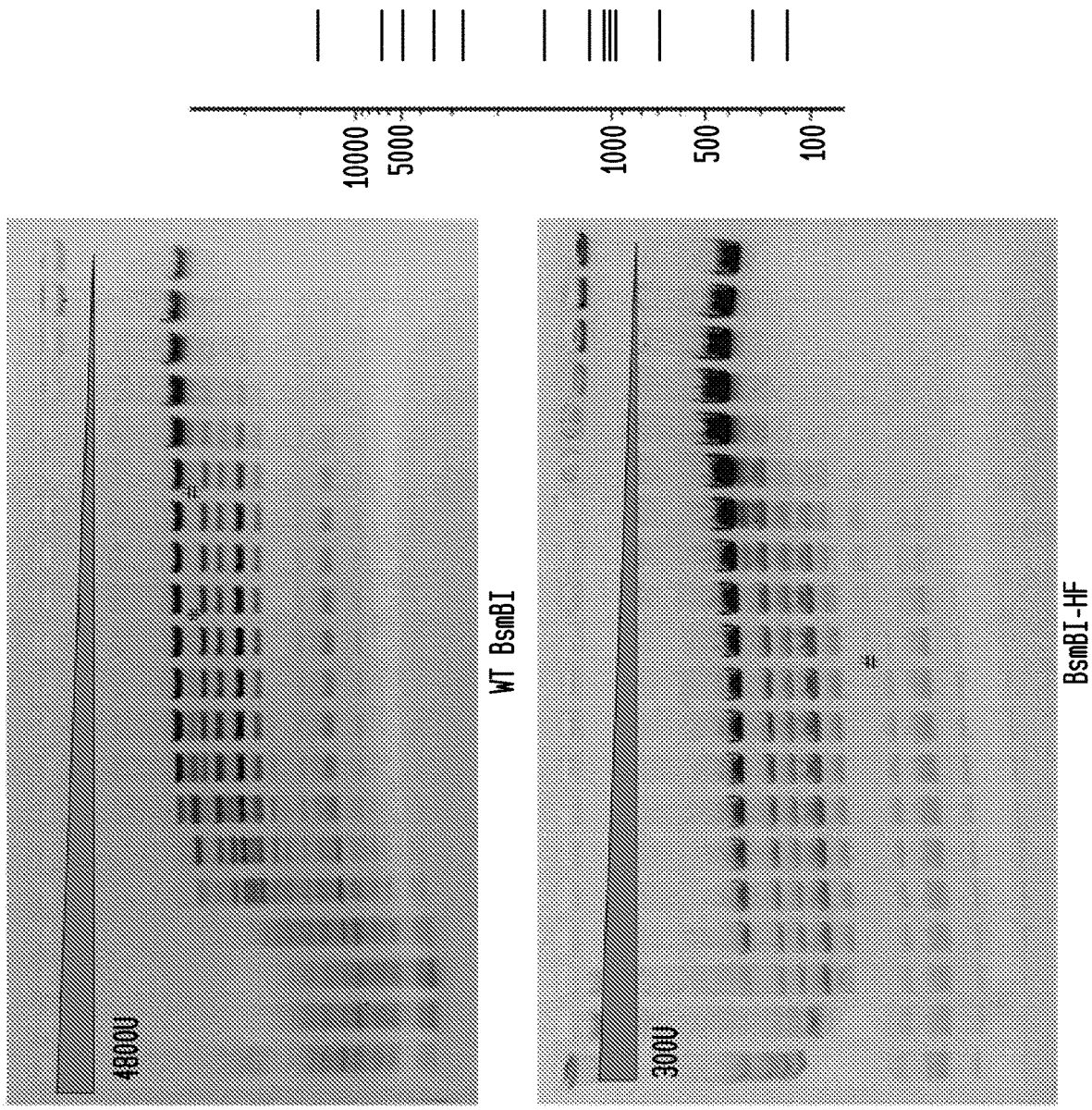

FIGS. 30A-B show cleavage of 1.2 µl lambda DNA substrate in a two-fold serial dilution using diluent A of BsmBI-HF (starting concentration: 300 U) and WT BsmBI (starting concentration 4,800 U) in NEB4 buffer. The reaction is at 55° C.

FIG. 30A shows cleavage by WT BsmBI.

FIG. 30B shows cleavage by BsmBI-HF.

FIGS. 31A-B show the DNA sequence (SEQ ID NO: 1) and protein sequence (SEQ ID NO:2) of MluCIM, respectively, for expression of EcoRI and MfeI.

FIG. 32 shows the DNA sequence (SEQ ID NO:3) of Hpy166IIM for expression of SalI.

FIGS. 33A-B show the DNA sequence (SEQ ID NO:4) and protein sequence (SEQ ID NO:5) of MfeI, respectively.

FIGS. 34A-B show the DNA sequence (SEQ ID NO:6) and protein sequence (SEQ ID NO:7) of BstXI, respectively.

FIGS. 35A-B show the DNA sequence (SEQ ID NO:8) and protein sequence (SEQ ID NO:9) of M.BstXI, respectively.

FIGS. 36A-B show the DNA sequence (SEQ ID NO: 10) and protein sequence (SEQ ID NO:11) of S.BstXI, respectively.

FIGS. 37A-B show the DNA sequence (SEQ ID NO: 12) and protein sequence (SEQ ID NO: 13) of PciI, respectively.

FIGS. 38A-B show the DNA sequence (SEQ ID NO: 14) and protein sequence (SEQ ID NO:15) of M.PciI, respectively.

FIG. 39 shows the DNA sequence (SEQ ID NO:17) encoding MI.EarI that recognizes CTCTTC and methylates at N4 cytosine or N6 adenine for cloning SapI and BspQI.

FIG. 40 shows the DNA sequence (SEQ ID NO:18) encoding M2.EarI that recognizes CTCTTC and methylates at N4 cytosine or N6 adenine for cloning SapI and BspQI.

Figure 41A:
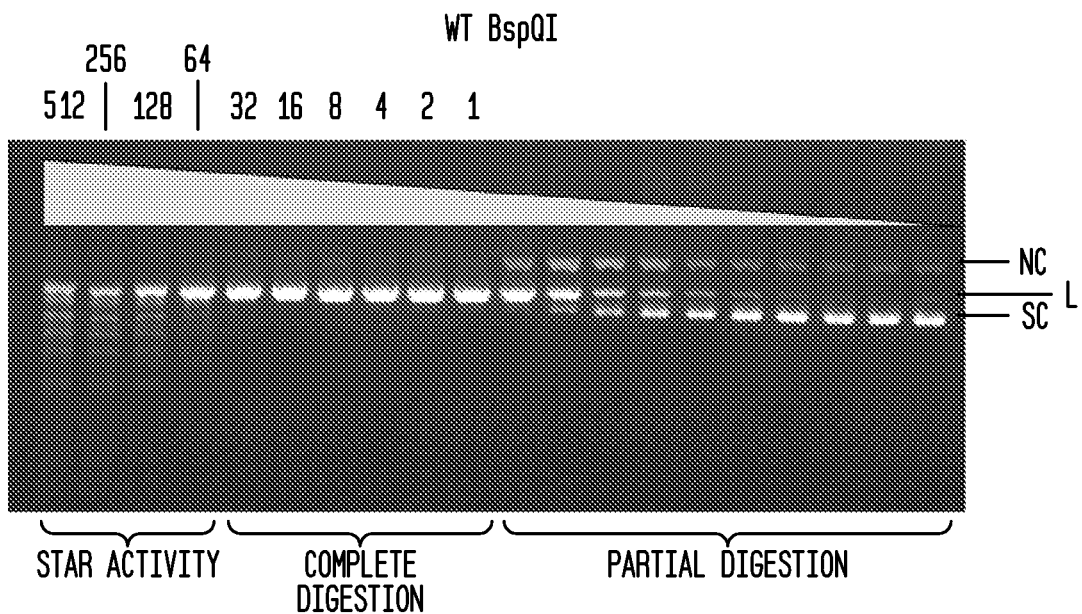
Figure 41B:
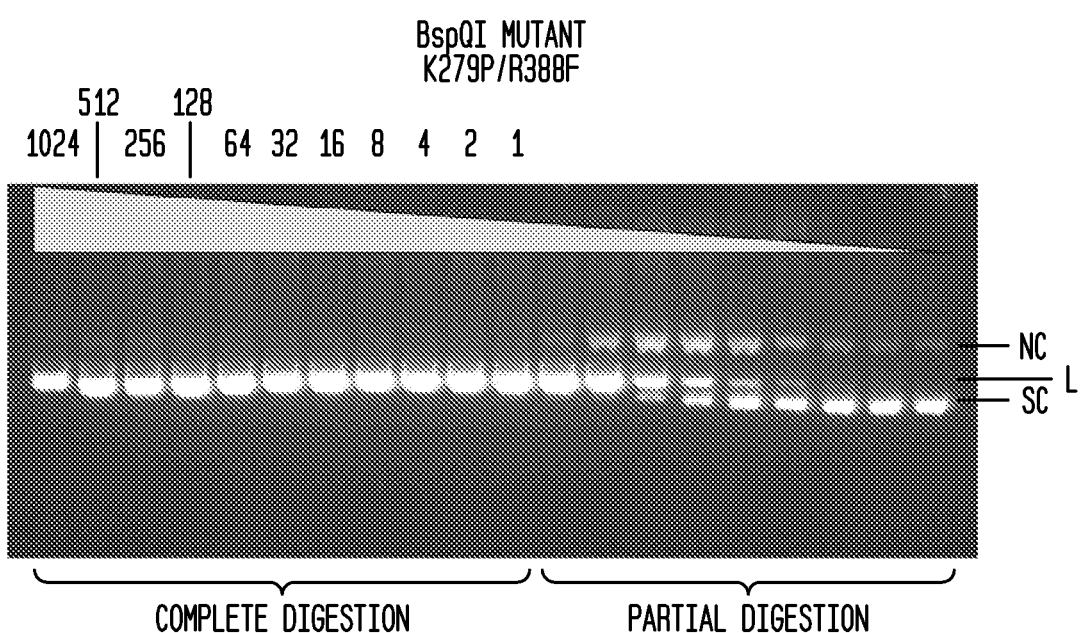

FIGS. 41A-B show agarose gels to determine the FI of 1 µl WT BspQI and 1 µl mutant (K279P/R388F) BspQI (starting concentrations 512 U and 1,024 U, respectively) by cleaving 1 µl pUC19 DNA substrate in a two-fold serial dilution using diluent A and NEB1 buffer plus 10% glycerol. The reaction was conducted at 50° C.

Figure 42:
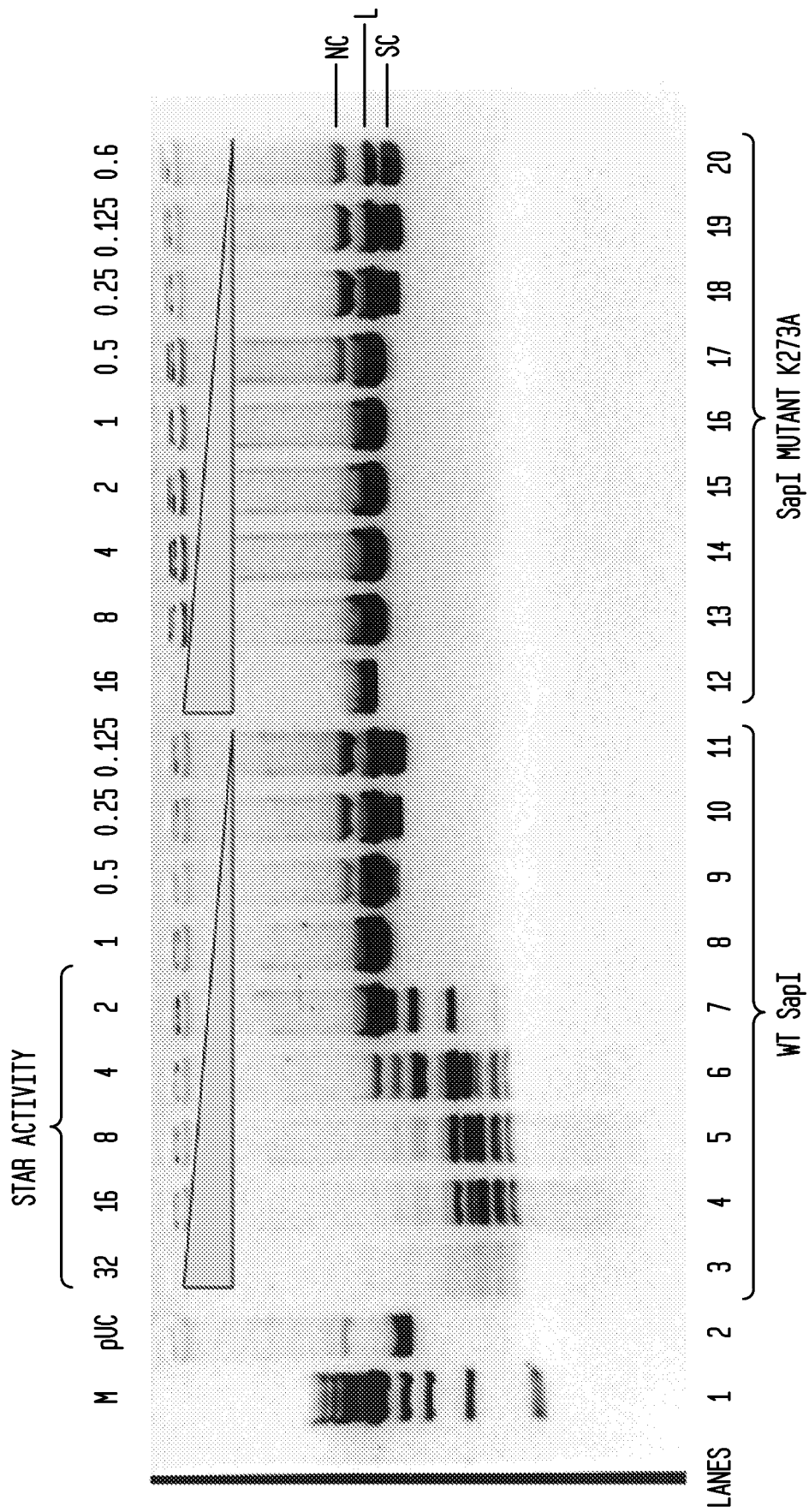

FIG. 42 shows agarose gels to determine the FI of 5 µl WT SapI and 5 µl mutant (K273A) SapI (starting concentrations 32 U and 16 U, respectively) by cleaving pUC19 DNA substrate in a two-fold serial dilution using diluent A and NEB2 buffer plus 25% DMSO.

Figure 43A:
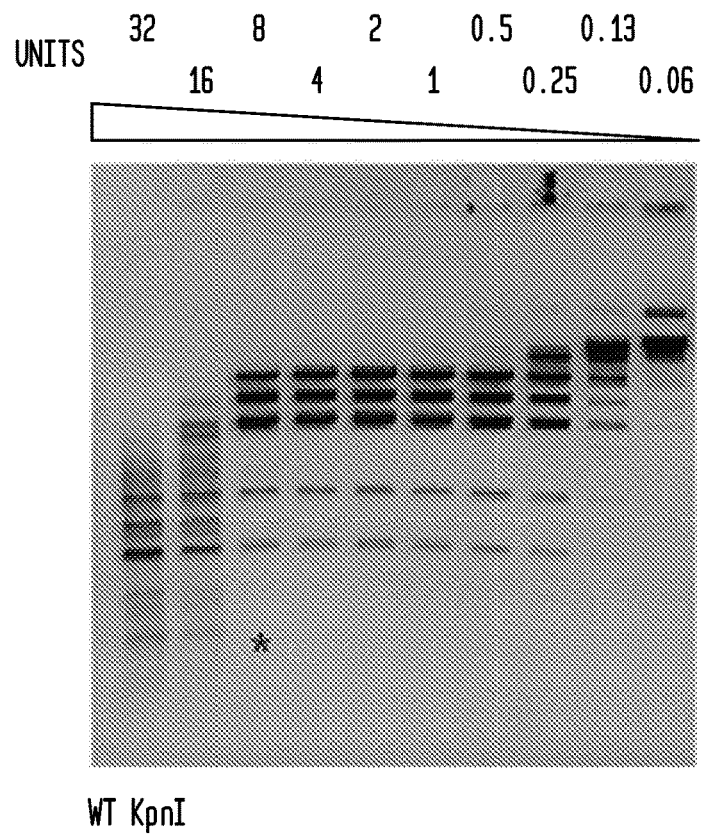
Figure 43B:
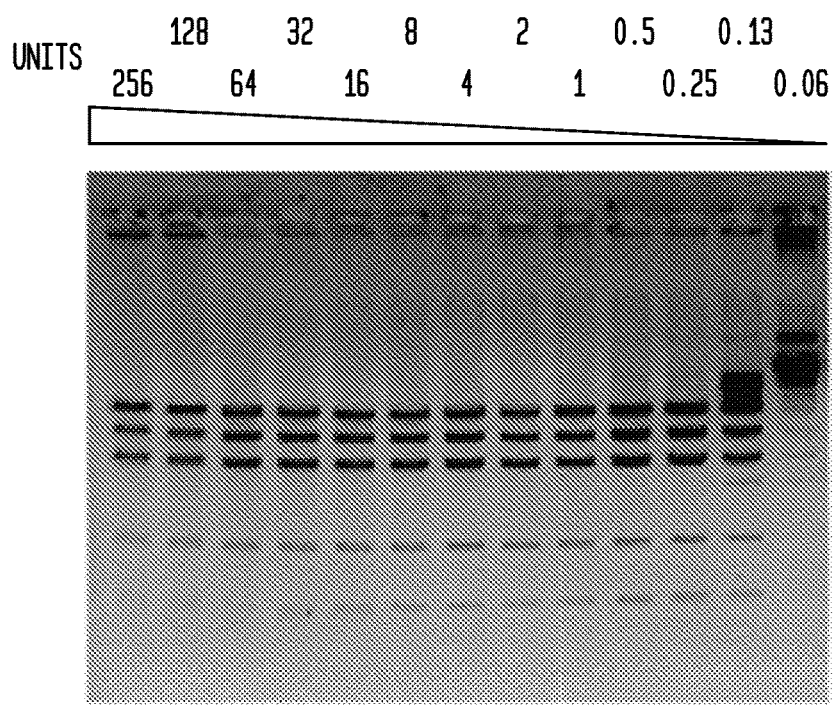

FIGS. 43A-B show catalytic and star activity of pXba by 5 µl WT KpnI and 5 µl D16N/E132A/D148E KpnI (initial concentrations 32 U and 256 U, respectively). The enzyme digested 2 µl pXba DNA substrate (0.5 µg) in a 2-fold serial dilution in NEB2 buffer using a diluent containing 10 mM Tris-HCl, pH 7.4, 50 mM KCl, 0.1 mM EDTA, 1 mM DTT and 50% glycerol with the total volume made up to 50 µl with water.

FIG. 43A shows the cleavage results of KpnI.

FIG. 43B shows the cleavage results of D16N/E132A/D148E KpnI.

FIG. 44A-G show the amino acid sequences of the enzymes in Table 1 and the DNA sequences of the enzymes in Table 1 that have not been previously disclosed.

DETAILED DESCRIPTION OF THE EMBODIMENTS

Embodiments of the invention provide a general method for selecting for restriction endonucleases with desired characteristics. The general method relies on a suitable assay for determining whether the desired restriction endonuclease has been created. In particular an embodiment of the general method provides a systematic screening method with a set of steps. This method has been deduced by performing many hundreds of reactions using many restriction endonucleases. The majority of the examples provided herein relate to identifying restriction endonucleases with reduced star activity but with cleavage activity that is at least similar to the WT restriction endonuclease. However, it is expected that the same methodology can be applied successfully to modifying other properties of the restriction endonucleases relating, for example, to improved cleavage activity in desired buffers, thermostability, rate of reaction in defined conditions, etc.

As discussed above, an end point of interest is to transform restriction endonucleases with star activity into high fidelity restriction endonucleases with significantly reduced star activity. Star activity refers to promiscuity in cleavage specificity by individual restriction endonucleases. The terms "reduction in star activity" and "increase in fidelity" are used interchangeably here. Although restriction endonucleases are characterized by their property of cleaving DNA at specific sequences, some restriction endonucleases additionally cleave DNA inefficiently at secondary sites in the DNA. This secondary cleavage may occur consistently or may arise only under certain conditions such as any of: increased concentrations, certain buffers, temperature, substrate type, storage, and incubation time.

It is generally acknowledged that little is known about the complex environment generated by the hundreds of amino acids that constitute a protein and determine specificity. One approach in the prior art has been to utilize crystallography to identify contact points between an enzyme and its substrate. Nonetheless, crystallography has limitations with respect to freezing a structure in time in an unnatural chemical environment.

The rules that determine the contribution of amino acids at any site in the protein and the role played by the structure of the substrate molecule has proved elusive using existing analytical techniques. For example, it is shown here that mutating an amino acid in a restriction endonuclease can cause all or partial loss of activity.

In this context, no structural explanation has been put forward to explain why star activity could increase with high glycerol concentration (>5% v/v), high enzyme to DNA ratio (usually >100 units of enzyme per µg of DNA), low ionic strength (<25 mM salt), high pH (>8.0), presence of organic solvent (such as DMSO, ethanol), and substitution of $Mg^{2+}$ with other divalent cations ($Mn^{2+}$, $Co^{2+}$). It was here recognized that because of the diversity of factors affecting star activity, it would be necessary to conduct comparisons of WT and mutant star activity under the same reaction conditions and in the same predetermined buffer and to develop a standard reaction condition in which any high fidelity enzyme must be capable of showing the described characteristics even if these characteristics were also observed in other reaction conditions.

Present embodiments of the invention are directed to generating modified restriction endonucleases with specific improved properties, namely enhanced cleavage fidelity without significant reduction in overall cleavage activity or significant loss of yield from the host cells that make the protein. The methods that have been developed here for finding mutants with improved properties have resulted from exhaustive experimentation and the properties of the resultant enzymes have been defined in the context of specified conditions. The methods described herein may be used for altering the enzymatic properties of any restriction endonuclease under predetermined conditions, but are not limited to the specific defined conditions.

| Restriction Endonuclease | Steps Used to Generate a High Fidelity Restriction Endonuclease |
|---|---|
| BamHI (Ex. 1) | Comparison of isoschizomer
Targeted 22 residues to mutate to Ala. 14 mutants obtained, 3 had improved fidelity
Saturation mutagenesis on 2 residues-K30 and E86
Recovered E86P as preferred mutant with greatest reduced star activity in selected buffers. Added mutations to E86P.
Second round of mutation (Arg, Lys, His, Asp, Glu, Ser, Thr) to Ala and Tyr to Phe. Selected E167 and Y165 for saturation mutagenesis and selected E167T and Y165F.
E163A/E167T was selected as preferred high fidelity mutant (BamHI-HF). |
| EcoRI (Ex. 2) | Comparison of isoschizomer
Targeted 42 charged residues to mutate to Ala. No high fidelity mutants
Second round of mutation: Target additional 32 charged residues to mutate to Ala: Identified K62A.
Saturation mutagenesis on K62A. EcoRI( K62E) was selected as a preferred high fidelity mutant (EcoRI-HF). |
| ScaI (Ex. 3) | Comparison of isoschizomers.
Targeted 58 charged residues to mutate to Ala. Identify 4 mutants
Preferred mutant of 4 is (H193A/S201F). This is selected as a preferred high fidelity mutant (ScaI-HF). |
| SalI (Ex. 4) | Target 86 charged residues and mutate to Ala. SalI (R107A) was preferentially selected as a preferred high fidelity mutant (SalI-HF). |
| SphI (Ex. 5) | Target 71 charged residues and mutate to Ala. SphI (K100A) was preferentially selected as a preferred high fidelity mutant (SphI-HF) |
| PstI (Ex. 6) | Target 92 charged amino acids and mutate to Ala. PstI (D91A) was preferentially selected as a preferred high fidelity mutant (PstI-HF) |
| NcoI (Ex. 7) | Target 66 charged residues and mutate to Ala. NcoI (A2T/R31A) was preferentially selected as a preferred high fidelity mutant (NcoI-HF). |
| NheI (Ex. 8) | Target 92 charged residues and mutate to Ala. NheI (E77A) was preferentially selected as a preferred high fidelity mutant (NheI-HF) |
| SspI (Ex. 9) | Target 81 charged residues and mutate to Ala. No preferential mutants obtained.
Target 95 residues to additional charged residues and hydroxylated residues to Ala except Tyr. Tyr mutated to Phe. SspI (Y98F) was preferentially selected as a preferred high fidelity mutant (SspI-HF) |
| NotI (Ex. 10) | Target 97 charged residues and mutate to Ala. K150A was preferentially selected as a preferred high fidelity mutant (NotIHF) |
| SacI (Ex. 11) | Target 101 charged residues and mutate to Ala. SacI (Q117H/R200A) was preferentially selected as a preferred high fidelity mutant (SacI-HF) where Q117H was a carry over mutation from template with no affect on activity |
| PvuII (Ex. 12) | Target 47 charged residues and mutate to Ala. No preferred mutants obtained
Target 19 hydroxylated residues - Ser/Thr and Tyr. Select T46A for further improvement
Saturation mutagenesis results in a preferred mutant T46G, T46H, T46K, T46Y. PvuII(T46G) was preferentially selected as a preferred high fidelity mutant (PvuII-HF) |
| MfeI (Ex. 13) | Target 60 charged residues and mutate to Ala. No preferred mutants obtained
Target 26 hydroxylated residues and mutate to Ala except for Tyr which was changed to Phe.
Target 38 residues (Cys, Phe, Met, Asn, Gln, Trp) and mutate to Ala
Identify Mfe (Q13A/F35Y) as a preferred high fidelity mutant (MfeI-HF) where F35Y is carried from the template |
| HindIII (Ex. 14) | Target 88 charged residues and mutate to Ala. No preferred mutants obtained
Target 103 residues (Cys Met Asn, Gln, Ser Thr Trp) and mutate to Ala and Tyr changed to Phe.
Identify HindIII (K198A) as a preferred high fidelity mutant (HindIII-HF) |
| SbfI (Ex. 15) | Target 78 charged residues mutated to Ala
Target 41 residues (Ser Thr) mutated to Ala/Tyr to Phe
Target 55 residues of Cys, Phe, Met Asn, Gln, Trp to Ala
SbfI (K251A) was selected as a preferred high fidelity mutant (SbfI-HF) |
| EagI (Ex. 16) | Target 152 residues (Asp, Glu, His, Lys, Arg, Ser, thr, Asn, and Gln changed to Ala and Tyr changed to Phe).
EagI H43A was selected as a preferred high fidelity mutant (EagIHF) |
| EcoRV (Ex. 17) | Target 162 residues (Cys,Asp, Glu, Phe, his, Lys, Met, Asn, Gln, Arg, Ser, Thr, to Ala and Trp to Phe)
EcoRV (D19A/E27A) was selected as a preferred high fidelity mutant (EcoRV-HF) |
| AvrII (Ex. 18) | Target 210 residues (Cys,Asp, Glu, Phe, his, Lys, Met, Asn, Gln, Arg, Ser, Thr, to Ala and Trp to Phe)
AvrII (Y104F) was selected as a preferred high fidelity mutant (AvrII-HF) |
| BstXI (Ex. 19) | Target 237 residues (Cys,Asp, Glu, Phe, his, Lys, Met, Asn, Gln, Arg, Ser, Thr, to Ala and Trp to Phe)
BstXI (N65A) was selected as a preferred high fidelity mutant (BstXI-HF) |
| PciI (Ex. 20) | Target 151 residues (Cys,Asp, Glu, Phe, his, Lys, Met, Asn, Gln, Arg, Ser, Thr, to Ala and Trp to Phe)
PciI (E78A/S133A) was selected as a preferred high fidelity mutant. (PciI-HF) This was spontaneous and not one of the 151 separate mutations |
| HpaI (Ex. 21) | Target 156 residues (Cys,Asp, Glu, Phe, his, Lys, Met, Asn, Gln, Arg, Ser, Thr, to Ala and Trp to Phe)
HpaI (E56A) was selected as a preferred high fidelity mutant (HpaI-HF) |
| AgeI (Ex. 22) | Target 149 residues (Cys,Asp, Glu, Phe, his, Lys, Met, Asn, Gln, Arg, Ser, Thr, to Ala and Trp to Phe)
AgeI (R139A) was selected as a preferred high fidelity mutant (AgeI-HF) |
| BsmBI (Ex. 23) | Target 358 residues (Cys,Asp, Glu, Phe, his, Lys, Met, Asn, Gln, Arg, Ser, Thr, to Ala and Trp to Phe)
BsmBI(N185Y/R232A) was selected as a preferred high fidelity mutant (BsmBI (HF) |
| BspQI (Ex. 24) | Target 122 residues (Arg, Lys, His, Glu, Asp, Gln, Asn, Cys)
Replace R at position 279 with Phe, Pro, Tyr, Glu, Asp or Leu.
Preferred mutations were R388F and K279P.
Created a double mutant BspQI(K279P/R388F) as preferred high fidelity mutant (BspQI-HF) |
| SapI (Ex. 25) | Find K273 and R380 in SapI corresponding to R388 and K279 in BspQI.
SapI (K273P/R380F) was selected as a preferred high fidelity mutant (SapI-HF) |
| KpnI (Ex. 26) | Target all residues (Asp, Glu, Arg, Lys, His, Ser, Thr, Tyr, Asn, Gln, Phe, Trp, Cys, Met) to Ala.
More mutation was done on site D16 and D148.
A combined D16N/E132A/D148E was selected as a preferred high fidelity mutant (KpnI-HF). |
| BsaI (Ex. 27) | Find 11 amino acids corresponding to the site in BsmBI.
BsaI (Y231F) was selected as a preferred high fidelity mutant (BsaI-HF). |

The method follows from the realization that amino acids responsible for cognate activity and star activity are different. The engineering of high fidelity restriction endonucleases described herein demonstrates that cognate activity and star activity can be separated and there are different critical amino acid residues that affect these different activities. The locations of amino acids that are here found to affect star activity are not necessarily found within the active site of the protein. The cleavage properties of any restriction endonuclease has been determined here for the first time by developing a criterion of success in the form of determining a FI (see also Wei et al. *Nucleic Acid Res.*, 36, 9, e50 (2008)) and an overall fidelity index improvement factor.

An "overall fidelity index improvement factor" refers to the highest FI for a mutant with maximum cleavage activity divided by the highest FI of the corresponding WT endonuclease with maximum cleavage activity within a selected set of buffers. The selected set may be of any size greater than one but practically will contain less than 10 different buffers and more preferably contains 4 buffers. The set may also include less than 4 buffers. The overall FI improvement factor of at least two should preferably be applicable for any mutant restriction endonuclease in the claimed invention additionally but not exclusively to the set of buffers consisting of NEB1, NEB2, NEB3 and NEB4.

A "similar cleavage activity" can be measured by reacting the same amount of enzyme with the same amount and type of substrate under the same conditions and visually comparing the cleavage profiles on a gel after electrophoresis such that the amount of cleavage product appears to be the same within a standard margin of error and wherein the quantitative similarity is more than 10%.

"Artificial" refers to "man-made".

"Standard conditions" refers to an overall FI improvement factor calculated from results obtained in NEB1-4 buffers.

The general method described herein has been exemplified with 27 restriction endonucleases: AgeI, AvrII, BamHI, BsaI, BsmBI, BspQI, BstXI, EagI, EcoRI, EcoRV, HindIII, HpaI, KpnI, MfeI, NcoI, NheI, NotI, PciI, PstI, PvuII, SacI, SalI, SapI, SbfI, ScaI, SphI and SspI restriction endonucleases. However, as mentioned above, the method is expected to be effective for the engineering of any restriction endonuclease that has significant star activity.

Embodiments of the method utilize a general approach to create mutant restriction endonucleases with reduced star activity. For certain enzymes, it has proven useful to mutate charged residues that are determined to be conserved between two isoschizomers (see for example SapI in Example 25). In general, however, the method involves a first step of identifying all the charged and polar residues in a protein sequence for the endonuclease. For example, charged amino acids and polar residues include the acidic residues Glu and Asp, the basic residues His, Lys and Arg, the amide residues Asn and Gln, the aromatic residues Phe, Tyr and Trp and the nucleophilic residue Cys. Individual residues are targeted and mutated to an Ala and the products of these targeted mutations are screened for the desired properties of increased fidelity. If none of the mutants obtained provide a satisfactory result, the next step is to target mutations to all the hydroxylated amino acids, namely, Ser, Thr and Tyr, the preferred mutation being Ser and Thr to Ala and Tyr to Phe. It is also possible to target mutations to both classes of residues at one time as was done for Examples 16-23. The mutation to Ala may be substituted by mutations to Val, Leu or Ile.

After these analyses, if one or more of the preferred mutants generated in the above steps still have substandard performance under the selected tests, these mutants can be selected and mutated again to each of the additional possible 18 amino acids. This is called saturation mutagenesis. Saturation mutagenesis provided the preferred high fidelity mutants for EcoRI (Example 2), BamHI in part (Example 1) and PvuII (Example 12). Depending on the results of saturation mutagenesis, the next step would be to introduce additional mutations either targeted or random or both into the restriction endonuclease. In Example 11, SacI-HF includes a random mutation generated fortuitously during inverse PCR. In Example 20, PciI-HF resulted from a random mutation and not from targeted mutations. In Example 26, BspQI-HF contains two mutations that were found to act synergistically in enhancing fidelity.

The use of various methods of targeted mutagenesis such as inverse PCR may involve the introduction of non-target mutations at secondary sites in the protein. These secondary mutations may fortuitously provide the desired properties (see Example 20). It is desirable to examine those mutated enzymes with multiple mutations to establish whether all the mutations are required for the observed effect. In Example 11, Q117H in the double mutant had no effect on activity. In Example 20, the additional spontaneous mutation appears to be solely responsible for the observed improved fidelity, whereas in Example 24, the individual mutations acted synergistically.

In some cases, a mutation may provide an additional advantage other than improved fidelity (see for example BamHI in which either E163A or P173A causes the enzyme to become more thermolabile).

The high fidelity/reduced star activity properties of the mutants provided in the Examples were selected according to their function in a set of standard buffers. Other mutations may be preferable if different buffer compositions were selected. However, the same methodology for finding mutants would apply. Table 4 lists mutations which apply to each restriction endonuclease and provide an overall FI improvement factor in the standard buffer.

The engineering of the high fidelity restriction endonucleases to provide an overall FI improvement factor of at least 2 involves one or more of the following steps:

1. Assessment of the Star Activity of the WT Restriction Endonuclease

In an embodiment of the invention, the extent of star activity of a restriction endonuclease is tested by means of the following protocol: the endonuclease activity is determined for an appropriate substrate using a high initial concentration of a stock endonuclease and serial dilutions thereof (for example, two-fold or three-fold dilutions). The initial concentration of restriction endonuclease is not important as long as it is sufficient to permit an observation of star activity in at least one concentration such that on dilution, the star activity is no longer detected.

An appropriate substrate contains nucleotide sequences that are cleaved by cognate endonuclease activity and where star activity can be observed. This substrate may be the vector containing the gene for the restriction endonuclease or a second DNA substrate. Examples of substrates used in Table 2 are pBC4, pXba, T7, lambda, and pBR322.

The concentration of stock restriction endonuclease is initially selected so that the star activity can be readily recognized and assayed in WT and mutated restriction endonucleases. Appropriate dilution buffers such as NEB diluent A, B or C is selected for performing the serial dilutions according to guidelines in the 2007-08 NEB catalog. The serially diluted restriction endonuclease is reacted with a predetermined concentration of the appropriate substrate in a total reaction volume that is determined by the size of the reaction vessel. For example, it is convenient to perform multiple reactions in microtiter plates where a 30 µl reaction mixture is an appropriate volume for each well. Hence, the examples generally utilize 0.6 µg of substrate in 30 µl, which is equivalent to 1 µg of substrate in 50 µl. The amount of substrate in the reaction mixture is not critical, but it is preferred that it be constant between reactions. The cleavage reaction occurs at a predetermined temperature (for example 25° C., 30° C., 37° C., 50° C., 55° C. or 65° C.) for a standard time such as one hour. The cleavage products can be determined by any standard technique, for example, by 0.8% agarose gel electrophoresis to determine the fidelity indices as defined above.

Not all restriction endonucleases have significant star activity as determined from their FI. However, if an endonuclease has a highest FI of no more than about 250 and a lowest F of less than 100, the restriction endonuclease is classified as having significant star activity. Such endonucleases are selected as a target of enzyme engineering to increase fidelity for a single substrate. In some cases, the restriction endonucleases with both FI over about 500 and FI less than about 100 are also engineered for better cleavage activity.

Table 2 below lists the FI of some engineered restriction endonucleases before engineering. All samples were analyzed on 0.8% agarose gel.

TABLE 2

| Enzyme | Diluent (NEB)*** | Sub-strate* | Temp ° C. | FI-1** | FI-2** | FI-3** | FI-4** |
|---|---|---|---|---|---|---|---|
| AgeI | C | pXba | 37 | 16 (1) | 8 (½) | 64 (⅛) | 8 (½) |
| AvrII | B | T7 | 37 | 64 (1) | 8 (1) | 32 (¼) | 32 (1) |
| BamHI | A | λ | 37 | 4 (½) | 4 (1) | 32 (1) | 4 (½) |
| BsaI | B | pBC4 | 50 | 8 (¼) | 120 (1) | 16 (¼) | 32 (1) |
| BsmBI | B | λ | 55 | 1 (⅛) | 8 (½) | 120 (1) | 4 (¼) |
| BspQI | B | λ | 50 | 2 (⅛) | 16 (1) | 32 (1) | 4 (¼) |
| BstXI | B | λ | 55 | 2 (½) | 2 (½) | 2 (⅛) | 4 (1) |
| EagI | B | pXba | 37 | 4 (¼) | 8 (½) | 250 (1) | 16 (1) |
| EcoRI | C | λ | 37 | 250 (½) | 4 (1) | 250 (1) | 4 (1) |
| EcoRV | A | pXba | 37 | 32 (1/16) | 120 (½) | 1000 (1) | 64 (¼) |
| HindIII | B | λ | 37 | 32 (¼) | 250 (1) | 4000 (¼) | 32 (½) |
| HpaI | A | λ | 37 | 32 (1/16) | 1 (¼) | 2 (⅛) | 16 (1) |
| KpnI | A | pXba | 37 | 16 (1) | 16 (¼) | 8 (1/16) | 4 (½) |
| MfeI | A | λ | 37 | 32 (1) | 16 (⅛) | 8 (1/16) | 32 (1) |
| NcoI | A | λ | 37 | 120 (1) | 32 (1) | 120 (¼) | 32 (1) |
| NheI | C | pXba | 37 | 32 (1) | 120 (¼) | 120 (⅛) | 32 (1) |
| NotI | C | pXba | 37 | ≥32000 (1/16) | 64 (1) | 500 (1) | 32 (¼) |
| PciI | A | pXba | 37 | 2000 (½) | 16 (¼) | 120 (1) | 8 (⅛) |
| PstI | C | λ | 37 | 64 (1) | 32 (1) | 120 (1) | 8 (½) |
| PvuII | A | pBR322 | 37 | 250 (1) | 16 (¼) | 8 (1/32) | ¼ (1) |
| SacI | A | pXba | 37 | 120 (1) | 120 (½) | 120 (1/32) | 32 (½) |
| SalI | A | λ (H3) | 37 | 8 (1/500) | 1 (1/16) | 32 (1) | 1 (1/120) |
| SapI | C | λ | 37 | 16 (¼) | 64 (½) | 32 (¼) | 16 (1) |
| SbfI | A | λ | 37 | 32 (1) | 8 (¼) | 8 (1/16) | 8 (½) |
| ScaI | A | λ | 37 | 1/16 (1/32) | ⅛ (1) | 4 (½) | 1/64 (1/16) |
| SphI | B | λ | 37 | 64 (1) | 32 (1) | 64 (¼) | 16 (½) |
| SspI | C | λ | 37 | 64 (1) | 16 (1) | 32 (¼) | 16 (1) |

*Substrate: λ is lambda phage DNA; λ (H3) is HindIII-digested lambda phage DNA; pXba is pUC19 with XbaI-digested fragment of Adeno Virus; pBC4: a shorter version of pXba; T7: T7 DNA
**FI-1 to FI-4: fidelity index of the enzyme in NEBuffer 1, 2, 3 and 4. The number in parenthesis is a value for relative cleavage activity of the mutant restriction endonuclease in a specified buffer in a set of buffers compared with the "best" cleavage activity of the same mutant restriction endonuclease in any of the buffers in the set of buffers.
The compositions of NEB buffers follow: NEB1: 10 mM Bis Tris Propane-HCl, 10 mM MgCl$_2$, 1 mM dithiothreitol (pH 7.0 at 25° C.); NEB2: 50 mM NaCl, 10 mM Tris-HCl, 10 mM MgCl$_2$, 1 mM dithiothreitol (pH 7.9 at 25° C.); NEB3: 100 mM NaCl, 50 mM Tris-HCl, 10 mM MgCl$_2$, 1 mM dithiothreitol (pH 7.9 at 25° C.); NEB4: 50 mM potassium acetate, 20 mM Tris-acetate, 10 mM magnesium acetate, 1 mM dithiothreitol (pH 7.9 at 25° C.).
***The compositions of NEB diluents follow. (Using diluents in the dilution instead of water will keep the glycerol concentration in the reaction as a constant.) Diluent A: 50 mM KCl, 10 mM Tris-HCl, 0.1 mM EDTA, 1 mM dithiothreitol, 200 mg/ml BSA, 50% glycerol (pH 7.4 at 25° C.); Diluent B: 300 mM NaCl, 10 mM Tris-HCl, 0.1 mM EDTA, 1 mM dithiothreitol, 500 mg/ml BSA, 50% glycerol (pH 7.4 at 25° C.); Diluent C: 250 mM NaCl, 10 mM Tris-HCl, 0.1 mM EDTA, 1 mM dithiothreitol, 0.15% Triton X-100, 200 mg/ml BSA, 50% glycerol (pH 7.4 at 25° C.).

2. Construction of High Expression Host Cell Strains

It is convenient if a host cell is capable of over-expressing the mutant restriction endonuclease for which reduced star activity is sought. If the restriction enzyme is highly expressed in E. coli, the star activity can be readily detected in the crude extract, which simplifies the screening for the high fidelity restriction endonuclease. However, the mutated restriction endonuclease can be expressed in any host cell providing that the host cell is protected in some way from toxicity arising from enzyme cleavage. This might include: the presence of a methylase; production in a compartment of the cell which provides a barrier to access to the genome (such as an inclusion body or the periplasm); in vitro synthesis; production in an emulsion (see U.S. patent application Ser. No. 12/035,872) absence of cleavage sites in the host genome; manufacture of the enzyme in component parts subject to intein mediated ligation (see U.S. Pat. No. 6,849,428), etc.

Over-expression of the mutated restriction endonucleases for purposes of production can be achieved using standard techniques of cloning, for example, use of an E. coli host, insertion of the endonuclease into a pUC19-derived expression vector, which is a high copy, and use of a relatively small plasmid that is capable of constant expression of recombinant protein. The vector may preferably contain a suitable promoter such as the lac promoter and a multicopy insertion site placed adjacent to the promoter. Alternatively, a promoter can be selected that requires IPTG induction of gene expression. If the activity in the crude extract is not sufficient, a column purification step for the restriction endonuclease in crude extract may be performed.

3. Mutagenesis of Restriction Endonuclease

DNA encoding each charged or polar group in the restriction endonuclease may be individually targeted and the mutated DNA cloned and prepared for testing. Multiple mutations may be introduced into individual restriction endonuclease genes. Targeted mutagenesis of restriction endonucleases may be achieved by any method known in the art. A convenient method used here is inverse PCR. In this approach, a pair of complementary primers that contains the targeted codon plus a plurality of nucleotides (for Example 18 nt) on both the 5' and 3' side of the codon is synthesized. The selection of suitable primers can be readily achieved by reviewing the gene sequence of the endonuclease of interest around the amino acid residue of interest. Access to gene sequences is provided through REBASE and GenBank. The sequences for the endonucleases described herein in the Examples are provided in FIGS. 31 to 38 and 44. The template for PCR is a plasmid containing the restriction endonuclease gene. The polymerase is preferably a high fidelity polymerase such as Vent® or Deep Vent™ DNA polymerase. By varying the annealing temperature and $Mg^{2+}$ concentration, successful introduction of most mutations can be achieved. The PCR amplification product is then purified and preferably digested by DpnI. In an embodiment of the invention, the digested product was transformed into competent host cells (for example, *E. coli*), which have been pre-modified with a corresponding methylase. Colonies from each mutant were picked and grown under similar conditions to those in which the WT is grown (for example, using similar growth medium, drug selection, and temperature). The resulting restriction endonucleases were screened for reduced star activity.

4. Screening for Mutant Restriction Endonucleases with Reduced Star Activity

Conditions such as buffer composition, temperature and diluent should be defined for determining star activity in a mutant restriction endonuclease. Tables 2 and 3 show the FI of recombinant endonucleases before and after mutation in four different buffers using three different diluents at 37° C. Accordingly, it is possible to determine which mutants have an overall desirable improved fidelity index factor of at least 2, more than 10, at least 50 or more than 500 and to select enzymes as preferred high fidelity mutants.

In an embodiment of the invention, the mutant restriction endonucleases were screened for activity in normal buffer conditions (no more than 5% glycerol) first. For those mutants with at least about 10% of activity of WT restriction endonuclease, activity was also determined in star activity promotion conditions that promoted star activity, for example, high glycerol concentration and optionally high pH. Preferably, the mutant with the least star activity but with acceptable cognate activity in normal buffers is selected. Plasmid can then be extracted and sequenced for the confirmation of the mutant. In some cases, the star activity is not easily measured, even with high glycerol and high pH conditions. Instead, the activity in different buffers is measured and compared, and the one with the highest cleavage activity ratio in NEB4 compared with NEB3 can be tested further for star activity improvement.

5. Saturation Mutagenesis on One Single Residue

As described in the previous section, the first step is to mutate a target amino acid in the restriction endonuclease to Ala. If the results are not satisfactory, saturation mutagenesis is performed. This is preferably performed by one of two methods. One method is to change the intended codon into NNN. After mutagenesis, multiple colonies are assayed under normal conditions and under conditions that promote star activity. Alternatively, a different codon can be selected for mutagenesis of each of the targeted amino acids for example: Ala: GCT; Cys: TGC; Asp: GAC; Glu: GAA; His: CAC; Ile: ATC; Lys: AAA; Leu: CTG; Met: ATG; Asn: AAC; Pro: CCG; Gln: CAG; Arg: CGT; Ser: TCC; Thr: ACC; Val: GTT; Trp: TGG and Tyr: TAC 6. Combination More than one mutation can be introduced into the restriction endonuclease gene if a single mutation does not sufficiently reduce the star activity. Mutation combination and saturation mutagenesis can be performed in any order.

7. Mutant Purification and Assessment of the Improvement

The high fidelity mutants may be purified in a variety of ways including use of different chromatography columns. For normal quality assessment, one FPLC heparin column is enough to eliminate the DNA and non-specific nucleases from the preparation. Multiple columns including ion exchange, hydrophobic, size exclusion and affinity columns can be used for further purification.

Purified high fidelity restriction endonucleases are measured for FI in four NEB buffers and compared with the FIs of the WT restriction endonuclease. The ratio of FI for the high fidelity restriction endonuclease in its optimal buffer to that of WT is the overall improvement factor.

\* The FI is a ratio of the highest concentration that does not show star activity to the lowest concentration that completes digestion of the substrate.

\*\* The number in parenthesis is a value for relative cleavage activity of the mutant restriction endonuclease in a specified buffer in a set of buffers compared with the greatest cleavage activity of the same mutant restriction endonuclease in any of the buffers in the set of buffers.

TABLE 3

FI* for exemplified restriction endonucleases

| Enzyme | Diluent (NEB) | Substrate* | Temp °C. | FI-1*** | FI-2** | FI-3** | FI-4** |
|---|---|---|---|---|---|---|---|
| AgeI-HF | C | pXba | 37 | ≥500 (1) | ≥250 (½) | ≥16 (1/16) | ≥250 (1) |
| AvrII-HF | B | T7 | 37 | 500 (1) | ≥500 (½) | ≥16 (1/64) | ≥1000 (1) |
| BamHI-HF | A | λ | 37 | ≥4000 (1) | ≥4000 (1) | ≥250 (1/16) | ≥4000 (1) |
| BsaI | B | pBC4 | 50 | ≥4000 (½) | ≥8000 (1) | 120 (1) | ≥8000 (1) |
| BsmBI | B | λ | 55 | 2 (1) | ≥500 (1) | ≥64 (⅛) | ≥500 (1) |
| BspQI-HF | A | pUC19 | 50 | ≥1000 (¼) | ≥1000 (¼) | ≥64 (1/64) | ≥4000 (1) |
| BstXI-HF | A | λ | 55 | ≥120 (½) | ≥250 (1) | ≥16 (1/16) | ≥250 (1) |
| EagI-HF | C | pXba | 37 | 250 (½) | 250 (1) | 250 (½) | 500 (1) |
| EcoRI-HF | C | λ | 37 | 2000 (⅛) | 4000 (¼) | 250 (1/250) | 16000 (1) |
| EcoRV-HF | A | pXba | 37 | ≥16000 (¼) | ≥64000 (1) | ≥32000 (½) | ≥64000 (1) |
| HindIII-HF | B | λ | 37 | ≥16000 (¼) | ≥64000 (1) | ≥16000 (¼) | ≥32000 (½) |
| HpaI-HF | A | λ | 37 | ≥32 (1/32) | ≥2000 (1) | 2 (⅛) | ≥2000 (1) |
| KpnI-HF | A | pXba | 37 | ≥4000 (1) | ≥1000 (¼) | ≥64 (1/64) | ≥4000 (1) |
| MfeI-HF | A | λ | 37 | ≥1000 (1) | ≥250 (¼) | ≥16 (1/64) | ≥500 (½) |
| NcoI-HF | A | λ | 37 | ≥4000 (¼) | ≥4000 (¼) | ≥1000 (1/16) | ≥64000 (1) |
| NheI-HF | C | pXba | 37 | ≥128000 (1) | ≥4000 (1/32) | ≥32 (1/2000) | ≥32000 (½) |
| NotI-HF | C | pXba | 37 | ≥8000 (1/16) | ≥128000 (1) | ≥4000 (1/64) | ≥64000 (½) |
| PciI-HF | A | pXba | 37 | NC | ≥2000 (1) | ≥2000 (1) | ≥1000 (1) |
| PstI-HF | C | λ | 37 | 1000 (⅛) | 4000 (½) | 4000 (¼) | 4000 (1) |
| PvuII-HF | A | pBR322 | 37 | ≥250 (1/120) | ≥2000 (1/16) | ≥250 (1/120) | 500 (1) |
| SacI-HF | A | pXba | 37 | ≥32000 (1) | ≥16000 (½) | ≥500 (1/64) | ≥32000 (1) |
| SalI-HF | A | λ (H3) | 37 | ≥8000 (⅛) | ≥64000 (1) | ≥4000 (1/16) | ≥32000 (½) |
| SbfI-HF | C | λ | 37 | 1000 (1) | 120 (½) | 8 (1/32) | 250 (1) |

TABLE 3-continued

FI* for exemplified restriction endonucleases

| Enzyme | Diluent (NEB) | Sub-strate* | Temp °C. | FI-1*** | FI-2** | FI-3** | FI-4** |
| --- | --- | --- | --- | --- | --- | --- | --- |
| ScaI-HF | A | λ | 37 | 4000 (⅛) | 1000 (1) | 2000 (1/32) | 1000 (1) |
| SphI-HF | B | λ | 37 | 4000 (⅛) | 2000 (1/16) | 250 (1/250) | 8000 (1) |
| SspI-HF | C | λ | 37 | ≥4000 (½) | 120 (½) | ≥32 (1/128) | 500 (1) |

TABLE 4

Mutations providing restriction endonucleases with high fidelity

| Restriction Endonuclease | Examples of mutants with overall improved FI factor ≥ 2 |
| --- | --- |
| AgeI | R139A; S201A* |
| AvrII | Y104F; M29A; E96A; K106A; S127A; F142A |
| BamHI | E163A/E167T; K30A; E86A; E86P; K87A; K87E; K87V; K87N; P144A; Y165F; E167A; E167R; E167K; E167L; E167I K30A/E86A; E86A/K106A; K30A/E86A/K106A; K30A/K87A; E86P/K87E; E86A/Y165F; K30A/E167A; E163S/E170T/P173A; E163S/E170T/P173A; E86P/K87T/K88N/ E163S/E170T/P173A; E86P/K87R/K88G/E163S/E170T/P173A;E86P/K87P/K88R/ E163S/E170T/P173A/E211K; E86P/K87T/K88R/ E163S/E170T/P173A/N158S; E86P/K87S/K88P/ E163S/E170T/P173A; E86P/K87G/K88S/ E163S/E170T/P173A; E86P/K87R/K88Q/ E163S/E170T/P173A; E86P/K87W/K88V; E86P/P173A |
| BsaI | Y231F |
| BsmBI | N185Y/R232A; H230A; D231A; R232A; |
| BspQI | K279P/R388F; K279A; K279F; K279P; K279Y; K279E; K279D R388A; R388F; R388Y; R388L; K279P/R388F; K279A/R388A; D244A |
| BstXI | N65A; Y57F; E75A; N76A; K199A; |
| EagI | H43A |
| EcoRI | K62A; K62S; K62L; R9A; K15A; R123A; K130A; R131A; R183A; S2Y; D135A; R187A; K62E |
| EcoRV | D19A; E27A; D19A/E27A |
| HindIII | S188P/E190A; K198A |
| HpaI | Y29F; E56A |
| KpnI | D148E; D16N/R119A/D148E; D2A/D16N/D148E; D16N/E134A/D148E; D16N/E132A/D148E |
| MfeI | Y173F; Q13A/F35Y |
| NcoI | D56A; H143A; E166A; R212A; D268A; A2T/R31A |
| NheI | E77A |
| NotI | K176A; R177A; R253A; K150A |
| PciI | E78A/S133A |
| PstI | E204G; K228A; K228A/A289V; D91A |
| PvuII | T46A; T46H; T46K; T46Y; T46G |
| SacI | Q117H/R154A/L284P; Q117H/R200A |
| SalI | R82A; K93A; K101A; R107A |
| SapI | K273P; R380A; K273P/R380A |
| SbfI | K251A |
| ScaI | R18A; R112A; E119A; H193A; S201F; H193A/S201F |
| SphI | D91A; D139A; D164A; K100A |
| SspI | H65A; K74A; E78A; E85A; E89A; K109A; E118A; R177A; K197A; Y98F |

The mutations for each enzyme are separated by a semicolon.

All references cited above and below, as well as U.S. provisional application Ser. No. 60/959,203, are incorporated by reference.

EXAMPLES

Where amino acids are referred to by a single letter code, this is intended to be standard nomenclature. The key to the code is provided for example in the NEB catalog 2007/2008 on page 280.

Plasmids used for cloning and as substrates have sequences as follows:

pLaczz2 (SEQ ID NO:102), pSyx20-lacIq (SEQ ID NO:105), pBC4 (SEQ ID NO:103), pXba (SEQ ID. NO:104) and pAGR3 (SEQ ID NO: 106). pACYC is described in GenBank XO 6403, T7 in GenBank NC001604, pUC18 in GenBank L09136, and pRRS in Skoglund et al. *Gene,* 88:1-5 (1990. pSX33 was constructed by inserting lacI gene into pLG339 at EcoRI site. pLG339 is described in Stoker, et al. *Gene* 19, 335-341 (1982).

All buffers identified as NEB buffers used herein are obtainable from New England Biolabs, Inc. (NEB), Ipswich, MA.

Example 1: Engineering of High Fidelity BamHI

1. Extraction of Plasmids Containing BamHI Methylase and BamHI Endonuclease

Competent *E. coli* host cells were transformed with pUC18-BamHIR and pACYC184-BamHIM and BamHIR was extracted by a standard Qiagen Mini-prep method using standard miniprep techniques (Qiagen, Valencia, CA).

2. Selection of Mutagenesis Target

BamHI and related restriction endonuclease OkrAI were cloned and sequenced. OkrAI was found to have significant star activity if the reaction occurred at 37° C. in NEB buffers (1, 2 and 4). The present analysis tested the assumption that the amino acid residue(s) responsible for the star activity were similar between BamHI and OkrAI endonuclease.

The complete protein sequence of BamHI (SEQ ID NO:19) is:

1  MEVEKEFITD EAKELLSKDK LIQQAYNEVK TSICSPIWPA TSKTFTINNT

51  EKNCNGVVPI KELCYTLLED TYNWYREKPL DILKLEKKKG GPIDVYKEFI

101  ENSELKRVGM EFETGNISSA HRSMNKLLLG LKHGEIDLAI ILMPIKQLAY

151  YLTDRVTNFE ELEPYFELTE GQPFIFIGFN AEAYNSNVPL IPKGSDGMSK

201  RSIKKWKDKV ENK

The complete protein sequence of OkrAI (SEQ ID NO:20) is:

1  MKIKRIEVLI NNGSVPGIPM ILNEIQDAIK TVSWPEGNNS FVINPVRKGN

51  GVKPIKNSCM RHLHQKGWAL EHPVRIKAEM RPGPLDAVKM IGGKAFALEW

101  ETGNISSSHR AINKMVMGML ERVIIGGVLI LPSRDMYNYL TDRVGNFREL

151  EPYFSVWRQF NLKDAYLAIV EIEHDSVDAQ VSLIPKGTDG RAIR

A "Bestfit" similarity analysis done by GCG for the protein sequence of BamHI and OkrAI endonuclease showed the following result where the upper protein sequence is BamHI and the bottom protein sequence is OkrAI:

```
bamhir.pep x okrair.pep
         .         .         .         .         .
 22 IQQAYNEVKTSICSPIWPATSKTFTINNTEKNCNGVVPIKELCYTLLEDT  71
    |  ||:. .T -  ||  ..|  ||   |   |||  ||T |    -
 18 IPMILNEIQDAIKTVSWPEGNNSFVINPVRKG.NGVKPIKNSCMRHLHQK  66

.         .         .         .         .
 72 YNWYREKPLDILKLEKKKGGPIDVYKEFIENSELKRVGMEFETGNISSAH  121
    |   | |.-| | |   : T|:|   | -|   |   :|.|T|||||T.T
 67 .GWALEHPVRI.KAEMRP.GPLDAVK.MIGG...KAFALEWETGNISSSH  109

.         .         .         .         .
122 RSMNKLLLGLKHGEIDLAIILMPIKQLAYYLTDRVTNFEELEPYFEL...  168
    |..T|:.-|:   |  : ::::|  : : ||T|| ||  |TT||| .--
110 RAINKMVMGMLERVIIGGVLILPSRDMYNYLTDRVGNFRELEPYFSVWRQ  159

.         .       .
169 ..TEGQPFIFIGFNAEAYNSNVPLIPKGSDGMSKR                 201 (SEQ ID NO: 21)
      .    :  :. ..|  |||||.||-. T
160 FNLKDAYLAIVEIEHDSVDAQVSLIPKGTDGRAIR                 194 (SEQ ID NO: 22)
```

The similar charged residues (D, E, H, K, R) in BamHI were found to be E28, K30, K52, K61, E77, K84, E86, K88, D94, K97, K106, E111, E113, H121, R122, K126, K146, D154, R155, E161, E163, E170, E182, K193, D196 and R201. These residues are underlined in the above comparison. Known mutants E77K, D94N, E111K and E113K were previously reported to be inactive (Xu, Shuang-yong et al. *J. Bacteriol.* 266: 4425-4429 (1991)) so they were excluded. The initial mutagenesis selection targeted 22 shared charged amino acid residue for mutation to Alanine: E28A, K30A, K52A, K61A, K84A, E86A, K88A, K97A, K106A, H121A, R122A, K126A, K146A, D154A, R155A, E161A, E163A, E170A, E182A, K193A, D196A and R201A.

3. Mutagenesis of BamHI

The point mutagenesis of the selected mutations was done by inverse PCR. The corresponding codons were all changed to GCA (alanine). The following primers were used for mutagenesis:

E28A
(SEQ ID NO: 23)
5'ATTCAACAAGCATACAATGCAGTTAAAACATCTATTGT3'

(SEQ ID NO: 24)
5'ACAAATAGATGTTTTAACTGCATTGTATGCTTGTTGAAT3'

K30A
(SEQ ID NO: 25)
5'CAAGCATACAATGAAGTTGCAACATCTATTTGTTCACCT3'

(SEQ ID NO: 26)
5'AGGTGAACAAATAGATGTTGCAACTTCATTGTATGCTTG3'

K52A
(SEQ ID NO: 27)
5'ACGATTAACAACACCGAAGCAAATTGTAACGGTGTAGTA3'

(SEQ ID NO: 28)
5'TACTACACCGTTACAATTTGCTTCGGTGTTGTTAATCGT3'

K61A
(SEQ ID NO: 29)
5'AACGGTGTAGTACCAATTGCAGAACTATGTTACACCTTA3'

(SEQ ID NO: 30)
5'TAAGGTGTAACATAGTTCTGCAATTGGTACTACACCGTT3'

K84A
(SEQ ID NO: 31)
5'AACCCCCTTGATATACTTGCACTTGAAAAGAAAAAGGT3'

(SEQ ID NO: 32)
5'ACCTTTTTTCTTTTCAAGTGCAAGTATATCAAGGGGTTT3'

E86A
(SEQ ID NO: 33)
5'GATATACTTAAACTTGCAAAGAAAAAAGGTGGTCCG3'

(SEQ ID NO: 34)
5'CGGACCACCTTTTTTCTTTGCAAGTTTAAGTATATCAAG3'

K88A
(SEQ ID NO: 35)
5'ATACTTAAACTTGAAAAGGCAAAAGGTGGTCCGATTGAT3'

(SEQ ID NO: 36)
5'ATCAATCGGACCACCTTTTGCCTTTTTCAAGTTTAAGTAT3'

K97A
(SEQ ID NO: 37)
5'GGTCCGATTGATGTTTATGCAGAGTTCATAGAAAACAGT3'

(SEQ ID NO: 38)
5'ACTGTTTTCTATGAACTCTGCATAAACATCAATCGGACC3'

K106A
(SEQ ID NO: 39)
5'ATAGAAAACAGTGAACTTGCACGTGTAGGTATGGAA3'

(SEQ ID NO: 40)
5'AAATTCCATACCTACACGTGCAAGTTCACTGTTTTCTAT3'

H121A
(SEQ ID NO: 41)
5'GGAAATATTAGTTCTGCCGCACGTTCAATGAACAAACTT3'

(SEQ ID NO: 42)
5'AAGTTTGTTCATTGAAACGTGCGGCAGAACTAATATTCC3'

R122A
(SEQ ID NO: 43)
5'AATATTAGTTCTGCCCACGCATCAATGAACAAACTTCTA3'

(SEQ ID NO: 44)
5'TAGAAGTTTGTTCATTGATGCGTGGGCAGAACTAATATT3'

K126A
(SEQ ID NO: 45)
5'GCCCACCGTTCAATGAACGCACTTCTATTAGGATTAAAACAT3'

(SEQ ID NO: 46)
5'ATGTTTTAATCCTAATAGAAGTGCGTTCATTGAACGGTGGGC3'

K146A
(SEQ ID NO: 47)
5'ATTATCCTTATGCCTATTGCACAATTGGCCTATTATCTT3'

(SEQ ID NO: 48)
5'AAGATAATAGGCCAATTGTGCAATAGGCATAAGGATAAT3'

D154A

-continued (SEQ ID NO: 49)
5'TTGGCCTATTATCTTACAGCACGTGTTACCAATTTCGAG3'

(SEQ ID NO: 50)
5'CTCGAAATTGGTAACACGTGCTGTAAGATAATAGGCCAA3'

R155A (SEQ ID NO: 51)
5'GCCTATTATCTTACAGATGCAGTTACCAATTTCGAGGAA3'

(SEQ ID NO: 52)
5'TTCCTCGAAATTGGTAACTGCATCTGTAAGATAATAGGC3'

E161A (SEQ ID NO: 53)
5'CGTGTTACCAATTTCGAGGCATTAGAACCTTATTTTGAA3'

(SEQ ID NO: 54)
5'TTCAAAATAAGGTTCTAATGCCTCGAAATTGGTAACACG3'

E163A (SEQ ID NO: 55)
5'ACCAATTTCGAGGAATTAGCACCTTATTTTGAACTTACT3'

(SEQ ID NO: 56)
5'AGTAAGTTCAAAATAAGGTGCTAATTCCTCGAAATTGGT3'

E170A (SEQ ID NO: 57)
5'CCTTATTTTGAACTTACTGCAGGACAACCATTTATTTTTATT3'

(SEQ ID NO: 58)
5'AATAAAAATAAATGGTTGTGCTGCAGTAAGTTCAAAATAAGG3'

E182A (SEQ ID NO: 59)
5'TTTATTTTTATTGGATTTAATGCTGCAGCTTATAATTCTAATGTC3'

(SEQ ID NO: 60)
5'GACATTAGAATTATAAGCTGCAGCATTAAATCCAATAAAAATAAA3'

K193A (SEQ ID NO: 61)
5'AATGTCCCTTTAATTCCCGCAGGTTCTGACGGTATGTCA3'

(SEQ ID NO: 62)
5'TGACATACCGTCAGAACCTGCGGGAATTAAAGGGACATT3'

D196A (SEQ ID NO: 63)
5'TTAATTCCCAAAGGTTCTGCAGGTATGTCAAAACGCTCA3'

(SEQ ID NO: 64)
5'TGAGCGTTTTGACATACCTGCAGAACCTTTGGGAATTAA3'

R201A (SEQ ID NO: 65)
5'TCTGACGGTATGTCAAAAGCATCAATTAAGAAATGGAAA3'

(SEQ ID NO: 66)
5'TTTCCATTTCTTAATTGATGCTTTTGACATACCGTCAGA3'

The PCR reaction in a reaction volume of 100 µl, contained 2 µl of each PCR primer, 1 µl pUC18-bamhiR, 400 µM dNTP, 4 units of Deep Vent™ DNA polymerase, and 10 µl 10×Thermopol buffer containing 0, 2, or 6 µl MgSO4 with additional water.

The PCR reaction conditions were 94° C. for 5 min, followed by 25 cycles of 94° C. 30 sec, 55° C. 30 sec, 72° C. 4 min and a final extension time at 72° C. for 7 mins. The PCR product was purified on a standard Qiagen spin column (Qiagen, Valencia, CA). Six to sixteen µl of PCR product was digested by 20 units of DpnI for 1 hour. The digested product was transformed into *E. coli* (pACYC-bamHIM).

After six PCR reactions, 14 out of the engineered 22 mutations were obtained: E28A, K30A, K61A, E86A, K97A, H121A, K126A, K146A, E161A, E163A, E170A, E182A, and R201A. Mutant proteins were extracted from cell lysates in an overnight culture and the activity was compared to WT BamHI. Normal enzyme activity was assayed in NEB2 buffer with or without 5% glycerol, while star activity was determined in NEB2 with 39.2% glycerol, though initially, lower percentage glycerol could be used. The substrate used for different reactions was pBR322, pUC19 or lambda DNA. The cleavage reaction was performed at 37° C. for 30 min or 1 hour. It was found that mutants K97A, H121A, K126A, E161A, E182A, R201A were inactive (less than 1% of 10 the WT BamHI activity) while E28A, K146A, E163A, E170A mutants had a similar level of activity including star activity to that of WT enzyme. Three mutants K30A, E86A and K126A were found to have significantly reduced star activity compared with WT BamHI. It was also found that K30A and E86A had similar overall cleavage activity to the WT enzyme while showing significant reduction in star activity. In contrast, K126A had only 25% of the overall cleavage activity of the WT enzyme and less significant improvement on star activity than observed for K30A an E86A.

A recheck on the pUC18-bamHIR plasmid revealed that the normal high copy plasmid had mutated to a low copy plasmid. A pair of primers was designed to transfer the bamHIR gene into the high copy plasmid:

(SEQ ID NO: 67)
5'GGTGGTGCATGCGGAGGTAAATAAATGGAAGTAGAAAAAGAGTTTATTACTGAT3'

(SEQ ID NO: 68)
5'GGTGGTGGTACCCTATTTGTTTTCAACTTTATCTTTCCATTTCTTAATTGA3'

The template was pUC18-bamhiR WT, with mutations at K30A, E86A or K126A. The PCR composition contained: 5 µl template, 2 µl primers each, 400 µM dNTP, 10 µl 10× Thermopol buffer, 4 units 2 µl Deep Vent™ polymerase, 72 µl H2O with 0, 2, 6 µl MgSO4. The PCR conditions were 94° C. for 5 min, followed by 25 cycles of 94° C. at 30 sec, 55° C. at 30 sec and 72° C. at 40 sec and a final extension period of 7 min. The PCR product was digested with SphI and KpnI and was ligated to pUC19 with the same pair of enzyme digestion. The ligated product was transformed into competent *E. coli*-containing pACYC-bamHIM. 26 colonies that contained the pUC19 version of BamHIR K30A and 12 of those that contained E86A were identified and grown. The activity of BamHI from these cultures was checked. All of them were active. Plasmids from five colonies of each mutation were extracted and the BamHIR plasmids from three of each mutation were sequenced. The identity of plasmids pUC19-BamHI(K30A) and pUC19-BamHI (E86A) were confirmed.

Those mutations that were unsuccessful in pUC18-BamHIR were repeated using the pUC19-BamHI(K30A) vector. The PCR mixture contained: 1 µl template and an amplification mixture containing 2 µl primers each, 400 µM dNTP, 10 µl 10×Thermopol buffer, 4 units 2 µl Deep Vent™ polymerase, 76 µl H2O with 0, 2, 6 µl 100 µM MgSO4. The PCR condition was 94° C. for 5 min, followed by 25 cycles of 94° C. for 30 sec, 55° C. for 30 sec and 72° C. for 3 min and 30 sec and a final extension period of 7 min. The PCR products were digested by DpnI and transformed to competent *E. coli* transformed with pACYC-BamHIM. The enzyme activities were checked on pUC19 substrate. The reaction composition was: 3 µl cell extract, 3 µl NEB2, 3 µl 50% glycerol, 0.5 µl 0.5 µg pUC19, 20.5 µl H2O. Reaction was at 37° C. for 1 hour. K30A/R122A, K30A/R155A and K30A/K193A were inactive. K30A/K52A and K30A/K88A were about ⅒ of the K30A activity. The normal activity of K30A/K106A, K30A/D154A and K30A/D196A were similar to that of K30A BamHI. The comparison of star activity of these three mutants with K30A at the high concentration glycerol (39.2%) showed that K30A/D196A had similar star activity as K30A, K30A/D154A even has more star activity than K30A, and K30A/K106A had less star activity than K30A. Attempts to isolate the K106A mutation of BamHI in the pUC19 vector failed because of cytotoxicity.

The mutation on the K30, E86 and K106 sites was combined using the inverse PCR: K30A/E86A, E86A/K106A, K30A/K106A and K30A/E86A/K106A. K30A/E86A appeared to be the preferred mutant. After purification, the FI was found to be improved for the BamHI mutant by 25% in all NEB buffers.

Further mutagenesis was done on the site of K30 and E86 randomly: For K30:

```
For K30:
                                    (SEQ ID NO: 69)
5'CAAGCATACAATGAAGTTNNNACATCTATTTGTTCACCT3'

(SEQ ID NO: 70)
5'AGGTGAACAAATAGATGTNNNAACTTCATTGTATGCTTG3'

For E86:
                                    (SEQ ID NO: 71)
5'GATATACTTAAACTTNNNAAGAAAAAAAGGTGGTCCG3'

(SEQ ID NO: 72)
5'CGGACCACCTTTTTTCTTNNNAAGTTTAAGTATATCAAG3'
```

The PCR composition was: 1 µl template (pUC19-BamHIR(K30A) or pUC19-BamHIR(E86A)) and the amplification mixture as described above was used. The PCR was performed at 94° C. 5 min, followed by 25 cycles of 94° C. 30 sec, 55° C. 30 sec and 72° C. 3 min and 30 sec and a final extension period of 7 min. The PCR products were digested by DpnI and transformed into *E. coli* (pACYC-BamHIM).

Total of 155 colonies were picked on K30 random mutations, and 158 colonies on E86 site. The colonies were grown overnight and made into cell extract. 0.5 µg pUC19 was digested with 1 µl cell extract in NEB 2 buffer with 42.5% glycerol, 37° C. 1 hour. The cell extract with apparent less star activity was re-assayed under 1, 4, 16 fold dilution on 0.5 µg pUC19 in NEB 2 buffer with 39.2% glycerol, 37° C. 30 min. For those mutants observed to have reduced star activity, the corresponding plasmids were extracted and sequenced to confirm the mutation. A total of 3 clones (#12, #66 and #82) contained the K30 mutation, and a total of 33 clones (#5, #15, #16, #19, #29, #47, #51, #55, #56, #58, #61, #69, #71, #73, #76, #82, #86, #88, #93, #94, #97, #98, #100, #104, #107, #113, #117, #118, #129, #132, #136, #139 and #151) were sequenced. After sequencing, #12 and #66 were found to contain the K30G mutation, and #82 the K30N mutation. Surprisingly, all 33 mutations are E86P mutation, just in different codons (CCA, CCT, CCC, CCG). Among these codons, the CCG occurred at the highest frequency in *E. coli* (clones #98, #136 and #139).

The cell extracts corresponding to K30G, K30N and K30A were serially diluted as 1, 2, 4, 8, 16 and 32 folds, while E86P and E86A were serially diluted 1, 2, 4, 8, 16, 32, 64, 128 and 256 fold. The serially diluted extracts were reacted with 0.5 µg pUC19 in NEB2 with 39.2% glycerol, 37° C. 30 min. Under extreme conditions, E86P appeared to be much superior to other mutants. At up to 32 times fold digestion, there was no significant star activity band. The difference between E86P and the K30 mutants (K30G, K30N and K30A) was so large that it was not additionally necessary to combine any of these mutations in the E86P mutant.

The activity of BamHI(E86P) was determined for 1 µg lambda DNA, substrate (also used for WT BamHI activity determination). The assay was performed in NEB1 buffer at 37° C. for 1 hour.

4. Detailed Comparison of BamHI(E86P) and WT BamHI

A. The Activity of BamHI(E86P) in Different NEB Buffers

The activity of purified BamHI(E86P) was determined in NEB1, NEB2, NEB3, NEB4 and NEB BamHI buffer, using lambda DNA substrate at 37° C. for 1 hour. BamHI(E86P) was most active in NEB1 buffer and NEB2, while having 50%, 50% and 25% activity levels in NEB3, NEB4, and BamHI buffer.

B. A Comparison of Cleavage Activity of BamHI(E86P) and WT BamHI on pUC19

There is one GGATCC site (BamHI site) and 6 AGATCC sites (BamHI star activity site) in pUC19 so that pUC19 was selected as a preferred substrate for comparison of the BamHI(E86P) and WT BamHI.

0.5 mg pUC19 was digested by WT BamHI and BamHI (E86P) in a serial dilution of 1, 3, 9, 27, 81, 243, 729, 2181, 6561, and 19683 folds with NEB dilution buffer A, in different buffers. WT BamHI showed star activity in every NEB normal buffer, while BamHI(E86P) showed no star activity bands at all (FIGS. 2-5). This demonstrated that BamHI(E86P) had greatly reduced star activity while retaining the cognate cleavage activity.

C. A Comparison of Cleavage Activity of BamHI(E86P) and WT BamHI on Lambda DNA Substrate To calculate the Fidelity Index, the restriction enzyme was diluted with dilution buffer, and the glycerol concentration was kept constantly at 5%. In the standard reaction condition used here, lambda DNA substrate concentration was 1 µg and the total reaction volume was 50 µl. In order to keep the enzyme volume at 10%, the enzyme was added in a volume of 5 µl. This is equivalent to 0.6 µg of substrate digested by 3 µl of restriction enzyme in a total volume of 30 µl. 0.6 mg lambda DNA was digested by 3 µl WT BamHI and BamHI (E86P) in a 1:2 serial dilution from 1 to 32768, in NEB1, NEB2, NEB3, NEB4 and NEB BamHI buffer at 37° C. for 1 hour.

TABLE 5

Fidelity Indices for WT and mutant BamHI in various buffers

| Buffer | BamHI(E86P) | | WT BamHI | | |
|---|---|---|---|---|---|
| | Activity | Fidelity Index | Activity | Fidelity Index | Improvement Factor |
| NEB1 | 100% | ≥4000 | 50% | 4 | ≥1000 |
| NEB2 | 100% | ≥4000 | 100% | 16 | ≥250 |
| NEB3 | 50% | ≥4000 | 100% | 32 | ≥125 |
| NEB4 | 50% | ≥4000 | 50% | 4 | ≥1000 |
| BamHI buffer | 25% | ≥2000 | 50% | 32 | ≥125 |

5. Further Improvement of BamHI for High Fidelity Mutants

At one hour level, the BamHI(E86P) appeared to be a good high fidelity BamHI mutant. However, when the reaction time was extended (e.g. overnight, or 14 hours), star activity bands appeared even though the star activity of E86P was not detected at one hour. (FIG. 3) The search for improved high fidelity BamHI was continued.

6. Mutations of Other Charged and Polar Residues

The other charged residues (Arg, Lys, His, Asp, Glu) were mutated to Ala at the positions of 2, 4, 5, 6, 10, 11, 13, 14, 18, 19, 20, 43, 51, 62, 69, 70, 76, 77, 78, 81, 87, 89, 94, 98, 101, 104, 107, 111, 113, 132, 133, 135, 137, 160, 167, 200, 204, 205, 207, 208, 209, 211, 213 in SEQ ID NO:19. The mutations were done on the template of pUC19-BamHI (K30A).

Other polar residues (Ser, Thr and Tyr) were mutated to Ala while Tyr was mutated to Phe at the positions of 9, 17, 26, 32, 36, 41, 42, 44, 46, 50, 65, 66, 71, 72, 75, 96, 103, 114, 118, 119, 123, 150, 151, 153, 157, 165, 169, 184, 186, 195, 199, 202 in SEQ ID NO: 19.

By using similar mutation and screen methods, the following mutations were discovered to have reduced star activity, K30A/K87A, E86P/K87E, E86A/Y165F, and K30A/E167A. E86P/K87E was identified as a mutant with improved properties in the presence of additional DMSO. However, the activity of this mutant in normal reaction buffer was much lower than that of WT BamHI.

The following combination of mutations was made: E86P/Y165F, E86P/E167A, E86P/Y165F/E167A, K30A/Y165F/E167A, K30G/Y165F/E167A, K30A/Y165F/E167A, E86A/Y165F/E167A. All had low activity.

Up to this point, it was found that E167A and Y165F had a strong effect, K87A had medium effect, and K30A and E86A had weak effect on the BamHI star activity. E86P is a special mutation that reduces star activity at 1 hour level but not overnight.

7. Mutation of E167 and Y165 to all Other Residues

E167 was mutated to all other residues in pUC19-BamHI by changing the codon to GCA for Ala, TGC for Cys, GAC for Asp, TTC for Phe, GGT for Gly, CAC for His, ATC for Ile, AAA for Lys, CTG for Leu, ATG for Met, AAC for Asn, CCG for Pro, CAG for Gln, CGT for Arg, TCC for Ser, ACC for Thr, GTT for Val, TGG for Trp, and TAC for Tyr.

After comparison of all the mutants, the E167T mutation was preferred, while E167R, E167K, E167L and E167I mutations showed improvement in reduced star activity compared with E167A.

Y165 was also mutated to all other amino acid residues by changing the corresponding codon to GCT for Ala, TGC for Cys, GAC for Asp, GAA for Glu, GGT for Gly, CAC for His, ATC for Ile, AAA for Lys, CTG for Leu, ATG for Met, AAC for Asn, CCG for Pro, CAG for Gln, CGT for Arg, TCC for Ser, ACC for Thr, GTT for Val, TGG for Trp.

After comparison of all the mutants, the presence of Y165F resulted in significant cleavage activity while other mutations of listed immediately above showed low activity or no cleavage activity.

8. Further Mutations on BamHI(E167T)

All charged and polar residues were mutated to Ala, on the template of puc19-BamHI(E167T), as the same procedure as above.

E163A/E167T as the preferred mutation was identified as BamHI-HF.

9. Comparison of BamHI-HF to WT BamHI

Introduction of a mutation at E163 resulted in reduced thermostability of the BamHI mutant, as did mutation P173A when added to other mutations responsible for reducing star activity.

BamHI-HF, unlike the BamHI(E86P), had no significant star activity in an overnight reaction in NEB1-4 buffers. FIG. 4 shows the results in NEB1 and NEB2. Hence BamHI (E163A/E167T) was selected as the preferred high fidelity BamHI.

The fidelity indices of BamHI-HF were measured in all of the four NEB buffers on lambda DNA substrate, with diluent A, at 37° C. and compared with the WT enzyme.

TABLE 6

Comparison of BamHI-HF and WT BamHI

| Buffer | BamHI-HF Activity | BamHI-HF Fidelity Index | WT BamHI Activity | WT BamHI Fidelity Index | Improvement Factor |
|---|---|---|---|---|---|
| NEB1 | 100% | ≥8000 | 50% | 4 | ≥1000 |
| NEB2 | 50% | ≥4000 | 100% | 16 | ≥250 |
| NEB3 | 12.5% | ≥250 | 100% | 32 | ≥8 |
| NEB4 | 50% | ≥4000 | 50% | 4 | ≥1000 |

BamHI-HF has a highest activity in NEB1, the fidelity index is ≥8000, WT BamHI has the highest activity in NEB2 and NEB3, and the highest FI is 32. The overall FI improvement factor, which is the ratio of the FI in the best buffer for each of the mutant and the WT enzyme, is ≥8000/32=250 fold.

10. Additional Mutations of BamHI

E163A/E167T/P173A was predicted to have a preferred reduction in star activity and additionally to be thermolabile.

(E86P/K87S/K88P/E163S/E170T/P173A) was tested. This mutant displayed 10-fold reduction in specific activity but had a compensating increased yield of protein from host cells.

Other BamHI mutants that shared reduced thermostability, reduced star activity and acceptable specific activity include:

E86P/K87R/K88G/E163S/E170T/P173A

E86P/K87P/K88R/E163S/E170T/P173A/E211K

E86P/K87T/K88R/E163S/E170T/P173A/N158S

E86P/K87S/K88P/E163S/E170T/P173A

E86P/K87G/K88S/E163S/E170T/P173A

E86P/K87R/K88Q/E163S/E170T/P173A

Example 2: Preparation of a High Fidelity EcoRI

1. Expression of EcoRI

PCR on EcoRI used the following primers: IDC-30 DNA

```
                                      (SEQ ID NO: 73)
GGTGGTGCATGCGGAGGTAAATAAATGTCTAATAAAAAACAGTCAAATAG
GCTA
```

```
                                      (SEQ ID NO: 74)
GGTGGTGGTACCTCACTTAGATCTAAGCTGTTCAAACAA
```

The PCR product was then digested with a second pair of restriction endonucleases—SphI and Acc65I, and ligated into the pUC19 digested with the same second pair of restriction endonucleases. The ligated plasmid was then be transformed into competent E. coli premodified with pACYC-MlucIM.

2. Mutagenesis of EcoRI

Initial selection of target amino acid residues resulted from a comparison of EcoRI with its isoschizomer RsrI, which is also known for its star activity.

EcoRI vs. RsrI

```
  4 KKQSNRLTEQHKLSQGVIGIFGDYAKAHDLAVGEVSKLVKKALSNEYPQL  53
    | |. || | .| | : ||| |. |||.: ||. |  |. ::||
 10 KGQALRLGIQQELGGGPLSIFGAAAQKHDLSIREVTAGVLTKLAEDFPNL  59

54 SFRYRDSIKKTEINEALKKIDPDLGGTLFVSNSSIKPDGGIVEVKDDYGE 103
    |. | |: | ||| |: || || |||  ..||:|||||| ||| :|
 60 EFQLRTSLTKKAINEKLRSFDPRLGQALFVESASIRPDGGITEVKDRHGN 109

104 WRVVLVAEAKHQGKDIINIRNGLLVGKRGDQDLMAAGNAIERSHKNISEI 153
    |||:|| |.|||| |: | |.| || ||| |||||||||| |||: |:
110 WRVILVGESKHQGNDVEKILAGVLQGKAKDQDFMAAGNAIERMHKNVLEL 159

154 ANFMLSESHFPYVLFLEGSNFLTENISITRPDGRVVNLEYNSGILNRLDR 203
    |:|| | |||||.||:|||| ||. :|||||||| : :.||.|||:||
160 RNYMLDEKHFPYVVFLQGSNFATESFEVTRPDGRVVKIVHDSGMLNRIDR 209

204 LTAANYGMPINSNLCINKFVNHKDKSIMLQAASIYTQGDGREWDSKIMFE 253
    .||.. || | | | | | |||:| . | .||
210 VTASSLSREINQNYCENIVVRAGSFDHMFQIASLYCK..AAPWTAGEMAE 257

254 IMFDISTTSLRVLGRDL 270 (SEQ ID NO: 75)
    | :. ||||:: ||
258 AMLAVAKTSLRIIADDL 274 (SEQ ID NO: 76)
```

Except for D91, E111 and K113, which were known active center residues, the 42 charged residues were identical or similar in the two endonucleases. The charged residues were as follows:

K4, R9, K15, K29, H31, D32, E37, E49, R56, R58, K63, E68, K71, D74, K89, E96, K98, K99, R105, H114, D118, K130, D133, D135, E144, R145, H147, K148, E152, E160, H162, E170, E177, R183, D185, R200, D202, R203, E253, R264, D269.

All of these charged residues were mutated to Ala (codon GCA, GCT, GCC or GCG) and the mutated genes amplified and cloned as follows:

The amplification mixture was the same as used in Example 1 (2 μl PCR primers each, 400 mM dNTP, 4 units of Deep Vent DNA polymerase, 10 μl 10× Thermopol buffer with additional 0, 2, 6 μl MgSO$_4$, and the total reaction volume was 100 μl) and was added to 1 μl pUC19-EcoRI). The PCR reaction conditions was 94° C. for 5 min, followed by 25 cycles of 94° C. for 30 sec, 55° C. for 30 sec, 72° C. for 3 min and 30 sec and a final extension time at 72° C. for 7 min. After PCR, the product was purified by the standard Qiagen spin column (Qiagen, Valencia, CA). 16 μl PCR product was digested by 20 units of DpnI for 1 hour. The digested product was transformed into a methylase protected competent *E. coli* preparation.

3. Screening EcoRI High Fidelity Mutants

Three colonies each were picked for each mutation and grown in LB with Ampicillin and Chloramphenicol for overnight. The activity assay was performed on pBR322 and lambda DNA to ensure the mutant had at least similar activity to WT EcoRI. Then these mutants were tested using 3 μl of cell extract in 2-fold serial dilution, 12 μl 50% glycerol, 3 μl of NEB1 buffer, 0.5 μl pBR322 and 11.5 μl water, reacted at 37° C. for one hour. However, none of the mutations improved the performance of star activity.

From this result, it was concluded that an effective mutation could not always be recognized as a homologous residue between isoschizomers.

4. Repeat Mutagenesis on the Rest of 32 Charged Residues

All remaining 32 charged residues were mutated into Ala as described in step 2 by targeting amino acid residues 5, 12, 14, 26, 40, 43, 44, 59, 62, 65, 72, 76, 100, 103, 117, 123, 131, 192, 221, 225, 226, 227, 228, 242, 244, 245, 247, 249, 257, 268, 272 and 277.

The numbers above correspond to amino acid positions in the EcoRI protein sequence (SEQ ID NO:83).

5. Repeat Selection

Four colonies were picked from each sample containing a different type of mutation and grown in 4 ml LB with CAM. After sonication, cell extracts were tested on lambda DNA substrate in normal glycerol condition in NEB1 buffer. Those extracts with similar activity were tested again on pUC19 substrate by adding 3 μl of cell extract in two-fold serial dilutions, in 3 μl of NEB2 buffer to 0.5 μl of pUC19 and 23.5 μl 50% glycerol to provide a final concentration of 39.2% glycerol in the reaction mixture.

Among all of these mutants, K62A was found to be the mutation with the least star activity and a high FI. R9A, K15A, R123A, K130A, R131A, R183A mutants all showed partial reduction in star activity. Interestingly, one clone containing the targeted mutation K5A showed a partial improvement. Additionally, a secondary mutation, S2Y was found after sequencing. Separation of these two mutations revealed that the effective mutation for this isolate was S2Y. D135A and R187A EcoRI also had much less star activity. However, the cleavage activity of these mutants was not optimal.

6. Comparison of EcoRI(K62A) with WT EcoRI

A side-by-side comparison was performed in a 3-fold serial dilution using NEB dilution buffer C, by digesting 0.6 μg of lambda DNA in four different NEB buffers (FIG. 6). EcoRI(K62A) had substantially less star activity than the WT EcoRI.

A more quantitative comparison was done by determining the Fidelity Index measurement for EcoRI(K62A) and WT EcoRI. The conditions for the fidelity index measurement was the same as for Table 2 using lambda DNA as substrate and, dilution buffer C. The reaction was incubated at 37° C. for 1 hour and the digestion products analyzed on an 0.8% agarose gel.

TABLE 7

Fidelity Index for EcoRI(K62A) and WT EcoRI

| | EcoRI(K62A) | | WT EcoRI | | |
|---|---|---|---|---|---|
| Buffer | Activity | Fidelity Index | Activity | Fidelity Index | Improvement Factor |
| NEB1 | 50% | 32000 | 50% | 250 | 128 |
| NEB2 | 50% | 8000 | 100% | 4 | 2000 |
| NEB3 | 12.5% | 4000 | 100% | 250 | 16 |
| NEB4 | 100% | 32000 | 100% | 4 | 8000 |
| EcoRI buffer | 12.5% | 4000 | 100% | 250 | 16 |

7. Further Mutation of EcoRI

Though it was not apparent that the EcoRI(K62A) had star activity on lambda DNA substrate, star activity was observed using Litmus28 substrate after a 10 hours digestion. EcoRI(K62A) in NEB4 had significantly reduced star activity compared with WT EcoRI in EcoRI buffer (FIG. 7).

Further improvements were investigated. EcoRI(K62) was mutated to all other amino acid residues by changing K to the corresponding codons as in the example 1. K62S and K62L were similar as K62A. EcoRI(K62E) had a ≥100 fold overall fidelity index improvement factor when compared with EcoRI(K62A) as shown in FIG. 6. EcoRI(K62E) was named EcoRI-HF.

8. Comparison of EcoRI-HF and WT EcoRI

A quantitative comparison was done by the FI measurement on EcoRI-HF and WT EcoRI in diluent C. The conditions for the FI measurement were the same as in Table 2 using lambda DNA as substrate. The reaction conditions were 37° C. for 1 hour and the results analyzed on a 0.8% agarose gel (FIG. 8).

TABLE 8

Comparison of EcoRI-HF and WT EcoRI

| | EcoRI-HF | | WT EcoRI | | |
|---|---|---|---|---|---|
| Buffer | Activity | Fidelity Index | Activity | Fidelity Index | Improvement Factor |
| NEB1 | 12.5% | 2000 | 50% | 250 | 8 |
| NEB2 | 100% | 4000 | 100% | 4 | 1000 |
| NEB3 | 0.4% | 250 | 100% | 250 | 1 |
| NEB4 | 100% | 16000 | 100% | 4 | 4000 |
| EcoRI buffer | 0.4% | 250 | 100% | 250 | 1 |

The overall fidelity index improvement factor was found to be 64 fold (16000 in NEB4 for EcoRI-HF to 250 of WT EcoRI in NEB3).

Example 3: Engineering a High Fidelity ScaI

1. Expression of ScaI

The sequence for ScaI restriction endonuclease and methylase are described in REBASE and in GenBank and is presented in FIG. 44 (SEQ ID NO:97). The genes expressing these enzymes were inserted into plasmids to produce pRRS-ScaI and pACYC184-ScaIM respectively. pACYC184-ScaIM was then transformed into competent *E. coli* host cells. The pRRS vector was derived from pUC19 and differs only in the presence of multiple cloning sites. pRRS-ScaIR was transformed into *E. coli* (pACYC-ScaIM) to make an expression strain. Plating and cell culture were performed at 30° C.

2. Mutagenesis of ScaI

ScaI has two sequenced isoschizomers: LlaDI and NmeSI. However, there was no known information on the star activity of LlaDI or NmeSI nor was there any information on the active site of these enzymes. Therefore all 58 charged residues were initially selected for targeted mutation at positions 4, 8, 11, 12, 14, 18, 25, 27, 30, 37, 39, 40, 43, 46, 51, 57, 61, 68, 72, 74, 80, 86, 97, 103, 108, 112, 114, 119, 120, 121, 127, 128, 129, 133, 135, 139, 140, 141, 147, 152, 156, 158, 159, 161, 162, 171, 172, 175, 179, 182, 184, 187, 172, 175, 192, 193, 195, 200, 222, 227 in the protein.

The numbers above correspond to amino acid positions in the ScaI protein sequence (SEQ ID NO:97).

The method of primer design and PCR is similar to that described in Example 1 for BamHI and Example 2 for EcoRI. Mutagenesis was achieved by varying annealing temperature and DNA polymerases. The PCR product was digested with DpnI and transformed into competent *E. coli* (pACYC184-ScaIM).

3. Selection of ScaI High Fidelity Mutants

Four colonies from each mutant of ScaI mutant were picked and grown in 4 ml LB with 100 µg/ml Amp and 33 µg/ml Cam at 30° C. overnight. Each cell culture was sonicated and the activity tested on lambda DNA in NEB2 buffer. Those that were apparently active were retested in 10, 100, and 1000 fold dilutions. Since ScaI has very significant star activity, the star activity bands were easily compared for the mutants versus the WT restriction endonuclease. Those with reduced star activity were retested with a two-fold serial dilution with NEB dilution buffer A. The FI was measured for each of the mutants. The FI was 1/8 for WT ScaI in NEB 2 buffer. Four mutants with similar activity levels were found to have greatly reduced star activity compared with WT ScaI. Mutant #6-3 ScaI had two fold more activity and the FI was 4 or 32 times better than WT ScaI. #26-2 ScaI has two fold more activity and an FI which was 8 or 64 times better than WT; #28-2 ScaI has 2 fold more activity and FI to be 120 or 1000 times better than WT, #54-3 has same activity as WT and FI to be 250 or 2000 times better than WT.

Four mutants: #6-3, #26-2, #28-2 and #54-3 ScaI were further tested in the presence of 36.7% glycerol for digestion of lambda DNA substrate. #54-3 showed a greater improvement in reduced star activity than the other three mutants.

After the plasmid was extracted, #6-3 was sequenced and found to have a mutation at R18A. #26-2 was sequenced and found to have a mutation at R112A. #28-2 was sequenced and found to have a mutation at E119A. These mutations were predicted. However, the #54-3 was found to have a double mutant-H193A/S201F. The S201F was a spontaneously secondary mutation that occurred during PCR, and was located outside the primer region of the H193A mutation.

To understand which residue was primarily responsible for the reduction in star activity a single mutation (S201F) was introduced into ScaI using the following primers:

```
                                          (SEQ ID NO: 77)
5'-GATTGGGTGGCGCAGAAATTTCAAACGGGCCAGCAGTCG-3'

(SEQ ID NO: 78)
5'-CGACTGCTGGCCCGTTTGAAATTTCTGCGCCACCCAATC-3'
```

The sequences for ScaI(H193A), ScaI(S201F) and ScaI (H193A/S201F) were confirmed. The three mutants and the WT ScaI were compared at the glycerol level of 5% and 37% (FIG. 9). S201F contributed significantly to the FI in contrast to H193A, which only contributed weakly. However, these two mutations appeared to be additive in improving the FI. S201F did not show star activity in 5% glycerol, but did show some star activity in 37% glycerol. H193A had some star activity in 5% glycerol, and significant star activity in 37% glycerol. However, with the combination of these two mutations, no star activity was detected in either 5% or 37% glycerol. This finding not only shows that the amino acids with hydroxyl group can be major active residue for star activity, but also that the right combination of the mutations can push the improvement in fidelity to a very high level. If mutations of charged residues fail to improve star activity, it is here observed that mutations on Ser, Thr and Tyr can be successful in improving the fidelity index. The ScaI(H193A/S201F) was labelled ScaI-HF.

4. Comparison of ScaI-HF and WT ScaI

ScaI-HF and WT ScaI were compared at a 2.5 fold serial dilution with NEB dilution buffer A in different NEB buffers on 1 μg lambda DNA in four different NEB buffers, 37° C., 1 hour (FIG. 10).

TABLE 9

Comparison of Fidelity Index for ScaI-HF and WT ScaI

| | ScaI-HF | | WT ScaI | | |
|---|---|---|---|---|---|
| Buffer | Activity | Fidelity Index | Activity | Fidelity Index | Improvement Factor |
| NEB1 | 12% | 250 | 6% | 1/64 | 16000 |
| NEB2 | 100% | 120 | 100% | 1/8 | 2000 |
| NEB3 | 3% | 2000 | 25% | 4 | 500 |
| NEB4 | 100% | 250 | 1% | 1/32 | 8000 |

ScaI-HF performed best in NEB2 and NEB4 buffers, in which the best FI was 250; WT ScaI performed best in NEB2 buffer, in which the FI was 1/8. The overall FI improvement factor was 250/(1/8)=4000.

Example 4: Engineering of High Fidelity SalI

1. Expression of SalI

SalI was expressed in *E. coli* transformed with placzz1-SalIR and pACYC-Hpy166IIM where placzzI is a pUC19 plasmid which utilizes the lac promoter to express the restriction endonuclease gene that is inserted into an adjacent multi-copy site. Hpy166IIM protects the outside four bases of SalI.

2. Mutagenesis of SalI 86 charged residues of SalI were mutated to Ala using the similar PCR methods in the previous examples: 5, 6, 8, 9, 12, 13, 19, 27, 31, 34, 35, 37, 42, 43, 45, 50, 60, 63, 65, 67, 73, 82, 83, 84, 90, 93, 97, 100, 101, 103, 107, 109, 111, 114, 116, 119, 126, 129, 131, 134, 140, 143, 145, 147, 148, 156, 157, 164, 168, 172, 173, 174, 180, 181, 186, 190, 191, 193, 210, 218, 226, 232, 235, 237, 238, 244, 246, 250, 256, 257, 258, 259, 260, 261, 264, 266, 271, 275, 297, 300, 304, 305, 306, 308, 309, 311.

The numbers above correspond to amino acid positions in the SalI protein sequence (SEQ ID NO:94).

The mutants were grown in LB with Amp and Cam at 30° C. overnight.

3. Selection of SalI-HF

The selection of SalI-HF was performed as described in the previous examples. The major difference was that the star activity of SalI could not be easily assayed in the crude extract, either in 5% glycerol or high glycerol concentration. Glycerol not only promoted the star activity of SalI, but also greatly inhibited the cognate activity.

Active mutants were assayed in both 5% glycerol and 37% glycerol on HindIII digested lambda DNA. The mutants #22, #26, #29, #31, #43 and #51 were tested for cleavage activity in all four NEB buffers. After several rounds of comparison in different conditions and substrates, #31, SalI(R107A) was found to be the preferred mutant, retaining high cleavage high activity, but displaying substantially reduced star activity. SalI(R107A) was labeled SalI-HF.

4. Comparison of SalI-HF and WT SalI

The FI of SalI-HF and WT SalI were determined (FIG. 11). The results are shown as Table 10 (below):

TABLE 10

Comparison of SalI-HF and WT SalI

| | SalI-HF | | WT SalI | | |
|---|---|---|---|---|---|
| Buffer | Activity | Fidelity Index | Activity | Fidelity Index | Improvement Factor |
| NEB1 | 50% | ≥1000 | 0.2% | 8 | 16000 |
| NEB2 | 100% | ≥2000 | 6% | 1/8 | 2000 |
| NEB3 | 25% | ≥500 | 100% | 4 | 500 |
| NEB4 | 100% | ≥2000 | 0.8% | 1/32 | 8000 |

SalI-HF performed best in NEB 2 and NEB 4 buffers, in which both FIs are 2000; WT SalI performed best in NEB 3 buffer, in which the FI was 4. The overall FI improvement factor was 2000/4=500.

Example 5: Engineering of High Fidelity SphI

1. Expression of SphI

SphI was expressed in *E. coli* (placzz1-SphIR, pACYC184-CviAIIM). CviAIIM protects the internal four bases of SphI. The transformed cells were grown in LB with Amp and Cam at 37° C. overnight.

2. Mutagenesis of SphI

All charged residues in SphI were mutated to Ala using the methods described in the Example 1 to Example 4. A total of 71 mutations were made: 3, 5, 12, 18, 21, 24, 25, 30, 31, 35, 43, 46, 51, 54, 57, 58, 60, 61, 72, 75, 77, 78, 87, 90, 91, 95, 100, 104, 107, 108, 110, 113, 120, 123, 124, 125, 129, 130, 131, 139, 140, 142, 146, 147, 155, 157, 159, 164, 170, 172, 173, 175, 178, 184, 186, 190, 194, 196, 197, 198, 206, 207, 209, 212, 215, 221, 227, 230, 231, 232, 235.

The numbers above correspond to amino acid positions in the SphI protein sequence (SEQ ID NO:98).

3. Selection of SphI-HF

Four colonies of each mutation were grown up in LB with Amp and Cam at 37° C. overnight. The activity selection was mainly on pBR322 in 5% glycerol and 30% glycerol in NEB2. With the experience of previous examples, the selection of high fidelity SphI was straightforward. SphI mutants D91A, K100A, D139A and D164A were found to significantly reduce star activity in SphI. Among them, K100A was the preferred mutation with the least star activity. SphI (K100A) was named as SphI-HF.

4. Comparison of SphI-HF and WT SphI

The comparison of SphI-HF and WT SphI was done side by side in their respective preferred buffers. SphI-HF was 2-fold serial diluted with NEB dilution buffer A and reacted in NEB4, and WT SphI was 2-fold serial diluted with NEB dilution buffer B. The digestion on lambda DNA is compared in FIG. 12.

TABLE 11

FI comparison of SphI-HF and WT SphI

| | SphI-HF | | WT SphI | | |
|---|---|---|---|---|---|
| Buffer | Activity | Fidelity Index | Activity | Fidelity Index | Improvement Factor |
| NEB1 | 50% | ≥1000 | 100% | 64 | ≥16 |
| NEB2 | 50% | ≥1000 | 100% | 32 | ≥32 |
| NEB3 | 3% | ≥120 | 25% | 64 | ≥2 |
| NEB4 | 100% | ≥2000 | 50% | 16 | ≥64 |

SphI-HF performed best in NEB4, in which FI is 2000; WT SphI performed best in NEB1 or NEB2, in which the preferred FI is 64. The overall FI improvement factor was >32.

Example 6: Engineering of High Fidelity PstI

1. Expression of PstI
PstI was expressed from *E. coli* (pACYC-HpyCH4VM, pPR594-PstIR). HpyCH4VM protects the internal four bases of PstI. pPR594 is a expression vector with Amp resistance and ptac promoter. The cell was grown in LB with Amp and Cam at 30° C., the culture was then induced by IPTG overnight.

2. Mutagenesis of PstI
92 charged residues were mutated to Ala using the method described in the previous examples. These were: 8, 10, 11, 14, 25, 26, 38, 40, 41, 44, 45, 47, 58, 61, 63, 66, 67, 69, 73, 74, 77, 78, 82, 85, 88, 91, 92, 94, 95, 99, 104, 105, 116, 119, 127, 128, 136, 142, 145, 146, 150, 151, 152, 156, 159, 169, 170, 174, 176, 179, 180, 184, 188, 191, 197, 202, 204, 207, 212, 214, 217, 218, 226, 227, 228, 231, 236, 237, 238, 239, 240, 246, 251, 257, 258, 261, 263, 273, 282, 284, 286, 287, 295, 297, 302, 305, 306, 309, 313, 314, 319 and 320.

The numbers above correspond to amino acid positions in the PstI protein sequence (SEQ ID NO:91).

After the PCR products were digested with DpnI, the samples were transformed into competent *E. coli* (pACYC-HpyCH4VM) and grown on LB plate with Amp and Cam.

3. Selection of PstI-HF
The selection of PstI-HF was similar to the previous samples. The normal activity enzyme activity was tested on lambda DNA with 5% glycerol, and the star activity was tested on pBR322 substrate in the condition of NEB4 buffer and 20% DMSO. DMSO enhanced the star activity more significantly than the same concentration glycerol. During the selection, #26, #56 and #65 had reduced star activity compared to the WT. When each was sequenced, the mutations were found to be D91A, E204G and K228A/A289V. Mutant #26 PstI(D91A) was labeled PstI-HF.

4. Comparison of PstI-HF and WT PstI
The FI of PstI-HF and WT PstI were measured separately on lambda DNA substrate in NEB1-4 buffers. The dilution buffer is NEB dilution buffer C. The comparison is shown as in the FIG. 13, and the result is listed in Table 12 (below).

TABLE 12

Comparison of PstI-HF and WT PstI

| | PstI-HF | | WT PstI | | |
|---|---|---|---|---|---|
| Buffer | Activity | Fidelity Index | Activity | Fidelity Index | Improvement Factor |
| NEB1 | 12.5% | ≥250 | 50% | 32 | ≥8 |
| NEB2 | 100% | ≥2000 | 25% | 16 | ≥125 |
| NEB3 | 25% | ≥500 | 100% | 120 | ≥2 |
| NEB4 | 100% | ≥2000 | 50% | 8 | ≥250 |

PstI-HF performed best in NEB2 and NEB4, in which the preferred FI is >2000, WT PstI performed best in NEB3, in which the FI was 120. The overall FI improvement factor was 2000/120=16 times.

Example 7: Engineering of High Fidelity NcoI

1. Expression of NcoI
Expression of NcoI was achieved in *E. coli* (pSYX20-NcoIM, pRRS-NcoIR). pRRS is a pUC19 derivative plasmid, and pSYX20 is a compatible low copy number plasmid with pRRS vector. The cells were grown at 30° C. overnight in the LB with Amp and Kanamycin (Kan).

2. Mutagenesis of NcoI
All 66 charged residues in NcoI were mutated to Ala. These residues were: 7, 8, 19, 22, 27, 30, 31, 32, 33, 37, 39, 42, 46, 55, 56, 61, 62, 64, 68, 69, 75, 84, 88, 89, 92, 93, 95, 97, 100, 116, 136, 144, 146, 162, 166, 170, 178, 183, 185, 187, 188, 189, 196, 199, 202, 204, 209, 211, 212, 213, 216, 219, 227, 229, 237, 241, 244, 250, 251, 257, 259, 261, 268, 279, 282, 285.

The numbers above correspond to amino acid positions in the NcoI protein sequence (SEQ ID NO:88).

The methods were the same as in the previous examples using inverse PCR followed by DpnI digestion. The treated product was then transformed into *E. coli* (pSYX20-NcoIM).

3. Selection of NcoI-HF
The selection of NcoI-HF was similar to that of PstI-HF. The activity was assayed as described above using lambda DNA as substrate with 5% glycerol. Star activity was determined using pBR322 or lambda in 19% DMSO. The following mutations were found to improve star activity: A2T/R31A, D56A, H143A, E166A, R212A and D268A. Among these mutants, NcoI(A2T/R31A) was selected as the NcoI-HF.

4. Comparison of NcoI-HF and WT NcoI
The FIs of NcoI-HF and WT NcoI were determined separately on lambda DNA in NEB1-4 buffers. The comparison is shown in FIG. 14, and the results listed in Table 13 (below).

TABLE 13

Comparison of NcoI-HF with WT NcoI

| | NcoI-HF | | WT NcoI | | |
|---|---|---|---|---|---|
| Buffer | Activity | Fidelity Index | Activity | Fidelity Index | Improvement Factor |
| NEB1 | 25% | ≥4000 | 100% | 120 | ≥32 |
| NEB2 | 25% | ≥4000 | 100% | 32 | ≥125 |
| NEB3 | 6.3% | ≥1000 | 25% | 120 | ≥8 |
| NEB4 | 100% | ≥16000 | 100% | 32 | ≥500 |

NcoI-HF showed the greatest reduction in star activity in NEB4, in which the preferred FI was 16000; WT NcoI performed best in NEB1, NEB2 and NEB4, in which the preferred FI was 120. The overall FI improvement factor was 16000/120=125.

Example 8: Engineering of High Fidelity NheI

1. Expression of NheI

NheI was expressed in *E. coli* transformed with pACYC-NheIM, and placzz1-NheIR. placzz1 is a pUC19 derivative plasmid. The cell was grown at 30° C. for overnight in the LB with Amp and Cam.

2. Mutagenesis of NheI

All 92 charged residues in NheI were mutated to Ala as the following residues: 5, 6, 7, 14, 17, 19, 22, 25, 28, 31, 38, 39, 42, 47, 49, 52, 56, 58, 59, 60, 64, 74, 75, 76, 77, 80, 91, 93, 104, 105, 110, 112, 116, 117, 123, 126, 130, 131, 133, 135, 137, 147, 149, 152, 159, 160, 165, 167, 170, 171, 174, 179, 183, 195, 202, 205, 207, 209, 210, 211, 214, 216, 218, 221, 225, 231, 241, 243, 244, 250, 252, 256, 257, 259, 264, 266, 267, 281, 285, 287, 288, 289, 291, 297, 300, 307, 313, 315, 318, 321, 324, 325.

The numbers above correspond to amino acid positions in the NheI protein sequence (SEQ ID NO:89).

The methods were the same as in the previous examples using inverse PCR followed by DpnI digestion. The treated product was then transformed into *E. coli* (pACYC-NheIM).

3. Selection of NheI-HF

Selection of NheI-HF was performed according to the previous examples. The standard and star activity assays contained pBR322 as a substrate in NEB4 buffer and 5% glycerol and 39% glycerol, respectively. Only one mutation was found to be significant in improving the NheI. This was E77A. NheI(E77A) was selected as the NheI-HF.

4. Comparison of NheI-HF and WT NheI

The FIs of NheI-HF and WT NheI were determined separately on pXba, a plasmid substrate containing the XbaI digested piece from Adeno virus in each of NEB1-4 buffers. The comparison is shown in FIG. 15, and the result is listed in Table 14 (below).

TABLE 14

Comparison of NheI-HF and WT NheI

| | NheI-HF | | WT NheI | | |
|---|---|---|---|---|---|
| Buffer | Activity | Fidelity Index | Activity | Fidelity Index | Improvement Factor |
| NEB1 | 100% | ≥128000 | 100% | 32 | ≥4000 |
| NEB2 | 3% | ≥4000 | 25% | 120 | ≥32 |
| NEB3 | 0.05% | ≥32 | 12.5% | 120 | ≥0.25 |
| NEB4 | 50% | ≥32000 | 100% | 32 | ≥1000 |

NheI-HF showed optimal activity in NEB1 buffer where its FI is ≥128,000. WT NheI has maximum activity in NEB1 and NEB4 buffers, where its best FI is 32. so, the overall FI improvement factor is ≥128,000/32=≥4000.

Example 9: Engineering of High Fidelity SspI

1. Expression of SspI

SspI was expressed from *E. coli* transformed with pACYC-SspIM, and placzz1-SspIR. placzz1 is a pUC19 derivative plasmid. The cells were grown at 30° C. overnight in LB with Amp and Cam.

2. Mutagenesis of SspI

All 81 charged residues in SspI were mutated to Ala: These were: 3, 8, 12, 13, 18, 19, 20, 35, 40, 42, 44, 47, 52, 60, 62, 65, 68, 69, 72, 74, 76, 77, 78, 79, 83, 85, 88, 89, 90, 96, 100, 108, 109, 118, 119, 127, 128, 129, 131, 132, 137, 144, 153, 154, 155, 156, 158, 165, 168, 170, 172, 177, 178, 179, 181, 185, 186, 187, 191, 194, 195, 197, 202, 204, 215, 222, 229, 237, 240, 246, 250, 256, 257, 259, 260, 264, 265, 267, 268, 269, 274.

The numbers above correspond to amino acid positions in the SspI protein sequence (SEQ ID NO:99).

The methods were the same as in the previous examples using inverse PCR followed by DpnI digestion. The treated product was then transformed into *E. coli* (pACYC-SspIM).

3. Selection of SspI High Fidelity Mutants

The standard cognate and star activity assays of NheI were performed using φX174 substrate in NEB 4 buffer and 5% glycerol and 39% glycerol respectively. Mutants #16 (H65A), #20(K74A), #23(E78A), #26(E85A), #28(E89A), #33(K109A), #34(E118A), #52(R177A), #62(K197A), #67 (D229A) all showed reduced star activity. K109A showed the greatest reduction in star activity. It was decided to seek further improvements in star activity.

4. Further Mutations

All residues originally identified as Tyr were mutated to Phe, while other residues Cys, Phe, Met, Asn, Gln, Ser, Thr, and Trp were mutated to Ala. This group included 95 residue mutations at the following positions: 2, 6, 7, 9, 10, 13, 22, 25, 26, 27, 29, 30, 32, 33, 34, 39, 41, 51, 53, 55, 56, 57, 58, 59, 61, 63, 71, 75, 81, 84, 87, 91, 94, 98, 104, 106, 107, 110, 111, 113, 114, 123, 125, 134, 136, 139, 140, 141, 142, 143, 146, 152, 157, 159, 160, 164, 173, 175, 180, 183, 190, 192, 193, 196, 198, 199, 201, 205, 207, 211, 214, 218, 219, 220, 221, 223, 225, 226, 227, 228, 230, 232, 233, 235, 238, 239, 241, 249, 254, 255, 272, 275, 276, 277, 280.

The numbers above correspond to amino acid positions in the SspI protein sequence (SEQ ID NO:113).

The PCRs and the selections were done by the same procedure as above. Among these mutants, it was found that Y98F had least star activity, and it was better than SspI (K109A) in this respect. The SspI(Y98F) was labelled SspI-HF and was deposited as the production strain.

5. Comparison of SspI-HF and WT SspI

The FIs of SspI-HF and WT SspI were determined separately using lambda DNA substrate in NEB1-4 buffers. The diluent was NEBC. The comparison is shown in FIG. 16, and the result is listed in Table 15 (below).

TABLE 15

Comparison of SspI-HF and WT SspI

| | SspI-HF | | WT SspI | | |
|---|---|---|---|---|---|
| Buffer | Activity | Fidelity Index | Activity | Fidelity Index | Improvement Factor |
| NEB1 | 50% | ≥4000 | 100% | 64 | ≥64 |
| NEB2 | 50% | 120 | 100% | 16 | ≥8 |
| NEB3 | 0.6% | ≥32 | 25% | 32 | ≥1 |
| NEB4 | 100% | 500 | 100% | 16 | ≥32 |

SspI-HF performed best in NEB4, in which the preferred FI was 500; WT SspI performed best in NEB1, NEB2 and NEB4, in which the preferred FI was 64. The overall FI improvement factor was 500/64=8.

Example 10: Engineering of High Fidelity NotI

1. Expression of NotI

NotI has significant star activity in NEB4 buffer and less in NEB3 buffer. NotI was engineered to reduce star activity in any NEB buffer. NotI was expressed in competent *E. coli* transformed with pACYC184-EagIM and placzz2-NotIR. The cells were grown at 37° C. for overnight in the LB with Amp and Cam.

2. Mutagenesis of NotI

All 97 charged residues in NotI were mutated to Ala as the following residues: 2, 4, 8, 10, 17, 21, 22, 26, 31, 34, 35, 36, 49, 52, 57, 59, 62, 72, 74, 75, 77, 84, 87, 96, 97, 105, 117, 121, 122, 125, 126, 129, 130, 133, 140, 141, 145, 150, 152, 156, 160, 165, 167, 174, 176, 177, 182, 187, 189, 193, 194, 200, 205, 208, 210, 219, 224, 225, 227, 236, 237, 245, 251, 253, 267, 271, 272, 280, 283, 290, 292, 294, 296, 304, 306, 308, 310, 314, 319, 321, 323, 327, 331, 335, 336, 339, 353, 354, 356, 358, 361, 365, 367, 368, 369, 370, 378, 382.

The numbers above correspond to amino acid positions in the NotI protein sequence (SEQ ID NO:90).

The method for introducing mutants into the enzyme was the same as in the previous examples using inverse PCR followed by DpnI digestion. The treated product was then transformed into *E. coli* containing pACYC-EagIM.

3. Selection of NotI-HF Selection of NotI-HF was performed as described in the previous examples. The standard cognate and star activity assays used pXba substrate in NEB 4 buffer and 5% glycerol and NEB ExoI buffer (67 mM Glycine-KOH, pH 9.5, 6.7 mM $MgCl_2$, 10 mM 2-mercaptoethanol) and 37% glycerol respectively. #37(K150A), #44 (K176A), #45(R177A), #63(R253A) all showed reduced star activity. K150A was the preferred mutation to reduce star activity. NotI(K150A) was selected as the NotI-HF.

4. Comparison of NotI-HF and WT NotI

The FIs of NotI-HF and WT NotI were determined separately using pXba substrate in NEB1-4 buffers. The comparison is shown in FIG. 17, and the results are listed in Table 16 (below).

TABLE 16

Comparison of NotI-HF and WT NotI

| | NotI-HF | | WT NotI | | |
|---|---|---|---|---|---|
| Buffer | Activity | Fidelity Index | Activity | Fidelity Index | Improvement Factor |
| NEB1 | 6% | ≥8000 | 6% | ≥8000 | ND |
| NEB2 | 100% | ≥128000 | 50% | 250 | ≥512 |
| NEB3 | 1.6% | ≥4000 | 100% | 4000 | ≥1 |
| NEB4 | 50% | ≥64000 | 12.5% | 32 | ≥2000 |

ND: Not determinable, for that both FI is an uncertain number over limit.

NotI-HF performed best in NEB2, in which the preferred FI was 128000; WT NheI performed best in NEB3, in which the preferred FI was 4000. The overall fidelity index improvement factor was 128000/4000=32. Engineering NotI not only further improved the FI of NotI, but also changed the optimal buffer.

Example 11: Engineering of High Fidelity SacI

1. Expression of SacI

SacI was expressed in *E. coli* transformed with pLG-SacIM and pRRS-SacIR. pRRS is a pUC19 derivative plasmid, pLG is a low copy compatible plasmid. The cells were grown at 30° C. overnight in LB with Amp and Kan.

2. Mutagenesis of SacI

All 101 charged residues in SacI were mutated to Ala as the following residues: 6, 7, 11, 15, 16, 19, 24, 25, 29, 30, 39, 40, 42, 45, 58, 61, 62, 63, 65, 67, 70, 71, 72, 74, 75, 76, 81, 85, 94, 98, 104, 105, 114, 116, 120, 123, 127, 129, 133, 134, 141, 143, 144, 145, 146, 150, 151, 154, 169, 170, 172, 181, 187, 196, 197, 200, 201, 211, 216, 220, 221, 224, 227, 228, 232, 238, 240, 246, 248, 250, 258, 270, 271, 277, 281, 288, 289, 295, 296, 297, 299, 303, 306, 313, 314, 321, 322, 324, 332, 336, 337, 340, 342, 344, 345, 347, 349, 350, 353, 357.

The numbers above correspond to amino acid positions in the SacI protein sequence (SEQ ID NO:93).

The methods were the same as in the previous examples using inverse PCR followed by DpnI digestion. The treated product was then transformed into *E. coli* (pLG-SacIM).

3. Selection of SacI-HF

Selection of SacI-HF was achieved using a method that was similar to the previous examples. The standard activity check used pUC19 with 5% glycerol in NEB4 and the star activity check was on pUC19 in NEB4 buffer with 39% glycerol. #52 SacI (Q117H/R154A/L284P) and #60 SacI (Q117H/R200A) both had reduced star activity, and SacI Q117H/R200A proved to be the preferred mutation. The Q117H was a carry over mutation from the template, which did not affect the activity of SacI. SacI(Q117H/R200A) was selected as the SacI-HF.

4. Comparison of SacI-HF and WT SacI

The FIs of SacI-HF and WT SacI were determined separately on pXba substrate in NEB1-4 buffers. The comparison is shown in FIG. 18, and the result is listed in Table 17 (below).

TABLE 17

Comparison of SacI-HF and WT SacI

| | SacI-HF | | WT SacI | | |
|---|---|---|---|---|---|
| Buffer | Activity | Fidelity Index | Activity | Fidelity Index | Improvement Factor |
| NEB1 | 25% | ≥2000 | 100% | 120 | ≥16 |
| NEB2 | 12.5% | ≥120 | 50% | 120 | ≥1 |
| NEB3 | 0.8% | ≥120 | 3% | 120 | ≥1 |
| NEB4 | 100% | 4000 | 100% | 32 | 120 |

SacI-HF performed best in NEB4, in which the FI was 4000; WT SacI performed best in NEB1 and NEB4, in which the preferred FI was 120. The overall FI improvement factor was 4000/120=32.

Example 12: Engineering of High Fidelity PvuII

1. Expression of PvuII PvuII was expressed in *E. coli* transformed with pACYC-PvuIIM and placzz2-PvuIIR. Placzz2 is a pUC19 derivative plasmid; pACYC is a low copy compatible plasmid. The cells were grown at 30° C. overnight in LB with Amp and Cam.

2. Mutagenesis of PvuII

All 47 charged residues in PvuII were mutated to Ala as the following residues: 3, 5, 8, 11, 15, 18, 21, 25, 26, 30, 34, 38, 54, 55, 58, 61, 66, 68, 70, 75, 78, 83, 84, 85, 93, 95, 105, 110, 114, 116, 118, 119, 121, 125, 126, 128, 129, 130, 134, 136, 137, 138, 143, 147, 151, 152, and 155.

The numbers above correspond to amino acid positions in the PvuII protein sequence (SEQ ID NO:92).

The methods were the same as in the previous examples using inverse PCR followed by DpnI digestion. The treated product was then transformed into *E. coli* (pACYC-PvuIIM).

3. Selection of PvuII High Fidelity Mutants

Selection of PvuII-HF was similar to the previous examples. The standard activity check used lambda DNA substrate with 5% glycerol in NEB4 and the star activity check was on pBR322 in NEB4 buffer with 39% glycerol. None of the mutants were qualified as high fidelity PvuII.

4. Additional Mutagenesis Steps

An additional mutagenesis step was mutation of all of the Ser, Thr into Ala, and Tyr to Phe in PvuII. The mutated positions were: 2, 19, 46, 49, 67, 71, 77, 81, 82, 94, 104, 113, 123, 124, 132, 133, 148, 154 and 157.

The methods were the same as in the previous examples using inverse PCR followed by DpnI digestion. The treated product was then transformed into *E. coli* (pACYC-PvuIIM).

The PvuII(T46) apped to have less star activity than the WT PvuII, however, further improvement was desired.

T46 was mutated to all other amino acid residues, by changing the codons to the corresponding amino acids. Among all these mutations, T46H, T46K, T46Y, T46G were all better than T46A. T46G is selected as the PvuII-HF.

5. Comparison of PvuII-HF and WT PvuII

The FIs of PvuII-HF and WT PvuII were determined separately on pBR322, with diluent A in NEB1-4 buffers. The comparison is shown in FIG. 19, and the result is listed in Table 18 (below).

TABLE 18

Comparison of PvuII-HF and WT PvuII

| Buffer | PvuII-HF Activity | PvuII-HF Fidelity Index | WT PvuII Activity | WT PvuII Fidelity Index | Improvement Factor |
|---|---|---|---|---|---|
| NEB1 | 3.1% | ≥250 | 100% | 250 | ≥1 |
| NEB2 | 12.5% | ≥1000 | 25% | 16 | ≥64 |
| NEB3 | 0.4% | ≥32 | 3.1% | 8 | ≥4 |
| NEB4 | 100% | 500 | 100% | ¼ | 2000 |

PvuII-HF performed best in NEB4, in which the FI was 500; WT PvuII performed best in NEB1 and NEB4, in which the preferred FI was 250. The overall FI improvement factor was 500/250=2. Though the overall FI improvement factor is not high for PvuII, the FI improved 2000 times in NEB4.

Example 13: Engineering of High Fidelity MfeI

1. Expression of MfeI

MfeI was expressed in *E. coli* transformed with pACYC-MluCIM and pRRS-MfeIR. pRRS is a pUC19 derivative plasmid, pACYC is a low copy compatible plasmid. MluCIM methylate AATT, which is the inner four nucleic acid sequence of the MfeI. The cells were grown at 37° C. overnight in LB with Amp and Cam.

2. Mutagenesis of MfeI

The mutagenesis of MfeI was done in three batches. The first batch is all of the charged residues, mutated into Ala as the following amino acid positions: 3, 5, 9, 19, 24, 36, 39, 44, 45, 47, 48, 50, 60, 61, 64, 65, 72, 83, 87, 90, 92, 93, 98, 100, 101, 103, 107, 109, 110, 115, 119, 120, 121, 124, 132, 135, 142, 143, 144, 153, 155, 158, 159, 161, 162, 164, 165, 171, 172, 175, 181, 184, 187, 188, 192, 195, 196, 198, 199, 200; The second batch is all of the residues with hydroxyl group: Ser, Thr and Tyr, with Ser and Thr changed into Ala and Tyr changed into Phe. The residues are at: 4, 7, 21, 28, 38, 40, 43, 53, 74, 75, 76, 81, 89, 91, 112, 122, 127, 134, 136, 157, 167, 170, 173, 177, 185, and 200. The third batch is the residues of Cys, Phe, Met, Asn, Gln, Trp all changed into Ala, the residues are at: 10, 12, 13, 25, 26, 29, 31, 32, 35, 51, 55, 67, 68, 77, 78, 84, 88, 96, 102, 105, 117, 123, 126, 141, 148, 149, 152, 168, 169, 174, 176, 178, 179, 180, 183, 191, 193, 194.

The numbers above correspond to amino acid positions in the MfeI protein sequence (SEQ ID NO:5).

The methods were the same as in the previous examples using inverse PCR followed by DpnI digestion. The treated product was then transformed into *E. coli* (pACYC-MluCIM).

3. Selection of MfeI-HF

Selection of MfeI-HF was achieved using a method that was similar to the previous examples. Cleavage activity was determined using φX174 substrate with 5% glycerol in NEB4 and star activity was determined using φX174 substrate in NEB4 buffer with 39% glycerol. A significant difficulty for this enzyme was that many mutations improved cleavage activity of the enzyme with reduced star activity, but required higher glycerol concentrations than the WT enzyme. MfeI(K50A) is one example, having reduced star activity and high cleavage activity in high concentration glycerol, while in lower glycerol concentrations, the activity was low. MfeI(Y173A) also reduced star activity. The preferred mutation was Q13A/F35Y. The mutation of F35Y was from the template, and Q13A was a targeted mutation. MfeI(Q13A/F35Y) was labelled MfeI-HF.

4. Comparison of MfeI-HF and WT MfeI

The FIs of MfeI-HF and WT MfeI were determined separately on lambda DNA substrate, with the dilution in NEB diluent A in NEB1-4 buffers. The comparison is shown in FIG. 20, and the result is listed in Table 19 (below).

TABLE 19

Comparison of MfeI-HF and WT MfeI

| Buffer | MfeI-HF Activity | MfeI-HF Fidelity Index | WT MfeI Activity | WT MfeI Fidelity Index | Improvement Factor |
|---|---|---|---|---|---|
| NEB1 | 100% | ≥1000 | 100% | 32 | ≥32 |
| NEB2 | 25% | ≥250 | 12.5% | 16 | ≥16 |
| NEB3 | 1.3% | ≥16 | 6.3% | 8 | ≥2 |
| NEB4 | 100% | ≥500 | 100% | 32 | ≥16 |

MfeI-HF performed best in NEB1 and NEB4, in which the preferred FI was 1000; WT MfeI performed best in NEB1 and NEB4, in which the preferred FI was 32. The overall FI improvement factor was 1000/32=32 fold.

Example 14: Engineering of High Fidelity HindIII

1. Expression of HindIII

HindIII was expressed in *E. coli* transformed with pUC19-HindIIIRM, which contains both HindIII endonuclease and methylase genes. The cells were grown at 30° C. overnight in LB with Amp.

2. Mutagenesis of HindIII 88 charged residues in HindIII were mutated to Ala. These were: 2, 3, 7, 8, 14, 20, 22, 34, 37, 39, 42, 45, 52, 55, 61, 62, 66, 69, 74, 84, 87, 89, 94, 100, 101, 109, 111, 114, 117, 120, 123, 124, 126, 128, 132, 134, 135, 136, 137, 138, 153, 158, 162, 163, 171, 172, 180, 182, 183, 190, 197, 198, 201, 202, 207, 209, 214, 215, 218, 222, 225, 227, 228, 229, 237, 238, 243, 244, 245, 249, 250, 251, 254, 255, 261, 265, 266, 267, 270, 274, 275, 281, 283, 286, 290, 293, 296, 297.

All residues Cys, Met, Asn, Gln, Ser, Thr, Trp were changed to Ala while Tyr was changed to Phe at the positions of 4, 11, 15, 17, 18, 19, 21, 23, 26, 27, 30, 31, 36, 38, 46, 57, 58, 59, 60, 63, 64, 76, 77, 80, 82, 83, 88, 91, 99, 102, 103, 104, 112, 113, 116, 118, 121, 122, 125, 131, 133, 139, 143, 146, 147, 148, 149, 151, 152, 154, 155, 157, 159, 160, 164, 168, 169, 170, 178, 184, 185, 187, 188, 189, 191, 193, 194, 195, 199, 200, 203, 204, 206, 210, 211, 212, 213, 216, 217, 219, 220, 221, 224, 230, 232, 233, 236, 240, 241, 246, 252, 253, 256, 258, 262, 263, 264, 277, 278, 279, 280, 284, 287, 288, 294, 295, 299.

The numbers above correspond to amino acid positions in the HindIII protein sequence (SEQ ID NO:85).

The methods were the same as in the previous examples using inverse PCR followed by DpnI digestion. The treated product was then transformed into E. coli strain ER3081.

3. Selection of HindIII-HF

Selection of HindIII-HF was achieved using a method that was similar to the previous examples. The standard activity check used lambda DNA with 5% glycerol in NEB4 and star activity was measured using lambda DNA substrate in NEB4 buffer with 39% glycerol. 2 mutants of HindIII were found to have reduced star activity. These were HindIII (K198A) and S188P/E190A. HindIII(K198A) was labelled HindIII-HF.

4. Comparison of HindIII-HF and WT HindIII

The FIs of HindIII-HF and WT HindIII were determined separately using lambda DNA substrate in each of NEB1-4 buffers with diluent B. The comparison is shown in FIG. 21, and the result is listed in Table 20 (below).

TABLE 20

| | Comparison of HindIII-HF and WT HindIII | | | | |
|---|---|---|---|---|---|
| | HindIII-HF | | WT HindIII | | |
| Buffer | Activity | Fidelity Index | Activity | Fidelity Index | Improvement Factor |
| NEB1 | 25% | ≥16000 | 25% | 32 | ≥500 |
| NEB2 | 100% | ≥64000 | 100% | 250 | ≥250 |
| NEB3 | 12.5% | ≥16000 | 25% | 4000 | ≥4 |
| NEB4 | 50% | ≥32000 | 50% | 32 | ≥1000 |

HindIII-HF performed best in NEB2, in which the preferred FI was 64000; WT HindIII performed best in NEB2, in which the preferred FI was 250. The overall FI improvement factor was 4000/120=32.

Example 15: Engineering of High Fidelity SbfI

1. Expression of SbfI

SbfI was expressed in E. coli transformed with pUC19-SbfIRM. The cells were grown at 30° C. overnight in LB with Amp.

2. Mutagenesis of SbfI 78 charged residues in SbfI were mutated to Ala. These were: 5, 8, 15, 18, 23, 27, 30, 34, 46, 49, 50, 53, 58, 63, 66, 70, 71, 74, 81, 82, 83, 85, 86, 87, 90, 94, 103, 115, 120, 121, 127, 132, 135, 136, 143, 144, 147, 150, 152, 154, 164, 169, 170, 183, 184, 187, 188, 192, 196, 204, 206, 208, 213, 214, 215, 218, 219, 226, 228, 230, 233, 237, 238, 239, 241, 248, 251, 253, 257, 258, 259, 260, 262, 266, 282, 284, 285, 288, 293, 297, 299, 304, 305, 307, 311, 316, and 322.

The residues of Ser and Thr in SbfI were also mutated into Ala. Tyr was mutated into Phe. The following positions were targeted: 3, 4, 5, 10, 13, 16, 31, 35, 38, 54, 55, 56, 68, 76, 78, 80, 88, 109, 111, 116, 119, 129, 131, 137, 146, 162, 174, 197, 198, 201, 205, 210, 224, 252, 263, 270, 272, 286, 298, 315, 321.

Another 55 residues of Cys, Phe, Met, Asn, Gln, Trp were also mutated to Ala at positions of: 2, 24, 26, 29, 32, 51, 62, 65, 67, 72, 84, 91, 92, 95, 97, 101, 104, 106, 110, 112, 114, 117, 124, 134, 140, 157, 160, 171, 178, 179, 185, 189, 193, 212, 217, 225, 231, 243, 245, 247, 256, 265, 268, 277, 279, 280, 281, 283, 287, 289, 290, 296, 301, 313 and 317.

The numbers above correspond to amino acid positions in the SbfI protein sequence (SEQ ID NO:96).

The methods were the same as in the previous examples using inverse PCR followed by DpnI digestion. The mutated products were transformed into E. coli strain ER2984.

3. Selection of SbfI-HF

Selection of SbfI-HF was achieved as described in previous examples. The standard activity check used lambda DNA with 5% glycerol in NEB4 and the star activity check was on lambda DNA in Exonuclease I buffer. SbfI(K251A) was labelled SbfI-HF.

4. Comparison of SbfI-HF and WT SbfI

The FIs of SbfI-HF and WT SbfI were determined separately on lambda DNA in NEB1-4 buffers with diluent C. The comparison is shown in FIG. 22, and the result is listed in Table 21 (below).

TABLE 21

| | Comparison of SbfI-HF and WT SbfI | | | | |
|---|---|---|---|---|---|
| | SbfI-HF | | WT SbfI | | |
| Buffer | Activity | Fidelity Index | Activity | Fidelity Index | Improvement Factor |
| NEB1 | 100% | 1000 | 100% | 16 | 64 |
| NEB2 | 50% | 120 | 50% | 32 | 4 |
| NEB3 | 3.5% | 8 | 25% | 120 | 1/16 |
| NEB4 | 100% | 250 | 12.5% | 8 | 32 |

SbfI-HF performed best in NEB1 and NEB4, in which the preferred FI was 1000; WT SbfI performed best in NEB1, in which the preferred FI was 8. The overall FI improvement factor was 1000/8=125 fold.

Example 16: Engineering of High Fidelity EagI

1. Expression of EagI

EagI was expressed in E. coli transformed with pBR322-EagIRM. The cells were grown at 30° C. overnight in LB with 20 µg/ml Tetracycline.

2. Mutagenesis of EagI

Asp, Glu, His, Lys, Arg, Ser, Thr, Asn and Gln residues were mutated to Ala. Tyr was mutated to Phe. These were the following residues: 2, 3, 4, 5, 6, 9, 13, 14, 17, 19, 21, 23, 27, 35, 36, 37, 40, 42, 43, 44, 45, 46, 49, 51, 53, 55, 56, 58, 60, 66, 67, 69, 71, 72, 73, 74, 75, 77, 78, 80, 82, 86, 87, 92, 93, 94, 95, 98, 99, 100, 102, 103, 104, 105, 112, 113, 114, 116, 117, 119, 122, 125, 127, 132, 134, 135, 137, 139, 140, 141, 145, 147, 148, 150, 152, 154, 155, 156, 157, 160, 162, 163, 164, 166, 169, 172, 173, 176, 177, 178, 179, 182, 185, 187, 188, 189, 193, 196, 197, 201, 202, 203, 204, 205, 206, 208, 209, 212, 217, 220, 221, 222, 224, 225, 230, 235, 236, 237, 238, 239, 240, 241, 243, 245, 246, 247, 248, 251, 255, 257, 258, 259, 260, 263, 264, 265, 266, 270, 272, 273, 275, 276, 277, 279, 280, 283, 286, 288, 289, 291, 295, 296.

The numbers above correspond to amino acid positions in the EagI protein sequence (SEQ ID NO:82).

The methods were the same as in the previous examples using inverse PCR followed by DpnI digestion. The treated product was then transformed into *E. coli* strain ER 3081 and grown on the LB agar plate with Tetracycline.

3. Selection of EagI-HF

Selection of EagI-HF was achieved using a method that was different to the previous examples which used high concentration of glycerol, high concentration of DMSO or high pH. Since the expression was too low to show the star activity in the crude extract, it would be very tedious to purify each of the mutants to check the star activity. From the previous examples, it was deduced that HF endonucleases tended to have increased cleavage activity in NEB4 compared to NEB3. Hence, the activity of EagI in the crude extract was measured in both NEB3 and NEB4; the one with highest ratio of NEB4/NEB3 was selected. EagI(H43A) was labelled EagI-HF.

4. Comparison of EagI-HF and WT EagI

The FIs of EagI-HF and WT EagI were determined separately on pXba substrate in each of NEB1-4 buffers. The comparison is shown in FIG. 23, and the result is listed in Table 22 (below).

TABLE 22

Comparison of EagI-HF and WT EagI

| Buffer | EagI-HF Activity | EagI-HF Fidelity Index | WT EagI Activity | WT EagI Fidelity Index | Improvement Factor |
|---|---|---|---|---|---|
| NEB1 | 50% | 250 | 25% | 4 | 64 |
| NEB2 | 100% | 250 | 50% | 8 | 32 |
| NEB3 | 50% | 250 | 100% | 250 | 1 |
| NEB4 | 100% | 500 | 100% | 16 | 16 |

EagI-HF performed best in NEB2 and NEB4, in which the preferred FI was 500; WT EagI performed best in NEB3 and NEB4, in which the preferred FI was 250. The overall FI improvement factor was 500/250=2.

Example 17: Engineering of High Fidelity EcoRV

1. Expression of EcoRV

EcoRV was expressed in *E. coli* strain transformed with pACYC-EcoRVM and placzz1-EcoRV. Placzz1 is a pUC19 derivative plasmid and pACYC is a low copy compatible plasmid. The cells were grown at 37° C. overnight in LB with Amp and Cam.

2. Mutagenesis of EcoRV

Cys, Asp, Glu, Phe, His, Lys, Met, Asn, Gln, Arg, Ser, Thr, and Trp residues were changed to Ala. Tyr was changed to Phe. These were: 2, 4, 5, 6, 9, 12, 13, 14, 15, 16, 17, 18, 19, 21, 25, 27, 29, 31, 35, 36, 37, 38, 41, 42, 44, 45, 47, 48, 49, 53, 54, 57, 58, 59, 61, 64, 65, 67, 68, 69, 70, 71, 72, 74, 75, 76, 78, 79, 81, 82, 84, 85, 86, 90, 92, 93, 94, 95, 96, 97, 98, 99, 100, 101, 102, 104, 105, 106, 110, 111, 112, 113, 114, 115, 116, 117, 118, 119, 120, 123, 125, 126, 127, 128, 131, 132, 136, 138, 139, 140, 143, 144, 145, 146, 147, 149, 150, 151, 152, 154, 155, 157, 158, 161, 163, 164, 167, 169, 171, 172, 173, 174, 179, 183, 185, 186, 187, 188, 191, 193, 195, 196, 197, 198, 199, 201, 203, 206, 207, 208, 209, 210, 211, 212, 214, 215, 216, 217, 218, 219, 220, 221, 222, 223, 224, 226, 227, 228, 229, 230, 231, 232, 234, 235, 236, 237, 238, 239, 241, 242, 244, and 245.

The numbers above correspond to amino acid positions in the EcoRV protein sequence (SEQ ID NO:84).

The methods were the same as in the previous examples using inverse PCR followed by DpnI digestion. The treated product was then transformed into *E. coli* (pACYC-EcoRVM).

3. Selection of EcoRV-HF

Selection of EcoRV-HF was achieved using a method that was similar to the previous examples. The standard activity check used pXba with 5% glycerol in NEB4 and the star activity check was on pXba in Exonuclease I buffer with 39% glycerol. EcoRV(D19A/E27A) was found to have reduced star activity compared with WT EcoRV. This mutant was labeled EcoRV-HF. For this mutant, the E27A was the targeted mutation, and D19A was a spontaneous mutation. The double mutant had greater reduction in star activity than either the D19A and E27A single mutant.

4. Comparison of EcoRV-HF and WT EcoRV

The FIs of EcoRV-HF and WT EcoRV were determined separately on pXba substrate in each of NEB1-4 buffers. The comparison is shown in FIG. 24, and the result is listed in Table 23 (below).

TABLE 23

Comparison of EcoRV-HF and WT EcoRV

| Buffer | EcoRV-HF Activity | EcoRV-HF Fidelity Index | WT EcoRV Activity | WT EcoRV Fidelity Index | Improvement Factor |
|---|---|---|---|---|---|
| NEB1 | 25% | ≥16000 | 6.3% | 32 | ≥500 |
| NEB2 | 100% | ≥64000 | 50% | 120 | ≥500 |
| NEB3 | 50% | ≥32000 | 100% | 1000 | ≥32 |
| NEB4 | 100% | ≥64000 | 25% | 64 | ≥1000 |

EcoRV-HF performed best in NEB2 and NEB4, in which the preferred FI was 64000; WT EcoRV performed best in NEB3, in which the preferred FI was 1000. The overall FI improvement factor was 64000/1000=64.

Example 18: Engineering of High Fidelity AvrII

1. Expression of AvrII

AvrII was expressed in *E. coli* transformed with pUC19-AvrIIRM. The cells were grown at 30° C. overnight in LB with Amp.

2. Mutagenesis of AvrII

Cys, Asp, Glu, Phe, His, Lys, Met, Asn, Gln, Arg, Ser, Thr, and Trp residues were mutated to Ala. Tyr was changed to Phe. These were: 2, 3, 4, 6, 8, 9, 10, 12, 15, 17, 19, 20, 22, 23, 27, 29, 30, 31, 32, 34, 36, 40, 41, 42, 43, 44, 46, 47, 48, 50, 51, 53, 55, 56, 57, 58, 59, 60, 65, 68, 70, 72, 74, 75, 76, 77, 79, 80, 82, 83, 84, 86, 87, 88, 94, 95, 96, 97, 100, 104, 105, 106, 107, 108, 110, 112, 113, 116, 117, 119 120, 121, 122, 123, 124, 126, 127, 129, 130, 131, 132, 134, 136, 139, 142, 143, 144, 145, 150, 151, 152, 153, 154, 156, 157, 158, 161, 163, 164, 165, 166, 168, 169, 173, 174, 177, 178, 181, 182, 184, 186, 187, 188, 189, 190, 191, 192, 195, 198, 200, 202, 206, 207, 211, 215, 216, 220, 223, 224, 226, 229, 230, 231, 232, 233, 234, 235, 236, 237, 239, 243, 244, 245, 246, 248, 249, 253, 255, 256, 260, 262, 264, 265, 266, 267, 268, 269, 270, 272, 274, 276, 277, 278, 279, 280, 281, 284, 285, 286, 288, 289, 290, 291, 299, 302, 303, 304, 305, 306, 308, 310, 312, 314, 315, 316, 318, 321, 322, 324, 325, 328, 331, 333, 335, 337, 338, 339, 340, 342, 343, 346, 347, 348, 350, 351, 353, 354, 355, 356, 358.

The numbers above correspond to amino acid positions in the AvrII protein sequence (SEQ ID NO:80).

The methods were the same as in the previous examples using inverse PCR followed by DpnI digestion. The treated product was then transformed into E. coli expression strain ER2984.

3. Selection of AvrII-HF

Selection of AvrII-HF was achieved using a method that was similar to the previous examples. The cleavage activity was determined using pBC4 with 5% glycerol in NEB4 and the star activity was measured using pBC4 in ExoI buffer with 39% glycerol. Mutants #16 (M29A), #57(E96A), #60 (Y104F), #62(K106A), #154(S127A), #170(F142A) all showed improvement. AvrII(Y104F) was labelled AvrII-HF.

4. Comparison of AvrII-HF and WT AvrII

The FIs of AvrII-HF and WT AvrII were determined separately on T7 DNA substrate with diluent B in each of NEB1-4 buffers. The comparison is shown in FIG. 25, and the result is listed in Table 24 (below).

TABLE 24

Comparison of AvrII-HF and WT AvrII

| Buffer | AvrII-HF Activity | AvrII-HF Fidelity Index | WT AvrII Activity | WT AvrII Fidelity Index | Improvement factor |
|---|---|---|---|---|---|
| NEB1 | 100% | 500 | 100% | 64 | ≥8 |
| NEB2 | 50% | ≥500 | 100% | 8 | ≥64 |
| NEB3 | 3.1% | ≥16 | 25% | 32 | ≥0.5 |
| NEB4 | 100% | 1000 | 100% | 32 | 32 |

AvrII-HF performed best in NEB1 and NEB4, in which the preferred FI was 1000; WT AvrII performed best in NEB1 and NEB4, in which the preferred FI was 64. The overall FI improvement factor was 1000/64=16.

Example 19: Engineering of High Fidelity BstXI

1. Expression of BstXI

BstXI was expressed in E. coli transformed with pACYCBstXIMS and pUC19-BstXIR. pACYC is a low copy compatible plasmid. The BstXI has to have both Methylase gene and the specificity gene to have a methylase function. The cells were grown at 37° C. overnight in LB with Amp and Cam.

2. Mutagenesis of BstXI 237 amino acid mutations were made in BstXI as follows. Cys, Asp, Glu, Phe, His, Lys, Met, Asn, Gln, Arg, Ser, Thr, Trp were mutated to Ala. Try was mutated to Phe. These were: 4, 6, 7, 9, 11, 12, 14, 15, 17, 18, 20, 21, 22, 23, 24, 26, 27, 29, 30, 31, 32, 33, 34, 35, 36, 37, 39, 40, 42, 43, 46, 48, 50, 53, 54, 57, 58, 59, 60, 62, 63, 64, 65, 66, 71, 72, 73, 75, 76, 78, 80, 81, 82, 83, 84, 86, 89, 91, 93, 94, 95, 96, 97, 98, 103. 105, 106, 108, 110, 111, 112, 114, 117, 118, 120, 123, 124, 125, 126, 127, 128, 129, 130, 131, 137, 138, 139, 141, 142, 144, 145, 146, 148, 151, 152, 153, 154, 155, 156, 159, 162, 163, 166, 168, 169, 171, 172, 173, 174, 175, 176, 177, 178, 182, 185, 188, 189, 191, 193, 194, 195, 196, 198, 199, 201, 204, 208, 209, 210, 211, 212, 214, 215, 216, 217, 218, 219, 220, 221, 223, 228, 229, 230, 233, 235, 236, 238, 239, 240, 244, 245, 248, 249, 250, 253, 254, 255, 258, 259, 260, 261, 263, 264, 265, 267, 268, 269, 272, 276, 277, 278, 279, 280, 282, 285, 286, 287, 288, 289, 291, 293, 294, 295, 300, 301, 302, 304, 305, 306, 308, 309, 312, 314, 317, 318, 319, 320, 323, 324, 325, 326, 330, 331, 333, 334, 335, 337, 343, 344, 345, 346, 347, 349, 353, 355, 356, 357, 358, 359, 360, 362, 363, 364, 365, 367, 369, 371, 373, 374, 376, 377, 378, 379, 380, 381, 382, and 383.

The numbers above correspond to amino acid positions in the BstXI protein sequence (SEQ ID NO:7).

The methods were the same as in the previous examples using inverse PCR followed by DpnI digestion. The treated product was then transformed into E. coli (pACYC-BstX-IMS).

3. Selection of BstXI-HF

Selection of BstXI-HF was achieved using a method that was similar to the previous examples. The cleavage activity was determined using pBC4 with 5% glycerol in NEB4 and the star activity was determined using pBC4 DNA substrate in NEB4 buffer with 39% glycerol. Mutants #36(Y57F), #44(N65A), #48(E75A), #49(N76A), and #124(K199A) all had reduced star activity. The BstXI(N65A) was labelled BstXI-HF.

4. Comparison of BstXI-HF and WT BstXI

The FIs of BstXI-HF and WT BstXI were determined separately on lambda DNA substrate with diluent A in each of NEB1-4 buffers. The comparison is shown in FIG. 26, and the result is listed in Table 25 (below).

TABLE 25

Comparison of BstXI-HF and WT BstXI

| Buffer | BstXI-HF Activity | BstXI-HF Fidelity Index | WT BstXI Activity | WT BstXI Fidelity Index | Improvement Factor |
|---|---|---|---|---|---|
| NEB1 | 50% | ≥120 | 6.3% | 4 | ≥32 |
| NEB2 | 100% | ≥250 | 100% | 32 | ≥8 |
| NEB3 | 6.3% | ≥16 | 100% | 2 | ≥8 |
| NEB4 | 100% | ≥250 | 100% | 32 | ≥32 |

BstXI-HF performed best in NEB2 and NEB4, in which the preferred FI was 250; WT BstXI performed best in NEB2, NEB3 and NEB4, in which the preferred FI was 32. The overall FI improvement factor was 250/32=8.

Example 20: Engineering of High Fidelity PciI

1. Expression of PciI

PciI was expressed in E. coli transformed with pACYC-PciIM and placzz1-PciIR. placzz1 is a pUC19 derivative plasmid, pACYC is a low copy compatible plasmid. The cells were grown at 37° C. overnight in LB with Amp and Cam.

2. Mutagenesis of PciI 151 amino acid residues in PciI were mutated with Cys, Asp, Glu, Phe, His, Lys, Met, Asn, Gln, Arg, Ser, Thr. Trp was changed to Ala and Tyr to Phe. These were: 2, 3, 4, 6, 8, 9, 10, 11, 12, 14, 17, 18, 19, 21, 24, 25, 26, 28, 29, 30, 31, 33, 34, 35, 36, 38, 39, 41, 44, 46, 47, 49, 50, 51, 54, 55, 56, 58, 59, 60, 63, 67, 68, 69, 71, 74, 75, 78, 80, 81, 82, 85, 86, 91, 92, 95, 97, 98, 101, 103, 104, 107, 109, 113, 114, 115, 118, 119, 120, 121, 122, 124, 126, 127, 129, 130, 131, 132, 133, 135, 136, 137, 138, 143, 145, 146, 147, 148, 149, 151, 152, 153, 154, 155, 157, 158, 159, 161, 164, 165, 167, 172, 175, 178, 179, 180, 182, 184, 185, 186, 190, 192, 193, 196, 197, 198, 199, 200, 202, 203, 206, 207, 209, 210, 215, 218, 221, 222, 228, 229, 230, 231, 232, 233, 234, 235, 237, 238, 239, 241, 242, 243, 244, 246, 247, 248, 253, 254, 255, 256.

The numbers above correspond to amino acid positions in the PciI protein sequence (SEQ ID NO:15).

The methods were the same as in the previous examples using inverse PCR followed by DpnI digestion. The treated product was then transformed into *E. coli* (pACYC-PciIM).

3. Selection of PciI-HF

Selection of PciI-HF was achieved using a method that was similar to the previous examples. The cleavage activity was determined using SalI-cut pBR322 with 5% glycerol in NEB4 and the star activity was determined using SalI-cut pBR322 in ExoI buffer with 39% glycerol. A double mutant PciI(E78A/S133A) had reduced star activity and strong cleavage activity. This mutant was not one of the targeted mutations described above, but was a fortuitous random event.

4. Comparison of PciI-HF and WT PciI

The FIs of PciI-HF and WT PciI were determined separately on pXba substrate with diluent A in each of NEB1-4 buffers. The comparison is shown in FIG. 27, and the result is listed in Table 26 (below).

TABLE 26

Comparison of PciI-HF and WT PciI

| | PciI-HF | | WT PciI | | |
|---|---|---|---|---|---|
| Buffer | Activity | Fidelity Index | Activity | Fidelity Index | Improvement Factor |
| NEB1 | NC | NC | 50% | 2000 | N/A |
| NEB2 | 100% | ≥2000 | 25% | 16 | ≥120 |
| NEB3 | 100% | ≥2000 | 100% | 120 | ≥16 |
| NEB4 | 100% | ≥1000 | 12.5% | 8 | ≥120 |

PciI-HF performed best in NEB2, NEB3 and NEB4, in which the preferred FI was 2000; WT PciI performed best in NEB3, in which the preferred FI was 120. The overall FI improvement factor was 2000/120=16.

Example 21: Engineering of High Fidelity HpaI

1. Expression of HpaI

HpaI was expressed in *E. coli* transformed with pACYC-MseIM and placzz1-HpaIR. placzz1 is a pUC19 derivative plasmid, pACYC is a low copy compatible plasmid. The cells were grown at 37° C. overnight in LB with Amp and Cam.

2. Mutagenesis of HpaI 156 amino acid residues in HpaI were mutated with Cys, Asp, Glu, Phe, His, Lys, Met, Asn, Gln, Arg, Ser, and Thr. Trp was changed to Ala and Tyr to Phe. These were: 7, 8, 9, 13, 14, 16, 17, 19, 20, 21, 22, 23, 26, 27, 29, 30, 33, 34, 35, 36, 37, 38, 40, 41, 42, 46, 47, 48, 50, 51, 56, 57, 59, 60, 65, 67, 69, 71, 72, 74, 75, 78, 79, 80, 81, 82, 83, 84, 85, 86, 89, 91, 93, 94, 95, 99, 100, 104, 105, 106, 108, 109, 110, 113, 115, 117, 119, 121, 122, 123, 124, 127, 128, 130, 131, 133, 135, 136, 137, 138, 139, 141, 142, 146, 147, 149, 150, 152, 156, 158, 159, 160, 162, 164, 165, 166, 167, 168, 169, 170, 172, 173, 176, 177, 180, 181, 182, 184, 185, 187, 188, 190, 191, 192, 193, 195, 196, 197, 202, 204, 206, 208, 209, 211, 212, 214, 215, 216, 217, 218, 219, 220, 221, 222, 223, 224, 225, 228, 230, 231, 233, 234, 235, 236, 237, 238, 240, 241, 242, 243, 244, 245, 247, 248, 249.

The numbers above correspond to amino acid positions in the HpaI protein sequence (SEQ ID NO:86).

The methods were the same as in the previous examples using inverse PCR followed by DpnI digestion. The treated product was then transformed into *E. coli* (pACYC-MseIM).

3. Selection of HpaI-HF

Selection of HpaI-HF was achieved using a method that was different to the previous examples. The cleavage activity and star activity were determined using lambda DNA substrate in NEB2 buffer. This HpaI has much more star activity in NEB2 than NEB4, and could be clearly observed in 5% glycerol.

HpaI(Y29F) and HpaI(E56A) were both preferred mutations with reduced star activity. HpaI(E56A) was labelled HpaI-HF.

4. Comparison of HpaI-HF and WT HpaI

The FIs of HpaI-HF and WT HpaI were determined separately on lambda DNA substrate with diluent A in each of NEB1-4 buffers. The comparison is shown in FIG. 28, and the result is listed in Table 27 (below).

TABLE 27

Comparison of HpaI-HF and WT HpaI

| | HpaI-HF | | WT HpaI | | |
|---|---|---|---|---|---|
| Buffer | Activity | Fidelity Index | Activity | Fidelity Index | Improvement Factor |
| NEB1 | 3.1% | ≥32 | 6.3% | 32 | ≥1 |
| NEB2 | 100% | ≥2000 | 25% | 1 | ≥2000 |
| NEB3 | 12.5% | 2 | 12.5% | 2 | 1 |
| NEB4 | 50% | ≥2000 | 100% | 16 | ≥120 |

HpaI-HF performed best in NEB2, in which the preferred FI was 2000; WT PciI performed best in NEB4, in which the preferred FI was 16. The overall FI improvement factor was 2000/16=120.

Example 22: Engineering of High Fidelity AgeI

1. Expression of AgeI

AgeI was expressed in *E. coli* transformed with pRRS-AgeIRM and psyx20-lacIq. pRRS is a pUC19 derivative plasmid, psyx20-lacIq is a low copy compatible plasmid with lacI expressed under lacIq promoter. The cells were grown at 37° C. in LB with Amp and Kan to 200 Klett units, and then induced at 25° C. with 0.5 mM IPTG overnight. The expression of AgeI was extremely difficult to achieve because it was unstable.

2. Mutagenesis of AgeI 149 amino acid residues in AgeI were mutated with Cys, Asp, Glu, Phe, His, Lys, Met, Asn, Gln, Arg, Ser, and Thr. Trp was changed to Ala and Tyr to Phe. These were: 2, 4, 6, 7, 9, 14, 16, 18, 19, 21, 22, 23, 24, 25, 26, 27, 29, 30, 31, 32, 37, 38, 40, 42, 43, 44, 45, 49, 51, 53, 55, 56, 58, 60, 62, 64, 65, 67, 68, 69, 72, 73, 75, 77, 78, 79, 82, 83, 85, 86, 87, 88, 90, 91, 92, 94, 96, 97, 102, 103, 104, 105, 110, 111, 114, 116, 119, 120, 122, 123, 128, 129, 130, 134, 135, 138, 139, 140, 142, 144, 146, 147, 148, 152, 153, 155, 157, 159, 166, 168, 170, 173, 174, 176, 177, 178, 182, 183, 185, 186, 188, 192, 195, 198, 200, 201, 206, 211, 212, 214, 217, 219, 220, 222, 223, 224, 225, 226, 227, 229, 231, 233, 234, 235, 237, 238, 239, 240, 241, 243, 245, 247, 248, 250, 251, 253, 255, 256, 258, 260, 262, 265, 266, 267, 268, 269, 271, 272

The methods were the same as in the previous examples using inverse PCR followed by DpnI digestion. The treated product was then transformed into *E. coli* (psyx20-lacIq).

The numbers above correspond to amino acid positions in the AgeI protein 5 sequence (SEQ ID NO:79).

3. Selection of AgeI-HF

Selection of AgeI-HF was achieved using a method that was similar to the previous examples. The standard activity check used pXba with 5% glycerol in NEB4 and the star activity check was on pXba in NEB4 buffer with 39% glycerol. Because of the difficulty of the expression system, this selection was repeated eight times before meaningful mutants were obtained. Two mutants, S201A and R139A had reduced star activity and R139A was labelled AgeI-HF.

4. Comparison of AgeI-HF and WT AgeI

The FIs of AgeI-HF and WT AgeI were determined separately on pXba substrate with diluent A in each of NEB1-4 buffers. The comparison is shown in FIG. 29, and the result is listed in Table 28 (below).

TABLE 28

Comparison of AgeI-HF and WT AgeI

| | AgeI-HF | | WT AgeI | | |
|---|---|---|---|---|---|
| Buffer | Activity | Fidelity Index | Activity | Fidelity Index | Improvement Factor |
| NEB1 | 100% | ≥500 | 100% | 16 | ≥32 |
| NEB2 | 50% | ≥250 | 50% | 8 | ≥32 |
| NEB3 | 6.3% | ≥16 | 12.5% | 64 | ≥0.25 |
| NEB4 | 100% | ≥250 | 50% | 8 | ≥32 |

AgeI-HF performed best in NEB1, and NEB4, in which the preferred FI was 500; WT AgeI performed best in NEB3, in which the preferred FI was 16. The overall FI improvement factor was 500/16=32.

Example 23: Engineering of High Fidelity BsmBI

1. Expression of BsmBI

BsmBI was expressed in *E. coli* transformed with pACYC-BsmAIM, ptaczz2-BsmBIR and psyx20-lacIq. Ptaczz2 is a pUC19 derivative plasmid which carries a inducible ptac promoter, pACYC is a low copy compatible plasmid. BsmAIM (GTCTC) covers BsmBI (CGTCTC) specificity. The psyx20-lacIq is a low copy vector with strong express of lacI. The cells were grown at 37° C. then induced in LB with Amp, Cam and Kan.

2. Mutagenesis of BsmBI 358 amino acid residues in BsmBI were mutated with Cys, Asp, Glu, Phe, His, Lys, Met, Asn, Gln, Arg, Ser, and Thr. Trp was changed to Ala and Tyr to Phe. These were: 8, 9, 12, 13, 14, 15, 17, 18, 19, 20, 21, 24, 25, 26, 27, 28, 29, 31, 33, 37, 38, 40, 42, 43, 44, 46, 47, 49, 50, 51, 52, 53, 54, 55, 56, 57, 58, 60, 61, 62, 63, 64, 65, 66, 67, 69, 70, 72, 76, 78, 79, 80, 81, 82, 83, 84, 88, 91, 93, 95, 96, 98, 99, 101, 103, 104, 105, 106, 109, 110, 111, 113, 114, 115, 117, 118, 119, 120, 121, 122, 124, 126, 127, 128, 130, 131, 132, 133, 134, 135, 138, 141, 143, 144, 145, 147, 149, 150, 154, 155, 157, 158, 160, 162, 163, 164, 165, 166, 167, 168, 169, 172, 174, 175, 176, 177, 179, 180, 181, 182, 184, 185, 186, 188, 189, 191, 194, 195, 197, 200, 201, 203, 205, 206, 207, 208, 211, 212, 213, 214, 215, 216, 217, 220, 221, 222, 223, 224, 225, 226, 228, 229, 230, 231, 232, 233, 235, 236, 237, 238, 239, 240, 242, 243, 247, 250, 251, 252, 257, 258, 260, 262, 263, 264, 265, 266, 268, 269, 271, 273, 274, 279, 280, 282, 283, 284, 287, 288, 289, 292, 294, 295, 296, 297, 299, 300, 301, 302, 303, 304, 305, 306, 307, 309, 310, 313, 314, 315, 316, 317, 318, 320, 321, 324, 325, 326, 328, 331, 332, 333, 334, 335, 336, 339, 340, 341, 342, 343, 344, 345, 348, 349, 351, 352, 353, 355, 356, 357, 358, 360, 361, 363, 364, 366, 367, 368, 370, 372, 375, 376, 377, 379, 381, 382, 384, 385, 386, 388, 389, 390, 393, 394, 395, 396, 398, 399, 400, 401, 402, 403, 404, 405, 406, 407, 408, 409, 410, 411, 412, 413, 414, 418, 421, 424, 425, 426, 428, 430, 431, 432, 433, 434, 436, 437, 438, 439, 442, 443, 444, 445, 446, 446, 448, 449, 450, 451, 452, 453, 454, 457, 458, 460, 461, 462, 464, 466, 467, 468, 470, 471, 472, 473, 474, 477, 478, 479, 480, 482, 483, 484, 485, 486, 487, 488, 489, 491, 492, 495, 496, 497, 498, 499, 500, 502, 503, 504, 505, 506, 507, 510, 511, 515, 516, 517, 518, 519, 522, 523.

The numbers above correspond to amino acid positions in the BsmBI protein sequence (SEQ ID NO:81).

The methods were the same as in the previous examples using inverse PCR followed by DpnI digestion. The treated product was then transformed into *E. coli* (pACYC-BsmAIM, psyx20-lacIq).

3. Selection of BsmBI-HF

Selection of BsmBI-HF was achieved using a method that was similar to the previous examples. The cleavage was determined using lambda DNA with 5% glycerol in NEB4 and the star activity was determined using Litmus28i in NEB4 buffer with 39% glycerol. Preferred mutants included H230A, D231A and N185Y/R232A. N185Y/R232A was labeled BsmBI-HF.

4. Comparison of BsmBI-HF and WT BsmBI

The FIs of BsmBI-HF and WT BsmBI were determined separately on lambda DNA substrate with diluent A in each of NEB1-4 buffers. The comparison is shown in FIG. 30, and the result is listed in Table 29 (below).

TABLE 29

Comparison of BsmBI-HF and WT BsmBI

| | BsmBI-HF | | WT BsmBI | | |
|---|---|---|---|---|---|
| Buffer | Activity | Fidelity Index | Activity | Fidelity Index | Improvement Factor |
| NEB1 | 100% | 32 | 12.5% | 1 | 32 |
| NEB2 | 100% | ≥500 | 50% | 8 | ≥64 |
| NEB3 | 12.5% | ≥64 | 100% | 120 | ≥0.5 |
| NEB4 | 100% | ≥500 | 25% | 4 | ≥120 |

BsmBI-HF performed best in NEB1, NEB2 and NEB4, in which the preferred FI was ≥500, WT BsmBI performed best in NEB3, in which the preferred FI was 120. The overall FI improvement factor was 500/120=4.

Example 24: Engineering BspQI Variants with Reduced Star Activity

1. Site-Directed Mutagenesis of BspQI Restriction Endonuclease

*E. coli* was transformed with pSX33-EarIM1M2 and pZZlacI-PspQI that was $Km^R$ and $Amp^R$). M.EarI (CTCTTC) also modifies BspQI site (GCTCTTC) and therefore pSX33-earIM1M2 (FIGS. 17 and 18) was used to co-transform and modify the *E. coli* chromosome. The WT amino acid sequence is shown in FIG. 16.

122 charged or non-charged amino acid residues in BspQI (Arg, Lys, His, Glu, Asp, Gln, Asn, Cys) were changed to Ala by site-directed mutagenesis. PCR was carried out under the following conditions: DNA denaturation, 98° C. for 30 sec, 1 cycle; DNA denaturation/primer annealing/extension, 98° C. for 10 sec, 55° C. to 65° C. for 30 sec, 72° C. for 2 min, for PCR 18 cycles; 72° C. for 15 min, 1 cycle. In 100 µl reactions, 2 units of Phusion™ DNA polymerase (NEB, Ipswich, MA), 1 mM dNTP, 10 ng to 100 ng template DNA, 20 µl 5× reaction buffer, 0.04 µM primers, sterile water to 100 µl total volume.

PCR DNA was digested with DpnI to destroy template DNA (Dam methylated) and co-transformed with pSX33-earIM1M2 into *E. coli*. Individual transformants were cultured overnight (5 ml LB, 50 µg/ml Km$^R$ and 100 µg/ml Amp$^R$) and split into two parts. One part (1.5 ml) was harvested by centrifugation and lysed by sonication in a sonication buffer (20 mM Tris-HCl, pH 7.5, 0.1 mM DTT, 50 mM NaCl, 10% glycerol). The cell extract was heated at 50° C. for 1 h and denatured E. coli proteins were removed by centrifugation. The clarified lysate was assayed for restriction activity and star activity on pUC19 DNA.

BspQI star activity assay condition: 1 µg pUC19 DNA, 5 µl of 10×NEB buffer 1, 25% DMSO, 2.5 µl clarified cell extract, sterile deionized water to 50 µl total volume and incubated at 50° C. for 1 h. Digested DNA was resolved by electrophoresis in 0.8 to 1% agarose gel.

The second part of the cell culture (uninduced) was harvested and plasmid DNA was prepared by Qiagen spin column purification procedure (Qiagen, Valencia, CA). The bspQIR alleles were sequenced by Big-dye dideoxy-terminator sequencing method to confirm the desired mutations. After identification of reduced star activity mutants, fresh transformants were obtained and IPTG-induced cultures were made. Restriction and star activity was assayed again to confirm the reduced star activity in comparison with the WT enzyme in all four buffers.

Among the 122 BspQI mutants constructed by site-directed mutagenesis, two BspQI variants, R388A and K279A, display reduced star activity. The star activity of R388A was reduced approximately 16-fold in buffer 1 and 10% glycerol. However, R388A still displayed star activity at high enzyme concentration. BspQI variant K279A also displayed reduced star activity (>8-fold improvement in reduced star activity).

To further reduce star activity at high enzyme concentration, R388 and K279 were substituted for Phe, Pro, Tyr, Glu, Asp, or Leu. IPTG-induced cell extracts of various R388X, and K279X mutants were assayed for restriction and star activity. It was found that R388F or K279P displayed the minimal star activity in either cell extracts or purified enzyme. The specific activity was not affected by the amino acid substitutions.

To still further reduce BspQI star activity, the two amino acid substitutions were combined into one mutant enzyme (double mutant, K279P/R388F) by site-directed mutagenesis. This double mutant lacks star activity in buffer 1 and buffer 2 with 10% glycerol (FIG. 41B).

TABLE 30

BspQI-HF vs WT BspQI

| Buffer | BspQI-HF Activity | BspQI-HF Fidelity Index | WT BspQI Activity | WT BspQI Fidelity Index | Improvement Factor |
|---|---|---|---|---|---|
| NEB1 | 25% | ≥1000 | 12.5% | 2 | ≥1000 |
| NEB2 | 25% | ≥1000 | 100% | 16 | ≥64 |
| NEB3 | 1.3% | ≥64 | 100% | 32 | ≥2 |
| NEB4 | 100% | ≥4000 | 50% | 4 | ≥1000 |

Example 25: Engineering SapI Variants with Reduced Star Activity

The conserved K279 and R388 amino acid residues were found in BspQI where corresponding positions are K273 and R380 in SapI. A 6×His tagged SapI expression clone was first constructed in pUC19. The SapI expression strain was E. coli transformed with pSX33-earIM1M2 and pUC-SapI that was Km$^R$ and Amp$^R$. Lys273 to Pro (K273P) and Arg 380 to Phe (R380F) amino acid substitutions were introduced into SapI by site-directed mutagenesis. SapI single mutant R380A was also constructed. Both SapI variants R380A and K273P/R380F showed reduced star activity when restriction activity and star activity reactions were performed (FIG. 42).

PCR, transformation, plasmid DNA preparation, and enzyme activity assay were carried out as described for BspQI, except that SapI activity was determined at 37° C. The 6×His-tagged SapI variant K273P/R380F was purified through Ni-NTA column chromatography and shown to display diminished star activity in the presence of 25% DMSO or 5% glycerol.

Example 26: Engineering KpnI High Fidelity Mutants

KpnI, which contains two activities, has been changed into a mutant with lower star activity (International Publication No. WO 07/027464). The example below describes novel mutants with improved star activity and similar cleavage activity to the wild-type.

Charged amino acid residues except the catalytic residues, (Asp, Glu, Arg, Lys and His) or polar amino acids (Ser, Thr, Tyr, Asn, Gln, Phe, Trp, Cys and Met) were individually mutated to Alanine.

Mutagenesis was carried out by inverse PCR using primers bearing the desired mutations. In general, inverse PCR was performed using 0.4 mM of each of the 4 dNTP, 1× ThermoPol Buffer (NEB), 20 ng of template DNA, 40 pmol of each of the primers and 4 U of Vent DNA polymerase (NEB) in a final volume of 100 µL.

Plasmids pUC19 or pAGR3 containing the KpnIR under the control of Plac or Ptac promoter, respectively, were used as template. PCRs were done with a temperature scheme of 94° C. for 4 minutes followed by 25 cycles of 94° C. for 30 seconds for denaturation, 55° C. for 30 seconds for annealing and 72° C. for 5 minutes for extension. The cycles were followed by incubation at 72° C. for 7 minutes before the reactions were treated by 20 U of DpnI (NEB) at 37° C. for 1 hour to degrade the template DNA. After inactivating DpnI at 80° C. for 20 minutes, 2 µl of the reaction was used to transform 50 µL of chemically competent NEBSalpha (NEB) pre-transformed by pSYX20-KpnIM. The transformed bacteria were plated onto LB plates containing 100 µg/ml of ampicillin and 30 µg/ml of kanamycin, and incubated at 37° C. for 12 to 15 hours. Three to four colonies of each construct were cultured in 1 ml of LB containing 100 µg/ml of ampicillin and 30 µg/ml of kanamycin at 37° C. for 12 to 15 hours with shaking of 200 rpm. The cultures were spun down and resuspended in 0.2 ml of sonication buffer (20 mM Tris-HCl, pH 8.3, 50 mM NaCl, 1 mM EDTA, 1 mM PMSF.) The resuspended cells were sonicated for 20 seconds, followed by centrifugation at 13,000 rpm at 4° C. for 5 min. Dilutions of the supernatant were made and 5 µL of which were assayed for KpnI cleavage activity.

For the screening of the mutants, an activity assay reaction was performed using 5 µL of 10- or 100-fold dilutions of the lysate supernatant, 0.5 ug of pXba DNA (NEB) and 1×NEBuffer 4 in a total volume of 50 µL. After incubating at 37° C. for 1 hour, the assay reactions were stopped by adding 10 ul of 6×DNA loading dye and analyzed by electrophoresis through 0.8% agarose gels in 1×TBE. Mutants that showed increased overall cleavage activity compared with the parent enzyme (KpnI D148E) were assayed for reduced star activity in a buffer containing 25% DMSO.

The assay was performed using 5 μL of dilutions of the enzymes incubated with 1 μg of pXba DNA (NEB) in the presence of 5% glycerol and 0.2 mg/ml of BSA in 1× NEBuffer 4 (total volume=50 μL). After incubation at 37° C. for 1 hour, the reactions were treated by 20 μg of proteinase K (NEB) at 37° C. for 15 minutes and then analyzed by electrophoresis through 0.8% agarose gels in 1×TBE. Divalent metal-dependent assays were carried out at 37° C. for 1 hour, using 50 U of enzyme and 1 μg of pXba DNA in a buffer containing 20 mM Tris HCl, 50 mM NaCl, pH 7.9, 1 mM DTT and increasing concentration of MgSO4/CaCl2)/MnCl2, followed by electrophoresis through 0.8% agarose gels in 1×TBE. The total reaction volume is 50 μL.

The result of random mutagenesis, was a preferred mutant, KpnI D148E, which showed lower star activity than the wild-type enzyme and KpnI D163I/K165A mutant described previously (International Publication No. WO 07/027464). However, KpnI D148E displayed star activity at high enzyme concentration. Double and triple mutants were constructed in D148E background to reduce this observed star activity. KpnI (D16N/E132A/D148E) was found to have lower star activity and higher specificity activity than mutant D148E. Amino acid substitutions D148 to E and E132 to A were introduced by site-directed mutagenesis. The D16 to N mutation was introduced by PCR. In standard reaction condition, one-hour incubation of purified enzymes with substrate DNA pXba (containing 6 KpnI sites) at 37° C.), resulted in the reduced star activity shown in Table 31.

TABLE 31

Fidelity indices for KpnI mutants

| | KpnI-HF | | WT KpnI | | |
|---|---|---|---|---|---|
| Buffer | Activity | Fidelity Index | Activity | Fidelity Index | Improvement Factor |
| NEB1 | 100% | ≥4000 | 100% | 16 | ≥250 |
| NEB2 | 50% | ≥2000 | 25% | 16 | ≥64 |
| NEB3 | 6.3% | ≥250 | 6.3% | 8 | ≥32 |
| NEB4 | 100% | ≥4000 | 50% | 4 | ≥1000 |

No star activity of pXba was observed for mutant D16N/E132A/D148E up to 4000U. Star activity observed for pBR322 substrate, which bears no KpnI site, was also diminished when cleaved with KpnI D148E and D16N/E132A/D148E.

Example 27: Engineering of High Fidelity BsaI

1. Expression of BsaI

BsaI was expressed in *E. coli* transformed with pACYC-BsmAIM, pUC19-BsaIR and psyx20-lacIq. pACYC is a low copy compatible plasmid. BsmAIM(GTCTC) covers BsmBI specificity(CGTCTC). The psyx20-lacIq is a low copy vector with strong express of lacI. The cells were grown at 37° C. then induced in LB with Amp, Cam and Kan.

2. Mutagenesis of BsaI

The amino acid of BsaI is similar to that of BsmBI. 11 amino acids around and at the corresponding previous effective site is mutated as R229A, S230A, Y231F, T232A, T233A, D234A, R235A, R236A, F238A, E239A, Y240F.

The methods were the same as in the previous examples using inverse PCR followed by DpnI digestion. The treated product was then transformed into *E. coli* (pACYC-BsmAIM, psyx20-lacIq).

3. Selection of BsaI-HF

Selection of BsaI-HF was achieved using a method that was similar to the previous examples. The standard activity check used lambda DNA with 5% glycerol in NEB4 and the star activity check was litmus28i in NEB4 buffer with 39% glycerol. One mutant, Y231F, out of the 11 designed ones, reduced star activity and labeled as BsaI-HF.

4. Comparison of BsaI-HF and WT BsaI

The FIs of BsaI-HF and WT BsaI were determined separately on lambda DNA with diluent A in NEB1-4 buffers. The result is listed in Table 32 (below).

TABLE 32

Comparison of BsaI-HF and WT BsaI

| | BsaI-HF | | WT BsaI | | |
|---|---|---|---|---|---|
| Buffer | Activity | Fidelity Index | Activity | Fidelity Index | Improvement Factor |
| NEB1 | 50% | ≥4000 | 25% | 8 | ≥500 |
| NEB2 | 100% | ≥8000 | 100% | 120 | ≥64 |
| NEB3 | 100% | 120 | 25% | 16 | 8 |
| NEB4 | 100% | ≥8000 | 100% | 32 | ≥250 |

BsaI-HF performed best in NEB2, NEB3 and NEB4, in which the best FI was 8000; WT BsaI performed best in NEB2 and NEB4, in which the best FI was 120. So the overall FI improvement factor was 8000/120=64.

What is claimed is:

1. A composition comprising a variant BspQI restriction endonuclease, wherein the variant BspQI restriction endonuclease comprises an amino acid sequence having one, two, or all three of the following substitutions:
   - a substitution at a position corresponding to 244 in SEQ ID NO: 16;
   - a substitution at a position corresponding to 279 in SEQ ID NO: 16; and
   - a substitution at a position corresponding to 388 in SEQ ID NO: 16.

2. A composition according to claim 1, wherein the substitution corresponding to position 244 is D244A.

3. A composition according to claim 1, wherein the substitution corresponding to position 279 is K279A, K279D, K279E, K279F, K279L, K279P, or K279Y.

4. A composition according to claim 1, wherein the substitution corresponding to position 279 is K279P.

5. A composition according to claim 1, wherein the substitution corresponding to position 388 is R388A, R388D, R388E, R388F, R388L, R388P, or R388Y.

6. A composition according to claim 1, wherein the substitution corresponding to position 388 is R388F.

7. A composition according to claim 1, wherein the variant BspQI restriction endonuclease comprises an amino acid sequence having the following substitutions:

a substitution at a position corresponding to 279 in SEQ ID NO: 16; and a substitution at a position corresponding to 388 in SEQ ID NO: 16.

8. The composition according to claim 7, wherein the substitutions at positions 279 and 388, are K279A and R388A.

9. The composition according to claim 7, wherein the substitutions at positions 279 and 388, are K279P and R388F.

* * * * *

SEQUENCE LISTING

<160> NUMBER OF SEQ ID NOS: 106

<210> SEQ ID NO 1
<211> LENGTH: 1089
<212> TYPE: DNA
<213> ORGANISM: Micrococcus luteus

<400> SEQUENCE: 1

```
atgatcaagt acttgggtag caagcggacg ctcgtgcccg tcctcggtga catcgcttcg      60
gcctctgaag caacagaggc ggttgacctg ttcactggca cgacgcgtgt ggcgcaagag     120
ttcaagcgtc gcgggcttcg agttcttgct aacgacatag cgacgtactc cgaggtttta     180
gcccagtgct atatcgccac caacgccag gaagttgacc gccgtgcgct cgaggccgct     240
ctggcggagc tgaacgcctt gcccggcgaa cctggatact tcacggaaac cttctgtgag     300
```

```
gcttctcgct acttccagcc caagaacggg gctcgggtgg atgcaatcag gaatgcgatc      360
gacgaccggt acgcggactc atggatgcga ccgatcctcc tcacgagctt gatgcttgcg      420
gccgaccgcg tcgactccac taccggagtg cagatggctt acctgaagca gtgggccgcg      480
cgtgcgcaca atgatctaga gttgcggctt ccagacctaa tcgcaggtga cggtgacgct      540
gctcgtgagg atgcggtgac tctcgcacaa gagctgcctc gcgtccagct gatgtacctt      600
gatcctccct ataaccagca caggtacttc accaactacc atatttggga gaccctgatt      660
cgttgggatg cccctgagag ttatgggatc gcctgtaagc gcattgactc tcgagatgat      720
gccaccaaga gccctataaa tatgaagcgg cgaatgcccg acgagatgcg tcgcctgctg      780
atgaccatca aggcggacct cgcggttgta tcttacaaca atgagtcgtg gattgatccg      840
gagacgatga tgtcgaccct gcgcgatgcg ggatatgagg acgtgcgtct gctcgctttc      900
gactataagc gctacgttgg ggctcaaatc gggatctaca atccctccgg ggaaaaggtc      960
ggtcgtgtga gtcacctccg aaacatcgag tatctctttc ttgcgggacc aacggagcgc     1020
gttgaggtgt gcgccgcgag tgttgaacac cgagcactac ccaaggaacc ggaactcacc     1080
gcgttctag                                                             1089
```

<210> SEQ ID NO 2
<211> LENGTH: 362
<212> TYPE: PRT
<213> ORGANISM: Micrococcus luteus

<400> SEQUENCE: 2

```
Met Ile Lys Tyr Leu Gly Ser Lys Arg Thr Leu Val Pro Val Leu Gly
1               5                   10                  15

Asp Ile Ala Ser Ala Ser Glu Ala Thr Glu Ala Val Asp Leu Phe Thr
            20                  25                  30

Gly Thr Thr Arg Val Ala Gln Glu Phe Lys Arg Arg Gly Leu Arg Val
        35                  40                  45

Leu Ala Asn Asp Ile Ala Thr Tyr Ser Glu Val Leu Ala Gln Cys Tyr
    50                  55                  60

Ile Ala Thr Asn Gly Gln Glu Val Asp Arg Arg Ala Leu Glu Ala Ala
65                  70                  75                  80

Leu Ala Glu Leu Asn Ala Leu Pro Gly Glu Pro Gly Tyr Phe Thr Glu
                85                  90                  95

Thr Phe Cys Glu Ala Ser Arg Tyr Phe Gln Pro Lys Asn Gly Ala Arg
            100                 105                 110

Val Asp Ala Ile Arg Asn Ala Ile Asp Asp Arg Tyr Ala Asp Ser Trp
        115                 120                 125

Met Arg Pro Ile Leu Leu Thr Ser Leu Met Leu Ala Ala Asp Arg Val
    130                 135                 140

Asp Ser Thr Thr Gly Val Gln Met Ala Tyr Leu Lys Gln Trp Ala Ala
145                 150                 155                 160

Arg Ala His Asn Asp Leu Glu Leu Arg Leu Pro Asp Leu Ile Ala Gly
                165                 170                 175

Asp Gly Asp Ala Ala Arg Glu Asp Ala Val Thr Leu Ala Gln Glu Leu
            180                 185                 190

Pro Arg Val Gln Leu Met Tyr Leu Asp Pro Pro Tyr Asn Gln His Arg
        195                 200                 205

Tyr Phe Thr Asn Tyr His Ile Trp Glu Thr Leu Ile Arg Trp Asp Ala
    210                 215                 220
```

| | | | | | | | | | | | | | | |
|---|---|---|---|---|---|---|---|---|---|---|---|---|---|---|
Pro | Glu | Ser | Tyr | Gly | Ile | Ala | Cys | Lys | Arg | Ile | Asp | Ser | Arg | Asp | Asp
225 | | | | 230 | | | | | 235 | | | | | 240

Ala Thr Lys Ser Pro Tyr Asn Met Lys Arg Arg Met Pro Asp Glu Met
245 250 255

Arg Arg Leu Leu Met Thr Ile Lys Ala Asp Leu Ala Val Val Ser Tyr
260 265 270

Asn Asn Glu Ser Trp Ile Asp Pro Glu Thr Met Met Ser Thr Leu Arg
275 280 285

Asp Ala Gly Tyr Glu Asp Val Arg Leu Leu Ala Phe Asp Tyr Lys Arg
290 295 300

Tyr Val Gly Ala Gln Ile Gly Ile Tyr Asn Pro Ser Gly Glu Lys Val
305 310 315 320

Gly Arg Val Ser His Leu Arg Asn Ile Glu Tyr Leu Phe Leu Ala Gly
325 330 335

Pro Thr Glu Arg Val Glu Val Cys Ala Ala Ser Val Glu His Arg Ala
340 345 350

Leu Pro Lys Glu Pro Glu Leu Thr Ala Phe
355 360

<210> SEQ ID NO 3
<211> LENGTH: 1146
<212> TYPE: DNA
<213> ORGANISM: Helicobacter pylori J166

<400> SEQUENCE: 3

```
ttggagaatt ttttgaataa tttagatatt aaaaccttag ggcaggtttt cacccctaaa      60
aagatagtgg atttcatgct cactctcaag cacaatcatg ggagtgtttt agagccaagc     120
gcgggcgatg ggagtttttt aaagcgctta aaaaaggctg tagggattga aatcgatcct     180
aaaatctgcc ctaaaaatgc cctttgcatg gactttttttg actaccctttt agaaaatcaa     240
tttgacacga ttattggcaa tccgccctat gtcaagcaca aggatattgc gccaagcacg     300
aaagaaaaac tccattacag ccttttttgat gaaaggagta atctatactt gttttttcata     360
gaaaaagcga tcaagcattt aaagcctaaa ggcgaattga ttttcatcac cccaagggat     420
ttttttaaaat ccacttctag cgtgaaatta acgaatgga tttacaaaga aggcacgata     480
acgcattttt ttgaattagg cgatcaaaag attttcccaa cgccatgcc taattgcgtg     540
attttttcgtt tttgtaaagg tgatttcagt agaatcacca cgatggttt gcaatttgtg     600
tgcaaaaaag gcattttgta tttcctcaac caatcttaca cgcaaaaatt aagcgaggtt     660
tttaaggtta aggtgggggc agtgagcggg tgcgataaga tttttaaaaa tgaaacatac     720
gggaatttag aatttgtcac ctcaatcacc aaaagaacca atgttttaga aaaaatggtt     780
tttgtcaata aacctaatga ttatttactc cagcataaag acagcttgat gcaaagaaag     840
attaaaaaat tcaatgaaag taattggttt gaatggggga ggatgcatca catatcccct     900
aaaaaacgca tttatgttaa cgccaaaacg cgccaaaaaa acccctttttt catccaccaa     960
tgccctaatt atgacggctc tatttttagcg ctattcccttt ataaccaaaa tttggattta    1020
caaaaccctct gcgataaact caacgctatc aactggcaag aattaggctt tgtgtgcggc    1080
gggcgttttt tgttttcgca gcgctctttta gaaaacgccc ttttgcctaa agacttttta    1140
aattag                                                                1146
```

<210> SEQ ID NO 4
<211> LENGTH: 609
<212> TYPE: DNA

<213> ORGANISM: Mycoplasma fermentans

<400> SEQUENCE: 4

```
atgggtaaat ctgaattaag tggaagatta aattggcaag cattggctgg attaaaagct      60
agtggtgctg aacaaaactt atataacgtg tttaacgctg tttttgaagg aactaaatac     120
gttttatacg agaagccaaa gcaccttaaa aatctatacg ctcaagtagt cttacctgat     180
gatgttatta agaaattttt aatcccttta attgatttat caactactca atggggtgtt     240
tctccagatt tcgcaataga aaatacagaa acgcataaaa ttcttttttgg tgaaattaaa   300
agacaagatg gatgggtaga aggtaaagat cctagtgctg caggggtaa tgcacatgag     360
agatcttgta aattatttac tcctggatta ttaaaagctt atagaacaat tggtggaatt     420
aacgatgaag atatattgcc attctgggtt gtattcgaag gtgatataac acgagatccc     480
aaaagagtaa gagaaattac tttctggtat gaccactatc aagataatta tttcatgtgg     540
cgaccaaatg aatcaggcga aaaattagtt caacacttca tgaaaaaatt aaaaaaatat     600
ttagattaa                                                             609
```

<210> SEQ ID NO 5
<211> LENGTH: 202
<212> TYPE: PRT
<213> ORGANISM: Mycoplasma fermentans

<400> SEQUENCE: 5

```
Met Gly Lys Ser Glu Leu Ser Gly Arg Leu Asn Trp Gln Ala Leu Ala
1               5                   10                  15
Gly Leu Lys Ala Ser Gly Ala Glu Gln Asn Leu Tyr Asn Val Phe Asn
            20                  25                  30
Ala Val Phe Glu Gly Thr Lys Tyr Val Leu Tyr Glu Lys Pro Lys His
        35                  40                  45
Leu Lys Asn Leu Tyr Ala Gln Val Val Leu Pro Asp Asp Val Ile Lys
    50                  55                  60
Glu Ile Phe Asn Pro Leu Ile Asp Leu Ser Thr Thr Gln Trp Gly Val
65                  70                  75                  80
Ser Pro Asp Phe Ala Ile Glu Asn Thr Glu Thr His Lys Ile Leu Phe
                85                  90                  95
Gly Glu Ile Lys Arg Gln Asp Gly Trp Val Glu Gly Lys Asp Pro Ser
            100                 105                 110
Ala Gly Arg Gly Asn Ala His Glu Arg Ser Cys Lys Leu Phe Thr Pro
        115                 120                 125
Gly Leu Leu Lys Ala Tyr Arg Thr Ile Gly Gly Ile Asn Asp Glu Glu
    130                 135                 140
Ile Leu Pro Phe Trp Val Val Phe Glu Gly Asp Ile Thr Arg Asp Pro
145                 150                 155                 160
Lys Arg Val Arg Glu Ile Thr Phe Trp Tyr Asp His Tyr Gln Asp Asn
                165                 170                 175
Tyr Phe Met Trp Arg Pro Asn Glu Ser Gly Glu Lys Leu Val Gln His
            180                 185                 190
Phe Asn Glu Lys Leu Lys Lys Tyr Leu Asp
        195                 200
```

<210> SEQ ID NO 6
<211> LENGTH: 1152
<212> TYPE: DNA
<213> ORGANISM: Bacillus stearothermophilus X1

<400> SEQUENCE: 6

```
atggctatta cattatgtga cataaatggt tgtagacttg agagaggaca tactggtaaa      60
cataataaat ttcctgaatt tgtatggact tctcaattta ataaaaaaga tattgataag     120
gtcaataaag caggatatgc aacaccaaga ggtggggaca aaggagccta tcagaaccat     180
gtttacagaa ataataaagt aattattcct tttgaaaggt tggaaaatgt taatttaaat     240
aactatcaag atggatatgt tattaggtta ttccctaatc agtactttga atcagccggg     300
gtagttaagc cggaattctt acaaccaaat tcatttgtta aagttgggga caatgcattt     360
attttatatc gcacacattc atcttttgag gaattacctc ctctaccaga ctggagggtt     420
agacatctaa aaaagaacgg taatatagtt accagaagaa gtaaggacgt aatcgatgct     480
ggacattatg tcttacgatt atcatcaatt agtaacaaaa aagaaagaaa agagggccct     540
cctcaaggta ttttgcacc tgaatatgca aatgcagaga ctaattatct gtcaaaagca     600
ttttagcct ggttaattat taaaactcaa aatagtccgt ataatgaaga acaattccaa     660
cacttaagag cgatcttaat tagtcataat ctcatcaata tttctcaact tgaagaaaag     720
gctattctaa agaatggtat cacatgctgc cctttatgcg agcaaattat tttttacgaa     780
cagctacacg aaatggtttc ttttgaaggt gcgtctggcc ttgcgaattc acaagaacag     840
gttgagggtg caactaggtc aacatcagtt aatttattcc atatggtacc attagtatat     900
gaaaccttgg aacacaaacc tgatcaaata gcatggggcc atgccatttg taatactaga     960
cttggtcaaa gagagtgcct gcctcttagt agactaaaac aagaaggtac gcccgttggt    1020
cttcttgatg aagattcgaa tcttgaagta ttaggatgga ttagtaaaga taagcaattt    1080
attcgtacag aaaatgggga agtttggatt aaaattacag atattgaatt taacgatgac    1140
tttgaagaat aa                                                       1152
```

<210> SEQ ID NO 7
<211> LENGTH: 383
<212> TYPE: PRT
<213> ORGANISM: Bacillus stearothermophilus X1

<400> SEQUENCE: 7

```
Met Ala Ile Thr Leu Cys Asp Ile Asn Gly Cys Arg Leu Glu Arg Gly
1               5                   10                  15

His Thr Gly Lys His Asn Lys Phe Pro Glu Phe Val Trp Thr Ser Gln
            20                  25                  30

Phe Asn Lys Lys Asp Ile Asp Lys Val Asn Lys Ala Gly Tyr Ala Thr
        35                  40                  45

Pro Arg Gly Gly Asp Lys Gly Ala Tyr Gln Asn His Val Tyr Arg Asn
    50                  55                  60

Asn Lys Val Ile Ile Pro Phe Glu Arg Leu Glu Asn Val Asn Leu Asn
65                  70                  75                  80

Asn Tyr Gln Asp Gly Tyr Val Ile Arg Leu Phe Pro Asn Gln Tyr Phe
                85                  90                  95

Glu Ser Ala Gly Val Val Lys Pro Glu Phe Leu Gln Pro Asn Ser Phe
            100                 105                 110

Val Lys Val Gly Asp Asn Ala Phe Ile Leu Tyr Arg Thr His Ser Ser
        115                 120                 125

Phe Glu Glu Leu Pro Pro Leu Pro Asp Trp Glu Val Arg His Leu Lys
    130                 135                 140

Lys Asn Gly Asn Ile Val Thr Arg Arg Ser Lys Asp Val Ile Asp Ala
145                 150                 155                 160
```

Gly His Tyr Val Leu Arg Leu Ser Ser Ile Ser Asn Lys Lys Glu Arg
                165                 170                 175

Lys Glu Gly Pro Pro Gln Gly Ile Phe Ala Pro Glu Tyr Ala Asn Ala
            180                 185                 190

Glu Thr Asn Tyr Leu Ser Lys Ala Phe Leu Ala Trp Leu Ile Ile Lys
        195                 200                 205

Thr Gln Asn Ser Pro Tyr Asn Glu Glu Gln Phe Gln His Leu Arg Ala
    210                 215                 220

Ile Leu Ile Ser His Asn Leu Ile Asn Ile Ser Gln Leu Glu Glu Lys
225                 230                 235                 240

Ala Ile Leu Lys Asn Gly Ile Thr Cys Cys Pro Leu Cys Glu Gln Ile
                245                 250                 255

Ile Phe Tyr Glu Gln Leu His Glu Met Val Ser Phe Glu Gly Ala Ser
            260                 265                 270

Gly Leu Ala Asn Ser Gln Glu Gln Val Glu Gly Ala Thr Arg Ser Thr
        275                 280                 285

Ser Val Asn Leu Phe His Met Val Pro Leu Val Tyr Glu Thr Leu Glu
    290                 295                 300

His Lys Pro Asp Gln Ile Ala Trp Gly His Ala Ile Cys Asn Thr Arg
305                 310                 315                 320

Leu Gly Gln Arg Glu Cys Leu Pro Leu Ser Arg Leu Lys Gln Glu Gly
                325                 330                 335

Thr Pro Val Gly Leu Leu Asp Glu Asp Ser Asn Leu Glu Val Leu Gly
            340                 345                 350

Trp Ile Ser Lys Asp Lys Gln Phe Ile Arg Thr Glu Asn Gly Glu Val
        355                 360                 365

Trp Ile Lys Ile Thr Asp Ile Glu Phe Asn Asp Asp Phe Glu Glu
    370                 375                 380

<210> SEQ ID NO 8
<211> LENGTH: 1536
<212> TYPE: DNA
<213> ORGANISM: Bacillus stearothermophilus X1
<220> FEATURE:
<221> NAME/KEY: misc_feature
<223> OTHER INFORMATION: DNA sequence of M.BstXI

<400> SEQUENCE: 8
atgatttttg ctgatattga atttgaaaaa gaactttttt cagctgctaa taaattaagg      60
ggaaaaattg ctccaagtga gtataagcat tatgttttgc ctttgatatt ccttagatat     120
ttatctctta ataccaaca aagaaggaat gaaattcaac aacagataaa tgattcaagg      180
gatcacaaga aaaatcaaga tgaagtgtta agatattgg aagacaggac tgaatacacc      240
aaagtaaatg ttttctatat tcctgaaaaa gctagttggg aatacttatt gaaaaattcc     300
gaaaatgata aaattaaaga atgatagat tcagctatgg aaatactgga aatgaatat      360 gacgagttaa aagtgttttt gccaaagata tataaaaact caaatatacc gaatgaagtt     420
attagtgatt tactaaaact attttctcaa gaagtatttt cagcacatga tggaagaaat     480
gttgatttat ggggagagt ttatgaatac tttataagta attttgctac tacagaaggt     540
actagaggtg gtgaatattt tacaccgtct tcaatcgtaa aattattggt agcaatgcta     600
gagcccatta aggtacagt ttatgatccg gcctgtggga caggaggaat gtttattcag      660
tctaataaat atagagaaaa taatcataac ttgtgttttg taggccagga acaaacgag      720 cttactatca aattggctaa atgaatgga attctacatg gaataaatcc tgaaattaga      780

```
caaggtgatt cattattaaa tgaccgttat ccagaattga aagctgaaat tgtaatatct    840
aatccaccgt ttaatatgaa ggattgggga gctgaacgcc tgccacttaa tgataagcga    900
ttaataggac cggtaacaaa cagtaatgca aattacatgt ggatacagca ttttctatac    960
catttaaaag atggtggttt agcaggattt gttattgcta atggagcttt gactagtaat   1020
ctggctgctg aaaaaattgt aaggaaacac ttaatagaca atgattatgt agattgtgtt   1080
gttcaattac ctgaaaaaat gttctttggt actggcattc caagtgcttt agtgttttta   1140
agtaagaatc gaaatggaag taacggccat gccaaaagag aaaagaggt tctatttatt   1200 gatgcaagcg ataagggaac attagtgggt aaaaagaata aaatatttt agatgatgaa   1260 ataaaagaaa ttgcagattt atatcattca tttaaatttt taaatgataa tgattataac   1320
catagtggtt tttacaaaaa ggttaacatt gaaaaaatcg tggaaaatga ttataaatta   1380
actccaactc tctatgtagg tgtaaaggaa gagactgaaa tggagaagcc atttagagaa   1440
atgataatag aatataaagc gatattagag caacaatttg aagaatcaaa caaactacag   1500
cagaaaatat taaagaattt agagggatta ttatga                              1536
```

<210> SEQ ID NO 9
<211> LENGTH: 511
<212> TYPE: PRT
<213> ORGANISM: Bacillus stearothermophilus X1
<220> FEATURE:
<221> NAME/KEY: misc_feature
<223> OTHER INFORMATION: protein sequence for M.BstXI

<400> SEQUENCE: 9

```
Met Ile Phe Ala Asp Ile Glu Phe Glu Lys Glu Leu Phe Ser Ala Ala
1               5                   10                  15

Asn Lys Leu Arg Gly Lys Ile Ala Pro Ser Glu Tyr Lys His Tyr Val
            20                  25                  30

Leu Pro Leu Ile Phe Leu Arg Tyr Leu Ser Leu Lys Tyr Gln Gln Arg
        35                  40                  45

Arg Asn Glu Ile Gln Gln Gln Ile Asn Asp Ser Arg Asp His Lys Lys
    50                  55                  60

Asn Gln Asp Glu Val Leu Lys Ile Leu Glu Asp Arg Thr Glu Tyr Thr
65                  70                  75                  80

Lys Val Asn Val Phe Tyr Ile Pro Glu Lys Ala Ser Trp Glu Tyr Leu
                85                  90                  95

Leu Lys Asn Ser Glu Asn Asp Lys Ile Lys Glu Met Ile Asp Ser Ala
            100                 105                 110

Met Glu Ile Leu Glu Asn Glu Tyr Asp Glu Leu Lys Gly Val Leu Pro
        115                 120                 125

Lys Ile Tyr Lys Asn Ser Asn Ile Pro Asn Glu Val Ile Ser Asp Leu
    130                 135                 140

Leu Lys Leu Phe Ser Gln Glu Val Phe Ser Ala His Asp Gly Arg Asn
145                 150                 155                 160

Val Asp Leu Leu Gly Arg Val Tyr Glu Tyr Phe Ile Ser Asn Phe Ala
                165                 170                 175

Thr Thr Glu Gly Thr Arg Gly Gly Glu Tyr Phe Thr Pro Ser Ser Ile
            180                 185                 190

Val Lys Leu Leu Val Ala Met Leu Glu Pro Ile Lys Gly Thr Val Tyr
        195                 200                 205

Asp Pro Ala Cys Gly Thr Gly Gly Met Phe Ile Gln Ser Asn Lys Tyr
    210                 215                 220
```

Arg Glu Asn Asn His Asn Leu Cys Phe Val Gly Gln Glu Gln Asn Glu
225                 230                 235                 240

Leu Thr Ile Lys Leu Ala Lys Met Asn Gly Ile Leu His Gly Ile Asn
            245                 250                 255

Pro Glu Ile Arg Gln Gly Asp Ser Leu Leu Asn Asp Arg Tyr Pro Glu
        260                 265                 270

Leu Lys Ala Glu Ile Val Ile Ser Asn Pro Pro Phe Asn Met Lys Asp
    275                 280                 285

Trp Gly Ala Glu Arg Leu Pro Leu Asn Asp Lys Arg Leu Ile Gly Pro
290                 295                 300

Val Thr Asn Ser Asn Ala Asn Tyr Met Trp Ile Gln His Phe Leu Tyr
305                 310                 315                 320

His Leu Lys Asp Gly Gly Leu Ala Gly Phe Val Ile Ala Asn Gly Ala
                325                 330                 335

Leu Thr Ser Asn Leu Ala Ala Glu Lys Ile Val Arg Lys His Leu Ile
            340                 345                 350

Asp Asn Asp Tyr Val Asp Cys Val Val Gln Leu Pro Glu Lys Met Phe
        355                 360                 365

Phe Gly Thr Gly Ile Pro Ser Ala Leu Val Phe Leu Ser Lys Asn Arg
    370                 375                 380

Asn Gly Ser Asn Gly His Ala Lys Arg Glu Lys Glu Val Leu Phe Ile
385                 390                 395                 400

Asp Ala Ser Asp Lys Gly Thr Leu Val Gly Lys Lys Asn Lys Ile Phe
                405                 410                 415

Leu Asp Asp Glu Ile Lys Glu Ile Ala Asp Leu Tyr His Ser Phe Lys
            420                 425                 430

Phe Leu Asn Asp Asn Asp Tyr Asn His Ser Gly Phe Tyr Lys Lys Val
        435                 440                 445

Asn Ile Glu Lys Ile Val Glu Asn Asp Tyr Lys Leu Thr Pro Thr Leu
    450                 455                 460

Tyr Val Gly Val Lys Glu Glu Thr Glu Met Glu Lys Pro Phe Arg Glu
465                 470                 475                 480

Met Ile Ile Glu Tyr Lys Ala Ile Leu Glu Gln Phe Glu Glu Ser
                485                 490                 495

Asn Lys Leu Gln Gln Lys Ile Leu Lys Asn Leu Glu Gly Leu Leu
            500                 505                 510

<210> SEQ ID NO 10
<211> LENGTH: 1179
<212> TYPE: DNA
<213> ORGANISM: Bacillus stearothermophilus X1
<220> FEATURE:
<221> NAME/KEY: misc_feature
<223> OTHER INFORMATION: DNA sequence of S.BstXI

<400> SEQUENCE: 10
atgaaaagta ctttgaagga atataaattg ggtgatatta ccgaagtcgt taatggtgcc      60
actccttcaa ctaaaaagcc tgagtactat gaaaatggta caattccatg gattactcct     120
aaagatttat caggctatta ctttaaatat atatctcatg gtaacgtaa tataacagag      180 cttggtctaa gaaatagttc agctaagttg ttaccaaaag gaactgtatt attttcctca     240
agagccccaa taggatacgt agcaatagct gataattggt taactacgaa ccagggattt     300
aaagttttta tatgtaatga ggagattatt tacaatgaat accttttatt ttttcttatt     360
gctaaaaggg attttattga acatttgcg aatgggagta cgtttaaaga gctttcatca     420

-continued

```
acttctgcaa agaatatacc aatcaatctt cctagtttag aagagcaaaa gaagattgtg      480
acaattttag gggatttgga tagaaagata gaattaaatt ataaaattat tgaaagctta      540
gaaaaaatag cagaaagaac atataaatat tggtttgtcg atgaattaaa tcaagatgaa      600
cagcacatcc gtaatggatg ggaaactgct aaaattggcg atgtggtgga acttttggga      660
gggggaaccc ctaaaacttc ggaaagtaag tattgggaag atggagatat taattggttt      720
actccttcag atttaacaaa aactagacag cttttttgtac gtgattctca aagaaaata      780 acaattgatg gacttaataa cagtgcagcg aaattaattc cccttattc cttgttaatg      840 tcaagtagag ctacaattgg cgagttggca attaatcaag aatctgctac tacaaatcaa      900
gggtttattg tattaatacc aaatgaaaaa atttctattt accaattata cttttgggct      960
aaacttaata agagcaaaat tatttcaatg gcaaatggta gtactttaa agaaattagt     1020 aagcgggatt ttaaatcttt ggagataata ttaccaaaaa atatagacac ttttaattca     1080
attatgcaag attattttag gaaaattgag gagttaattg atgaaataaa aatcttaaaa     1140
accgcaagag ataatttaat tccaaaactt ataaaatga                           1179
```

<210> SEQ ID NO 11
<211> LENGTH: 392
<212> TYPE: PRT
<213> ORGANISM: Bacillus stearothermophilus X1
<220> FEATURE:
<221> NAME/KEY: misc_feature
<223> OTHER INFORMATION: protein sequence for S.BstXI

<400> SEQUENCE: 11

```
Met Lys Ser Thr Leu Lys Glu Tyr Lys Leu Gly Asp Ile Thr Glu Val
1               5                   10                  15

Val Asn Gly Ala Thr Pro Ser Thr Lys Lys Pro Glu Tyr Tyr Glu Asn
            20                  25                  30

Gly Thr Ile Pro Trp Ile Thr Pro Lys Asp Leu Ser Gly Tyr Tyr Phe
        35                  40                  45

Lys Tyr Ile Ser His Gly Glu Arg Asn Ile Thr Glu Leu Gly Leu Arg
    50                  55                  60

Asn Ser Ser Ala Lys Leu Leu Pro Lys Gly Thr Val Leu Phe Ser Ser
65                  70                  75                  80

Arg Ala Pro Ile Gly Tyr Val Ala Ile Ala Asp Asn Trp Leu Thr Thr
                85                  90                  95

Asn Gln Gly Phe Lys Ser Phe Ile Cys Asn Glu Glu Ile Ile Tyr Asn
            100                 105                 110

Glu Tyr Leu Tyr Tyr Phe Leu Ile Ala Lys Arg Asp Phe Ile Glu Thr
        115                 120                 125

Phe Ala Asn Gly Ser Thr Phe Lys Glu Leu Ser Ser Thr Ser Ala Lys
    130                 135                 140

Asn Ile Pro Ile Asn Leu Pro Ser Leu Glu Glu Gln Lys Lys Ile Val
145                 150                 155                 160

Thr Ile Leu Gly Asp Leu Asp Arg Lys Ile Glu Leu Asn Tyr Lys Ile
                165                 170                 175

Ile Glu Ser Leu Glu Lys Ile Ala Glu Arg Thr Tyr Lys Tyr Trp Phe
            180                 185                 190

Val Asp Glu Leu Asn Gln Asp Glu Gln His Ile Arg Asn Gly Trp Glu
        195                 200                 205

Thr Ala Lys Ile Gly Asp Val Val Glu Leu Leu Gly Gly Gly Thr Pro
    210                 215                 220
```

Lys Thr Ser Glu Ser Lys Tyr Trp Glu Asp Gly Asp Ile Asn Trp Phe
225                 230                 235                 240

Thr Pro Ser Asp Leu Thr Lys Thr Arg Gln Leu Phe Val Arg Asp Ser
            245                 250                 255

Gln Arg Lys Ile Thr Ile Asp Gly Leu Asn Asn Ser Ala Ala Lys Leu
        260                 265                 270

Ile Pro Pro Tyr Ser Leu Leu Met Ser Ser Arg Ala Thr Ile Gly Glu
    275                 280                 285

Leu Ala Ile Asn Gln Glu Ser Ala Thr Thr Asn Gln Gly Phe Ile Val
290                 295                 300

Leu Ile Pro Asn Glu Lys Ile Ser Ile Tyr Gln Leu Tyr Phe Trp Ala
305                 310                 315                 320

Lys Leu Asn Lys Ser Lys Ile Ile Ser Met Ala Asn Gly Ser Thr Phe
            325                 330                 335

Lys Glu Ile Ser Lys Arg Asp Phe Lys Ser Leu Glu Ile Ile Leu Pro
        340                 345                 350

Lys Asn Ile Asp Thr Phe Asn Ser Ile Met Gln Asp Tyr Phe Arg Lys
    355                 360                 365

Ile Glu Glu Leu Ile Asp Glu Ile Lys Ile Leu Lys Thr Ala Arg Asp
    370                 375                 380

Asn Leu Ile Pro Lys Leu Ile Lys
385                 390

<210> SEQ ID NO 12
<211> LENGTH: 770
<212> TYPE: DNA
<213> ORGANISM: planococcus citreus SE-F45

<400> SEQUENCE: 12
atgaaacagt tgcagatcc ttttgaaaga agattccttg atgcaattga acatcatctt      60
gatggaattt ctgagaaaat aaaaaaagac tttacacaca aaacttttt aaaagaattg     120 aatggcctta aggtgataa agtctatcat gacttaggct tgataccgc tgaatatact     180 ctggtacgtc ttataggaag aatgagcata agcgttggga aaggctggg ggagatatac     240 gataaagtcc ctcgttatgt tgctgccgcg cgatttggtc ttcaaccaaa tcaaattgca     300
gaagtatttg atggtcttga gttagatata gctttgcgca atagcctttt gtcagatgat     360
gataaaattc acataaaaaa ataactgaa aagatgtcag gcgaaacata ctcgggaatc     420
ggaatcgaaa ttcgttataa ctttaatcca aatgacagtt cccgtttaag aaaagacgtc     480
gatgtagctt ctaaattgtc ggccgcgggg ttatttcctg tttatttaat atttagctct     540
ctcagtccta ggaatgatgc aatagcccgt cttaaaagag ggggatggag ctttaaacag     600
gggcaggaag ccttagactt ccttaccgaa cttttaggag tggatattgg gtctgtttta     660
tctgacccaa taatagccgc agaaactagg gagaaaacat caaaaattat gaagtctata     720
tttgaatcag aggcattcca atctgttata ccgggagagt ggagtaaact                770

<210> SEQ ID NO 13
<211> LENGTH: 257
<212> TYPE: PRT
<213> ORGANISM: planococcus citreus SE-F45

<400> SEQUENCE: 13

Met Lys Gln Phe Ala Asp Pro Phe Glu Arg Arg Phe Leu Asp Ala Ile
1               5                   10                  15

```
Glu His His Leu Asp Gly Ile Ser Glu Lys Ile Lys Lys Asp Phe Thr
         20                  25                  30

His Lys Asn Phe Leu Lys Glu Leu Asn Gly Leu Lys Gly Asp Lys Val
     35                  40                  45

Tyr His Asp Leu Gly Phe Asp Thr Ala Glu Tyr Thr Leu Val Arg Leu
 50                  55                  60

Ile Gly Arg Met Ser Ile Ser Val Gly Arg Arg Leu Gly Glu Ile Tyr
 65                  70                  75                  80

Asp Lys Val Pro Arg Tyr Val Ala Ala Arg Phe Gly Leu Gln Pro
                 85                  90                  95

Asn Gln Ile Ala Glu Val Phe Asp Gly Leu Glu Leu Asp Ile Ala Leu
         100                 105                 110

Arg Asn Ser Leu Leu Ser Asp Asp Lys Ile His Ile Lys Lys Ile
     115                 120                 125

Thr Glu Lys Met Ser Gly Glu Thr Tyr Ser Gly Ile Gly Ile Glu Ile
         130                 135                 140

Arg Tyr Asn Phe Asn Pro Asn Asp Ser Arg Leu Arg Lys Asp Val
145                 150                 155                 160

Asp Val Ala Ser Lys Leu Ser Ala Ala Gly Leu Phe Pro Val Tyr Leu
                 165                 170                 175

Ile Phe Ser Ser Leu Ser Pro Arg Asn Asp Ala Ile Ala Arg Leu Lys
         180                 185                 190

Arg Gly Gly Trp Ser Phe Lys Gln Gly Gln Glu Ala Leu Asp Phe Leu
             195                 200                 205

Thr Glu Leu Leu Gly Val Asp Ile Gly Ser Val Leu Ser Asp Pro Ile
     210                 215                 220

Ile Ala Ala Glu Thr Arg Glu Lys Thr Ser Lys Ile Met Lys Ser Ile
225                 230                 235                 240

Phe Glu Ser Glu Ala Phe Gln Ser Val Ile Pro Gly Glu Trp Ser Lys
                 245                 250                 255

Leu
```

<210> SEQ ID NO 14
<211> LENGTH: 1347
<212> TYPE: DNA
<213> ORGANISM: planococcus citreus SE-F45
<220> FEATURE:
<221> NAME/KEY: misc_feature
<223> OTHER INFORMATION: DNA sequence for M.PciI

<400> SEQUENCE: 14

| | | |
|---|---|---|
| atgacaaatt tttcgcactc agctctaacg agctacgatc ttctcgggca tgaaattgtc | 60 |
| caagattctg aagctgttag ctcgggtcca tatctggtca gctatgaccc gatccctgta | 120 |
| cgtcggtcta cattcctagc tggactgtca gagaacgttc actcgtggtt tcgtctcaca | 180 |
| ccaagtttcg gaccggatct agttcgaaca atcatcaaac agatgaatct gcgccgcac | 240 |
| tcacacatcc atgacccttt ctcaggagcc gggactaccg cgattgaggc ttcgttagag | 300 |
| ggctatgaag caagctgcgt agaagttaat ccgtttctct acttcgtggg aaaacatcc | 360 |
| atagattggt ctatcaatgc tgatgatgct gcagcgcagc tagaaagcat aaaaataaa | 420 |
| tattatagca tgtctgcaac cgctactttg ataacatag ccgacctagg aatagatata | 480 |
| ccaaaaatac acaatattca tcggtggtgg agaaacgatg ttcttaaaga tatattagtc | 540 |
| ctaaaatctt ctatcagatc ttgcacacaa gataagtatt gttccttttt tgagctagcc | 600 |
| ctagctgcag ttctcgttcc agatttgaca aatgtaacgc taggaaaact acaactgcac | 660 |

-continued

```
tttgtaaaca aagacgataa agagataaac gtctggccta catatgaatc tcatgcaaaa    720
aaaatgattc acgacttgtc attaattaat aagcaaaatt tcgattttt gcccaagatt     780 atttatggtg attcaactca aaatcaaca tttagcgagg tggcagggat agatgctata     840
ataacatccc ctccgtaccc taataggtac agctatattt ggaatactcg ccctcacctg    900
tacattcttg atatgatttc cgaagcaaaa gaggcttcgc aaatagatcg tagaacgatt    960
ggtggaacat ggggggacagc aacttccgaa ttaggaaagg gtatattttc tccaatcaat   1020
gctgtagtca aagacgcgct tgaaggggtt cacgaaagaa tcgccggttc cgatcaactc    1080
atggcaaact atgtaactca ttattttaat cggctctttt tacatataga agctataaaa    1140
ccatcactta atccaaaagc aaagcttgct tatgttgttg ggaactcttg gattaagggc    1200
gaatatgtag ccactgacgt aatcttagca aaaattatcg aagggcttt gccaggctca     1260 tcaattgatg gtcttcatcg tttccgtcgc cggaacagtg gaaagaatct ctttgaaact    1320
atagtttact ccactctccc ggtataa                                         1347
```

<210> SEQ ID NO 15
<211> LENGTH: 448
<212> TYPE: PRT
<213> ORGANISM: planococcus citreus SE-F45
<220> FEATURE:
<221> NAME/KEY: misc_feature
<223> OTHER INFORMATION: Protein sequence for M.PciI

<400> SEQUENCE: 15

```
Met Thr Asn Phe Ser His Ser Ala Leu Thr Ser Tyr Asp Leu Leu Gly
1               5                   10                  15

His Glu Ile Val Gln Asp Ser Glu Ala Val Ser Ser Gly Pro Tyr Leu
            20                  25                  30

Val Ser Tyr Asp Pro Ile Pro Val Arg Arg Ser Thr Phe Leu Ala Gly
        35                  40                  45

Leu Ser Glu Asn Val His Ser Trp Phe Arg Leu Thr Pro Ser Phe Gly
    50                  55                  60

Pro Asp Leu Val Arg Thr Ile Ile Lys Gln Met Asn Leu Ala Pro His
65                  70                  75                  80

Ser His Ile His Asp Pro Phe Ser Gly Ala Gly Thr Thr Ala Ile Glu
                85                  90                  95

Ala Ser Leu Glu Gly Tyr Glu Ala Ser Cys Val Glu Val Asn Pro Phe
            100                 105                 110

Leu Tyr Phe Val Gly Lys Thr Ser Ile Asp Trp Ser Ile Asn Ala Asp
        115                 120                 125

Asp Ala Ala Ala Gln Leu Glu Ser Ile Lys Asn Lys Tyr Tyr Ser Met
    130                 135                 140

Ser Ala Thr Ala Thr Leu Asp Asn Ile Ala Asp Leu Gly Ile Asp Ile
145                 150                 155                 160

Pro Lys Ile His Asn Ile His Arg Trp Trp Arg Asn Asp Val Leu Lys
                165                 170                 175

Asp Ile Leu Val Leu Lys Ser Ser Ile Arg Ser Cys Thr Gln Asp Lys
            180                 185                 190

Tyr Cys Ser Phe Phe Glu Leu Ala Leu Ala Val Leu Val Pro Asp
        195                 200                 205

Leu Thr Asn Val Thr Leu Gly Lys Leu Gln Leu His Phe Val Asn Lys
    210                 215                 220

Asp Asp Lys Glu Ile Asn Val Trp Pro Thr Tyr Glu Ser His Ala Lys
```

-continued

```
225                 230                 235                 240

Lys Met Ile His Asp Leu Ser Leu Ile Asn Lys Gln Asn Phe Glu Phe
                245                 250                 255

Leu Pro Lys Ile Ile Tyr Gly Asp Ser Thr Gln Lys Ser Thr Phe Ser
            260                 265                 270

Glu Val Ala Gly Ile Asp Ala Ile Ile Thr Ser Pro Pro Tyr Pro Asn
        275                 280                 285

Arg Tyr Ser Tyr Ile Trp Asn Thr Arg Pro His Leu Tyr Ile Leu Asp
    290                 295                 300

Met Ile Ser Glu Ala Lys Glu Ala Ser Gln Ile Asp Arg Arg Thr Ile
305                 310                 315                 320

Gly Gly Thr Trp Gly Thr Ala Thr Ser Glu Leu Gly Lys Gly Ile Phe
                325                 330                 335

Ser Pro Ile Asn Ala Val Val Lys Asp Ala Leu Glu Gly Val His Glu
            340                 345                 350

Arg Ile Ala Gly Ser Asp Gln Leu Met Ala Asn Tyr Val Thr His Tyr
        355                 360                 365

Phe Asn Arg Leu Phe Leu His Ile Glu Ala Ile Lys Pro Ser Leu Asn
    370                 375                 380

Pro Lys Ala Lys Leu Ala Tyr Val Val Gly Asn Ser Trp Ile Lys Gly
385                 390                 395                 400

Glu Tyr Val Ala Thr Asp Val Ile Leu Ala Lys Ile Ile Glu Gly Ala
                405                 410                 415

Leu Pro Gly Ser Ser Ile Asp Gly Leu His Arg Phe Arg Arg Arg Asn
            420                 425                 430

Ser Gly Lys Asn Leu Phe Glu Thr Ile Val Tyr Ser Thr Leu Pro Val
        435                 440                 445

<210> SEQ ID NO 16
<211> LENGTH: 430
<212> TYPE: PRT
<213> ORGANISM: Bacillus sphaericus

<400> SEQUENCE: 16

Met Arg Arg Leu Ala Lys Asn Ser Arg Asn Asp Ser Tyr Leu Ser Asn
1               5                   10                  15

Arg Asp Tyr Gln Glu Ile Val Arg Glu Asn Thr Thr Thr Ile Ser Phe
            20                  25                  30

Pro Leu Lys Glu Lys His Thr Leu Thr Leu Thr Lys Lys Ile Gly Leu
        35                  40                  45

Asn Gln Thr Ala Gly Phe Gly Gly Trp Phe Phe Pro Asp Ser Pro Cys
    50                  55                  60

Leu Leu Thr Val Thr Val Leu Ser Ser Phe Gly Thr Lys Val Thr Ser
65                  70                  75                  80

Lys Thr Phe Ser Leu Ser Lys Asp Trp Asn Arg Val Gly Leu Ala Trp
                85                  90                  95

Ile Asn Glu His Ser Ser Asp Thr Met Ser Ile Val Leu Glu Phe Ser
            100                 105                 110

Asp Val Glu Ile Val His Thr Trp Gly Leu Thr Cys Asp Val Phe Asn
        115                 120                 125

Val His Glu Leu Ile Ile Asp Ala Ile Glu Asp Gln Asn Lys Leu Ile
    130                 135                 140

Asp Val Leu Asn Gln Glu His Leu Ser Pro Glu Thr Tyr Tyr Leu Asn
145                 150                 155                 160
```

His Asp Ser Asp Thr Asp Leu Ile Glu Asn Leu Glu Ser Thr Glu Glu
                165                 170                 175

Ile Lys Ile Val Asn Gln Ser Gln Lys Gln Ile Ser Leu Lys Lys Cys
            180                 185                 190

Cys Tyr Cys Gln Arg Tyr Met Pro Val Asn Ile Leu Val Arg Ser Asn
        195                 200                 205

Ser Ser Phe His Lys His Lys Ser Lys Lys Thr Gly Phe Gln Asn Glu
    210                 215                 220

Cys Arg Ala Cys Lys Lys Trp Arg Ile Asn Asn Ser Phe Asn Pro Val
225                 230                 235                 240

Arg Thr Lys Asp Gln Leu His Glu Ser Ala Val Ile Thr Arg Glu Lys
                245                 250                 255

Lys Ile Leu Leu Lys Glu Pro Glu Ile Leu Gln Lys Ile Lys Asn Arg
            260                 265                 270

Asn Asn Gly Glu Gly Leu Lys Ser Ile Ile Trp Lys Lys Phe Asp Lys
        275                 280                 285

Lys Cys Phe Asn Cys Glu Lys Glu Leu Thr Ile Glu Glu Val Arg Leu
    290                 295                 300

Asp His Thr Arg Pro Leu Ala Tyr Leu Trp Pro Ile Asp Glu His Ala
305                 310                 315                 320

Thr Cys Leu Cys Glu Lys Cys Asn Asn Thr Lys His Asp Met Phe Pro
                325                 330                 335

Ile Asp Phe Tyr Gln Gly Asp Glu Asp Lys Leu Arg Arg Leu Ala Arg
            340                 345                 350

Ile Thr Gly Leu Asp Tyr Glu Ser Leu Val Lys Arg Asp Val Asn Glu
        355                 360                 365

Val Glu Leu Ala Arg Ile Ile Asn Asn Ile Glu Asp Phe Ala Thr Asn
    370                 375                 380

Val Glu Ala Arg Thr Phe Arg Ser Ile Arg Asn Lys Val Lys Glu Val
385                 390                 395                 400

Arg Pro Asp Thr Asp Leu Phe Glu Ile Leu Lys Ser Lys Asn Ile Asn
                405                 410                 415

Leu Tyr Asn Glu Leu Gln Tyr Glu Leu Leu Thr Arg Lys Asp
            420                 425                 430

<210> SEQ ID NO 17
<211> LENGTH: 1245
<212> TYPE: DNA
<213> ORGANISM: Enterobacter aerogenes

<400> SEQUENCE: 17
gtgaatcaga aaatgaaaa atcatttatg cgtttgcaat caacctttag cggtggcaaa      60
ggtagtccaa tgcatgattg gtacccatat ttagagggtt attctcccga atttgtgaaa    120
tgcttgattt cacgatttgc tcctaaagcc aaaacaattt tagatccatt ttgtggctct    180
ggaacaacag ccattgtttc cgttttagag ggtttaaata attactattg cgaagtaaac    240
cctttatgcc aatatattat tgaaactaaa ctaatagctt taacattaag cgaagaagaa    300
aaaacaaaat tagtaaatga actttattct atttctaatg aaataactaa tgtactcaaa    360
ccttctgcaa ccgagacaga tctagagaaa tcatttaaat ccgttttttgg taatacgaaa    420 ttttttgagg atcacatatt taagatata cttagttatc aatgttacat tagctctatc    480
gaagatgaaa tcttaagag acttctgaca atagcaggga ttagatcgtt aatcccttcc    540
tcgttattgg taagacgagg tgatttacga ttcaagacac aaaaagaatt agagaaaggc    600

```
aaccagggct ttcgctttca tgtacaaaaa agcttagaat taattgccag tgatttatta        660
gacattacgg aaggtagtgg tttagctacc ttcttatgtg atgatgccaa agaaatatct        720
gggaataacc tgattgatgc tgtaataaca agcccgccat atttaaatgg cacaaattat        780
tttagaaata ctaaaattga actttggttt tagggaaat taaagaccaa atcagatcta         840
agacattata gggatttagc tattaccagt ggtattaacg atgtaactaa aggtaaaagc        900
ttatcttcaa ataatactat tatctcagaa ataccattat tatctgaatg tattaaagaa        960
ctaagcataa aagagtatga tagtcgtatt tcaatgatgg ttgaaaacta cttttgggac      1020
atgttcaaat tcttatcaaa actcccaaaa ttactaacta atgatgcgac tatctgtata      1080
gatttaggtg attctgttta ttgtaacgtc tacatcccta cacaagatat tttgaaagaa      1140
atgatgtcaa agttaggttt tgaagagaac gaaagggtca ttcttcgtga acgaaaatcc      1200
cgcaatggaa caaagttagt ccagactgtt caggttttta atga                       1245
```

```
<210> SEQ ID NO 18
<211> LENGTH: 1140
<212> TYPE: DNA
<213> ORGANISM: Enterobacter aerogenes

<400> SEQUENCE: 18
```

```
atgaaaaata aatattttag taaaaaatgg gagcaattca agaaagaatt accccatcaa        60
tcaggtgaaa tggtaaagag aaattggggc ataactggc actctatgtg ttcataccaa        120
gggaaactta aaccatcaat agctagatct ttaattgata cattcatgcc atcaagtaag      180
ggacgtatat tagatgtctt ctcaggtgtt ggcaccattc ctttcgaagc aagattactt      240
ggtcatactg catatggatt tgatattagt ccagcagcag ttaatatttc acgcgcaaaa      300
ctagaagtta taagtaaaaa tgaaatccaa gaggtaatta ataaattatc tgattttatt      360
gagcaaaaca aaaattcaat agattataac gaacataatt taataaggtt taatggttca      420
attgaatcct atttcatcc tgaaactttt aaggaaatac tgtgtgctcg taaattcttt      480
ttaataaaag gtgaattaaa tgcatctgaa tcgttagtac agtcatgttt attacatatt      540
ttacatggta atcgtccgta tgcattgagt agaaagtccc atcctattac accttcgcg      600 cctactggag attttatata cagtaattta gttataaagt taatcaaaaa agttgaaaga      660
gtcttgcaaa attctgatgg tatcccagat actggcagca aagtatttta tcaggactct      720
acaaaaagtt ggcctgaaga agtaaataat ttagatgcaa ttataacatc acctccattt      780
tatgatagta cccgtttcta ttcagcaaat tggatgcgat tatggttttc tggttgggaa      840
aaagatgact tccaaacgaa gccaaaagat tttgtggacg aaactcagaa aaaaagcttt      900
gaaatatatg ataatatatt caaacaatct caacaatgct aaaaaaaga tggcgttttt      960 ttaatgcacg ttggcaaaag taaaaaaagt gatatggcag acaaattgc taaaattggt    1020 agtaattatc ttagccttat agatatattt gacgaaagtg ttgaacattg cgaaagtcac    1080
ggaattaaag acaaaggcac gacaacccat catcagtacc ttgtctttac gaaagattag   1140
```

```
<210> SEQ ID NO 19
<211> LENGTH: 213
<212> TYPE: PRT
<213> ORGANISM: Bacillus amyloliquefaciens H

<400> SEQUENCE: 19
```

```
Met Glu Val Glu Lys Glu Phe Ile Thr Asp Glu Ala Lys Glu Leu Leu
1               5                   10                  15
```

```
Ser Lys Asp Lys Leu Ile Gln Gln Ala Tyr Asn Glu Val Lys Thr Ser
            20                  25                  30

Ile Cys Ser Pro Ile Trp Pro Ala Thr Ser Lys Thr Phe Thr Ile Asn
        35                  40                  45

Asn Thr Glu Lys Asn Cys Asn Gly Val Val Pro Ile Lys Glu Leu Cys
    50                  55                  60

Tyr Thr Leu Leu Glu Asp Thr Tyr Asn Trp Tyr Arg Glu Lys Pro Leu
65                  70                  75                  80

Asp Ile Leu Lys Leu Glu Lys Lys Gly Gly Pro Ile Asp Val Tyr
                85                  90                  95

Lys Glu Phe Ile Glu Asn Ser Glu Leu Lys Arg Val Gly Met Glu Phe
                100                 105                 110

Glu Thr Gly Asn Ile Ser Ser Ala His Arg Ser Met Asn Lys Leu Leu
            115                 120                 125

Leu Gly Leu Lys His Gly Glu Ile Asp Leu Ala Ile Ile Leu Met Pro
    130                 135                 140

Ile Lys Gln Leu Ala Tyr Tyr Leu Thr Asp Arg Val Thr Asn Phe Glu
145                 150                 155                 160

Glu Leu Glu Pro Tyr Phe Glu Leu Thr Glu Gly Gln Pro Phe Ile Phe
                165                 170                 175

Ile Gly Phe Asn Ala Glu Ala Tyr Asn Ser Asn Val Pro Leu Ile Pro
            180                 185                 190

Lys Gly Ser Asp Gly Met Ser Lys Arg Ser Ile Lys Lys Trp Lys Asp
        195                 200                 205

Lys Val Glu Asn Lys
        210

<210> SEQ ID NO 20
<211> LENGTH: 194
<212> TYPE: PRT
<213> ORGANISM: Oceanospirillum kriegii

<400> SEQUENCE: 20

Met Lys Ile Lys Arg Ile Glu Val Leu Ile Asn Asn Gly Ser Val Pro
1               5                   10                  15

Gly Ile Pro Met Ile Leu Asn Glu Ile Gln Asp Ala Ile Lys Thr Val
            20                  25                  30

Ser Trp Pro Glu Gly Asn Asn Ser Phe Val Ile Asn Pro Val Arg Lys
        35                  40                  45

Gly Asn Gly Val Lys Pro Ile Lys Asn Ser Cys Met Arg His Leu His
    50                  55                  60

Gln Lys Gly Trp Ala Leu Glu His Pro Val Arg Ile Lys Ala Glu Met
65                  70                  75                  80

Arg Pro Gly Pro Leu Asp Ala Val Lys Met Ile Gly Gly Lys Ala Phe
                85                  90                  95

Ala Leu Glu Trp Glu Thr Gly Asn Ile Ser Ser Ser His Arg Ala Ile
            100                 105                 110

Asn Lys Met Val Met Gly Met Leu Glu Arg Val Ile Gly Gly Val
        115                 120                 125

Leu Ile Leu Pro Ser Arg Asp Met Tyr Asn Tyr Leu Thr Asp Arg Val
    130                 135                 140

Gly Asn Phe Arg Glu Leu Glu Pro Tyr Phe Ser Val Trp Arg Gln Phe
145                 150                 155                 160

Asn Leu Lys Asp Ala Tyr Leu Ala Ile Val Glu Ile Glu His Asp Ser
                165                 170                 175
```

Val Asp Ala Gln Val Ser Leu Ile Pro Lys Gly Thr Asp Gly Arg Ala
            180                 185                 190

Ile Arg

<210> SEQ ID NO 21
<211> LENGTH: 180
<212> TYPE: PRT
<213> ORGANISM: Bacillus amyloliquefaciens H
<220> FEATURE:
<221> NAME/KEY: MISC_FEATURE
<222> LOCATION: (1)..(180)
<223> OTHER INFORMATION: Residues 1-180 correspond to residues 22-201 of
      the protein sequence of BamHI (seq id no. 19)

<400> SEQUENCE: 21

Ile Gln Gln Ala Tyr Asn Glu Val Lys Thr Ser Ile Cys Ser Pro Ile
1               5                   10                  15

Trp Pro Ala Thr Ser Lys Thr Phe Thr Ile Asn Asn Thr Glu Lys Asn
            20                  25                  30

Cys Asn Gly Val Val Pro Ile Lys Glu Leu Cys Tyr Thr Leu Leu Glu
        35                  40                  45

Asp Thr Tyr Asn Trp Tyr Arg Glu Lys Pro Leu Asp Ile Leu Lys Leu
    50                  55                  60

Glu Lys Lys Lys Gly Gly Pro Ile Asp Val Tyr Lys Glu Phe Ile Glu
65                  70                  75                  80

Asn Ser Glu Leu Lys Arg Val Gly Met Glu Phe Glu Thr Gly Asn Ile
                85                  90                  95

Ser Ser Ala His Arg Ser Met Asn Lys Leu Leu Leu Gly Leu Lys His
            100                 105                 110

Gly Glu Ile Asp Leu Ala Ile Ile Leu Met Pro Ile Lys Gln Leu Ala
        115                 120                 125

Tyr Tyr Leu Thr Asp Arg Val Thr Asn Phe Glu Glu Leu Gly Pro Tyr
    130                 135                 140

Phe Glu Leu Thr Glu Gly Gln Pro Phe Ile Phe Ile Gly Phe Asn Ala
145                 150                 155                 160

Glu Ala Tyr Asn Ser Asn Val Pro Leu Ile Pro Lys Gly Ser Asp Gly
                165                 170                 175

Met Ser Lys Arg
            180

<210> SEQ ID NO 22
<211> LENGTH: 177
<212> TYPE: PRT
<213> ORGANISM: Oceanospirillum kriegii
<220> FEATURE:
<221> NAME/KEY: MISC_FEATURE
<222> LOCATION: (1)..(177)
<223> OTHER INFORMATION: Residues 1-177 correspond to residues 18-194 of
      the protein sequence of OkrAI (seq id no. 20)

<400> SEQUENCE: 22

Ile Pro Met Ile Leu Asn Glu Ile Gln Asp Ala Ile Lys Thr Val Ser
1               5                   10                  15

Trp Pro Glu Gly Asn Asn Ser Phe Val Ile Asn Pro Arg Lys Gly
            20                  25                  30

Asn Gly Val Lys Pro Ile Lys Asn Ser Cys Met Arg His Leu His Gln
        35                  40                  45

Lys Gly Trp Ala Leu Glu His Pro Val Arg Ile Lys Ala Glu Met Arg
    50                  55                  60

Pro Gly Pro Leu Asp Ala Val Lys Met Ile Gly Gly Lys Ala Phe Ala
65                  70                  75                  80

Leu Glu Trp Glu Thr Gly Asn Ile Ser Ser His Arg Ala Ile Asn
            85                  90                  95

Lys Met Val Met Gly Met Leu Glu Arg Val Ile Ile Gly Gly Val Leu
            100                 105                 110

Ile Leu Pro Ser Arg Asp Met Tyr Asn Tyr Leu Thr Asp Arg Val Gly
        115                 120                 125

Asn Phe Arg Glu Leu Glu Pro Tyr Phe Ser Val Trp Arg Gln Phe Asn
    130                 135                 140

Leu Lys Asp Ala Tyr Leu Ala Ile Val Glu Ile Glu His Asp Ser Val
145                 150                 155                 160

Asp Ala Gln Val Ser Leu Ile Pro Lys Gly Thr Asp Gly Arg Ala Ile
                165                 170                 175

Arg

<210> SEQ ID NO 23
<211> LENGTH: 38
<212> TYPE: DNA
<213> ORGANISM: artificial
<220> FEATURE:
<223> OTHER INFORMATION: primer

<400> SEQUENCE: 23
attcaacaag catacaatgc agttaaaaca tctattgt                              38

<210> SEQ ID NO 24
<211> LENGTH: 39
<212> TYPE: DNA
<213> ORGANISM: artificial
<220> FEATURE:
<223> OTHER INFORMATION: primer

<400> SEQUENCE: 24
acaaatagat gttttaactg cattgtatgc ttgttgaat                             39

<210> SEQ ID NO 25
<211> LENGTH: 39
<212> TYPE: DNA
<213> ORGANISM: artificial
<220> FEATURE:
<223> OTHER INFORMATION: primer

<400> SEQUENCE: 25
caagcataca atgaagttgc aacatctatt tgttcacct                             39

<210> SEQ ID NO 26
<211> LENGTH: 39
<212> TYPE: DNA
<213> ORGANISM: artificial
<220> FEATURE:
<223> OTHER INFORMATION: primer

<400> SEQUENCE: 26
aggtgaacaa atagatgttg caacttcatt gtatgcttg                             39

<210> SEQ ID NO 27
<211> LENGTH: 39
<212> TYPE: DNA
<213> ORGANISM: artificial
<220> FEATURE:
<223> OTHER INFORMATION: primer

<400> SEQUENCE: 27
acgattaaca acaccgaagc aaattgtaac ggtgtagta                                   39

<210> SEQ ID NO 28
<211> LENGTH: 40
<212> TYPE: DNA
<213> ORGANISM: artificial
<220> FEATURE:
<223> OTHER INFORMATION: primer

<400> SEQUENCE: 28
acgattaaca acaccgaagc aaattgtaac ggtgtagtat                                  40

<210> SEQ ID NO 29
<211> LENGTH: 39
<212> TYPE: DNA
<213> ORGANISM: artificial
<220> FEATURE:
<223> OTHER INFORMATION: primer

<400> SEQUENCE: 29
aacggtgtag taccaattgc agaactatgt tacacctta                                   39

<210> SEQ ID NO 30
<211> LENGTH: 39
<212> TYPE: DNA
<213> ORGANISM: artificial
<220> FEATURE:
<223> OTHER INFORMATION: primer

<400> SEQUENCE: 30
taaggtgtaa catagttctg caattggtac tacaccgtt                                   39

<210> SEQ ID NO 31
<211> LENGTH: 39
<212> TYPE: DNA
<213> ORGANISM: artificial
<220> FEATURE:
<223> OTHER INFORMATION: primer

<400> SEQUENCE: 31 aaccccttg atatacttgc acttgaaaag aaaaaaggt                                    39

<210> SEQ ID NO 32
<211> LENGTH: 39
<212> TYPE: DNA
<213> ORGANISM: artificial
<220> FEATURE:
<223> OTHER INFORMATION: primer

<400> SEQUENCE: 32 acctttttc ttttcaagtg caagtatatc aagggttt                                     39

<210> SEQ ID NO 33
<211> LENGTH: 36
<212> TYPE: DNA
<213> ORGANISM: artificial
<220> FEATURE:
<223> OTHER INFORMATION: primer

<400> SEQUENCE: 33
gatatactta aacttgcaaa gaaaaaaggt ggtccg                                      36

<210> SEQ ID NO 34

```
<211> LENGTH: 39
<212> TYPE: DNA
<213> ORGANISM: artificial
<220> FEATURE:
<223> OTHER INFORMATION: primer

<400> SEQUENCE: 34
cggaccacct tttttctttg caagtttaag tatatcaag                              39

<210> SEQ ID NO 35
<211> LENGTH: 39
<212> TYPE: DNA
<213> ORGANISM: artificial
<220> FEATURE:
<223> OTHER INFORMATION: primer

<400> SEQUENCE: 35
atacttaaac ttgaaaaggc aaaaggtggt ccgattgat                              39

<210> SEQ ID NO 36
<211> LENGTH: 40
<212> TYPE: DNA
<213> ORGANISM: artificial
<220> FEATURE:
<223> OTHER INFORMATION: primer

<400> SEQUENCE: 36
atcaatcgga ccacctttttg cctttttcaa gtttaagtat                            40

<210> SEQ ID NO 37
<211> LENGTH: 39
<212> TYPE: DNA
<213> ORGANISM: artificial
<220> FEATURE:
<223> OTHER INFORMATION: primer

<400> SEQUENCE: 37
ggtccgattg atgtttatgc agagttcata gaaaacagt                              39

<210> SEQ ID NO 38
<211> LENGTH: 39
<212> TYPE: DNA
<213> ORGANISM: artificial
<220> FEATURE:
<223> OTHER INFORMATION: primer

<400> SEQUENCE: 38
actgttttct atgaactctg cataaacatc aatcggacc                              39

<210> SEQ ID NO 39
<211> LENGTH: 37
<212> TYPE: DNA
<213> ORGANISM: artificial
<220> FEATURE:
<223> OTHER INFORMATION: primer

<400> SEQUENCE: 39
atagaaaaac agtgaacttg cacgtgtagg tatggaa                                37

<210> SEQ ID NO 40
<211> LENGTH: 39
<212> TYPE: DNA
<213> ORGANISM: artificial
<220> FEATURE:
<223> OTHER INFORMATION: primer

<400> SEQUENCE: 40
```
aaattccata cctacacgtg caagttcact gttttctat                                39

<210> SEQ ID NO 41
<211> LENGTH: 39
<212> TYPE: DNA
<213> ORGANISM: artificial
<220> FEATURE:
<223> OTHER INFORMATION: primer

<400> SEQUENCE: 41
ggaaatatta gttctgccgc acgttcaatg aacaaactt                                39

<210> SEQ ID NO 42
<211> LENGTH: 39
<212> TYPE: DNA
<213> ORGANISM: artificial
<220> FEATURE:
<223> OTHER INFORMATION: primer

<400> SEQUENCE: 42
aagtttgttc attgaaacgt gcggcagaac taatattcc                                39

<210> SEQ ID NO 43
<211> LENGTH: 39
<212> TYPE: DNA
<213> ORGANISM: artificial
<220> FEATURE:
<223> OTHER INFORMATION: primer

<400> SEQUENCE: 43
aatattagtt ctgcccacgc atcaatgaac aaacttcta                                39

<210> SEQ ID NO 44
<211> LENGTH: 39
<212> TYPE: DNA
<213> ORGANISM: artificial
<220> FEATURE:
<223> OTHER INFORMATION: primer

<400> SEQUENCE: 44
tagaagtttg ttcattgatg cgtgggcaga actaatatt                                39

<210> SEQ ID NO 45
<211> LENGTH: 42
<212> TYPE: DNA
<213> ORGANISM: artificial
<220> FEATURE:
<223> OTHER INFORMATION: primer

<400> SEQUENCE: 45
gcccaccgtt caatgaacgc acttctatta ggattaaaac at                            42

<210> SEQ ID NO 46
<211> LENGTH: 42
<212> TYPE: DNA
<213> ORGANISM: artificial
<220> FEATURE:
<223> OTHER INFORMATION: primer

<400> SEQUENCE: 46
atgttttaat cctaatagaa gtgcggtcat tgaacggtgg gc                            42

<210> SEQ ID NO 47
<211> LENGTH: 39
<212> TYPE: DNA

```
<213> ORGANISM: artificial
<220> FEATURE:
<223> OTHER INFORMATION: primer

<400> SEQUENCE: 47
attatcctta tgcctattgc acaattggcc tattatctt                              39

<210> SEQ ID NO 48
<211> LENGTH: 39
<212> TYPE: DNA
<213> ORGANISM: artificial
<220> FEATURE:
<223> OTHER INFORMATION: primer

<400> SEQUENCE: 48
aagataatag gccaattgtg cataggcat aaggataat                               39

<210> SEQ ID NO 49
<211> LENGTH: 39
<212> TYPE: DNA
<213> ORGANISM: artificial
<220> FEATURE:
<223> OTHER INFORMATION: primer

<400> SEQUENCE: 49
ttggcctatt atcttacagc acgtgttacc aatttcgag                              39

<210> SEQ ID NO 50
<211> LENGTH: 39
<212> TYPE: DNA
<213> ORGANISM: artificial
<220> FEATURE:
<223> OTHER INFORMATION: primer

<400> SEQUENCE: 50
ctcgaaattg gtaacacgtg ctgtaagata ataggccaa                              39

<210> SEQ ID NO 51
<211> LENGTH: 39
<212> TYPE: DNA
<213> ORGANISM: artificial
<220> FEATURE:
<223> OTHER INFORMATION: primer

<400> SEQUENCE: 51
gcctattatc ttacagatgc agttaccaat ttcgaggaa                              39

<210> SEQ ID NO 52
<211> LENGTH: 39
<212> TYPE: DNA
<213> ORGANISM: artificial
<220> FEATURE:
<223> OTHER INFORMATION: primer

<400> SEQUENCE: 52
ttcctcgaaa ttggtaactg catctgtaag ataataggc                              39

<210> SEQ ID NO 53
<211> LENGTH: 39
<212> TYPE: DNA
<213> ORGANISM: artificial
<220> FEATURE:
<223> OTHER INFORMATION: primer

<400> SEQUENCE: 53
cgtgttacca atttcgaggc attagaacct tattttgaa                              39
```

-continued

<210> SEQ ID NO 54
<211> LENGTH: 39
<212> TYPE: DNA
<213> ORGANISM: artificial
<220> FEATURE:
<223> OTHER INFORMATION: primer

<400> SEQUENCE: 54
ttcaaaataa ggttctaatg cctcgaaatt ggtaacacg                              39

<210> SEQ ID NO 55
<211> LENGTH: 39
<212> TYPE: DNA
<213> ORGANISM: artificial
<220> FEATURE:
<223> OTHER INFORMATION: primer

<400> SEQUENCE: 55
accaatttcg aggaattagc accttatttt gaacttact                              39

<210> SEQ ID NO 56
<211> LENGTH: 39
<212> TYPE: DNA
<213> ORGANISM: artificial
<220> FEATURE:
<223> OTHER INFORMATION: primer

<400> SEQUENCE: 56
agtaagttca aaataaggtg ctaattcctc gaaattggt                              39

<210> SEQ ID NO 57
<211> LENGTH: 42
<212> TYPE: DNA
<213> ORGANISM: artificial
<220> FEATURE:
<223> OTHER INFORMATION: primer

<400> SEQUENCE: 57
ccttattttg aacttactgc aggacaacca tttattttta tt                          42

<210> SEQ ID NO 58
<211> LENGTH: 42
<212> TYPE: DNA
<213> ORGANISM: artificial
<220> FEATURE:
<223> OTHER INFORMATION: primer

<400> SEQUENCE: 58
aataaaaata aatggttgtg ctgcagtaag ttcaaaataa gg                          42

<210> SEQ ID NO 59
<211> LENGTH: 45
<212> TYPE: DNA
<213> ORGANISM: artificial
<220> FEATURE:
<223> OTHER INFORMATION: primer

<400> SEQUENCE: 59 tttatttta ttggatttaa tgctgcagct tataattcta atgtc                        45

<210> SEQ ID NO 60
<211> LENGTH: 45
<212> TYPE: DNA
<213> ORGANISM: artificial
<220> FEATURE:

<223> OTHER INFORMATION: primer

<400> SEQUENCE: 60
gacattagaa ttataagctg cagcattaaa tccaataaaa ataaa        45

<210> SEQ ID NO 61
<211> LENGTH: 39
<212> TYPE: DNA
<213> ORGANISM: artificial
<220> FEATURE:
<223> OTHER INFORMATION: primer

<400> SEQUENCE: 61
aatgtccctt taattcccgc aggttctgac ggtatgtca        39

<210> SEQ ID NO 62
<211> LENGTH: 39
<212> TYPE: DNA
<213> ORGANISM: artificial
<220> FEATURE:
<223> OTHER INFORMATION: primer

<400> SEQUENCE: 62
tgacataccg tcagaacctg cgggaattaa agggacatt        39

<210> SEQ ID NO 63
<211> LENGTH: 39
<212> TYPE: DNA
<213> ORGANISM: artificial
<220> FEATURE:
<223> OTHER INFORMATION: primer

<400> SEQUENCE: 63
ttaattccca aggttctgc aggtatgtca aaacgctca        39

<210> SEQ ID NO 64
<211> LENGTH: 39
<212> TYPE: DNA
<213> ORGANISM: artificial
<220> FEATURE:
<223> OTHER INFORMATION: primer

<400> SEQUENCE: 64
tgagcgtttt gacatacctg cagaaccttt gggaattaa        39

<210> SEQ ID NO 65
<211> LENGTH: 39
<212> TYPE: DNA
<213> ORGANISM: artificial
<220> FEATURE:
<223> OTHER INFORMATION: primer

<400> SEQUENCE: 65
tctgacggta tgtcaaaagc atcaattaag aaatggaaa        39

<210> SEQ ID NO 66
<211> LENGTH: 39
<212> TYPE: DNA
<213> ORGANISM: artificial
<220> FEATURE:
<223> OTHER INFORMATION: primer

<400> SEQUENCE: 66
tttccatttc ttaattgatg cttttgacat accgtcaga        39

-continued

```
<210> SEQ ID NO 67
<211> LENGTH: 54
<212> TYPE: DNA
<213> ORGANISM: artificial
<220> FEATURE:
<223> OTHER INFORMATION: primer

<400> SEQUENCE: 67
ggtggtgcat gcggaggtaa ataaatggaa gtagaaaaag agtttattac tgat      54

<210> SEQ ID NO 68
<211> LENGTH: 51
<212> TYPE: DNA
<213> ORGANISM: artificial
<220> FEATURE:
<223> OTHER INFORMATION: primer

<400> SEQUENCE: 68
ggtggtggta ccctatttgt tttcaacttt atctttccat ttcttaattg a         51

<210> SEQ ID NO 69
<211> LENGTH: 39
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (19)..(21)
<223> OTHER INFORMATION: n=a, c, g or t

<400> SEQUENCE: 69
caagcataca atgaagttnn nacatctatt tgttcacct                       39

<210> SEQ ID NO 70
<211> LENGTH: 39
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (19)..(21)
<223> OTHER INFORMATION: n=a. c. g or t

<400> SEQUENCE: 70
aggtgaacaa atagatgtnn naacttcatt gtatgcttg                       39

<210> SEQ ID NO 71
<211> LENGTH: 37
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (16)..(18)
<220> FEATURE:
<221> NAME/KEY: misc_feature
<222> LOCATION: (16)..(18)
<223> OTHER INFORMATION: n=a, c, g, or t

<400> SEQUENCE: 71
gatatactta aacttnnnaa gaaaaaaagg tggtccg                         37

<210> SEQ ID NO 72
<211> LENGTH: 39
<212> TYPE: DNA
<213> ORGANISM: artificial
```

```
<220> FEATURE:
<223> OTHER INFORMATION: primer
<220> FEATURE:
<221> NAME/KEY: misc_feature
<222> LOCATION: (19)..(21)
<220> FEATURE:
<221> NAME/KEY: misc_feature
<222> LOCATION: (19)..(21)
<223> OTHER INFORMATION: n=a, c, g, or t

<400> SEQUENCE: 72
cggaccacct tttttcttnn naagtttaag tatatcaag                          39

<210> SEQ ID NO 73
<211> LENGTH: 54
<212> TYPE: DNA
<213> ORGANISM: artificial
<220> FEATURE:
<223> OTHER INFORMATION: primer

<400> SEQUENCE: 73
ggtggtgcat gcggaggtaa ataaatgtct aataaaaaac agtcaaatag gcta         54

<210> SEQ ID NO 74
<211> LENGTH: 39
<212> TYPE: DNA
<213> ORGANISM: artificial
<220> FEATURE:
<223> OTHER INFORMATION: primer

<400> SEQUENCE: 74
ggtggtggta cctcacttag atctaagctg ttcaaacaa                          39

<210> SEQ ID NO 75
<211> LENGTH: 267
<212> TYPE: PRT
<213> ORGANISM: Escherichia coli RY13
<220> FEATURE:
<221> NAME/KEY: MISC_FEATURE
<222> LOCATION: (1)..(267)
<223> OTHER INFORMATION: Amino acid residues 1-267 correspond to
      residues 4-270 of the protein sequence of EcoRI

<400> SEQUENCE: 75
```

Lys Lys Gln Ser Asn Arg Leu Thr Glu Gln His Lys Leu Ser Gln Gly
1               5                   10                  15

Val Ile Gly Ile Phe Gly Asp Tyr Ala Lys Ala His Asp Leu Ala Val
            20                  25                  30

Gly Glu Val Ser Lys Leu Val Lys Lys Ala Leu Ser Asn Glu Tyr Pro
        35                  40                  45

Gln Leu Ser Phe Arg Tyr Arg Asp Ser Ile Lys Lys Thr Glu Ile Asn
    50                  55                  60

Glu Ala Leu Lys Lys Ile Asp Pro Asp Leu Gly Gly Thr Leu Phe Val
65                  70                  75                  80

Ser Asn Ser Ser Ile Lys Pro Asp Gly Gly Ile Val Glu Val Lys Asp
                85                  90                  95

Asp Tyr Gly Glu Trp Arg Val Val Leu Val Ala Glu Ala Lys His Gln
            100                 105                 110

Gly Lys Asp Ile Ile Asn Ile Arg Asn Gly Leu Leu Val Gly Lys Arg
        115                 120                 125

Gly Asp Gln Asp Leu Met Ala Ala Gly Asn Ala Ile Glu Arg Ser His
    130                 135                 140

Lys Asn Ile Ser Glu Ile Ala Asn Phe Met Leu Ser Glu Ser His Phe

```
           145                 150                 155                 160
Pro Tyr Val Leu Phe Leu Glu Gly Ser Asn Phe Leu Thr Glu Asn Ile
                165                 170                 175

Ser Ile Thr Arg Pro Asp Gly Arg Val Val Asn Leu Glu Tyr Asn Ser
                180                 185                 190

Gly Ile Leu Asn Arg Leu Asp Arg Leu Thr Ala Ala Asn Tyr Gly Met
                195                 200                 205

Pro Ile Asn Ser Asn Leu Cys Ile Asn Lys Phe Val Asn His Lys Asp
210                 215                 220

Lys Ser Ile Met Leu Gln Ala Ala Ser Ile Tyr Thr Gln Gly Asp Gly
225                 230                 235                 240

Arg Glu Trp Asp Ser Lys Ile Met Phe Glu Ile Met Phe Asp Ile Ser
                245                 250                 255

Thr Thr Ser Leu Arg Val Leu Gly Arg Asp Leu
                260                 265

<210> SEQ ID NO 76
<211> LENGTH: 265
<212> TYPE: PRT
<213> ORGANISM: Rhodopseudomonas sphaeroides
<220> FEATURE:
<221> NAME/KEY: MISC_FEATURE
<222> LOCATION: (1)..(265)
<223> OTHER INFORMATION: amino acid residues 1-265 correspond to
      residues 10-274 of the protein sequence of RsrI

<400> SEQUENCE: 76

Lys Gly Gln Ala Leu Arg Leu Gly Ile Gln Gln Glu Leu Gly Gly
1               5                   10                  15

Pro Leu Ser Ile Phe Gly Ala Ala Gln Lys His Asp Leu Ser Ile
                20                  25                  30

Arg Glu Val Thr Ala Gly Val Leu Thr Lys Leu Ala Glu Asp Phe Pro
                35                  40                  45

Asn Leu Glu Phe Gln Leu Arg Thr Ser Leu Thr Lys Lys Ala Ile Asn
    50                  55                  60

Glu Lys Leu Arg Ser Phe Asp Pro Arg Leu Gly Gln Ala Leu Phe Val
65                  70                  75                  80

Glu Ser Ala Ser Ile Arg Pro Asp Gly Gly Ile Thr Glu Val Lys Asp
                85                  90                  95

Arg His Gly Asn Trp Arg Val Ile Leu Val Gly Glu Ser Lys His Gln
                100                 105                 110

Gly Asn Asp Val Glu Lys Ile Leu Ala Gly Val Leu Gln Gly Lys Ala
                115                 120                 125

Lys Asp Gln Asp Phe Met Ala Ala Gly Asn Ala Ile Glu Arg Met His
130                 135                 140

Lys Asn Val Leu Glu Leu Arg Asn Tyr Met Leu Asp Glu Lys His Phe
145                 150                 155                 160

Pro Tyr Val Val Phe Leu Gln Gly Ser Asn Phe Ala Thr Glu Ser Phe
                165                 170                 175

Glu Val Thr Arg Pro Asp Gly Arg Val Val Lys Ile Val His Asp Ser
                180                 185                 190

Gly Met Leu Asn Arg Ile Asp Arg Val Thr Ala Ser Ser Leu Ser Arg
                195                 200                 205

Glu Ile Asn Gln Asn Tyr Cys Glu Asn Ile Val Val Arg Ala Gly Ser
210                 215                 220

Phe Asp His Met Phe Gln Ile Ala Ser Leu Tyr Cys Lys Ala Ala Pro
```

```
                225                 230                 235                 240

Trp Thr Ala Gly Glu Met Ala Glu Ala Met Leu Ala Val Ala Lys Thr
                    245                 250                 255

Ser Leu Arg Ile Ile Ala Asp Asp Leu
                260                 265

<210> SEQ ID NO 77
<211> LENGTH: 39
<212> TYPE: DNA
<213> ORGANISM: artificial
<220> FEATURE:
<223> OTHER INFORMATION: primer

<400> SEQUENCE: 77
gattgggtgg cgcagaaatt tcaaacgggc cagcagtcg                              39

<210> SEQ ID NO 78
<211> LENGTH: 39
<212> TYPE: DNA
<213> ORGANISM: artificial
<220> FEATURE:
<223> OTHER INFORMATION: primer

<400> SEQUENCE: 78
cgactgctgg cccgtttgaa atttctgcgc cacccaatc                              39

<210> SEQ ID NO 79
<211> LENGTH: 272
<212> TYPE: PRT
<213> ORGANISM: Agrobacterium gelatinovorum

<400> SEQUENCE: 79

Met Arg Leu Asp Leu Asp Phe Gly Arg Gly Leu Val Ala His Val Met
1               5                   10                  15

Leu Asp Asn Val Ser Glu Glu Gln Tyr Gln Gln Ile Ser Asp Tyr Phe
            20                  25                  30

Val Pro Leu Val Asn Lys Pro Lys Leu Lys Ser Arg Asp Ala Ile Gly
        35                  40                  45

Gln Ala Phe Val Met Ala Thr Glu Val Cys Pro Asp Ala Asn Pro Ser
    50                  55                  60

Asp Leu Trp His His Val Leu Tyr Arg Ile Tyr Ile Arg Glu Lys Ile
65                  70                  75                  80

Gly Thr Asp Pro Ser Gln Ser Trp Val Arg Thr Ser Gly Glu Ala Phe
                85                  90                  95

Glu Val Ala Leu Val Glu Arg Tyr Asn Pro Val Leu Ala Arg His Gly
            100                 105                 110

Ile Arg Leu Thr Ala Leu Phe Lys Gly Gln Lys Gly Leu Ala Leu Thr
        115                 120                 125

Arg Met Gly Val Ala Asp Arg Val Gly Ser Arg Lys Val Asp Val Met
    130                 135                 140

Ile Glu Lys Gln Gly Gly Gly Arg Ser Pro Ala Glu Gly Phe Gly
145                 150                 155                 160

Val Val Gly Gly Ile His Ala Lys Val Ser Leu Ala Glu Arg Val Ser
                165                 170                 175

Asp Asp Ile Pro Ala Ser Arg Ile Met Met Gly Glu Gly Leu Leu Ser
            180                 185                 190

Val Leu Ser Thr Leu Asp Val Lys Ser Phe Pro Pro Pro His Gly Asp
        195                 200                 205
```

```
Leu Val Asn Arg Gly Glu Leu Gly Thr Pro Asp Arg Pro Ser Asp Lys
            210                 215                 220

Arg Asn Tyr Ile Glu Gly His Gly Asp Phe Ser Ala Cys Phe Ser Tyr
225                 230                 235                 240

Asn Leu Arg Thr Pro Pro Ser Asn Ala Thr Thr Pro Ser Gly Arg His
                245                 250                 255

Ile Tyr Val Ser Ala Ser Leu Val Arg Thr Thr Ser Ser Pro Thr Thr
                260                 265                 270

<210> SEQ ID NO 80
<211> LENGTH: 358
<212> TYPE: PRT
<213> ORGANISM: Anabaena variabilis

<400> SEQUENCE: 80

Met Glu Glu Asp Leu Asp Leu Ser Glu Asn Ile Glu Ala Ala Ser Ala
1               5                   10                  15

Glu Leu Thr Thr Leu Tyr Gln Val Ala Ala Asp Ala Met Lys Asp Tyr
                20                  25                  30

Ile Glu Ile Tyr Leu Ala Leu Ser Lys Gln Ser Asp Gly Phe Ser Asn
            35                  40                  45

Ile Asn Asn Leu Asp Leu Thr Ser Arg Asn Arg Arg Leu Val Val Ile
50                  55                  60

His Gly Leu Ser Leu Glu Leu Asp Pro Asp Thr Ser Thr Pro Glu Glu
65                  70                  75                  80

Ile Lys Arg Glu Ala Glu Arg Met Leu Ala Ile Ala Leu Asp Thr Glu
                85                  90                  95

Ser Ala Ile Thr Ala Gly Val Tyr Glu Lys Met Arg Leu Phe Ala Ser
            100                 105                 110

Ser Leu Val Asp Gln Leu Phe Glu Gln Thr Asp Glu Leu Asn Ser Leu
            115                 120                 125

Ser Ser Glu Tyr Leu Ser Ala Asn Pro Gly Phe Leu Pro Phe Phe Gln
130                 135                 140

Gln Leu Ala Gly Leu Arg Ser Lys Ser Glu Leu Lys Arg Glu Val Gly
145                 150                 155                 160

Asn Ala Ser Asp Asn Ser Ile Ser Lys Ala Val Ala Glu Arg Ile Leu
                165                 170                 175

Glu Arg Ile Ile Arg Asn Leu Arg Ile Arg Thr Phe Ser Lys Glu Lys
            180                 185                 190

Leu Leu Gln Ala Val Glu Pro Thr Leu Glu Gly Ile Val Arg Asp Leu
            195                 200                 205

Val Gly Lys Val Leu Leu Glu Asn Ile Val Ala Asp Ala Leu Ser Asp
210                 215                 220

Leu Gln Val Pro Phe Met Arg Glu Ser Glu Tyr Gln Ser Leu Lys Gly
225                 230                 235                 240

Val Ile Tyr Asp Phe Arg Ala Asp Phe Val Ile Pro Asp Ala Gln Asn
                245                 250                 255

Pro Ile Ala Phe Ile Glu Val Arg Lys Ser Ser Thr Arg His Ala Ser
            260                 265                 270

Leu Tyr Ala Lys Asp Lys Met Phe Ser Ala Ile Asn Trp Lys Gly Lys
            275                 280                 285

Asn Lys Arg Leu Leu Gly Ile Leu Val Val Glu Gly Pro Trp Thr Arg
            290                 295                 300

Glu Thr Leu Arg Val Met Ala Asn Val Phe Asp Tyr Val Thr Pro Leu
305                 310                 315                 320
```

Thr Arg Val Ser Gln Val Ala Glu Ala Ile Arg Ala Tyr Leu Asp Gly
            325                 330                 335

Asp Lys Thr Arg Leu Lys Trp Leu Val Asn Phe Ser Ile Glu Glu Ala
            340                 345                 350

Asp His Asp Asn Ile Thr
            355

<210> SEQ ID NO 81
<211> LENGTH: 530
<212> TYPE: PRT
<213> ORGANISM: Bacillus stearothermophilus B61

<400> SEQUENCE: 81

Met Ala Lys Tyr Gly Arg Gly Lys Phe Leu Pro His Gln Asn Tyr Ile
1               5                   10                  15

Asp Tyr Met His Phe Ile Val Asn His Lys Asn Tyr Ser Gly Met Pro
            20                  25                  30

Asn Ala Ile Gly Glu Asp Gly Arg Ile Asn Trp Gln Val Ser Ser Gly
        35                  40                  45

Lys Thr Thr Ser Phe Tyr Glu Tyr Tyr Gln Ala Arg Phe Glu Trp Trp
    50                  55                  60

Glu Lys Lys Ala Asp Glu Leu Asn Leu Pro Gly Thr Gly Asn Ser Asn
65                  70                  75                  80

Lys Arg Phe Ser Leu Ala Ala Arg Leu Ile His Pro Thr Gly Gln Arg
                85                  90                  95

Pro Cys Arg Leu Cys Gly Lys Tyr Gln Tyr Val Gly Tyr Met Tyr Val
            100                 105                 110

Ser His Asn Leu Tyr Lys Arg Trp Ser Lys Ile Thr Gly Arg Glu Asp
        115                 120                 125

Leu Phe Phe Lys Lys Gln Asn Ile Ile Glu Ala Ala Asn Ile Phe Lys
    130                 135                 140

Ser Ile Met Gly Glu Gln Ala Leu Ile Asn Glu Leu Thr Thr Ile Phe
145                 150                 155                 160

Pro Glu Arg Lys Asp Tyr Phe Asn Arg Leu Pro Asn Ile Glu Asp Phe
                165                 170                 175

Phe Val Ser Ser Ser His Ile Lys Asn Asn Gly Asn Tyr Ile Ser Pro
            180                 185                 190

Gly Phe Met Ala Asn Pro Pro Asp Arg Leu Asp Gly Phe His Asp Tyr
        195                 200                 205

Gly Ile Cys Cys Arg Lys Glu Lys Asp Pro Gly Arg His Asp Asp Asn
    210                 215                 220

Met Arg Leu Tyr Asn His Asp Arg Arg Ala Phe Met Trp Trp Ser Glu
225                 230                 235                 240

Gly Asp Trp Ala Leu Ala Asp Ala Leu Tyr Asn Lys Ala Gly Ala Gly
                245                 250                 255

Lys Cys Ala Asp Pro Asp Cys Gln Lys Glu Val Glu Lys Ile Ser Pro
            260                 265                 270

Asp His Val Gly Pro Ile Ser Cys Gly Phe Lys Gln Ile Pro Phe Phe
        275                 280                 285

Lys Pro Leu Cys Ala Ser Cys Asn Ser Ala Lys Asn Arg Arg Phe Ser
    290                 295                 300

Tyr Gln Asp Val Lys Glu Leu Leu Lys Tyr Glu Asn Tyr Thr Gly Asp
305                 310                 315                 320

Ser Val Ala Ser Trp Gln Val Arg Ala Leu Trp Asp Asn Cys Lys His

|   |   |   | 325 |   |   |   | 330 |   |   |   | 335 |   |
|---|---|---|---|---|---|---|---|---|---|---|---|---|

Leu Val Lys Asn Asp Asp Asp Ser Lys Leu Leu Ser Asn Leu Met Arg
          340               345               350

Ser Leu Gln Asp Tyr Tyr Leu Arg Ser Leu Tyr Lys Leu Phe Ser Asn
          355               360               365

Gly Phe Ala His Leu Leu Ser Tyr Phe Leu Thr Pro Glu Tyr Ala His
          370               375               380

Tyr Lys Ile Thr Phe Glu Gly Leu Asn Thr Ser Thr Leu Glu Tyr Glu
385               390               395               400

Arg Tyr Tyr Lys Thr Phe Lys Lys Thr Lys Ser Thr Ser Ser Leu Ala
          405               410               415

Ala Arg Ile Val Arg Ile Ala Phe Glu Glu Leu Glu Ile Tyr Asn Ser
          420               425               430

Lys Asp Ile Asn Glu Arg Lys Leu Ile Lys Phe Asp Thr Ser Ser Trp
          435               440               445

Glu Lys Asp Phe Glu Asn Ile Ile Ser Tyr Ala Thr Lys Asn Leu Ser
          450               455               460

Leu Asp Glu Glu Ala Ser Lys Trp Asn Lys Val Leu Thr Asp Lys Asn
465               470               475               480

Leu Ser Ser Thr Glu Lys Asp Lys Lys Ile Ser Ser Leu Leu Glu Asp
          485               490               495

Lys Asn Tyr Glu Val Tyr Lys Lys Gln Phe Tyr Ile Leu Lys Asp Leu
          500               505               510

Leu Val Glu His Phe Asn Lys Ile Gly Glu Gln Ile Ala Lys Asp Tyr
          515               520               525

Met Lys
    530

<210> SEQ ID NO 82
<211> LENGTH: 301
<212> TYPE: PRT
<213> ORGANISM: Enterobacter agglomerans

<400> SEQUENCE: 82

Met Lys Lys Arg Arg Asp Leu Val Glu Val Phe Gly Tyr Asn Pro Met
1               5                   10                  15

Asp Leu Ser Pro Glu Val Arg Ala Leu Trp Asn Leu Gly Ala Cys Pro
            20                  25                  30

Phe Leu Asn Lys Glu Cys Ile Lys Ile Asn His Asp Gln Thr Ile Ile
            35                  40                  45

Tyr Gly Thr Cys Ser Val Thr Ser Pro Tyr Gly Asp Val Ile Ile Cys
        50                  55                  60

Pro Asn Arg Leu Tyr Ala Asn Asp Tyr Glu Thr Leu His Lys Val Ser
65                  70                  75                  80

Arg Asp Ala Phe Gly Asp Val Pro Phe Leu Thr Tyr Ser Asn Phe
            85                  90                  95

Ile Lys Tyr Arg Ala Thr Tyr Lys Asp Cys Ile Val Ala Leu Gly Lys
            100                 105                 110

Asn Ser Gly Lys Glu Val Gln Val Gly Arg Ala Leu Ser Met Asp Trp
            115                 120                 125

Val Leu Val Arg Ile Thr Asp Gly Glu Leu Lys Glu Tyr Val Gly Val
            130                 135                 140

Glu Ile Gln Ser Ile Asp Ile Thr Gly Asn Tyr Arg Asp Ala Trp His
145                 150                 155                 160

```
Ala Tyr Lys Asn Leu Lys Pro Ile Asp Ile Asp Asn Leu Pro Thr
            165                 170                 175

Ser Gln His Gly Leu Asn Trp Ala Asn Val His Lys Arg Leu Ile Pro
        180                 185                 190

Gln Ile Ile Arg Lys Gly Val Val Tyr Ser Arg Ser Asn Tyr Val Lys
            195                 200                 205

Lys Gly Leu Tyr Phe Ile Leu Pro Glu Ile Val Tyr Asn Lys Phe Glu
        210                 215                 220

Asp Val Ile Gly Ala Asp Ile Pro Leu Leu Lys Thr Gln Thr Asn Lys
225                 230                 235                 240

Ser Ile Thr Val His Thr Tyr Ser Leu Gly Glu Pro Ala Ala Asn Gly
            245                 250                 255

Glu Gln Arg Lys Leu Ile Ser Glu Arg Glu Ile Ile Phe Asp Leu Asp
        260                 265                 270

Glu Phe Ser Lys Arg Phe Thr Thr Gly Pro Asn Leu Pro Lys Gly Asp
            275                 280                 285

Asp Leu Asp Ala Val Ile Lys Lys Ala Leu Gly Met Met
        290                 295                 300

<210> SEQ ID NO 83
<211> LENGTH: 277
<212> TYPE: PRT
<213> ORGANISM: Escherichia coli RY13

<400> SEQUENCE: 83

Met Ser Asn Lys Lys Gln Ser Asn Arg Leu Thr Glu Gln His Lys Leu
1               5                   10                  15

Ser Gln Gly Val Ile Gly Ile Phe Gly Asp Tyr Ala Lys Ala His Asp
            20                  25                  30

Leu Ala Val Gly Glu Val Ser Lys Leu Val Lys Lys Ala Leu Ser Asn
        35                  40                  45

Glu Tyr Pro Gln Leu Ser Phe Arg Tyr Arg Asp Ser Ile Lys Lys Thr
    50                  55                  60

Glu Ile Asn Glu Ala Leu Lys Lys Ile Asp Pro Asp Leu Gly Gly Thr
65                  70                  75                  80

Leu Phe Val Ser Asn Ser Ser Ile Lys Pro Asp Gly Gly Ile Val Glu
                85                  90                  95

Val Lys Asp Asp Tyr Gly Glu Trp Arg Val Val Leu Val Ala Glu Ala
            100                 105                 110

Lys His Gln Gly Lys Asp Ile Ile Asn Ile Arg Asn Gly Leu Leu Val
        115                 120                 125

Gly Lys Arg Gly Asp Gln Asp Leu Met Ala Ala Gly Asn Ala Ile Glu
    130                 135                 140

Arg Ser His Lys Asn Ile Ser Glu Ile Ala Asn Phe Met Leu Ser Glu
145                 150                 155                 160

Ser His Phe Pro Tyr Val Leu Phe Leu Glu Gly Ser Asn Phe Leu Thr
                165                 170                 175

Glu Asn Ile Ser Ile Thr Arg Pro Asp Gly Arg Val Val Asn Leu Glu
            180                 185                 190

Tyr Asn Ser Gly Ile Leu Asn Arg Leu Asp Arg Leu Thr Ala Ala Asn
        195                 200                 205

Tyr Gly Met Pro Ile Asn Ser Asn Leu Cys Ile Asn Lys Phe Val Asn
    210                 215                 220

His Lys Asp Lys Ser Ile Met Leu Gln Ala Ala Ser Ile Tyr Thr Gln
225                 230                 235                 240
```

```
Gly Asp Gly Arg Glu Trp Asp Ser Lys Ile Met Phe Glu Ile Met Phe
                245                 250                 255

Asp Ile Ser Thr Thr Ser Leu Arg Val Leu Gly Arg Asp Leu Phe Glu
            260                 265                 270

Gln Leu Thr Ser Lys
        275
```

<210> SEQ ID NO 84
<211> LENGTH: 245
<212> TYPE: PRT
<213> ORGANISM: Escherichia coli J62 pLG74

<400> SEQUENCE: 84

```
Met Ser Leu Arg Ser Asp Leu Ile Asn Ala Leu Tyr Asp Glu Asn Gln
1               5                   10                  15

Lys Tyr Asp Val Cys Gly Ile Ile Ser Ala Glu Gly Lys Ile Tyr Pro
            20                  25                  30

Leu Gly Ser Asp Thr Lys Val Leu Ser Thr Ile Phe Glu Leu Phe Ser
        35                  40                  45

Arg Pro Ile Ile Asn Lys Ile Ala Glu Lys His Gly Tyr Ile Val Glu
    50                  55                  60

Glu Pro Lys Gln Gln Asn His Tyr Pro Asp Phe Thr Leu Tyr Lys Pro
65                  70                  75                  80

Ser Glu Pro Asn Lys Ile Ala Ile Asp Ile Lys Thr Thr Tyr Thr
                85                  90                  95

Asn Lys Glu Asn Glu Lys Ile Lys Phe Thr Leu Gly Tyr Thr Ser
            100                 105                 110

Phe Ile Arg Asn Asn Thr Lys Asn Ile Val Tyr Pro Phe Asp Gln Tyr
        115                 120                 125

Ile Ala His Trp Ile Ile Gly Tyr Val Tyr Thr Arg Val Ala Thr Arg
    130                 135                 140

Lys Ser Ser Leu Lys Thr Tyr Asn Ile Asn Glu Leu Asn Glu Ile Pro
145                 150                 155                 160

Lys Pro Tyr Lys Gly Val Lys Val Phe Leu Gln Asp Lys Trp Val Ile
                165                 170                 175

Ala Gly Asp Leu Ala Gly Ser Gly Asn Thr Thr Asn Ile Gly Ser Ile
            180                 185                 190

His Ala His Tyr Lys Asp Phe Val Glu Gly Lys Gly Ile Phe Asp Ser
        195                 200                 205

Glu Asp Glu Phe Leu Asp Tyr Trp Arg Asn Tyr Glu Arg Thr Ser Gln
    210                 215                 220

Leu Arg Asn Asp Lys Tyr Asn Asn Ile Ser Glu Tyr Arg Asn Trp Ile
225                 230                 235                 240

Tyr Arg Gly Arg Lys
            245
```

<210> SEQ ID NO 85
<211> LENGTH: 300
<212> TYPE: PRT
<213> ORGANISM: Haemophilus influenzae Rd (exo-mutant)

<400> SEQUENCE: 85

```
Met Lys Lys Ser Ala Leu Glu Lys Leu Leu Ser Leu Ile Glu Asn Leu
1               5                   10                  15

Thr Asn Gln Glu Phe Lys Gln Ala Thr Asn Ser Leu Ile Ser Phe Ile
            20                  25                  30
```

Tyr Lys Leu Asn Arg Asn Glu Val Ile Glu Leu Val Arg Ser Ile Gly
            35                  40                  45

Ile Leu Pro Glu Ala Ile Lys Pro Ser Ser Thr Gln Glu Lys Leu Phe
 50                  55                  60

Ser Lys Ala Gly Asp Ile Val Leu Ala Lys Ala Phe Gln Leu Leu Asn
 65                  70                  75                  80

Leu Asn Ser Lys Pro Leu Glu Gln Arg Gly Asn Ala Gly Asp Val Ile
            85                  90                  95

Ala Leu Ser Lys Glu Phe Asn Tyr Gly Leu Val Ala Asp Ala Lys Ser
           100                 105                 110

Phe Arg Leu Ser Arg Thr Ala Lys Asn Gln Lys Asp Phe Lys Val Lys
           115                 120                 125

Ala Leu Ser Glu Trp Arg Glu Asp Lys Asp Tyr Ala Val Leu Thr Ala
           130                 135                 140

Pro Phe Phe Gln Tyr Pro Thr Thr Lys Ser Gln Ile Phe Lys Gln Ser
145                 150                 155                 160

Leu Asp Glu Asn Val Leu Leu Phe Ser Trp Glu His Leu Ala Ile Leu
                165                 170                 175

Leu Gln Leu Asp Leu Glu Glu Thr Asn Ile Phe Pro Phe Glu Gln Leu
           180                 185                 190

Trp Asn Phe Pro Lys Lys Gln Ser Lys Thr Ser Val Ser Asp Ala
           195                 200                 205

Glu Asn Asn Phe Met Arg Asp Phe Asn Lys Tyr Phe Met Asp Leu Phe
210                 215                 220

Lys Ile Asp Lys Asp Thr Leu Asn Gln Leu Leu Gln Lys Glu Ile Asn
225                 230                 235                 240

Phe Ile Glu Glu Arg Ser Leu Ile Glu Lys Glu Tyr Trp Lys Lys Gln
                245                 250                 255

Ile Asn Ile Ile Lys Asn Phe Thr Arg Glu Glu Ala Ile Glu Ala Leu
           260                 265                 270

Leu Lys Asp Ile Asn Met Ser Ser Lys Ile Glu Thr Ile Asp Ser Phe
           275                 280                 285

Ile Lys Gly Ile Lys Ser Asn Asp Arg Leu Tyr Leu
           290                 295                 300

<210> SEQ ID NO 86
<211> LENGTH: 254
<212> TYPE: PRT
<213> ORGANISM: Haemophilus parainfluenzae

<400> SEQUENCE: 86

Met Lys Tyr Glu Glu Ile Asn Phe Lys Val Pro Val Glu Ser Pro Tyr
 1               5                  10                  15

Tyr Pro Asn Tyr Ser Gln Cys Val Ile Glu Arg Ile Tyr Ser Ile Leu
             20                  25                  30

Arg Asn Gln Lys Asp Met Gly Asp Arg Ile Ile Asn Thr Asn
            35                  40                  45

Leu Lys Lys Gly Leu Pro Leu Glu Asn Ile Asn Lys Ile Ala Gly Pro
 50                  55                  60

Met Ile Glu Ala Trp Ala Glu Glu Val Phe Ser Gly Ile Arg Asp Asn
 65                  70                  75                  80

Arg Asp Asn Gln Tyr Asn Leu Ile Asn Val Glu Ala Gln Glu Arg Leu
             85                  90                  95

Gly Ile Ser Asp Ile Ile Leu Gln Phe Gln Val Asn Asn Asn Val Ile

```
            100                 105                 110
Thr Gly Asn Val Asp Val Lys Ala Thr Ser Asn Asp Ile Pro Asp Ser
            115                 120                 125

Gly Lys Ser Pro Asn Ile Thr Ser Phe Ser Arg Ile Arg Thr Ala Tyr
130                 135                 140

Val Lys Asp Pro Asn Phe Ile Phe Ile Ile Leu Ser Ile Lys His Ser
145                 150                 155                 160

Val Tyr Val Lys Arg Asn Glu Tyr Thr Asn Leu Met Asp Gly Ile Met
                165                 170                 175

Gln Ile Ile Asp Phe Asn Val Tyr Asp Leu Lys Tyr Ile Ser Asp Ser
                180                 185                 190

Asp Ile Ser Tyr Asn Pro Ala Leu Gly Thr Gly Gln Ile Gln Ile Lys
                195                 200                 205

Asp Ile His Tyr Val Ser Ser Gln Lys Arg Thr Thr Trp Gln Met Cys
                210                 215                 220

Gln Leu Leu Asp Leu Lys Tyr Leu Arg Ser Lys Lys Arg Thr Ile Glu
225                 230                 235                 240

Gln Phe Tyr Asn Glu Ala Lys Arg Asn Lys Trp Ile Lys Asp
                245                 250

<210> SEQ ID NO 87
<211> LENGTH: 218
<212> TYPE: PRT
<213> ORGANISM: Klebsiella pnermoniae OK8

<400> SEQUENCE: 87

Met Asp Val Phe Asp Lys Val Tyr Ser Asp Asp Asn Ser Tyr Asp
1               5                   10                  15

Gln Lys Thr Val Ser Gln Arg Ile Glu Ala Leu Phe Leu Asn Asn Leu
                20                  25                  30

Gly Lys Val Val Thr Arg Gln Gln Ile Ile Arg Ala Ala Thr Asp Pro
            35                  40                  45

Lys Thr Gly Lys Gln Pro Glu Asn Trp His Gln Arg Leu Ser Glu Leu
50                  55                  60

Arg Thr Asp Lys Gly Tyr Thr Ile Leu Ser Trp Arg Asp Met Lys Val
65                  70                  75                  80

Leu Ala Pro Gln Glu Tyr Ile Met Pro His Ala Thr Arg Arg Pro Lys
                85                  90                  95

Ala Ala Lys Arg Val Leu Pro Thr Lys Glu Thr Trp Glu Gln Val Leu
                100                 105                 110

Asp Arg Ala Asn Tyr Ser Cys Glu Trp Gln Glu Asp Gly Gln His Cys
                115                 120                 125

Gly Leu Val Glu Gly Asp Ile Asp Pro Ile Gly Gly Thr Val Lys
            130                 135                 140

Leu Thr Pro Asp His Met Thr Pro His Ser Ile Asp Pro Ala Thr Asp
145                 150                 155                 160

Val Asn Asp Pro Lys Met Trp Gln Ala Leu Cys Gly Arg His Gln Val
                165                 170                 175

Met Lys Lys Asn Tyr Trp Asp Ser Asn Asn Gly Lys Ile Asn Val Ile
                180                 185                 190

Gly Ile Leu Gln Ser Val Asn Glu Lys Gln Lys Asn Asp Ala Leu Glu
            195                 200                 205

Phe Leu Leu Asn Tyr Tyr Gly Leu Lys Arg
    210                 215
```

```
<210> SEQ ID NO 88
<211> LENGTH: 288
<212> TYPE: PRT
<213> ORGANISM: Nocardia corallina

<400> SEQUENCE: 88

Met Ala Thr Ala Pro Gly His Leu Leu Gly Gln Ile Ile Gly Asn Val
1               5                   10                  15

Met Glu Glu Ala Leu Lys Pro Val Leu Gln Glu Met Ala Asp Arg His
                20                  25                  30

Asp Leu Tyr Leu Asp Ser Lys Gly Leu Arg Pro Gly Val Arg Ser Gly
            35                  40                  45

Ala Leu Val Thr Trp Thr Asp Asp Leu Gly Asn Asn His Asp Leu Asp
        50                  55                  60

Phe Val Leu Glu Arg Gly Gly Ser Ala Thr Lys Ala Gly Asn Pro Ala
65                  70                  75                  80

Ala Phe Ile Glu Ala Ala Trp Arg Arg Tyr Thr Lys His Ser Lys Ala
                85                  90                  95

Lys Ala Gln Glu Ile Gln Gly Ala Val Leu Pro Val Leu Ala Ala Trp
            100                 105                 110

Asn Asn Val Lys Pro Thr Pro Ala Ala Val Val Ala Gly Gln Trp Thr
        115                 120                 125

Ala Pro Ser Leu Gln Gln Met Arg Ser Asn Gly Phe Val Val Leu His
130                 135                 140

Leu His Phe Pro Thr Thr Ala Gln Val Phe Gly Gly Asn Gly Ile Asn
145                 150                 155                 160

Ile Glu Gly Thr Gly Glu Gly Thr Pro Asp Ala Phe Trp Gln Gln Gln
                165                 170                 175

Cys Asp Ala Tyr Thr Ser Lys Ser Glu Ala Asp Lys Asp Ser Leu Ala
            180                 185                 190

Thr Ala Leu Arg Thr Ala His Ala Gln Glu Phe Arg Thr Phe Val Ala
        195                 200                 205

Glu Leu Glu Arg Arg Val Val Arg Ala Ile Asp Tyr Val Val Val Thr
210                 215                 220

Pro Leu His Gly His Gly Ser Gln Tyr Thr Ser Ile Glu Asn Ala Ile
225                 230                 235                 240

Glu Ala Val Arg Thr Tyr Ser Cys Gly Glu Glu Ser Ala Pro Phe Leu
                245                 250                 255

Arg Phe Glu Ile Arg Ile Ser Tyr Thr Asn Gly Asp Val Ile Gln Ala
            260                 265                 270

Thr Phe Gly Ser Ser Ser Asp Ala Ile Glu Phe Leu Asp Thr Phe Asn
        275                 280                 285

<210> SEQ ID NO 89
<211> LENGTH: 328
<212> TYPE: PRT
<213> ORGANISM: Neisseria mucosa

<400> SEQUENCE: 89

Met Ser Ser Tyr His Asp Asp Leu Asn Ile Leu Asn Val Asp Phe Asn
1               5                   10                  15

His Leu Arg Leu Thr Glu Leu Ile Lys Leu Ala Asp Gln Ala Glu Pro
                20                  25                  30

Phe Tyr Leu Trp Val Glu Lys Ile Phe Arg Gln Val Ser Gly Arg Ala
            35                  40                  45
```

```
Asp Ser Leu Glu Thr Ile Ile Glu Val Glu Arg Val Val Leu Lys
    50                  55                  60

Met Ala Ile Leu Thr Cys Phe Thr Ser Asp Lys Glu Leu Pro Lys
65                  70                  75                  80

Leu Phe Asn Gly Val Gly Val Pro Tyr Pro His Ile Lys Ala Cys Tyr
                    85                  90                  95

Phe Phe Phe Ala Trp Leu Val Arg Asp Ala Ala Thr Gln Arg Leu Asp
                100                 105                 110

Pro Leu Ile Arg Glu Ala Phe Thr Gln Leu Lys Ser Ile His Pro Gln
                115                 120                 125

Met Lys Lys Thr Glu Leu Glu Ser Glu Ile Phe Ser Gln Leu Leu Val
130                 135                 140

Asn Tyr Arg Asn Glu Leu Ile His Phe Ser Trp Pro Val Ile Arg Glu
145                 150                 155                 160

Val Leu Ile Ser Arg Leu Glu Gly Ser Arg Arg Ala Ala Arg Gly Ser
                165                 170                 175

Tyr Leu Glu Leu Phe Val Arg Thr Ala Leu Ala Gln Ser Ile Thr Tyr
                180                 185                 190

Phe Tyr Lys Ile Tyr Gly Asn Tyr Gly Lys Phe Leu Asp Val Lys Ile
                195                 200                 205

His Asp Lys Pro Leu Lys Val Lys Asn Arg Thr Tyr Asp Val Val Ala
210                 215                 220

Glu Leu Ile Gly Asn Asn His Asn Thr Gln Tyr Leu Ile Leu Pro Val
225                 230                 235                 240

Lys Thr Arg Glu Thr Gln Gly Gly His Ala His Leu Phe Thr Arg
                245                 250                 255

Asp Ile Glu Gln Ser Asn Asn Asp Ile Arg Glu Leu Tyr Pro Asn Ala
                260                 265                 270

Val Ile Ala Pro Val Ile Ala Glu Asn Trp Ser Asp Thr Glu Lys
                275                 280                 285

Asp Leu Glu Asn Val Gly Tyr Asn Asp Ile Phe His Phe Ser Val Asn
                290                 295                 300

Pro Asn Arg Phe Ala Gly Phe Ser Asp Val Glu Gln Ile Arg Leu Asn
305                 310                 315                 320

Arg Leu Val Glu Arg Ile Leu Leu
                325

<210> SEQ ID NO 90
<211> LENGTH: 383
<212> TYPE: PRT
<213> ORGANISM: Nocardia otitidis-caviarum

<400> SEQUENCE: 90

Met Arg Ser Asp Thr Ser Val Glu Pro Glu Gly Ala Asn Phe Ile Ala
1               5                   10                  15

Glu Phe Phe Gly His Arg Val Tyr Pro Glu Val Val Ser Thr Glu Ala
                20                  25                  30

Ala Arg Asn Asp Gln Ala Thr Gly Thr Cys Pro Phe Leu Thr Ala Ala
                35                  40                  45

Lys Leu Val Glu Thr Ser Cys Val Lys Ala Glu Thr Ser Arg Gly Val
                50                  55                  60

Cys Val Val Asn Thr Ala Val Asp Asn Glu Arg Tyr Asp Trp Leu Val
65                  70                  75                  80

Cys Pro Asn Arg Ala Leu Asp Pro Leu Phe Met Ser Ala Ala Ser Arg
                85                  90                  95
```

-continued

```
Lys Leu Phe Gly Tyr Gly Pro Thr Glu Pro Leu Gln Phe Ile Ala Ala
            100                 105                 110

Pro Thr Leu Ala Asp Gln Ala Val Arg Asp Gly Ile Arg Glu Trp Leu
        115                 120                 125

Asp Arg Gly Val His Val Ala Tyr Phe Gln Glu Lys Leu Gly Gly
130                 135                 140

Glu Leu Ser Ile Ser Lys Thr Asp Ser Ser Pro Glu Phe Ser Phe Asp
145                 150                 155                 160

Trp Thr Leu Ala Glu Val Glu Ser Ile Tyr Pro Val Pro Lys Ile Lys
                165                 170                 175

Arg Tyr Gly Val Leu Glu Ile Gln Thr Met Asp Phe His Gly Ser Tyr
            180                 185                 190

Lys His Ala Val Gly Ala Ile Asp Ile Ala Leu Val Glu Gly Ile Asp
        195                 200                 205

Phe His Gly Trp Leu Pro Thr Pro Ala Gly Arg Ala Ala Leu Ser Lys
    210                 215                 220

Lys Met Glu Gly Pro Asn Leu Ser Asn Val Phe Lys Arg Thr Phe Tyr
225                 230                 235                 240

Gln Met Ala Tyr Lys Phe Ala Leu Ser Gly His Gln Arg Cys Ala Gly
                245                 250                 255

Thr Gly Phe Ala Ile Pro Gln Ser Val Trp Lys Ser Trp Leu Arg His
            260                 265                 270

Leu Ala Asn Pro Thr Leu Ile Asp Asn Gly Asp Gly Thr Phe Ser Leu
        275                 280                 285

Gly Asp Thr Arg Asn Asp Ser Glu Asn Ala Trp Ile Phe Val Phe Glu
    290                 295                 300

Leu Asp Pro Asp Thr Asp Ala Ser Pro Arg Pro Leu Ala Pro His Leu
305                 310                 315                 320

Glu Ile Arg Val Asn Val Asp Thr Leu Ile Asp Leu Ala Leu Arg Glu
                325                 330                 335

Ser Pro Arg Ala Ala Leu Gly Pro Ser Gly Pro Val Ala Thr Phe Thr
            340                 345                 350

Asp Lys Val Glu Ala Arg Met Leu Arg Phe Trp Pro Lys Thr Arg Arg
        355                 360                 365

Arg Arg Ser Thr Thr Pro Gly Gly Gln Arg Gly Leu Phe Asp Ala
    370                 375                 380

<210> SEQ ID NO 91
<211> LENGTH: 326
<212> TYPE: PRT
<213> ORGANISM: Providencia stuartii 164

<400> SEQUENCE: 91

Met Lys Glu Leu Lys Leu Lys Glu Ala Lys Glu Ile Leu Lys Ala Leu
1               5                   10                  15

Gly Leu Pro Pro Gln Gln Tyr Asn Asp Arg Ser Gly Trp Val Leu Leu
            20                  25                  30

Ala Leu Ala Asn Ile Lys Pro Glu Asp Ser Trp Lys Glu Ala Lys Ala
        35                  40                  45

Pro Leu Leu Pro Thr Val Ser Ile Met Glu Phe Ile Arg Thr Glu Tyr
    50                  55                  60

Gly Lys Asp Tyr Lys Pro Asn Ser Arg Glu Thr Ile Arg Arg Gln Thr
65                  70                  75                  80

Leu His Gln Phe Glu Gln Ala Arg Ile Val Asp Arg Asn Arg Asp Leu
```

```
                    85                  90                  95
Pro Ser Arg Ala Thr Asn Ser Lys Asp Asn Asn Tyr Ser Leu Asn Gln
                100                 105                 110

Val Ile Ile Asp Ile Leu His Asn Tyr Pro Asn Gly Asn Trp Lys Glu
            115                 120                 125

Leu Ile Gln Gln Phe Leu Thr His Val Pro Ser Leu Gln Glu Leu Tyr
        130                 135                 140

Glu Arg Ala Leu Ala Arg Asp Arg Ile Pro Ile Lys Leu Leu Asp Gly
145                 150                 155                 160

Thr Gln Ile Ser Leu Ser Pro Gly Glu His Asn Gln Leu His Ala Asp
                165                 170                 175

Ile Val His Glu Phe Cys Pro Arg Phe Val Gly Asp Met Gly Lys Ile
            180                 185                 190

Leu Tyr Ile Gly Asp Thr Ala Ser Ser Arg Asn Glu Gly Gly Lys Leu
        195                 200                 205

Met Val Leu Asp Ser Glu Tyr Leu Lys Lys Leu Gly Val Pro Pro Met
210                 215                 220

Ser His Asp Lys Leu Pro Asp Val Val Tyr Asp Glu Lys Arg Lys
225                 230                 235                 240

Trp Leu Phe Leu Ile Glu Ala Val Thr Ser His Gly Pro Ile Ser Pro
                245                 250                 255

Lys Arg Trp Leu Glu Leu Glu Ala Ala Leu Ser Ser Cys Thr Val Gly
            260                 265                 270

Lys Val Tyr Val Thr Ala Phe Pro Thr Arg Thr Glu Phe Arg Lys Asn
        275                 280                 285

Ala Ala Asn Ile Ala Trp Glu Thr Glu Val Trp Ile Ala Asp Asn Pro
290                 295                 300

Asp His Met Val His Phe Asn Gly Asp Arg Phe Leu Gly Pro His Asp
305                 310                 315                 320

Lys Lys Pro Glu Leu Ser
                325

<210> SEQ ID NO 92
<211> LENGTH: 157
<212> TYPE: PRT
<213> ORGANISM: Proteus vulgaris

<400> SEQUENCE: 92

Met Ser His Pro Asp Leu Asn Lys Leu Leu Glu Leu Trp Pro His Ile
1               5                   10                  15

Gln Glu Tyr Gln Asp Leu Ala Leu Lys His Gly Ile Asn Asp Ile Phe
            20                  25                  30

Gln Asp Asn Gly Gly Lys Leu Leu Gln Val Leu Leu Ile Thr Gly Leu
        35                  40                  45

Thr Val Leu Pro Gly Arg Glu Gly Asn Asp Ala Val Asp Asn Ala Gly
50                  55                  60

Gln Glu Tyr Glu Leu Lys Ser Ile Asn Ile Asp Leu Thr Lys Gly Phe
65                  70                  75                  80

Ser Thr His His His Met Asn Pro Val Ile Ala Lys Tyr Arg Gln
                85                  90                  95

Val Pro Trp Ile Phe Ala Ile Tyr Arg Gly Ile Ala Ile Glu Ala Ile
            100                 105                 110

Tyr Arg Leu Glu Pro Lys Asp Leu Glu Phe Tyr Tyr Asp Lys Trp Glu
        115                 120                 125
```

```
Arg Lys Trp Tyr Ser Asp Gly His Lys Asp Ile Asn Asn Pro Lys Ile
    130                 135                 140

Pro Val Lys Tyr Val Met Glu His Gly Thr Lys Ile Tyr
145                 150                 155

<210> SEQ ID NO 93
<211> LENGTH: 358
<212> TYPE: PRT
<213> ORGANISM: Streptomyces achromogenes

<400> SEQUENCE: 93

Met Gly Ile Thr Ile Lys Lys Ser Thr Ala Glu Gln Val Leu Arg Lys
1               5                   10                  15

Ala Tyr Glu Ala Ala Ala Ser Asp Asp Val Phe Leu Glu Asp Trp Ile
                20                  25                  30

Phe Leu Ala Thr Ser Leu Arg Glu Val Asp Ala Pro Arg Thr Tyr Thr
            35                  40                  45

Ala Ala Leu Val Thr Ala Leu Leu Ala Arg Ala Cys Asp Asp Arg Val
        50                  55                  60

Asp Pro Arg Ser Ile Lys Glu Lys Tyr Asp Asp Arg Ala Phe Ser Leu
65                  70                  75                  80

Arg Thr Leu Cys His Gly Val Val Pro Met Ser Val Glu Leu Gly
                85                  90                  95

Phe Asp Leu Gly Ala Thr Gly Arg Glu Pro Ile Asn Asn Gln Pro Phe
            100                 105                 110

Phe Arg Tyr Asp Gln Tyr Ser Glu Ile Val Arg Val Gln Thr Lys Ala
        115                 120                 125

Arg Pro Tyr Leu Asp Arg Val Ser Ser Ala Leu Ala Arg Val Asp Glu
    130                 135                 140

Glu Asp Tyr Ser Thr Glu Glu Ser Phe Arg Ala Leu Val Ala Val Leu
145                 150                 155                 160

Ala Val Cys Ile Ser Val Ala Asn Lys Lys Gln Arg Val Ala Val Gly
                165                 170                 175

Ser Ala Ile Val Glu Ala Ser Leu Ile Ala Glu Thr Gln Ser Phe Val
            180                 185                 190

Val Ser Gly His Asp Val Pro Arg Lys Leu Gln Ala Cys Val Ala Ala
        195                 200                 205

Gly Leu Asp Met Val Tyr Ser Glu Val Val Ser Arg Arg Ile Asn Asp
    210                 215                 220

Pro Ser Arg Asp Phe Pro Gly Asp Val Gln Val Ile Leu Asp Gly Asp
225                 230                 235                 240

Pro Leu Leu Thr Val Glu Val Arg Gly Lys Ser Val Ser Trp Glu Gly
                245                 250                 255

Leu Glu Gln Phe Val Ser Ser Ala Thr Tyr Ala Gly Phe Arg Arg Val
            260                 265                 270

Ala Leu Met Val Asp Ala Ala Ser His Val Ser Leu Met Ser Ala Asp
        275                 280                 285

Asp Leu Thr Ser Ala Leu Glu Arg Lys Tyr Glu Cys Ile Val Lys Val
    290                 295                 300

Asn Glu Ser Val Ser Ser Phe Leu Arg Asp Val Phe Trp Ser Pro
305                 310                 315                 320

Arg Asp Val His Ser Ile Leu Ser Ala Phe Pro Glu Ala Met Tyr Arg
                325                 330                 335

Arg Met Ile Glu Ile Glu Val Arg Glu Pro Glu Leu Asp Arg Trp Ala
            340                 345                 350
```

```
Glu Ile Phe Pro Glu Thr
        355

<210> SEQ ID NO 94
<211> LENGTH: 315
<212> TYPE: PRT
<213> ORGANISM: Streptomyces albus G

<400> SEQUENCE: 94

Met Ile Asn Ala Asp Lys Pro His Arg Trp Asn Asp Val Gln Ala
1               5                   10                  15

Ser Val Arg Leu Tyr Asn Gln Trp Phe Leu Asp Ala Ala Pro Lys Ala
            20                  25                  30

Tyr Arg Asp Thr Arg Gln Leu Thr Ile Asp Glu Val Glu Gln Ala Phe
            35                  40                  45

Gln Arg Thr Ala Asn Met Thr Ser Ile Thr Pro Glu Val Leu Lys Ala
        50                  55                  60

His Pro Lys Thr Leu Ala Thr Leu Arg Met Ser Thr Ala Pro Pro Ile
65                  70                  75                  80

Ala Arg Asp Arg Leu Val Gly Leu Ser His Gly Ser Lys Ser Leu Leu
                85                  90                  95

Asp Thr Met Glu Lys Gly Lys Leu Pro Pro Arg Met Lys Gly Asp Val
            100                 105                 110

Leu Asp Thr His Leu Ala Lys Met Cys Ala Val Leu Thr Asp Leu Leu
            115                 120                 125

Asp Leu Asp Leu Phe His Trp Tyr Pro Thr Gly Glu Pro Ala Glu Pro
130                 135                 140

Arg Gln Arg Glu Leu Ala Ala Thr Val Val Ala Asp Arg Leu Cys Gly
145                 150                 155                 160

Ala Ile Ala Asp Pro Ile Val Arg Asn Ala Gln Glu Arg Arg Gln Leu
                165                 170                 175

Ala Leu Ile Glu Glu Trp Leu Leu Ala Arg Gly Tyr Thr Lys Lys Thr
            180                 185                 190

His Ser Ala Ser Leu Pro Leu Asn Thr Met Gln Pro Gly Thr Phe Ser
            195                 200                 205

Phe Arg Gln Asn Val Val Gly Ser Asp Leu Pro Val Asn Ile Pro
        210                 215                 220

Val Asp Ala Val Ile Gln Pro His Thr Pro His Ser His Lys Leu Pro
225                 230                 235                 240

Ile Leu Ile Glu Ala Lys Ser Ala Gly Asp Phe Thr Asn Thr Asn Lys
                245                 250                 255

Arg Arg Lys Glu Glu Ala Thr Lys Ile His Gln Leu Gln Leu Lys Tyr
            260                 265                 270

Gly Asn Glu Ile Ser Leu Thr Leu Phe Leu Cys Gly Tyr Phe Asn Thr
        275                 280                 285

Gly Tyr Leu Gly Tyr Ser Ala Ala Glu Gly Leu Asp Trp Val Trp Glu
    290                 295                 300

His Arg Ile Asp Asp Leu Glu Ala Ala Gly Ala
305                 310                 315

<210> SEQ ID NO 95
<211> LENGTH: 432
<212> TYPE: PRT
<213> ORGANISM: Saccharopolyspora sp.

<400> SEQUENCE: 95
```

-continued

```
Met Arg Arg Leu Ala Thr Gln Arg Arg Glu Asp Ala Tyr Lys Ser Asn
1               5                   10                  15

Arg Asp Tyr Gln Thr Val His Glu Ala Gln Ser Leu Arg Val Asn Ser
            20                  25                  30

Thr Asp Asp Asn Leu Ser Leu Phe Leu Leu Lys Asp Ile Ser Pro
        35                  40                  45

Arg Glu Asp Ser Lys Asn Ile Val Gly Phe Gly Phe Val Lys Pro
    50                  55                  60

Glu Ile Ala Thr Thr Met Ala Leu Thr Leu Thr Thr Asp Ile Asp Lys
65                  70                  75                  80

Gln Ile Lys Ser Val Pro Leu Ser Ser Asn Trp Asn Arg Ile Ser Ile
                85                  90                  95

Val Ala Lys Phe Ala Ser Asn Pro Ser Val Ser Ile Thr Leu Gly Phe
                100                 105                 110

Asp Gln Thr Pro Trp Val Asp Phe Trp Gly Ile Asn Ser Asp Asp Ile
            115                 120                 125

Gly Leu Ser Phe Val Ser Asp Ala Val Pro Leu Glu Met Ser Met Ile
        130                 135                 140

Asp Ser Ile His Ile Ala Pro Glu Thr Leu Tyr Leu Asp His Ser Ser
145                 150                 155                 160

Ala Cys Leu Leu Asp Ile Asp Pro Val Glu Ser Thr Arg Phe Lys Thr
                165                 170                 175

Gly His Gly Asp Pro Leu Ser Leu Lys Lys Cys Ser Tyr Cys Gly Arg
                180                 185                 190

Leu Leu Pro Ile Asp Leu Glu Arg Pro Gly Lys Leu Ser Phe His Lys
                195                 200                 205

His Arg Ala Lys Ile Thr Asn His Gln Asn Glu Cys Arg Ser Cys Lys
210                 215                 220

Lys Trp Arg Ile Asn Asn Ser Phe Asn Pro Met Arg Thr Ile Asp Gln
225                 230                 235                 240

Leu Asn Glu Ser Ala Leu Ile Thr Arg Glu Arg Lys Ile Phe Leu Gln
                245                 250                 255

Glu Pro Glu Ile Leu Gln Glu Ile Lys Asp Arg Thr Gly Ala Gly Leu
                260                 265                 270

Lys Ser Gln Val Trp Glu Arg Phe His Arg Lys Cys Phe Asn Cys Arg
                275                 280                 285

Lys Asp Leu Lys Leu Ser Glu Val Gln Leu Asp His Thr Arg Pro Leu
                290                 295                 300

Ala Tyr Leu Trp Pro Ile Asp Glu His Ala Thr Cys Leu Cys Ala Gln
305                 310                 315                 320

Cys Asn Asn Thr Lys Lys Asp Arg Phe Pro Val Asp Phe Tyr Ser Glu
                325                 330                 335

Gln Gln Ile Arg Glu Leu Ser Asp Ile Cys Gly Leu Pro Tyr Gln Asp
                340                 345                 350

Leu Cys Ala Arg Ser Leu Asn Leu Asp Gln Leu Asp Arg Ile Glu Arg
                355                 360                 365

Asn Ile Ala Glu Phe Ser Lys Glu Trp Asp Val Arg Thr Phe Ala Ser
                370                 375                 380

Thr Ala Arg Arg Ile Ser Glu Val Tyr Pro Ala Arg Asp Leu Phe Glu
385                 390                 395                 400

Thr Leu Lys Lys Glu Ser Glu Ser Ala Tyr Asn Lys Ile Ile Glu Lys
                405                 410                 415
```

```
Leu Lys Glu Arg Pro Asp Ala Leu Leu Asp Glu Ala Leu Pro Leu Asp
            420                 425                 430
```

<210> SEQ ID NO 96
<211> LENGTH: 323
<212> TYPE: PRT
<213> ORGANISM: Streptomyces species Bf-61

<400> SEQUENCE: 96

```
Met Asn Ser Ser Asp Gly Ile Asp Gly Thr Val Ala Ser Ile Asp Thr
1               5                   10                  15

Ala Arg Ala Leu Leu Lys Arg Phe Gly Phe Asp Ala Gln Arg Tyr Asn
            20                  25                  30

Val Arg Ser Ala Val Thr Leu Leu Ala Leu Ala Gly Leu Lys Pro Gly
        35                  40                  45

Asp Arg Trp Val Asp Ser Thr Thr Pro Arg Leu Gly Val Gln Lys Ile
    50                  55                  60

Met Asp Trp Ser Gly Glu His Trp Ala Lys Pro Tyr Ala Thr Gly Ser
65                  70                  75                  80

Arg Glu Asp Phe Arg Lys Lys Thr Leu Arg Gln Trp Val Asp Asn Gly
                85                  90                  95

Phe Ala Val Leu Asn Ala Asp Asn Leu Asn Ile Ala Thr Asn Ser Gln
            100                 105                 110

Leu Asn Glu Tyr Cys Leu Ser Asp Glu Ala Leu Gln Ala Leu Arg Ala
        115                 120                 125

Tyr Gly Thr Glu Gly Phe Glu Glu Ser Leu Val Val Phe Leu Asp Glu
    130                 135                 140

Ala Ser Lys Ala Val Lys Ala Arg Ala Glu Ala Leu Gln Ala Ala Met
145                 150                 155                 160

Ile Ser Val Asp Leu Pro Gly Gly Glu Glu Phe Leu Leu Ser Pro Ala
                165                 170                 175

Gly Gln Asn Pro Leu Leu Lys Lys Met Val Glu Glu Phe Val Pro Arg
            180                 185                 190

Phe Ala Pro Arg Ser Thr Val Leu Tyr Leu Gly Asp Thr Arg Gly Lys
        195                 200                 205

His Ser Leu Phe Glu Arg Glu Ile Phe Glu Glu Val Leu Gly Leu Thr
    210                 215                 220

Phe Asp Pro His Gly Arg Met Pro Asp Leu Ile Leu His Asp Glu Val
225                 230                 235                 240

Arg Gly Trp Leu Phe Leu Met Glu Ala Val Lys Ser Lys Gly Pro Phe
                245                 250                 255

Asp Glu Glu Arg His Arg Ser Leu Gln Glu Leu Phe Val Thr Pro Ser
            260                 265                 270

Ala Gly Leu Ile Phe Val Asn Cys Phe Glu Asn Arg Glu Ser Met Arg
        275                 280                 285

Gln Trp Leu Pro Glu Leu Ala Trp Glu Thr Glu Ala Trp Val Ala Glu
    290                 295                 300

Asp Pro Asp His Leu Ile His Leu Asn Gly Ser Arg Phe Leu Gly Pro
305                 310                 315                 320

Tyr Glu Arg
```

<210> SEQ ID NO 97
<211> LENGTH: 227
<212> TYPE: PRT
<213> ORGANISM: Streptomyces caespitosus

<400> SEQUENCE: 97

```
Met Ile Asn Asp Gln Leu Pro Arg Trp Val Arg Glu Ala Arg Val Gly
1               5                   10                  15

Thr Arg Thr Gly Gly Pro Ala Met Arg Pro Lys Thr Ser Asp Ser Pro
            20                  25                  30

Tyr Phe Gly Trp Asp Ser Glu Asp Trp Pro Glu Val Thr Arg Gln Leu
        35                  40                  45

Leu Ser Glu Gln Pro Leu Ser Gly Asp Thr Leu Val Asp Ala Val Leu
    50                  55                  60

Ala Ser Trp Glu Ser Ile Phe Glu Ser Arg Leu Gly Ser Gly Phe His
65                  70                  75                  80

Ile Gly Thr Gln Ile Arg Pro Thr Pro Gln Ile Met Gly Phe Leu Leu
                85                  90                  95

His Ala Leu Ile Pro Leu Glu Leu Ala Asn Gly Asp Pro Ser Trp Arg
            100                 105                 110

Ala Asp Leu Asn Ser Ser Glu Lys Asp Leu Val Tyr Gln Pro Asp His
        115                 120                 125

Lys Tyr Ser Ile Glu Met Lys Thr Ser Ser His Lys Asp Gln Ile Phe
    130                 135                 140

Gly Asn Arg Ser Phe Gly Val Glu Asn Pro Gly Lys Gly Lys Lys Ala
145                 150                 155                 160

Lys Asp Gly Tyr Tyr Val Ala Val Asn Phe Glu Lys Trp Ser Asp Ala
                165                 170                 175

Pro Gly Arg Leu Pro Arg Ile Arg Thr Ile Arg Tyr Gly Trp Leu Asp
            180                 185                 190

His Thr Asp Trp Val Ala Gln Lys Ser Gln Thr Gly Gln Gln Ser Ser
        195                 200                 205

Leu Pro Ala Val Val Ser Asn Thr Gln Leu Leu Ala Ile His Thr Gly
    210                 215                 220

Gly Gln Arg
225
```

<210> SEQ ID NO 98
<211> LENGTH: 235
<212> TYPE: PRT
<213> ORGANISM: Streptomyces phaeochromogenes

<400> SEQUENCE: 98

```
Met Thr Ser Lys Asp Pro Ile Val Leu Ser Ala Asp Gln Ile Ala Trp
1               5                   10                  15

Leu Arg Gln Leu Lys Met Ser Lys Arg Ala Ala Leu Val Arg Asp Tyr
            20                  25                  30

Ile Leu Glu Tyr Gly Ala Val Thr Thr Gly Lys Leu Ala Glu Leu Gly
        35                  40                  45

Tyr Ser His Pro Pro Arg Ala Ala Arg Asp Leu Lys Asp Ala Gly Ala
    50                  55                  60

Gly Val Val Thr Ile Met Val Lys Gly Pro Asp Gly Arg Met Ala
65                  70                  75                  80

Ser Tyr Ala Phe Asn Gly Lys Ala Asn Glu Asp Gly Ala Gly Arg Val
                85                  90                  95

Val Ile Pro Lys Ala Phe Gly Glu Ala Leu Lys Arg Ala His Gly Gly
            100                 105                 110

Lys Cys Ala Val Cys Tyr Gly Asp Phe Ser Glu Arg Glu Leu Gln Cys
        115                 120                 125
```

```
Asp His Arg Val Pro Phe Ala Ile Ala Gly Asp Lys Pro Lys Leu Val
130                 135                 140

Gln Glu Asp Phe Met Pro Leu Cys Ala Ser Asp Asn Arg Ala Lys Ser
145                 150                 155                 160

Trp Ser Cys Glu Asn Cys Pro Asn Trp Glu Leu Lys Asp Glu Asp Thr
                165                 170                 175

Cys Arg Ser Cys Phe Trp Ala Ser Pro Glu Asn Tyr Thr His Val Ser
                180                 185                 190

Thr Arg Pro Glu Arg Arg Ile Asn Leu Leu Phe Gln Gly Asp Glu Val
                195                 200                 205

Glu Ile Phe Asp Ala Leu Lys Asn Ala Ala Ala Asn Glu Gly Val Ser
210                 215                 220

Leu Thr Glu Ala Thr Lys Arg Lys Leu Ala Asp
225                 230                 235

<210> SEQ ID NO 99
<211> LENGTH: 281
<212> TYPE: PRT
<213> ORGANISM: Sphaerotilus species

<400> SEQUENCE: 99

Met Ser Lys Ala Ala Tyr Gln Asp Phe Thr Lys Arg Phe Ser Leu Leu
1               5                   10                  15

Ile Lys Lys His Pro Asn Leu Ile Thr Met Thr Leu Ser Asn Ile Phe
                20                  25                  30

Thr Met Arg Leu Ile Gly Asn Lys Thr His Gly Asp Leu Ala Glu Ile
            35                  40                  45

Ala Ile Ser Glu Phe Ile Asn Gln Tyr Met Tyr Asp Phe Lys Ser Ile
50                  55                  60

His Val Gly Lys Asp Leu Tyr Arg Ala Lys Ser Lys Glu Glu Asp Ile
65                  70                  75                  80

Thr Val Glu Asn Glu Ile Thr Lys Glu Lys Phe Pro Ile Ser Leu Lys
                85                  90                  95

Ala Tyr Gly Asp Gly Pro Leu Gln Leu Ser Thr Asp Lys Asn Phe Leu
            100                 105                 110

Met Tyr Pro Leu Leu Glu Glu Ile Gly Ala Phe Ile Asn Ala Lys Glu
        115                 120                 125

Lys Ile Glu Glu Ile Phe Ala Asn Glu Ala Phe Ser Cys Phe Ser Glu
130                 135                 140

Ile Asn Val Leu Pro Leu Ile Tyr Asp Glu Lys Arg Gln Arg Cys Asn
145                 150                 155                 160

Ile Leu Val Phe Asp Ala Ala Arg Ala Arg Ala Glu Thr Ala Tyr Ile
                165                 170                 175

Arg Lys Glu Thr Glu Gly Ser Gly Arg Lys His Pro Ala Tyr Arg Phe
            180                 185                 190

Phe Asp Lys Asn Lys Asn Tyr Ile Cys Glu Val Arg Tyr Gly Asn Ala
        195                 200                 205

Ala Ala Asn Ala Leu Gln Arg Gly Leu Trp Thr Asn Thr Lys Asn Ala
210                 215                 220

Thr Ser Phe Phe Asp Ser Val Thr Asn Gly Trp Val Asp Tyr Ser His
225                 230                 235                 240

Asn Leu Val Leu Val Lys Leu Leu Ser His Ala Leu Val Ser Ser Arg
                245                 250                 255

Lys Gly His Glu Ala Ala Leu Glu Glu Ile Lys Lys Asp Ile Leu Gln
            260                 265                 270
```

Leu Lys Gln Thr Asn Gly Ile Asn Val
          275                 280

<210> SEQ ID NO 100
<211> LENGTH: 1077
<212> TYPE: DNA
<213> ORGANISM: Anabaena variabilis

<400> SEQUENCE: 100

| | | | | | |
|---|---|---|---|---|---|
| atggaagaag | accttgattt | atctgaaaat | atcgaagctg | catctgcgga | gcttacgact | 60 |
| ctttatcagg | tagctgctga | tgctatgaaa | gattatattg | aaatctatct | tgcgctgagt | 120 |
| aaacagtctg | atgggttttc | aaatattaac | aatcttgact | taacttctcg | taacaggcgt | 180 |
| ttggtagtta | tacatggact | ttcgttagag | ttagatccag | atacttcgac | tccagaggaa | 240 |
| attaaacgtg | aagctgaacg | aatgctagcg | atagctcttg | atacagagtc | agcaattacg | 300 |
| gcaggagtat | atgaaaaaat | gcgtctcttc | gcaagctctt | tagtagatca | gctatttgaa | 360 |
| caaacggatg | aacttaattc | attatcatcg | gaatatttgt | cagcaaatcc | aggattttg | 420 |
| ccgttttcc | agcagttggc | ggggcttaga | agtaaatcag | agttaaagag | agaagtagga | 480 |
| aatgcctctg | acaatagtat | ttctaaagcg | gttgcagaga | gaatattaga | gcgcattata | 540 |
| cgtaacttga | gaattcgcac | tttttccaaa | gagaaactat | acaagctgt | tgagcctact | 600 |
| ttagaaggaa | tagtcaggga | tctcgtagga | aaagtgttat | tggaaaatat | agttgctgat | 660 |
| gctttatctg | atttacaagt | tccttcatg | cgtgaatcag | agtatcaaag | ccttaaagga | 720 |
| gtgatttatg | atttccgcgc | tgattttgtg | ataccagacg | cacaaaatcc | aattgctttt | 780 |
| atcgaggtgc | gaaaaagctc | tacacgacat | gcgtcactct | atgccaagga | taagatgttt | 840 |
| tcagcgatta | ttggaaagg | aaaaaataaa | aggctttgg | gtattttggt | tgtggaagga | 900 |
| ccttggacaa | gagaaactct | tcgcgtcatg | gcaaatgtgt | ttgattacgt | tacacccttta | 960 |
| actcgtgttt | cccaagttgc | agaagctatc | agagcatatc | tagatgggga | taaaacgaga | 1020 |
| ctgaagtggt | tagttaattt | cagtattgaa | gaagcagacc | acgacaacat | aacctaa | 1077 |

<210> SEQ ID NO 101
<211> LENGTH: 1293
<212> TYPE: DNA
<213> ORGANISM: Bacillus sphaericus

<400> SEQUENCE: 101

| | | | | | |
|---|---|---|---|---|---|
| atgagacgat | tagcaaaaaa | ttcacggaac | gacagttatt | taagtaatag | ggattaccag | 60 |
| gaaatcgtga | gggaaaatac | cactacaata | tcgtttccct | taaaagaaaa | acatactctg | 120 |
| actttaacga | aaaaaatagg | gctaaatcag | actgctggat | tcggaggatg | gtttttccct | 180 |
| gattcaccat | gttattaac | agtaactgta | ctatcctctt | tcggtacaaa | ggtaacttct | 240 |
| aaaacccttta | gccttctaa | agattggaat | cgtgttgggc | ttgcttggat | taacgagcat | 300 |
| tcgagtgaca | ccataagcat | tgtcctagag | tttagtgatg | tggaaatagt | tcatacatgg | 360 |
| ggacttacat | gtgatgtttt | taatgtccat | gaattaatta | ttgatgctat | agaagatcaa | 420 |
| aataaactaa | tagacgtgct | aaatcaagaa | catttatctc | ctgaaacata | ttatttaaac | 480 |
| catgactctg | atactgattt | aattgagaat | ttggaatcta | cagaagagat | aaagatagtt | 540 |
| aaccaaagcc | aaaagcaaat | ctcttttaaaa | aaatgctgtt | attgtcaacg | ttatatgcct | 600 |
| gtgaacatat | tagttcgttc | aaattcatca | tttcataaac | acaagagtaa | gaaaactggt | 660 |
| tttcaaaatg | aatgtcgggc | ttgtaagaag | tgtgagaataa | ataattcatt | caatccagtc | 720 |

```
agaacaaaag accaactaca tgaatcagca gttattacac gtgaaaaaaa aatattactt    780
aaagaacctg aatattaca gaaatcaaa aatagaaata acgtgaggg cttaaaaagt     840 attatatgga aaaatttga taaaaaatgc tttaattgtg aaaagaatt aaccattgaa     900 gaggtacgcc tagaccatac aagaccactt gcttatctgt ggcctatcga tgaacacgca    960
acttgtttat gtgaaaaatg caacaataca aacatgata tgtttcctat cgattttat    1020 caaggggacg aagacaaatt aagacgttta gctagaatta cggggttaga ttatgaatct   1080
ctagttaaga gggacgtaaa tgaagttgaa cttgcaagaa taatcaataa cattgaagac   1140
tttgcaacta atgtagaggc acgtactttt cgctcaataa gaaataaagt aaaagaagta   1200
cgtcccgata ctgacctatt tgaaattctt aaatctaaaa atattaattt atataatgaa   1260
cttcaatatg aacttcttac ccgtaaggat taa                                1293
```

<210> SEQ ID NO 102
<211> LENGTH: 2189
<212> TYPE: DNA
<213> ORGANISM: artificial
<220> FEATURE:
<223> OTHER INFORMATION: plasmid placzz2

<400> SEQUENCE: 102

```
ctggcgaaag gggatgtgc tgcaaggcga ttaagttggg taacgccagg gttttcccag     60
tcacgacgtt gtaaaacgac ggccagtgaa ttcgagctcg gtacccgggg gcgcgccgga   120
tccttaatta agtctagagt cgactgttta acctgcagg catgcaagct tggcgtaatc   180
atggtcatat gttaacctcc ggcgtaatca tggtcatagc tgtttcctgt gtgaaattgt   240
tatccgctca caattccaca caacatacga gccggaagca taaagtgtaa agcctggggt   300
gcctaatgag tgagctaact cacattaatt gcgttgcgct cactgcccgc tttccagtcg   360
ggaaacctgt cgtgccagca tgtgagcaaa aggccagcaa aaggccagga accgtaaaaa   420
ggccgcgttg ctggcgtttt tccataggct ccgcccccct gacgagcatc acaaaaatcg   480
acgctcaagt cagaggtggc gaaacccgac aggactataa agataccagg cgtttccccc   540
tggaagctcc ctcgtgcgct ctcctgttcc gaccctgccg cttaccggat acctgtccgc   600
ctttctccct tcgggaagcg tggcgctttc tcatagctca cgctgtaggt atctcagttc   660
ggtgtaggtc gttcgctcca agctgggctg tgtgcacgaa ccccccgttc agcccgaccg   720
ctgcgcctta ccggtaact atcgtcttga gtccaacccg gtaagacacg acttatcgcc   780
actggcagca gccactggta acaggattag cagagcgagg tatgtaggcg gtgctacaga   840
gttcttgaag tggtggccta actacggcta cactagaagg acagtatttg gtatctgcgc   900
tctgctgaag ccagttacct tcggaaaaag agttggtagc tcttgatccg gcaaacaaac   960
caccgctggt agcggtggtt tttttgtttg caagcagcag attacgcgca gaaaaaaagg  1020
atctcaagaa gatcctttga tcttttctac ggggtctgac gctcagtgga acgaaaactc  1080
acgttaaggg attttggtca tgagattatc aaaaaggatc ttcacctaga tccttttaaa  1140
ttaaaaatga agttttaaat caatctaaag tatatatgag taaacttggt ctgacagtta  1200
ccaatgctta atcagtgagg cacctatctc agcgatctgt ctatttcgtt catccatagt  1260
tgcctgactc cccgtcgtgt agataactac gatacgggag ggcttaccat ctggccccag  1320
tgctgcaatg ataccgcgag acccacgctc accggctcca gatttatcag caataaacca  1380
gccagccgga agggccgagc gcagaagtgg tcctgcaact ttatccgcct ccatccagtc  1440
```

| | |
|---|---|
| tattaattgt tgccgggaag ctagagtaag tagttcgcca gttaatagtt tgcgcaacgt | 1500 |
| tgttgccatt gctacaggca tcgtggtgtc acgctcgtcg tttggtatgg cttcattcag | 1560 |
| ctccggttcc caacgatcaa ggcgagttac atgatccccc atgttgtgca aaaaagcggt | 1620 |
| tagctccttc ggtcctccga tcgttgtcag aagtaagttg gccgcagtgt tatcactcat | 1680 |
| ggttatggca gcactgcata attctcttac tgtcatgcca tccgtaagat gcttttctgt | 1740 |
| gactggtgag tactcaacca agtcattctg agaatagtgt atgcggcgac cgagttgctc | 1800 |
| ttgcccggcg tcaatacggg ataataccgc gccacatagc agaactttaa aagtgctcat | 1860 |
| cattggaaaa cgttcttcgg ggcgaaaact ctcaaggatc ttaccgctgt tgagatccag | 1920 |
| ttcgatgtaa cccactcgtg cacccaactg atcttcagca tcttttactt tcaccagcgt | 1980 |
| ttctgggtga gcaaaaacag gaaggcaaaa tgccgcaaaa aagggaataa gggcgacacg | 2040 |
| gaaatgttga atactcatac tcttcctttt tcaatattat tgaagcattt atcagggtta | 2100 |
| ttgtctcatg agcggataca tatttgaatg tatttagaaa aataaacaaa taggggttcc | 2160 |
| gcgcacattt ccccgaaaag tgccacctg | 2189 |

<210> SEQ ID NO 103
<211> LENGTH: 10673
<212> TYPE: DNA
<213> ORGANISM: artificial
<220> FEATURE:
<223> OTHER INFORMATION: plasmid pBC4

<400> SEQUENCE: 103

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acccggggat | 420 |
| cctctagagt cgaaccccgg atccggccgt ccgccgtgat ccatgcggtt accgcccgcg | 480 |
| tgtcgaaccc aggtgtgcga cgtcagacaa cgggggagcg ctccttttgg cttccttcca | 540 |
| ggcgcggcgg ctgctgcgct agcttttttg gccactggcc gcgcgcggcg taagcggtta | 600 |
| ggctggaaag cgaaagcatt aagtggctcg ctccctgtag ccggagggtt attttccaag | 660 |
| ggttgagtcg caggaccccc ggttcgagtc tcgggccggc cggactgcgg cgaacggggg | 720 |
| tttgcctccc cgtcatgcaa gaccccgctt gcaaattcct ccggaaacag ggacgagccc | 780 |
| cttttttgct tttcccagat gcatccggtg ctgcggcaga tgcgcccccc tcctcagcag | 840 |
| cggcaagagc aagagcagcg gcagacatgc agggcaccct cccctctcc taccgcgtca | 900 |
| ggaggggcaa catccgcggc tgacgcgcg gcagatggtg attacgaacc cccgcggcgc | 960 |
| cgggcccggc actacctgga cttggaggag ggcgagggcc tggcgcggct aggagcgccc | 1020 |
| tctcctgagc gacacccaag ggtgcagctg aagcgtgaca cgcgcgaggc gtacgtgccg | 1080 |
| cggcagaacc tgtttcgcga ccgcgaggga gaggagcccg aggagatgcg ggatcgaaag | 1140 |
| ttccacgcag ggcgcgagtt gcggcatggc ctgaaccgcg agcggttgct gcgcgaggag | 1200 |
| gactttgagc ccgacgcgcg gaccgggatt agtcccgcgc gcgcacacgt ggcggccgcc | 1260 |
| gacctggtaa ccgcgtacga gcagacggtg aaccaggaga ttaactttca aaaaagcttt | 1320 |

```
aacaaccacg tgcgcacgct tgtggcgcgc gaggaggtgg ctataggact gatgcatctg    1380
tgggactttg taagcgcgct ggagcaaaac ccaaatagca agccgctcat ggcgcagctg    1440
ttccttatag tgcagcacag cagggacaac gaggcattca gggatgcgct gctaaacata    1500
gtagagcccg agggccgctg gctgctcgat ttgataaaca ttctgcagag catagtggtg    1560
caggagcgca gcttgagcct ggctgacaag gtggccgcca ttaactattc catgctcagt    1620
ctgggcaagt tttacgcccg caagatatac catacccctt acgttcccat agacaaggag    1680
gtaaagatcg aggggttcta catgcgcatg gcgttgaagg tgcttacctt gagcgacgac    1740
ctgggcgttt atcgcaacga gcgcatccac aaggccgtga gcgtgagccg gcggcgcgag    1800
ctcagcgacc gcgagctgat gcacagcctg caaagggccc tggctggcac gggcagcggc    1860
gatagagagg ccgagtccta ctttgacgcg ggcgctgacc tgcgctgggc cccaagccga    1920
cgcgccctgg aggcagctgg ggccggacct gggctggcgg tggcacccgc gcgcgctggc    1980
aacgtcggcg gcgtggagga atatgacgag gacgatgagt acgagccaga ggacggcgag    2040
tactaagcgg tgatgtttct gatcagatga tgcaagacgc aacggacccg gcggtgcggg    2100
cggcgctgca gagccagccg tccggcctta actccacgga cgactggcgc caggtcatgg    2160
accgcatcat gtcgctgact gcgcgtaacc ctgacgcgtt ccggcagcag ccgcaggcca    2220
accggctctc cgcaattctg gaagcggtgg tcccggcgcg cgcaaacccc acgcacgaga    2280
aggtgctggc gatcgtaaac gcgctggccg aaaacagggc catccggccc gatgaggccg    2340
gcctggtcta cgacgcgctg cttcagcgcg tggctcgtta caacagcggc aacgtgcaga    2400
ccaacctgga ccggctggtg ggggatgtgc gcgaggccgt ggcgcagcgt gagcgcgcgc    2460
agcagcaggg caacctgggc tccatggttg cactaaacgc cttcctgagt acacagcccg    2520
ccaacgtgcc gcgggacag gaggactaca ccaactttgt gagcgcactg cggctaatgg    2580
tgactgagac accgcaaagt gaggtgtacc agtccgggcc agactatttt ttccagacca    2640
gtagacaagg cctgcagacc gtaaacctga gccaggcttt caagaacttg caggggctgt    2700
ggggggtgcg ggctcccaca ggcgaccgcg cgaccgtgtc tagcttgctg acgcccaact    2760
cgcgcctgtt gctgctgcta atagcgccct tcacggacag tggcagcgtg tcccgggaca    2820 cataccctagg tcacttgctg acactgtacc gcgaggccat aggtcaggcg catgtggacg    2880
agcatacttt ccaggagatt acaagtgtca gccgcgcgct ggggcaggag gacacgggca    2940
gcctggaggc aaccctgaac tacctgctga ccaaccggcg gcagaagatc ccctcgttgc    3000
acagtttaaa cagcgaggag gagcgcatct tgcgctatgt gcagcagagc gtgagcctta    3060
acctgatgcg cgacggggta acgcccagcg tggcgctgga catgaccgcg cgcaacatgg    3120
aaccgggcat gtatgcctca aaccggccgt ttatcaatcg cctaatggac tacttgcatc    3180
gcgcggccgc cgtgaacccc gagtatttca ccaatgccat cttgaacccg cactggctac    3240
cgccccctgg tttctacacc gggggatttg aggtgcccga gggtaacgat ggattcctct    3300
gggacgacat agacgacagc gtgttttccc cgcaaccgca gaccctgcta gagttgcaac    3360
agcgcgagca ggcagaggcg gcgctgcgaa aggaaagctt ccgcaggcca agcagcttgt    3420
ccgatctagg cgctgcggcc ccgcggtcag atgcgagtag cccatttcca agcttgatag    3480
ggtcttttac cagcactcgc accacccgcc cgcgcctgct gggcgaggag gagtacctaa    3540
acaactcgct gctgcagccg cagcgcgaaa agaacctgcc tccggcattt cccaacaacg    3600
ggatagagag cctagtggac aagatgagta gatggaagac gtatgcgcag gagcacaggg    3660
```

```
atgtgcccgg cccgcgcccg cccacccgtc gtcaaaggca cgaccgtcag cggggtctgg    3720
tgtgggagga cgatgactcg gcagacgaca gcagcgtcct ggatttggga gggagtggca    3780
acccgtttgc gcaccttcgc cccaggctgg ggagaatgtt ttaaaaaaaa aaaaaaaag    3840
catgatgcaa aataaaaaac tcaccaaggc catggcaccg agcgttggtt ttcttgtatt    3900
ccccttagta tgcagcgcgc ggcgatgtat gaggaaggtc ctcctccctc ctacgagagc    3960
gtggtgagcg cggcgccagt ggcggcggcg ctgggttccc ccttcgatgc tcccctggac    4020
ccgccgtttg tgcctccgcg gtacctgcgg cctaccgggg ggagaaacag catccgttac    4080
tctgagttgg cacccctatt cgacaccacc cgtgtgtacc ttgtggacaa caagtcaacg    4140
gatgtggcat ccctgaacta ccagaacgac cacagcaact ttctaaccac ggtcattcaa    4200
aacaatgact acagcccggg ggaggcaagc acacagacca tcaatcttga cgaccgttcg    4260
cactggggcg gcgacctgaa aaccatcctg cataccaaca tgccaaatgt gaacgagttc    4320
atgtttacca ataagtttaa ggcgcgggtg atggtgtcgc gctcgcttac taaggacaaa    4380
caggtggagc tgaaatatga gtgggtggag ttcacgctgc ccgagggcaa ctactccgag    4440
accatgacca tagaccttat gaacaacgcg atcgtggagc actacttgaa agtgggcagg    4500
cagaacgggg ttctggaaag cgacatcggg gtaaagtttg acacccgcaa cttcagactg    4560
gggtttgacc cagtcactgg tcttgtcatg cctggggtat atacaaacga agccttccat    4620
ccagacatca ttttgctgcc aggatgcggg gtggacttca cccacagccg cctgagcaac    4680
ttgttgggca tccgcaagcg gcaacccttc caggagggct taaggatcac ctacgatgac    4740
ctggagggtg gtaacattcc cgcactgttg gatgtggacg cctaccaggc aagcttaaaa    4800
gatgacaccg aacagggcgg ggatggcgca ggcggcggca acaacagtgg cagcggcgcg    4860
gaagagaact ccaacgcggc agccgcggca atgcagccgg tggaggacat gaacgatcat    4920
gccattcgcg cgacaccttt tgccacacgg gcggaggaga agcgcgctga ggccgaggca    4980
gcggcagaag ctgccgcccc cgctgcgcaa cccgaggtcg agaagcctca aagaaaccg    5040
gtgatcaaac ccctgacaga ggacagcaag aaacgcagtt acaacctaat aagcaatgac    5100
agcaccttca cccagtaccg cagctggtac cttgcataca actacggcga ccctcagacc    5160
gggatccgct catggaccct cctttgcact cctgacgtaa cctgcggctc ggagcaggtc    5220
tactggtcgt tgccagacat gatgcaagac cccgtgacct tccgctccac gagccagatc    5280
agcaactttc cggtggtggg cgccgagctg ttgcccgtgc actccaagag cttctacaac    5340
gaccaggccg tctactccca gctcatccgc cagtttacct ctctgaccca cgtgttcaat    5400
cgctttcccg agaaccagat tttggcgcgc ccgccagccc ccaccatcac caccgtcagt    5460
gaaaacgttc ctgctctcac agatcacggg acgctaccgc tgcgcaacag catcggagga    5520
gtccagcgag tgaccattac tgacgccaga cgccgcacct gccctacgt ttacaaggcc    5580
ctgggcatag tctcgccgcg cgtcctatcg agccgcactt tttgagcaaa catgtccatc    5640
cttatatcgc ccagcaataa cacaggctgg ggcctgcgct tcccaagcaa gatgtttggc    5700
ggggcaaaga agcgctccga ccaacaccca gtgcgcgtgc gcgggcacta ccgcgcgccc    5760
tggggcgcgc acaaacgcgg ccgcactggg cgcaccaccg tcgatgacgc cattgacgcg    5820
gtggtggagg aggcgcgcaa ctacacgccc acgccgccac cagtgtccac agtggacgcg    5880
gccattcaga ccgtggtgcg cggagcccgg cgttatgcta aaatgaagag acggcggagg    5940
cgcgtagcac gtcgccaccg ccgccgaccc ggcactgccg cccaacgcgc ggcggcggcc    6000
ctgcttaacc gcgcacgtcg caccggccga cgggcggcca tgcgggccgc tcgaaggctg    6060
```

```
gccgcgggta ttgtcactgt gcccccagg tccaggcgac gagcggccgc cgcagcagcc    6120
gcggccatta gtgctatgac tcagggtcgc aggggcaacg tgtactgggt gcgcgactcg    6180
gttagcggcc tgcgcgtgcc cgtgcgcacc cgccccccgc gcaactagat tgcaagaaaa    6240
aactacttag actcgtactg ttgtatgtat ccagcggcgg cggcgcgcaa cgaagctatg    6300
tccaagcgca aaatcaaaga agagatgctc caggtcatcg cgccggagat ctatggcccc    6360
ccgaagaagg aagagcagga ttacaagccc cgaaagctaa agcgggtcaa aaagaaaaag    6420
aaagatgatg atgatgatga acttgacgac gaggtggaac tgctgcacgc aaccgcgccc    6480
aggcggcggg tacagtggaa aggtcgacgc gtaagacgtg ttttgcgacc cggcaccacc    6540
gtagttttta cgcccggtga gcgctccacc cgcacctaca agcgcgtgta tgatgaggtg    6600
tacggcgacg aggacctgct tgagcaggcc aacgagcgcc tcggggagtt tgcctacgga    6660
aagcggcata aggacatgtt ggcgttgccg ctggacgagg gcaacccaac acctagccta    6720
aagcccgtga cactgcagca ggtgctgccc acgcttgcac cgtccgaaga aaagcgcggc    6780
ctaaagcgcg agtctggtga cttggcaccc accgtgcagc tgatggtacc caagcgccag    6840
cgactggaag atgtcttgga aaaaatgacc gtggagcctg gctggagcc cgaggtccgc    6900 gtgcggccaa tcaagcaggt ggcaccggga ctgggcgtgc agaccgtgga cgttcagata    6960
cccaccacca gtagcactag tattgccact gccacagagg gcatggagac acaaacgtcc    7020
ccggttgcct cggcggtggc agatgccgcg gtgcaggcgg ccgctgcggc cgcgtccaaa    7080
acctctacgg aggtgcaaac ggacccgtgg atgtttcgcg tttcagcccc ccggcgcccg    7140
cgccgttcca ggaagtacgg caccgccagc gcactactgc ccgaatatgc cctacatcct    7200
tccatcgcgc ctaccccgg ctatcgtggc tacacctacc gccccagaag acgagcgact    7260
acccgacgcc gaaccaccac tggaacccgc cgccgccgtc gccgtcgcca gcccgtgctg    7320
gccccgattt ccgtgcgcag ggtggctcgc gaaggaggca ggaccctggt gctgccaaca    7380
gcgcgctacc accccagcat cgtttaaaag ccggtctttg tggttcttgc agatatggcc    7440
ctcacctgcc gcctccgttt cccggtgccg ggattccgag gaagaatgca ccgtaggagg    7500
ggcatggccg gccacggcct gacgggcggc atgcgtcgtg cgcaccaccg gcggcggcgc    7560
gcgtcgcacc gtcgcatgcg cggcggtatc ctgcccctcc ttattccact gatcgccgcg    7620
gcgattggcg ccgtgcccgg aattgcatcc gtggccttgc aggcgcagag acactgatta    7680
aaaacaagtt gcatgtggaa aaatcaaaat aaaagtctg gagtctcacg ctcgcttggt    7740
cctgtaacta ttttgtagaa tggaagacat caactttgcg tctctggccc cgcgacacgg    7800
ctcgcgcccg ttcatgggaa actggcaaga tatcggcacc agcaatatga gcggtggcgc    7860
cttcagctgg ggctcgctgt ggagcggcat taaaaatttc ggttccacca ttaagaacta    7920
tggcagcaag gcctggaaca gcagcacagg ccagatgctg agggacaagt tgaaagagca    7980
aaatttccaa caaaaggtgg tagatggcct ggcctctggc attagcgggg tggtggacct    8040
ggccaaccag gcagtgcaaa ataagattaa cagtaagctt gatccccgcc ctcccgtaga    8100
ggagcctcca ccggccgtgg agacagtgtc tccagagggg cgtggcgaaa agcgtccgcg    8160
gcccgacagg gaagaaactc tggtgacgca aatagatgag cctccctcgt acgaggaggc    8220
actaaagcaa ggcctgccca ccacccgtcc catcgcgccc atggctaccg gagtgctggg    8280
ccagcacaca cctgtaacgc tggacctgcc tccccccgct gacacccagc agaaacctgt    8340
gctgccaggg ccgtccgccg ttgttgtaac ccgccctagc cgcgcgtccc tgcgccgtgc    8400
```

```
cgccagcggt ccgcgatcga cctgcaggca tgcaagcttg gcgtaatcat ggtcatagct    8460
gtttcctgtg tgaaattgtt atccgctcac aattccacac aacatacgag ccggaagcat    8520
aaagtgtaaa gcctggggtg cctaatgagt gagctaactc acattaattg cgttgcgctc    8580
actgcccgct ttccagtcgg gaaacctgtc gtgccagctg cattaatgaa tcggccaacg    8640
cgcggggaga ggcggtttgc gtattgggcg ctcttccgct tcctcgctca ctgactcgct    8700
gcgctcggtc gttcggctgc ggcgagcggt atcagctcac tcaaaggcgg taatacggtt    8760
atccacagaa tcaggggata acgcaggaaa gaacatgtga gcaaaaggcc agcaaaaggc    8820
caggaaccgt aaaaaggccg cgttgctggc gtttttccat aggctccgcc ccctgacga    8880
gcatcacaaa aatcgacgct caagtcagag gtggcgaaac ccgacaggac tataaagata    8940
ccaggcgttt ccccctggaa gctccctcgt gcgctctcct gttccgaccc tgccgcttac    9000
cggatacctg tccgcctttc tcccttcggg aagcgtggcg ctttctcaat gctcacgctg    9060
taggtatctc agttcggtgt aggtcgttcg ctccaagctg ggctgtgtgc acgaaccccc    9120
cgttcagccc gaccgctgcg ccttatccgg taactatcgt cttgagtcca acccggtaag    9180
acacgactta tcgccactgg cagcagccac tggtaacagg attagcagag cgaggtatgt    9240
aggcggtgct acagagttct tgaagtggtg gcctaactac ggctacacta aggacagt     9300
atttggtatc tgcgctctgc tgaagccagt taccttcgga aaaagagttg gtagctcttg    9360
atccggcaaa caaccaccg ctggtagcgg tggtttttt gtttgcaagc agcagattac    9420
gcgcagaaaa aaaggatctc aagaagatcc tttgatcttt tctacggggt ctgacgctca    9480
gtggaacgaa aactcacgtt aagggatttt ggtcatgaga ttatcaaaaa ggatcttcac    9540
ctagatcctt ttaaattaaa aatgaagttt taaatcaatc taagtatat atgagtaaac    9600
ttggtctgac agttaccaat gcttaatcag tgaggcacct atctcagcga tctgtctatt    9660
tcgttcatcc atagttgcct gactccccgt cgtgtagata actacgatac gggagggctt    9720
accatctggc cccagtgctg caatgatacc gcgagaccca cgctcaccgg ctccagattt    9780
atcagcaata aaccagccag ccggaagggc cgagcgcaga agtggtcctg caactttatc    9840
cgcctccatc cagtctatta attgttgccg ggaagctaga gtaagtagtt cgccagttaa    9900
tagtttgcgc aacgttgttg ccattgctac aggcatcgtg gtgtcacgct cgtcgtttgg    9960
tatggcttca ttcagctccg gttcccaacg atcaaggcga gttacatgat cccccatgtt   10020
gtgcaaaaaa gcggttagct ccttcggtcc tccgatcgtt gtcagaagta agttggccgc   10080
agtgttatca ctcatggtta tggcagcact gcataattct cttactgtca tgccatccgt   10140
aagatgcttt tctgtgactg gtgagtactc aaccaagtca ttctgagaat agtgtatgcg   10200
gcgaccgagt tgctcttgcc cggcgtcaat acgggataat accgcgccac atagcagaac   10260
tttaaaagtg ctcatcattg gaaaacgttc ttcgggcga aaactctcaa ggatcttacc   10320
gctgttgaga tccagttcga tgtaacccac tcgtgcaccc aactgatctt cagcatcttt   10380
tactttcacc agcgtttctg ggtgagcaaa aacaggaagg caaaatgccg caaaaaggg   10440
aataagggcg acacggaaat gttgaatact catactcttc cttttcaat attattgaag   10500
catttatcag ggttattgtc tcatgagcgg atacatattt gaatgtattt agaaaaataa   10560
acaaataggg gttccgcgca catttccccg aaaagtgcca cctgacgtct aagaaaccat   10620
tattatcatg acattaacct ataaaaatag gcgtatcacg aggccctttc gtc          10673
```

<210> SEQ ID NO 104
<211> LENGTH: 22563

```
<212> TYPE: DNA
<213> ORGANISM: artificial
<220> FEATURE:
<223> OTHER INFORMATION: plasmid pXba

<400> SEQUENCE: 104
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
ccttctagac cgtgcaaaag gagagcctgt aagcgggcac tcttccgtgg tctggtggat     480
aaattcgcaa gggtatcatg gcggacgacc ggggttcgaa ccccggatcc ggccgtccgc     540
cgtgatccat gcggttaccg cccgcgtgtc gaacccaggt gtgcgacgtc agacaacggg     600
ggagcgctcc ttttggcttc cttccaggcg cggcggctgc tgcgctagct tttttggcca     660
ctggccgcgc gcggcgtaag cggttaggct ggaaagcgaa agcattaagt ggctcgctcc     720
ctgtagccgg agggttattt tccaagggtt gagtcgcagg accccggtt cgagtctcgg      780
gccggccgga ctgcggcgaa cggggtttg cctccccgtc atgcaagacc ccgcttgcaa      840
attcctccgg aaacagggac gagcccctt tttgcttttc ccagatgcat ccggtgctgc      900
ggcagatgcg ccccctcct cagcagcggc aagagcaaga gcagcggcag acatgcaggg      960
caccctcccc ttctcctacc gcgtcaggag gggcaacatc cgcggctgac gcggcggcag    1020
atggtgatta cgaaccccg cggcgccggg cccggcacta cctggacttg gaggagggcg     1080
agggcctggc gcggctagga gcgccctctc ctgagcgaca cccaagggtg cagctgaagc    1140
gtgacacgcg cgaggcgtac gtgccgcggc agaacctgtt tcgcgaccgc gagggagagg    1200
agcccgagga gatgcgggat cgaaagttcc acgcagggcg cgagttgcgg catggcctga    1260
accgcgagcg gttgctgcgc gaggaggact ttgagcccga cgcgcggacc gggattagtc    1320
ccgcgcgcgc acacgtggcg gccgccgacc tggtaaccgc gtacgagcag acggtgaacc    1380
aggagattaa ctttcaaaaa gctttaaca accacgtgcg cacgcttgtg gcgcgcgagg     1440
aggtggctat aggactgatg catctgtggg actttgtaag cgcgctggag caaaacccaa    1500
atagcaagcc gctcatggcg cagctgttcc ttatagtgca gcacagcagg acaacgagg     1560
cattcaggga tgcgctgcta aacatagtag agcccgaggg ccgctggctg ctcgatttga    1620
taaacattct gcagagcata gtggtgcagg agcgcagctt gagcctggct gacaaggtgg    1680
ccgccattaa ctattccatg ctcagtctgg gcaagtttta cgcccgcaag ataaccata    1740
cccccttacgt tccatagac aaggaggtaa agatcgaggg gttctacatg cgcatggcgt    1800
tgaaggtgct taccttgagc gacgacctgg gcgtttatcg caacgagcgc atccacaagg    1860
ccgtgagcgt gagccggcgg cgcgagctca gcgaccgcga gctgatgcac agcctgcaaa    1920
gggccctggc tggcacgggc agcggcgata gagaggccga gtcctacttt gacgcgggcg    1980
ctgacctgcg ctgggcccca agccgacgcg ccctggaggc agctggggcc ggacctgggc    2040
tggcggtggc acccgcgcgc gctggcaacg tcggcgcgt ggaggaatat gacgaggacg     2100
atgagtacga gccagaggac ggcgagtact aagcggtgat gtttctgatc agatgatgca    2160
```

```
agacgcaacg gacccggcgg tgcgggcggc gctgcagagc cagccgtccg gccttaactc    2220
cacggacgac tggcgccagg tcatggaccg catcatgtcg ctgactgcgc gtaaccctga    2280
cgcgttccgg cagcagccgc aggccaaccg gctctccgca attctggaag cggtggtccc    2340
ggcgcgcgca aaccccacgc acgagaaggt gctggcgatc gtaaacgcgc tggccgaaaa    2400
cagggccatc cggcccgatg aggccggcct ggtctacgac gcgctgcttc agcgcgtggc    2460
tcgttacaac agcggcaacg tgcagaccaa cctggaccgg ctggtggggg atgtgcgcga    2520
ggccgtggcg cagcgtgagc gcgcgcagca gcagggcaac ctgggctcca tggttgcact    2580
aaacgccttc ctgagtacac agcccgccaa cgtgccgcgg ggacaggagg actacaccaa    2640
ctttgtgagc gcactgcggc taatggtgac tgagacaccg caaagtgagg tgtaccagtc    2700
cgggccagac tattttttcc agaccagtag acaaggcctg cagaccgtaa acctgagcca    2760
ggctttcaag aacttgcagg ggctgtgggg ggtgcgggct cccacaggcg accgcgcgac    2820
cgtgtctagc ttgctgacgc ccaactcgcc cctgttgctg ctgctaatag cgcccttcac    2880
ggacagtggc agcgtgtccc gggacacata cctaggtcac ttgctgacac tgtaccgcga    2940
ggccataggt caggcgcatg tggacgagca tactttccag gagattacaa gtgtcagccg    3000
cgcgctgggg caggaggaca cgggcagcct ggaggcaacc ctgaactacc tgctgaccaa    3060
ccggcggcag aagatcccct cgttgcacag tttaaacagc gaggaggagc gcatcttgcg    3120
ctatgtgcag cagagcgtga gccttaacct gatgcgcgac ggggtaacgc ccagcgtggc    3180
gctggacatg accgcgcgca acatggaacc gggcatgtat gcctcaaacc ggccgtttat    3240
caatcgccta atggactact tgcatcgcgc ggccgccgtg aaccccgagt atttcaccaa    3300
tgccatcttg aacccgcact ggctaccgcc ccctggtttc tacaccgggg gatttgaggt    3360
gcccgagggt aacgatggat tcctctggga cgacatagac gacagcgtgt ttccccgca    3420
accgcagacc ctgctagagt tgcaacagcg cgagcaggca gaggcggcgc tgcgaaagga    3480
aagcttccgc aggccaagca gcttgtccga tctaggcgct gcggccccgc ggtcagatgc    3540
gagtagccca tttccaagct tgatagggtc ttttaccagc actcgcacca cccgcccgcg    3600
cctgctgggc gaggaggagt acctaaacaa ctcgctgctg cagccgcagc gcgaaaagaa    3660
cctgcctccg gcatttccca acaacgggat agagagccta gtggacaaga tgagtagatg    3720
gaagacgtat gcgcaggagc acagggatgt gcccggcccg cgcccgccca cccgtcgtca    3780
aaggcacgac cgtcagcggg gtctggtgtg ggaggacgat gactcggcag acgacagcag    3840
cgtcctggat ttgggaggga gtggcaaccc gtttgcgcac cttcgcccca ggctggggag    3900
aatgttttaa aaaaaaaaa aaaagcatg atgcaaaata aaaaactcac caaggccatg    3960
gcaccgagcg ttggttttct tgtattcccc ttagtatgca gcgcgcggcg atgtatgagg    4020
aaggtcctcc tccctcctac gagagcgtgg tgagcgcggc gccagtggcg gcggcgctgg    4080
gttccccctt cgatgctccc ctggaccgc cgtttgtgcc tccgcggtac ctgcggccta    4140
ccgggggga aaacagcatc cgttactctg agttggcacc cctattcgac accacccgtg    4200
tgtaccttgt ggacaacaag tcaacggatg tggcatccct gaactaccag aacgaccaca    4260
gcaactttct aaccacggtc attcaaaaca atgactacag cccgggggag gcaagcacac    4320
agaccatcaa tcttgacgac cgttcgcact ggggcggcga cctgaaaacc atcctgcata    4380
ccaacatgcc aaatgtgaac gagttcatgt ttaccaataa gtttaaggcg cgggtgatgg    4440
tgtcgcgctc gcttactaag gacaaacagg tggagctgaa atatgagtgg gtggagttca    4500
cgctgcccga gggcaactac tccgagacca tgaccataga ccttatgaac aacgcgatcg    4560
```

```
tggagcacta cttgaaagtg ggcaggcaga acggggttct ggaaagcgac atcggggtaa    4620
agtttgacac ccgcaacttc agactggggt ttgacccagt cactggtctt gtcatgcctg    4680
gggtatatac aaacgaagcc ttccatccag acatcatttt gctgccagga tgcggggtgg    4740
acttcaccca cagccgcctg agcaacttgt tgggcatccg caagcggcaa cccttccagg    4800
agggctttag gatcacctac gatgacctgg agggtggtaa cattcccgca ctgttggatg    4860
tggacgccta ccaggcaagc ttaaaagatg acaccgaaca gggcggggat ggcgcaggcg    4920
gcggcaacaa cagtggcagc ggcgcggaag agaactccaa cgcggcagcc gcggcaatgc    4980
agccggtgga ggacatgaac gatcatgcca ttcgcggcga cacctttgcc acacgggcgg    5040
aggagaagcg cgctgaggcc gaggcagcgg cagaagctgc cgcccccgct gcgcaacccg    5100
aggtcgagaa gcctcagaag aaaccggtga tcaaacccct gacagaggac agcaagaaac    5160
gcagttacaa cctaataagc aatgacagca ccttcaccca gtaccgcagc tggtaccttg    5220
catacaacta cggcgaccct cagaccggga tccgctcatg gaccctcctt tgcactcctg    5280
acgtaacctg cggctcggag caggtctact ggtcgttgcc agacatgatg caagaccccg    5340
tgaccttccg ctccacgagc cagatcagca actttccggt ggtgggcgcc gagctgttgc    5400
ccgtgcactc caagagcttc tacaacgacc aggccgtcta ctcccagctc atccgccagt    5460
ttacctctct gacccacgtg ttcaatcgct ttcccgagaa ccagattttg gcgcgcccgc    5520
cagcccccac catcaccacc gtcagtgaaa acgttcctgc tctcacagat cacgggacgc    5580
taccgctgcg caacagcatc ggaggagtcc agcgagtgac cattactgac gccagacgcc    5640
gcacctgccc ctacgtttac aaggccctgg gcatagtctc gccgcgcgtc ctatcgagcc    5700 gcacttttg agcaaacatg tccatcctta tatcgcccag caataacaca ggctggggcc    5760
tgcgcttccc aagcaagatg tttggcgggg caaagaagcg ctccgaccaa cacccagtgc    5820
gcgtgcgcgg gcactaccgc gcgccctggg gcgcgcacaa acgcggccgc actgggcgca    5880
ccaccgtcga tgacgccatt gacgcggtgg tggaggaggc gcgcaactac acgcccacgc    5940
cgccaccagt gtccacagtg gacgcggcca ttcagaccgt ggtgcgcgga gcccggcgtt    6000
atgctaaaat gaagagacgg cggaggcgcg tagcacgtcg ccaccgccgc cgacccggca    6060
ctgccgccca acgcgcggcg gcggcccctgc ttaaccgcgc acgtcgcacc ggccgacggg    6120
cggccatgcg ggccgctcga aggctggccg cgggtattgt cactgtgccc ccaggtccga    6180
ggcgacgagc ggccgccgca gcagccgcgg ccattagtgc tatgactcag ggtcgcaggg    6240
gcaacgtgta ctgggtgcgc gactcggtta gcggcctgcg cgtgcccgtg cgcacccgcc    6300
ccccgcgcaa ctagattgca agaaaaaact acttagactc gtactgttgt atgtatccag    6360
cggcggcggc gcgcaacgaa gctatgtcca agcgcaaaat caaagaagag atgctccagg    6420
tcatcgcgcc ggagatctat ggccccccga agaaggaaga gcaggattac aagccccgaa    6480
agctaaagcg ggtcaaaaag aaaaagaaag atgatgatga tgatgaactt gacgacgagg    6540
tggaactgct gcacgcaacc gcgcccaggc ggcgggtaca gtggaaaggt cgacgcgtaa    6600
gacgtgtttt gcgaccccgg ccaccgctag ttttttacgcc cggtgagcgc tccaccccgca    6660 cctacaagcg cgtgtatgat gaggtgtacg gcgacgagga cctgcttgag caggccaacg    6720
agcgcctcgg ggagtttgcc tacggaaagc ggcataagga catgttggcg ttccgctgg    6780 acagggcaa cccaacacct agcctaaagc ccgtgacact gcagcaggtg ctgcccacgc    6840
ttgcaccgtc cgaagaaaag cgcggcctaa agcgcgagtc tggtgacttg gcacccaccg    6900
```

```
tgcagctgat ggtacccaag cgccagcgac tggaagatgt cttggaaaaa atgaccgtgg    6960
agcctgggct ggagcccgag gtccgcgtgc ggccaatcaa gcaggtggca ccgggactgg    7020
gcgtgcagac cgtggacgtt cagatacccca ccaccagtag cactagtatt gccactgcca   7080
cagagggcat ggagacacaa acgtcccgg ttgcctcggc ggtggcagat gccgcggtgc    7140
aggcggccgc tgcggccgcg tccaaaacct ctacggaggt gcaaacggac ccgtggatgt    7200
ttcgcgtttc agccccccgg cgcccgcgcc gttccaggaa gtacggcacc gccagcgcac    7260
tactgcccga atatgcccta catccttcca tcgcgcctac ccccggctat cgtggctaca    7320
cctaccgccc cagaagacga gcgactaccc gacgccgaac caccactgga acccgccgcc    7380
gccgtcgccg tcgccagccc gtgctggccc cgatttccgt gcgcagggtg gctcgcgaag    7440
gaggcaggac cctggtgctg ccaacagcgc gctaccaccc cagcatcgtt taaaagccgg    7500
tctttgtggt tcttgcagat atggccctca cctgccgcct ccgtttcccg gtgccgggat    7560
tccgaggaag aatgcaccgt aggagggca tggccggcca cggcctgacg ggcggcatgc    7620
gtcgtgcgca ccaccggcgg cggcgcgcgt cgcaccgtcg catgcgcggc ggtatcctgc    7680
ccctccttat tccactgatc gccgcggcga ttggcgccgt gcccggaatt gcatccgtgg    7740
ccttgcaggc gcagagacac tgattaaaaa caagttgcat gtggaaaaat caaaataaaa    7800
agtctggagt ctcacgctcg cttggtcctg taactatttt gtagaatgga agacatcaac    7860
tttgcgtctc tggccccgcg acacggctcg cgcccgttca tggaaactg gcaagatatc    7920 ggcaccagca atatgagcgg tggcgccttc agctggggct cgctgtggag cggcattaaa    7980
aatttcggtt ccaccattaa gaactatggc agcaaggcct ggaacagcag cacaggccag    8040
atgctgaggg acaagttgaa agagcaaaat ttccaacaaa aggtggtaga tggcctggcc    8100
tctggcatta gcggggtggt ggacctggcc aaccaggcag tgcaaaataa gattaacagt    8160
aagcttgatc cccgccctcc cgtagaggag cctccaccgg ccgtggagac agtgtctcca    8220
gaggggcgtg gcgaaaagcg tccgcggccc gacaggggaag aaactctggt gacgcaaata    8280
gatgagcctc cctcgtacga ggaggcacta agcaaggcc tgcccaccac ccgtcccatc    8340
gcgcccatgg ctaccggagt gctgggccag cacacacctg taacgctgga cctgcctccc    8400
cccgctgaca cccagcagaa acctgtgctg ccagggccgt ccgccgttgt tgtaacccgc    8460
cctagccgcg cgtccctgcg ccgtgccgcc agcggtccgc gatcgatgcg gcccgtagcc    8520
agtggcaact ggcaaagcac actgaacagc atcgtgggtc tgggggtgca atccctgaag    8580
cgccgacgat gcttctaaat agctaacgtg tcgtatgtgt catgtatgcg tccatgtcgc    8640
cgccagagga gctgctgagc cgccgtgcgc ccgctttcca agatggctac cccttcgatg    8700
atgccgcagt ggtcttacat gcacatctcg ggccaggacg cctcggagta cctgagcccc    8760
gggctggtgc agtttgcccg cgccaccgag acgtacttca gcctgaataa caagtttaga    8820
aaccccacgg tggcacctac gcacgacgta accacagacc ggtcccagcg tttgacgctg    8880
cggttcatcc ctgtggaccg cgaggatacc gcgtactcgt acaaagcgcg gttcacccctg    8940 gctgtgggtg acaaccgtgt gcttgatatg gcttccacgt actttgacat ccgcggcgtg    9000
ctggacaggg gcctacttt taagccctac tccggcactg cctacaacgc tctagctccc    9060
aagggcgctc ctaactcctg tgagtgggaa caaaccgaag atagcggccg gcagttgcc    9120 gaggatgaag aagaggaaga tgaagatgaa gaagaggaag aagaagagca aaacgctcga    9180
gatcaggcta ctaagaaaac acatgtctat gcccaggctc ctttgtctgg agaaacaatt    9240
acaaaaagcg ggctacaaat aggatcagac aatgcagaaa cacaagctaa acctgtatac    9300
```

```
gcagatcctt cctatcaacc agaacctcaa attggcgaat ctcagtggaa cgaagctgat   9360
gctaatgcgg caggagggag agtgcttaaa aaaacaactc ccatgaaacc atgctatgga   9420
tcttatgcca ggcctacaaa tccttttggt ggtcaatccg ttctggttcc ggatgaaaaa   9480
ggggtgcctc ttccaaaggt tgacttgcaa ttcttctcaa atactacctc tttgaacgac   9540
cggcaaggca atgctactaa accaaaagtg gttttgtaca gtgaagatgt aaatatggaa   9600
accccagaca cacatctgtc ttacaaacct ggaaaaggtg atgaaaattc taaagctatg   9660
ttgggtcaac aatctatgcc aaacagaccc aattacattg ctttcaggga caattttatt   9720
ggcctaatgt attataacag cactggcaac atgggtgttc ttgctggtca ggcatcgcag   9780
ctaaatgccg tggtagattt gcaagacaga aacacagagc tgtcctatca actcttgctt   9840
gattccatag gtgatagaac cagatatttt tctatgtgga atcaggctgt agacagctat   9900
gatccagatg ttagaatcat tgaaaaccat ggaactgagg atgaattgcc aaattattgt   9960
tttcctcttg ggggtattgg ggtaactgac acctatcaag ctattaaggc taatggcaat  10020
ggctcaggcg ataatggaga tactacatgg acaaaagatg aaacttttgc aacacgtaat  10080
gaaataggag tgggtaacaa cttttgccatg gaaattaacc taaatgccaa cctatggaga  10140
aatttccttt actccaatat tgcgctgtac ctgccagaca agctaaaata caaccccacc  10200
aatgtggaaa tatctgacaa ccccaacacc tacgactaca tgaacaagcg agtggtggct  10260
cccgggcttg tagactgcta cattaacctt ggggcgcgct ggtctctgga ctacatggac  10320
aacgttaatc cctttaacca ccaccgcaat gcgggcctcc gttatcgctc catgttgttg  10380
ggaaacggcc gctacgtgcc ctttcacatt caggtgcccc aaaagttttt tgccattaaa  10440
aacctcctcc tcctgccagg ctcatataca tatgaatgga acttcaggaa ggatgttaac  10500
atggttctgc agagctctct gggaaacgat cttagagttg acggggctag cattaagttt  10560
gacagcattt gtctttacgc caccttcttc cccatggccc acaacacggc ctccacgctg  10620
gaagccatgc tcagaaatga caccaacgac cagtcccttta atgactacct ttccgccgcc  10680
aacatgctat accccatacc cgccaacgcc accaacgtgc ccatctccat cccatcgcgc  10740
aactgggcag catttcgcgg ttgggccttc acacgcttga agacaaagga aaccccttcc  10800
ctgggatcag gctacgaccc ttactacacc tactctggct ccataccata ccttgacgga  10860
accttctatc ttaatcacac ctttaagaag gtggccatta cctttgactc ttctgttagc  10920
tggccgggca cgaccgcct gcttactccc aatgagtttg agattaaacg ctcagttgac  10980
ggggagggct acaacgtagc tcagtgcaac atgaccaagg actggttcct ggtgcagatg  11040
ttggccaact acaatattgg ctaccagggc ttctacattc cagaaagcta caaggaccgc  11100
atgtactcgt tcttcagaaa cttccagccc atgagccggc aagtggttga cgatactaaa  11160
tacaaggagt atcagcaggt tggaattctt caccagcata acaactcagg attcgtaggc  11220
tacctcgctc ccaccatgcg cgagggacag gcttaccccg ccaacgtgcc ctacccacta  11280
ataggcaaaa ccgcggttga cagtattacc cagaaaaagt ttctttgcga tcgcacccct  11340
tggcgcatcc cattctccag taactttatg tccatgggcg cactcacaga cctgggccaa  11400
aaccttctct acgccaactc cgcccacgcg ctagacatga cttttgaggt ggatcccatg  11460
gacgagccca cccttctttta tgttttgttt gaagtctttg acgtggtccg tgtgcaccag  11520
ccgcaccgcg cgtcatcga gaccgtgtac ctgcgcacgc ccttctcggc cggcaacgcc  11580
acaacataaa agaagcaagc aacatcaaca acagctgccg ccatgggctc cagtgagcag  11640
```

```
gaactgaaag ccattgtcaa agatcttggt tgtgggccat attttttggg cacctatgac    11700
aagcgctttc caggctttgt ttctccacac aagctcgcct gcgccatagt caatacggcc    11760
ggtcgcgaga ctgggggcgt acactggatg gcctttgcct ggaacccgcg ctcaaaaaca    11820
tgctacctct ttgagcccct tggcttttct gaccaacgac tcaagcaggt ttaccagttt    11880
gagtacgagt cactcctgcg ccgtagcgcc attgcttctt cccccgaccg ctgtataacg    11940
ctggaaaagt ccacccaaag cgtgcagggg cccaactcgg ccgcctgtgg actattctgc    12000
tgcatgtttc tccacgcctt tgccaactgg ccccaaactc ccatggatca aaccccacc    12060 atgaaccttta ttaccggggt acccaactcc atgcttaaca gtccccaggt acagcccacc    12120
ctgcgtcgca accaggaaca gctctacagc ttcctggagc gccactcgcc ctacttccgc    12180
agccacagtg cgcagattag gagcgccact tcttttttgtc acttgaaaaa catgtaaaaa    12240
taatgtacta ggagacactt tcaataaagg caaatgtttt tatttgtaca ctctcgggtg    12300
attatttacc ccccacccctt gccgtctgcg ccgtttaaaa atcaaagggg ttctgccgcg    12360
catcgctatg cgccactggc agggacacgt tgcgatactg tgtttagtg ctccacttaa    12420 actcaggcac aaccatccgc ggcagctcgg tgaagttttc actccacagg ctgcgcacca    12480
tcaccaacgc gtttagcagg tcgggcgccg atatcttgaa gtcgcagttg gggcctccgc    12540
cctgcgcgcg cgagttgcga tacacagggt tgcagcactg gaacactatc agcgccgggt    12600
ggtgcacgct ggccagcacg ctcttgtcgg agatcagatc cgcgtccagg tcctccgcgt    12660
tgctcagggc gaacggagtc aactttggta gctgccttcc caaaagggt gcatgcccag    12720 gctttgagtt gcactcgcac cgtagtggca tcagaaggtg accgtgcccg gtctgggcgt    12780
taggatacag cgcctgcatg aaagccttga tctgcttaaa agccacctga gcctttgcgc    12840
cttcagagaa gaacatgccg caagacttgc cggaaaactg attggccgga caggccgcgt    12900
catgcacgca gcaccttgcg tcggtgttgg agatctgcac cacatttcgg ccccaccggt    12960
tcttcacgat cttggccttg ctagactgct ccttcagcgc gcgctgcccg ttttcgctcg    13020
tcacatccat ttcaatcacg tgctccttat ttatcataat gctcccgtgt agacacttaa    13080
gctcgccttc gatctcagcg cagcggtgca gccacaacgc gcagcccgtg ggctcgtggt    13140
gcttgtaggt tacctctgca aacgactgca ggtacgcctg caggaatcgc ccatcatcg    13200 tcacaaaggt cttgttgctg gtgaaggtca gctgcaaccc gcggtgctcc tcgtttagcc    13260
aggtcttgca tacggccgcc agagcttcca cttggtcagg cagtagcttg aagtttgcct    13320
ttagatcgtt atccacgtgg tacttgtcca tcaacgcgcg cgcagcctcc atgcccttct    13380
cccacgcaga cacgatcggc aggctcagcg ggtttatcac cgtgctttca ctttccgctt    13440
cactggactc ttccttttcc tcttgcgtcc gcataccccg cgccactggg tcgtcttcat    13500
tcagccgccg caccgtgcgc ttacctccct tgccgtgctt gattagcacc ggtgggttgc    13560
tgaaacccac catttgtagc gccacatctt ctctttcttc ctcgctgtcc acgatcacct    13620
ctggggatgg cgggcgctcg ggcttgggag agggggcgctt ctttttcttt ttggacgcaa    13680
tggccaaatc cgccgtcgag gtcgatggcc gcgggctggg tgtgcgcggc accagcgcat    13740
cttgtgacga gtcttcttcg tcctcggact cgagacgccg cctcagccgc tttttttgggg    13800 gcgcgcgggg aggcggcggc gacggcgacg gggacgacac gtcctccatg gttggtggac    13860
gtcgcgccgc accgcgtccg cgctcggggg tggtttcgcg ctgctcctct tcccgactgg    13920
ccatttcctt ctcctatagg cagaaaaaga tcatggagtc agtcgagaag gaggacagcc    13980
taaccgcccc ctttgagttc gccaccaccg cctccaccga tgccgccaac gcgcctacca    14040
```

```
ccttccccgt cgaggcaccc ccgcttgagg aggaggaagt gattatcgag caggacccag    14100
gttttgtaag cgaagacgac gaggatcgct cagtaccaac agaggataaa aagcaagacc    14160
aggacgacgc agaggcaaac gaggaacaag tcgggcgggg ggaccaaagg catggcgact    14220
acctagatgt gggagacgac gtgctgttga agcatctgca gcgccagtgc gccattatct    14280
gcgacgcgtt gcaagagcgc agcgatgtgc ccctcgccat agcggatgtc agccttgcct    14340
acgaacgcca cctgttctca ccgcgcgtac cccccaaacg ccaagaaaac ggcacatgcg    14400
agcccaaccc gcgcctcaac ttctaccccg tatttgccgt gccagaggtg cttgccacct    14460
atcacatctt tttccaaaac tgcaagatac ccctatcctg ccgtgccaac cgcagccgag    14520
cggacaagca gctggccttg cggcagggcg ctgtcatacc tgatatcgcc tcgctcgacg    14580
aagtgccaaa aatctttgag ggtcttggac gcgacgagaa acgcgcggca aacgctctgc    14640
aacaagaaaa cagcgaaaat gaaagtcact gtggagtgct ggtggaactt gagggtgaca    14700
acgcgcgcct agccgtgctg aaacgcagca tcgaggtcac ccactttgcc tacccggcac    14760
ttaacctacc ccccaaggtt atgagcacag tcatgagcga gctgatcgtg cgccgtgcac    14820
gacccctgga gagggatgca aacttgcaag aacaaaccga ggagggccta cccgcagttg    14880
gcgatgagca gctggcgcgc tggcttgaga cgcgcgagcc tgccgacttg gaggagcgac    14940
gcaagctaat gatggccgca gtgcttgtta ccgtggagct tgagtgcatg cagcggttct    15000
ttgctgaccc ggagatgcag cgcaagctag aggaaacgtt gcactacacc tttcgccagg    15060
gctacgtgcg ccaggcctgc aaaatttcca acgtggagct ctgcaacctg gtctcctacc    15120 ttggaattttt gcacgaaaac cgcctcgggc aaaacgtgct tcattccacg ctcaagggcg    15180
aggcgcgccg cgactacgtc cgcgactgcg tttacttatt tctgtgctac acctggcaaa    15240
cggccatggg cgtgtggcag caatgcctgg aggagcgcaa cctaaaggag ctgcagaagc    15300
tgctaaagca aaacttgaag gacctatgga cggccttcaa cgagcgctcc gtggccgcgc    15360
acctggcgga cattatcttc cccgaacgcc tgcttaaaac cctgcaacag ggtctgccag    15420
acttcaccag tcaaagcatg ttgcaaaact ttaggaactt tatcctagag cgttcaggaa    15480
ttctgcccgc cacctgctgt gcgcttccta gcgactttgt gcccattaag taccgtgaat    15540
gccctccgcc gctttggggt cactgctacc ttctgcagct agccaactac cttgcctacc    15600
actccgacat catggaagac gtgagcggtg acggcctact ggagtgtcac tgtcgctgca    15660
acctatgcac cccgcaccgc tccctggtct gcaattcgca actgcttagc gaaagtcaaa    15720
ttatcggtac ctttgagctg cagggtccct cgcctgacga aaagtccgcg ctccgggggt    15780
tgaaactcac tccggggctg tggacgtcgg cttaccttcg caaatttgta cctgaggact    15840
accacgccca cgagattagg ttctacgaag accaatcccg cccgcaaat gcggagctta    15900 ccgcctgcgt cattacccag ggccacatcc ttggccaatt gcaagccatc aacaaagccc    15960
gccaagagtt tctgctacga aagggacggg gggtttacct ggaccccag tccgcgagg    16020 agctcaaccc aatccccccg ccgccgcagc cctatcagca gccgcgggcc cttgcttccc    16080
aggatggcac ccaaaaagaa gctgcagctg ccgccgccgc cacccacgga cgaggaggaa    16140
tactgggaca gtcaggcaga ggaggttttg gacgaggagg aggagatgat ggaagactgg    16200
gacagcctag acgaagcttc cgaggccgaa gaggtgtcag acgaaacacc gtcaccctcg    16260
gtcgcattcc cctcgccggc gccccagaaa ttggcaaccg ttcccagcat cgctacaacc    16320
tccgctcctc aggcgccgcc ggcactgcct gttcgccgac ccaaccgtag atgggacacc    16380
```

```
actggaacca gggccggtaa gtctaagcag ccgccgccgt tagcccaaga gcaacaacag    16440
cgccaaggct accgctcgtg gcgcgggcac aagaacgcca tagttgcttg cttgcaagac    16500
tgtgggggca acatctcctt cgcccgccgc tttcttctct accatcacgg cgtggccttc    16560
ccccgtaaca tcctgcatta ctaccgtcat ctctacagcc cctactgcac cggcggcagc    16620
ggcagcggca gcaacagcag cggtcacaca gaagcaaagg cgaccggata gcaagactct    16680
gacaaagccc aagaaatcca cagcggcggc agcagcagga ggaggagcgc tgcgtctggc    16740
gcccaacgaa cccgtatcga cccgcgagct tagaaatagg attttttccca ctctgtatgc    16800 tatatttcaa caaagcaggg gccaagaaca agagctgaaa ataaaaaaca ggtctctgcg    16860
ctccctcacc cgcagctgcc tgtatcacaa aagcgaagat cagcttcggc gcacgctgga    16920
agacgcggag gctctcttca gcaaatactg cgcgctgact cttaaggact agtttcgcgc    16980
cctttctcaa atttaagcgc gaaaactacg tcatctccag cggccacacc cggcgccagc    17040
acctgtcgtc agcgccatta tgagcaagga aattcccacg ccctacatgt ggagttacca    17100
gccacaaatg ggacttgcgg ctggagctgc ccaagactac tcaacccgaa taaactacat    17160
gagcgcggga ccccacatga tatcccgggt caacggaatc cgcgcccacc gaaaccgaat    17220
tctcctcgaa caggcggcta ttaccaccac acctcgtaat aaccttaatc cccgtagttg    17280
gcccgctgcc ctggtgtacc aggaaagtcc cgctcccacc actgtggtac ttcccagaga    17340
cgcccaggcc gaagttcaga tgactaactc aggggcgcag cttgcgggcg ctttcgtca    17400 cagggtgcgg tcgcccgggc agggtataac tcacctgaaa atcagagggc gaggtattca    17460
gctcaacgac gagtcggtga gctcctctct tggtctccgt ccggacggga catttcagat    17520
cggcggcgct ggccgctctt catttacgcc ccgtcaggcg atcctaactc tgcagacctc    17580
gtcctcggag ccgcgctccg gaggcattgg aactctacaa tttattgagg agttcgtgcc    17640
ttcggtttac ttcaaccccct tttctggacc tcccggccac tacccggacc agtttattcc    17700
caactttgac gcggtgaaag actcggcgga cggctacgac tgaatgacca gtggagaggc    17760
agagcgactg cgcctgacac acctcgacca ctgccgccgc cacaagtgct tgcccgcgg    17820 ctccggtgag ttttgttact ttgaattgcc cgaagagcat atcgagggcc cggcgcacgg    17880
cgtccggctc accacccagg tagagcttac acgtagcctg attcgggagt ttaccaagcg    17940 cccccctgcta gtggagcggg agcggggtcc ctgtgttctg accgtggttt gcaactgtcc    18000
taaccctgga ttacatcaag atctttgttg tcatctctgt gctgagtata ataaatacag    18060
aaattagaat ctactggggc tcctgtcgcc atcctgtgaa cgccaccgtt tttacccacc    18120
caaagcagac caaagcaaac ctcacctccg gtttgcacaa gcgggccaat aagtaccta    18180 cctggtactt taacggctct tcatttgtaa tttacaacag tttccagcga gacgaagtaa    18240
gtttgccaca caaccttctc ggcttcaact acaccgtcaa gaaaaacacc accaccacca    18300
ccctcctcac ctgccgggaa cgtacgagtg cgtcaccggt tgctgcgccc acacctacag    18360
cctgagcgta accagacatt actcccattt ttccaaaaca ggaggtgagc tcaactcccg    18420
gaactcaggt caaaaaagca ttttgcgggg tgctgggatt ttttaattaa gtatatgagc    18480
aattcaagta actctacaag cttgtctaat ttttctggaa ttggggtcgg ggttatcctt    18540
actcttgtaa ttctgtttat tcttatacta gcacttctgt gccttagggt tgccgcctgc    18600
tgcacgcacg tttgtaccta ttgtcagctt tttaaacgct gggggcaaca tccaagatga    18660
ggtacatgat tttaggcttg ctcgcccttg cggcagtctg cagcgctgcc aaaaaggttg    18720
agtttaagga accagcttgc aatgttacat ttaaatcaga agctaatgaa tgcactactc    18780
```

```
ttataaaatg caccacagaa catgaaaagc ttattattcg ccacaaagac aaaattggca   18840
agtatgctgt atatgctatt tggcagccag gtgacactaa cgactataat gtcacagtct   18900
tccaaggtga aaatcgtaaa acttttatgt ataaatttcc attttatgaa atgtgcgata   18960
ttaccatgta catgagcaaa cagtacaagt tgtggccccc acaaaagtgt ttagagaaca   19020
ctggcacctt tgttccacc gctctgctta ttacagcgct tgctttggta tgtaccttac    19080
tttatctcaa atacaaaagc agacgcagtt ttattgatga aaagaaaatg ccttgatttt   19140
ccgcttgctt gtattcccct ggacaattta ctctatgtgg gatatgctcc aggcgggcaa   19200
gattataccc acaaccttca aatcaaactt tcctggacgt tagcgcctga tttctgccag   19260
cgcctgcact gcaaatttga tcaaacccag cttcagcttg cctgctccag agatgaccgg   19320
ctcaaccatc gcgcccacaa cggactatcg caacaccact gctaccggac taacatctgc   19380
cctaaattta ccccaagttc atgcctttgt caatgactgg gcgagcttgg acatgtggtg   19440
gttttccata gcgcttatgt ttgtttgcct tattattatg tggcttattt gttgcctaaa   19500
gcgcagacgc gccagacccc ccatctatag gcctatcatt gtgctcaacc cacacaatga   19560
aaaaattcat agattggacg gtctgaaacc atgttctctt cttttacagt atgattaaat   19620
gagacatgat tcctcgagtt cttatattat tgacccttgt tgcgcttttc tgtgcgtgct   19680
ctacattggc cgcggtcgct cacatcgaag tagattgcat cccaccttc acagtttacc    19740 tgctttacgg atttgtcacc cttatcctca tctgcagcct cgtcactgta gtcatcgcct   19800
tcattcagtt cattgactgg gtttgtgtgc gcattgcgta cctcaggcac catccgcaat   19860
acagagacag gactatagct gatcttctca gaattcttta attatgaaac ggagtgtcat   19920
ttttgttttg ctgattttt gcgccctacc tgtgctttgc tcccaaacct cagcgcctcc     19980
caaaagacat atttcctgca gattcactca aatatggaac attcccagct gctacaacaa   20040
acagagcgat ttgtcagaag cctggttata cgccatcatc tctgtcatgg tttttttgcag  20100 taccattttt gccctagcca tatatccata ccttgacatt ggctggaatg ccatagatgc   20160
catgaaccac cctactttcc cagtgcccgc tgtcatacca ctgcaacagg ttattgcccc   20220
aatcaatcag cctcgccccc cttctcccac ccccactgag attagctact ttaatttgac   20280
aggtggagat gactgaatct ctagagtcga cctgcaggca tgcaagcttg gcgtaatcat   20340
ggtcatagct gtttcctgtg tgaaattgtt atccgctcac aattccacac aacatacgag   20400
ccggaagcat aaagtgtaaa gcctggggtg cctaatgagt gagctaactc acattaattg   20460
cgttgcgctc actgcccgct ttccagtcgg gaaacctgtc gtgccagctg cattaatgaa   20520
tcggccaacg cgcggggaga ggcggtttgc gtattgggcg ctcttccgct tcctcgctca   20580
ctgactcgct gcgctcggtc gttcggctgc ggcgagcggt atcagctcac tcaaaggcgg   20640
taatacggtt atccacagaa tcaggggata acgcaggaaa gaacatgtga gcaaaaggcc   20700
agcaaaaggc caggaaccgt aaaaaggccg cgttgctggc gtttttccat aggctccgcc   20760
cccctgacga gcatcacaaa aatcgacgct caagtcagag gtggcgaaac ccgacaggac   20820
tataaagata ccaggcgttt ccccctggaa gctccctcgt gcgctctcct gttccgaccc   20880
tgccgcttac cggatacctg tccgcctttc tcccttcggg aagcgtggcg ctttctcaat   20940
gctcacgctg taggtatctc agttcggtgt aggtcgttcg ctccaagctg ggctgtgtgc   21000
acgaaccccc cgttcagccc gaccgctgcg ccttatccgg taactatcgt cttgagtcca   21060
acccggtaag acacgactta tcgccactgg cagcagccac tggtaacagg attagcagag   21120
```

| | |
|---|---:|
| cgaggtatgt aggcggtgct acagagttct tgaagtggtg gcctaactac ggctacacta | 21180 |
| gaaggacagt atttggtatc tgcgctctgc tgaagccagt taccttcgga aaaagagttg | 21240 |
| gtagctcttg atccggcaaa caaaccaccg ctggtagcgg tggtttttt gtttgcaagc | 21300 |
| agcagattac gcgcagaaaa aaaggatctc aagaagatcc tttgatcttt tctacggggt | 21360 |
| ctgacgctca gtggaacgaa aactcacgtt aagggatttt ggtcatgaga ttatcaaaaa | 21420 |
| ggatcttcac ctagatcctt ttaaattaaa aatgaagttt taaatcaatc taagtatat | 21480 |
| atgagtaaac ttggtctgac agttaccaat gcttaatcag tgaggcacct atctcagcga | 21540 |
| tctgtctatt tcgttcatcc atagttgcct gactccccgt cgtgtagata actacgatac | 21600 |
| gggagggctt accatctggc cccagtgctg caatgatacc gcgagaccca cgctcaccgg | 21660 |
| ctccagattt atcagcaata aaccagccag ccggaagggc cgagcgcaga gtggtcctg | 21720 |
| caactttatc cgcctccatc cagtctatta attgttgccg ggaagctaga gtaagtagtt | 21780 |
| cgccagttaa tagtttgcgc aacgttgttg ccattgctac aggcatcgtg gtgtcacgct | 21840 |
| cgtcgtttgg tatggcttca ttcagctccg gttcccaacg atcaaggcga gttacatgat | 21900 |
| cccccatgtt gtgcaaaaaa gcggttagct ccttcggtcc tccgatcgtt gtcagaagta | 21960 |
| agttggccgc agtgttatca ctcatggtta tggcagcact gcataattct cttactgtca | 22020 |
| tgccatccgt aagatgcttt tctgtgactg gtgagtactc aaccaagtca ttctgagaat | 22080 |
| agtgtatgcg gcgaccgagt tgctcttgcc cggcgtcaat acgggataat accgcgccac | 22140 |
| atagcagaac tttaaaagtg ctcatcattg gaaaacgttc ttcggggcga aaactctcaa | 22200 |
| ggatcttacc gctgttgaga tccagttcga tgtaacccac tcgtgcaccc aactgatctt | 22260 |
| cagcatcttt tactttcacc agcgtttctg ggtgagcaaa aacaggaagg caaaatgccg | 22320 |
| caaaaaaggg aataagggcg acacggaaat gttgaatact catactcttc ctttttcaat | 22380 |
| attattgaag catttatcag ggttattgtc tcatgagcgg atacatattt gaatgtattt | 22440 |
| agaaaaataa acaaataggg gttccgcgca catttccccg aaaagtgcca cctgacgtct | 22500 |
| aagaaaccat tattatcatg acattaacct ataaaaatag gcgtatcacg aggccctttc | 22560 |
| gtc | 22563 |

```
<210> SEQ ID NO 105
<211> LENGTH: 8350
<212> TYPE: DNA
<213> ORGANISM: artificial
<220> FEATURE:
<223> OTHER INFORMATION: plasmid psyx20-lacIq

<400> SEQUENCE: 105
```

| | |
|---|---:|
| cagctggcgt aatagcgaag aggcccgcac cgatcgccct tcccaacagt tgcgcagcct | 60 |
| gaatggcgaa tgggacgcgc cctgtagcgg cgcattaagc gcggcgggtg tggtggttac | 120 |
| gcgcagcgtg accgctacac ttgccagcgc cctagcgccc gctcctttcg ctttcttccc | 180 |
| ttcctttctc gccacgttcg ccggctttcc ccgtcaagct ctaaatcggg gctcccttt | 240 |
| agggttccga tttagtgctt tacggcacct cgaccccaaa aaacttgatt agggtgatgg | 300 |
| ttcacgtagt gggccatcgc cctgatagac ggtttttcgc cctttgacgt tggagtccac | 360 |
| gttctttaat agtggactct tgttccaaac tggaacaaca ctcaaccta tctcggtcta | 420 |
| ttcttttgat ttataaggga ttttgccgat ttcggcctat tggttaaaaa atgagctgat | 480 |
| ttaacaaaaa tttaacgcga attttaacaa aattcgaccg atgcccttga gagccttcaa | 540 |
| cccagtcagc tccttccggt gggcgcgggg catgactatc gtcgccgcac ttatgactgt | 600 |

| | |
|---|---|
| cttctttatc atgcaactcg taggacaggt gccggcagcg ctctgggtca ttttcggcga | 660 |
| ggaccgcttt cgctggagcg cgacgatgat cggcctgtcg cttgcggtat tcggaatctt | 720 |
| gcacgccctc gctcaagcct tcgtcactgg tcccgccacc aaacgtttcg gcgagaagca | 780 |
| ggccattatc gccggcatgg cggccgacgc gctgggctac gtcttgctgg cgttcgcgac | 840 |
| gcgaggctgg atggccttcc ccattatgat tcttctcgct tccggcggca tcgggatgcc | 900 |
| cgcgttgcag gccatgctgt ccaggcaggt agatgacgac catcagggac agcttcaagg | 960 |
| atcgctcgcg gctcttacca gcctaacttc gatcattgga ccgctgatcg tcacggcgat | 1020 |
| ttatgccgcc tcggcgagca catggaacgg gttggcatgg attgtaggcg ccgccctata | 1080 |
| ccttgtctgc ctccccgcgt tgcgtcgcgg tgcatggagc cgggccacct cgacctgaat | 1140 |
| ggaagccggg ggcacctcgc taacggattc accactccgc agacccgcca taaaacgccc | 1200 |
| tgagaagccc gtgacgggct tttcttgtat tatgggtagt ttccttgcat gaatccataa | 1260 |
| aaggcgcctg tagtgccatt taccccccatt cactgccaga gccgtgagcg cagcgaactg | 1320 |
| aatgtcacga aaagacagc gactcaggtg cctgatggtc ggagacaaaa ggaatattca | 1380 |
| gcgatttgcc cgagcttgcg agggtgctac ttaagccttt agggttttaa ggtctgtttt | 1440 |
| gtagaggagc aaacagcgtt tgcgacatcc ttttgtaata ctgcggaact gactaaagta | 1500 |
| gtgagttata cacagggctg ggatctattc tttttatctt tttttattct ttctttattc | 1560 |
| tataaattat aaccacttga atataaacaa aaaaaacaca caaaggtcta gcggaattta | 1620 |
| cagagggtct agcagaattt acaagttttc cagcaaaggt ctagcagaat ttacagatac | 1680 |
| ccacaactca aggaaaagg actagtaatt atcattgact agcccatctc aattggtata | 1740 |
| gtgattaaaa tcacctagac caattgagat gtatgtctga attagttgtt ttcaaagcaa | 1800 |
| atgaactagc gattagtcgc tatgacttaa cggagcatga aaccaagcta attttatgct | 1860 |
| gtgtggcact actcaacccc acgattgaaa accctacaag gaaagaacgg acggtatcgt | 1920 |
| tcacttataa ccaatacgct cagatgatga acatcagtag ggaaaatgct tatggtgtat | 1980 |
| tagctaaagc aaccagagag ctgatgacga gaactgtgga atcaggaat cctttggtta | 2040 |
| aaggctttga gattttccag tggacaaact atgccaagtt ctcaagcgaa aaattagaat | 2100 |
| tagtttttag tgaagagata ttgccttatc ttttccagtt aaaaaaattc ataaaatata | 2160 |
| atctggaaca tgttaagtct tttgaaaaca aatactctat gaggatttat gagtggttat | 2220 |
| taaaagaact aacacaaaag aaaactcaca aggcaaatat agagattagc cttgatgaat | 2280 |
| ttaagttcat gttaatgctt gaaaataact accatgagtt taaaaggctt aaccaatggg | 2340 |
| ttttgaaacc aataagtaaa gatttaaaca cttacagcaa tatgaaattg gtggttgata | 2400 |
| agcgaggccg cccgactgat acgttgattt tccaagttga actagataga caaatggatc | 2460 |
| tcgtaaccga acttgagaac aaccagataa aaatgaatgg tgacaaaata ccaacaacca | 2520 |
| ttacatcaga ttcctaccta cataacggac taagaaaaac actacacgat gctttaactg | 2580 |
| caaaaattca gctcaccagt tttgaggcaa aatttttgag tgacatgcaa agtaagtatg | 2640 |
| atctcaatgg ttcgttctca tggctcacgc aaaaacaacg aaccacacta gagaacatac | 2700 |
| tggctaaata cggaaggatc tgaggttctt atggctcttg tatctatcag tgaagcatca | 2760 |
| agactaacaa acaaaagtag aacaactgtt caccgttaca tatcaaaggg aaaactgtcc | 2820 |
| atatgcacag atgaaaacgg tgtaaaaaag atagatacat cagagctttt acgagttttt | 2880 |
| ggtgcattca aagctgttca ccatgaacag atcgacaatg taacagatga acagcatgta | 2940 |

```
acacctaata gaacaggtga aaccagtaaa acaaagcaac tagaacatga aattgaacac    3000
ctgagacaac ttgttacagc tcaacagtca cacatagaca gcctgaaaca ggcgatgctg    3060
cttatcgaat caaagctgcc gacaacacgg gagccagtga cgcctcccgt ggggaaaaaa    3120
tcatggcaat tctggaagaa atagcgcttt cagccggcaa accggctgaa gccggatctg    3180
cgattctgat aacaaactag caacaccaga acagcccgtt tgcgggcagc aaaacccgta    3240
cttttggacg ttccggcggt tttttgtggc gagtggtgtt cgggcggtgc gcgattattg    3300
aagcatttat cagggttatt gtctcatgag cggatacata tttgaatgta tttagaaaaa    3360
taaacaaata ggggttccgc gcacatttcc ccgaaaagtg ccacctgacg tctaagaaac    3420
cattattatc atgacattaa cctataaaaa taggcgtatc acgaggccct ttcgtcttca    3480
agaattcgcg cgcgaaggcc aagcggcatg catttacgtt gacaccatcg aatggcgcaa    3540
aacctttcgc ggtatggcat gatagcgccc ggaagagagt caattcaggg tggtgaatgt    3600
gaaaccagta acgttatacg atgtcgcaga gtatgccggt gtctcttatc agaccgtttc    3660
ccgcgtggtg aaccaggcca gccacgtttc tgcgaaaacg cgggaaaaag tggaagcggc    3720
gatggcggag ctgaattaca ttcccaaccg cgtggcacaa caactggcgg gcaaacagtc    3780
gttgctgatt ggcgttgcca cctccagtct ggccctgcac gcgccgtcgc aaattgtcgc    3840
ggcgattaaa tctcgcgccg atcaactggg tgccagcgtg gtggtgtcga tggtagaacg    3900
aagcggcgtc gaagcctgta aagcggcggt gcacaatctt ctcgcgcaac gcgtcagtgg    3960
gctgatcatt aactatccgc tggatgacca ggatgccatt gctgtggaag ctgcctgcac    4020
taatgttccg gcgttatttc ttgatgtctc tgaccagaca cccatcaaca gtattatttt    4080
ctcccatgaa gacggtacgc gactgggcgt ggagcatctg gtcgcattgg gtcaccagca    4140
aatcgcgctg ttagcgggcc cattaagttc tgtctcggcg cgtctgcgtc tggctggctg    4200
gcataaatat ctcactcgca atcaaattca gccgatagcg gaacgggaag cgactggag     4260 tgccatgtcc ggttttcaac aaaccatgca aatgctgaat gagggcatcg ttcccactgc    4320
gatgctggtt gccaacgatc agatggcgct gggcgcaatg cgcgccatta ccgagtccgg    4380
gctgcgcgtt ggtgcggata tctcggtagt gggatacgac gataccgaag acagctcatg    4440
ttatatcccg ccgtcaacca ccatcaaaca ggattttcgc ctgctggggc aaaccagcgt    4500
ggaccgcttc tgcaactct ctcagggcca ggcggtgaag gcaatcagc tgttgcccgt      4560 ctcactggtg aaaagaaaaa ccaccctggc gcccaatacg caaaccgcct ctccccgcgc    4620
gttggccgat tcattaatgc agctggcacg acaggtttcc cgactggaaa gcgggcagtg    4680
agcgcaacgc aattaatgtg agttagctca ctcattaggc gaattctcat gtttgacagc    4740
ttatcatcga taagctttaa tgcggtagtt tatcacagtt aaattgctaa cgcagtcagg    4800
caccgtgtat gaaatctaac aatgcgctca tcgtcatcct cggcaccgtc accctggatg    4860
ctgtaggcat aggcttggtt atgccggtac tgccgggcct cttgcgggat atcgtccatt    4920
ccgacagcat cgccagtcac tatggcgtgc tgctagcgct atatgcgttg atgcaatttc    4980
tatgcgcacc cgttctcgga gcactgtccg accgctttgg ccgccgccca gtcctgctcg    5040
cttcgctact tggagccact atcgactacg cgatcatggc gaccacaccc gtcctgtgga    5100
tcctctacgc cggacgcatc gtggccggca tcaccggcgc cacaggtgcg gttgctggcg    5160
cctatatcgc cgacatcacc gatggggaag atcgggctcg ccacttcggg ctcatgagcg    5220
cttgtttcgg cgtgggtatg gtggcaggcc ccgtggccgg gggactgttg gcgccatct    5280 ccttgcatgc accattcctt gcggcggcgg tgctcaacgg cctcaaccta ctactgggct    5340
```

```
gcttcctaat gcaggaatcg cataagggag agcgtcgacc gatgcccttg agagccttca    5400
acccagtcag ctccttccgg tgggcgcggg gcatgactat cgtcgccgca cttatgactg    5460
tcttctttat catgcaactc gtaggacagg tgccggcagc gctctgggtc attttcggcg    5520
aggaccgctt tcgctggagc gcgacgatga tcggcctgtc gcttgcgta ttcggaatct     5580
tgcacgccct cgctcaagcc ttcgtcactg gtcccgccac caaacgtttc ggcgagaagc    5640
aggccattat cgccggcatg gcggccgacg cgctgggcta cgtcttgctg gcgttcgcga    5700
cgcgaggctg gatggccttc cccattatga ttcttctcgc ttccggcggc atcgggatgc    5760
ccgcgttgca ggccatgctg tccaggcagg tagatgacga ccatcaggga cagcttcaag    5820
gatcgctcgc ggctcttacc agcctaactt cgatcattgg accgctgatc gtcacggcga    5880
tttatgccgc ctcggcgagc acatggaacg ggttggcatg gattgtaggc gccgccctat    5940
accttgtctg cctccccgcg ttgcgtcgcg gtgcatggag ccgggccacc tcgacctgaa    6000
tggaagccgg cggcacctcg ctaacggatt caccactcca agaattggag ccaatcaatt    6060
cttgcggaga actgtgaatg cgcaaaccaa cccttggcag aacatatcca tcgcgtccgc    6120
catctccagc agccgcacgc ggcgcatctc gggcagcgtt gggtcctggc cacgggtgcg    6180
catgatcgtg ctcctgtcgt tgaggacccg gctaggctgg cggggttgcc ttactggtta    6240
gcagaatgaa tcaccgatac gcgagcgaac gtgaagcgac tgctgctgca aaacgtctgc    6300
gacctgagca acaacatgaa tggtcttcgg tttccgtgtt tcgtaaagtc tggaaacgcg    6360
gaagtcagcg ccctgcacca ttatgttccg gatctgcatc gcaggatgct gctggctacc    6420
ctgtggaaca cctacatctg tattaacgaa gcgctggcat tgaccctgag tgatttttct    6480
ctggtcccgc cgcatccata ccgccagttg tttaccctca caacgttcca gtaaccgggc    6540
atgttcatca tcagtaaccc gtatcgtgag catcctctct cgtttcatcg gtatcattac    6600
ccccatgaac agaaatcccc cttacacgga ggcatcagtg accaaacagg aaaaaaccgc    6660
ccttaacatg gcccgcttta tcagaagcca gacattaacg cttctggaga aactcaacga    6720
gctggacgcg gatgaacagg cagacatctg tgaatcgctt cacgaccacg ctgatgagct    6780
ttaccgcagc gcgcagggtc agcctgaata cgcgtttaat gaccagcaca gtcgtgatgg    6840
caaggtcaga atagcgctga ggtctgcctc gtgaagaagg tgttgctgac tcataccagg    6900
cctgaatcgc cccatcatcc agccagaaag tgagggagcc acggttgatg agagctttgt    6960
tgtaggtgga ccagttggtg attttgaact tttgctttgc cacggaacgg tctgcgttgt    7020
cgggaagatg cgtgatctga tccttcaact cagcaaaagt tcgatttatt caacaaagcc    7080
acgttgtgtc tcaaaatctc tgatgttaca ttgcacaaga taaaaatata tcatcatgaa    7140
caataaaact gtctgcttac ataaacagta atacaagggg tgttatgagc catattcaac    7200
gggaaacgtc ttgctcgagg ccgcgattaa attccaacat ggatgctgat ttatatgggt    7260
ataaatgggc tcgcgataat gtcgggcaat caggtgcgac aatctatcga ttgtatggga    7320
agcccgatgc gccagagttg tttctgaaac atggcaaagg tagcgttgcc aatgatgtta    7380
cagatgagat ggtcagacta aactggctga cggaatttat gcctcttccg accatcaagc    7440
attttatccg tactcctgat gatgcatggt tactcaccac tgcgatcccc gggaaaacag    7500
cattccaggt attagaagaa tatcctgatt caggtgaaaa tattgttgat gcgctggcag    7560
tgttcctgcg ccggttgcat tcgattcctg tttgtaattg tcctttaac agcgatcgcg    7620
tatttcgtct cgctcaggcg caatcacgaa tgaataacgg tttggttgat gcgagtgatt    7680
```

| | |
|---|---|
| ttgatgacga gcgtaatggc tggcctgttg aacaagtctg gaaagaaatg cataagcttt | 7740 |
| tgccattctc accggattca gtcgtcactc atggtgattt ctcacttgat aaccttattt | 7800 |
| ttgacgaggg gaaattaata ggttgtattg atgttggacg agtcggaatc gcagaccgat | 7860 |
| accaggatct tgccatccta tggaactgcc tcggtgagtt ttctccttca ttacagaaac | 7920 |
| ggcttttca aaaatatggt attgataatc ctgatatgaa taaattgcag tttcatttga | 7980 |
| tgctcgatga gttttctaa tcagaattgg ttaattggtt gtaacactgg cagagcatta | 8040 |
| cgctgacttg acgggacggc ggctttgttg aataaatcga acttttgctg agttgaagga | 8100 |
| tcagatcacg catcttcccg acaacgcaga ccgttccgtg gcaaagcaaa agttcaaaat | 8160 |
| caccaactgg tccacctaca acaaagctct catcaaccgt ggctccctca ctttctggct | 8220 |
| ggatgatggg gcgattcagg cctggtatga gtcagcaaca ccttcttcac gaggcagacc | 8280 |
| tcagcgctat tctgaccttg ccatcacgac tgtgctggtc attaaacgcg tattcaggct | 8340 |
| gaccctgcgc | 8350 |

<210> SEQ ID NO 106
<211> LENGTH: 3190
<212> TYPE: DNA
<213> ORGANISM: artificial
<220> FEATURE:
<223> OTHER INFORMATION: plasmid pAGR3

<400> SEQUENCE: 106

| | |
|---|---|
| aagtgaccaa acaggaaaaa accgccctta acatggcccg ctttatcaga agccagacat | 60 |
| taacgcttct ggagaaactc aacgagctgg acgcggatga acaggcagac atctgtgaat | 120 |
| cgcttcacga ccacgctgat gagctttacc gcagctgcct cgcgcgtttc ggtgatgacg | 180 |
| gtgaaaacct ctgacacatg cagctcccgg agacggtcac agcttgtctg taagcggatg | 240 |
| ccgggagcag acaagcccgt cagggcgcgt cagcgggtgt tggcgggtgt cggggcgcag | 300 |
| ccatgaccca gtcacgtagc gatagcggag tgtatactgg cttaactatg cggcatcaga | 360 |
| gcagattgta ctgagagtgc accatatgcg gtgtgaaata ccgcacagat gcgtaaggag | 420 |
| aaaataccgc atcaggcgct cttccgcttc ctcgctcact gactcgctgc gctcggtcgt | 480 |
| tcggctgcgg cgagcggtat cagctcactc aaaggcggta atacggttat ccacagaatc | 540 |
| aggggataac gcaggaaaga acatgtgagc aaaaggccag caaaaggcca ggaaccgtaa | 600 |
| aaaggccgcg ttgctggcgt ttttccatag gctccgcccc cctgacgagc atcacaaaaa | 660 |
| tcgacgctca agtcagaggt ggcgaaaccc gacaggacta taaagatacc aggcgtttcc | 720 |
| ccctggaagc tccctcgtgc gctctcctgt tccgaccctg ccgcttaccg gatacctgtc | 780 |
| cgcctttctc ccttcgggaa gcgtggcgct ttctcatagc tcacgctgta ggtatctcag | 840 |
| ttcggtgtag gtcgttcgct ccaagctggg ctgtgtgcac gaacccccg ttcagcccga | 900 |
| ccgctgcgcc ttatccggta actatcgtct tgagtccaac ccggtaagac acgacttatc | 960 |
| gccactggca gcagccactg gtaacaggat tagcagagcg aggtatgtag gcggtgctac | 1020 |
| agagttcttg aagtggtggc ctaactacgg ctacactaga aggacagtat ttggtatctg | 1080 |
| cgctctgctg aagccagtta ccttcggaaa aagagttggt agctcttgat ccggcaaaca | 1140 |
| aaccaccgct ggtagcggtg ttttttgt ttgcaagcag cagattacgc gcagaaaaaa | 1200 |
| aggatctcaa gaagatcctt tgatcttttc tacgggtct gacgctcagt ggaacgaaaa | 1260 |
| ctcacgttaa gggattttgg tcatgagatt atcaaaaagg atcttcacct agatcctttt | 1320 |
| aaattaaaaa tgaagtttta atcaatcta agtatatat gagtaaactt ggtctgacag | 1380 |

```
ttaccaatgc ttaatcagtg aggcacctat ctcagcgatc tgtctatttc gttcatccat    1440
agttgcctga ctccccgtcg tgtagataac tacgatacgg gagggcttac catctggccc    1500
cagtgctgca atgataccgc gagacccacg ctcaccggct ccagatttat cagcaataaa    1560
ccagccagcc ggaagggccg agcgcagaag tggtcctgca actttatccg cctccatcca    1620
gtctattaat tgttgccggg aagctagagt aagtagttcg ccagttaata gtttgcgcaa    1680
cgttgttgcc attgctgcag gcatcgtggt gtcacgctcg tcgtttggta tggcttcatt    1740
cagctccggt tcccaacgat caaggcgagt tacatgatcc cccatgttgt gcaaaaaagc    1800
ggttagctcc ttcggtcctc cgatcgttgt cagaagtaag ttggccgcag tgttatcact    1860
catggttatg gcagcactgc ataattctct tactgtcatg ccatccgtaa gatgcttttc    1920
tgtgactggt gagtactcaa ccaagtcatt ctgagaatag tgtatgcggc gaccgagttg    1980
ctcttgcccg gcgtcaacac gggataatac cgcgccacat agcagaactt taaaagtgct    2040
catcattgga aaacgttctt cggggcgaaa actctcaagg atcttaccgc tgttgagatc    2100
cagttcgatg taacccactc gtgcacccaa ctgatcttca gcatcttta ctttcaccag     2160 cgtttctggg tgagcaaaaa caggaaggca aaatgccgca aaaagggaa taagggcgac     2220 acggaaatgt tgaatactca tactcttcct ttttcaatat tattgaagca tttatcaggg    2280
ttattgtctc atgagcggat acatatttga atgtatttag aaaaataaac aaataggggt    2340
tccgcgcaca tttccccgaa aagtgccacc tgacgtctaa gaaaccatta ttatcatgac    2400
attaacctat aaaaataggc gtatcacgag gccctttcgt cttcaagaat taattcccaa    2460
ttccaggcat caaataaaac gaaaggctca gtcgaaagac tgggcctttc gttttatctg    2520
ttgtttgtcg gtgaacgctc tcctgagtag gacaaatccg ccgggagcgg atttgaacgt    2580
tgcgaagcaa cggcccggag ggtggcgggc aggacgcccg ccataaactg ccaggaatta    2640
attccaggca tcaaataaaa cgaaaggctc agtcgaaaga ctgggccttt cgttttatct    2700
gttgtttgtc ggtgaacgct ctcctgagta ggacaaatcc gccgggagcg gatttgaacg    2760
ttgcgaagca acggcccgga gggtggcggg caggacgccc gccataaact gccaggaatt    2820
aattccaggc atcaaataaa acgaaaggct cagtcgaaag actgggcctt tcgttttatc    2880
tgttgtttgt cggtgaacgc tctcctgagt aggacaaatc cgccgggagc ggatttgaac    2940
gttgcgaagc aacggcccgg agggtggcgg gcaggacgcc cgccataaac tgccaggaat    3000
taattccagg catcaaataa aacgaaaggc tcagtcgaaa gactgggcct ttcgttttat    3060
ctgttgtttg tcggtgaacg ctctcctgag taggacaaat ccgccgggag cggatttgaa    3120
cgttgcgaag caacggcccg gagggtggcg ggcaggacgc ccgccataaa ctgccaggaa    3180
ttggggatcg                                                           3190
```